United States Patent
Watters et al.

(10) Patent No.: US 10,513,546 B2
(45) Date of Patent: Dec. 24, 2019

(54) CRP CAPTURE/DETECTION OF GRAM POSITIVE BACTERIA

(71) Applicant: PRESIDENT AND FELLOWS OF HARVARD COLLEGE, Cambridge, MA (US)

(72) Inventors: Alexander L. Watters, North Andover, MA (US); Donald E. Ingber, Boston, MA (US); Mark J. Cartwright, West Newton, MA (US); Michael Super, Lexington, MA (US); Martin Rottman, St. Cloud (FR); Evangelia Murray, Worcester, MA (US); Brendon Dusel, West Roxbury, MA (US)

(73) Assignee: PRESIDENT AND FELLOWS OF HARVARD COLLEGE, Cambridge, MA (US)

( * ) Notice: Subject to any disclaimer, the term of this patent is extended or adjusted under 35 U.S.C. 154(b) by 0 days.

(21) Appl. No.: 15/105,298

(22) PCT Filed: Dec. 18, 2014

(86) PCT No.: PCT/US2014/071293
§ 371 (c)(1),
(2) Date: Jun. 16, 2016

(87) PCT Pub. No.: WO2015/095604
PCT Pub. Date: Jun. 25, 2015

(65) Prior Publication Data
US 2016/0311877 A1    Oct. 27, 2016

Related U.S. Application Data

(60) Provisional application No. 61/917,705, filed on Dec. 18, 2013.

(51) Int. Cl.
| | | |
|---|---|---|
| *C07K 14/47* | (2006.01) | |
| *G01N 33/569* | (2006.01) | |
| *A61K 47/42* | (2017.01) | |
| *G01N 33/68* | (2006.01) | |
| *A61K 38/00* | (2006.01) | |

(52) U.S. Cl.
CPC .......... *C07K 14/4737* (2013.01); *A61K 47/42* (2013.01); *C07K 14/4726* (2013.01); *G01N 33/569* (2013.01); *G01N 33/56911* (2013.01); *G01N 33/56916* (2013.01); *G01N 33/56938* (2013.01); *G01N 33/56944* (2013.01); *G01N 33/6854* (2013.01); *A61K 38/00* (2013.01); *C07K 2319/30* (2013.01); *C07K 2319/33* (2013.01); *G01N 2333/4737* (2013.01)

(58) Field of Classification Search
None
See application file for complete search history.

(56) References Cited

U.S. PATENT DOCUMENTS

| | | |
|---|---|---|
| 4,425,330 A | 1/1984 | Norcross et al. |
| 5,137,810 A | 8/1992 | Sizemore et al. |
| 5,270,199 A | 12/1993 | Ezekowitz |
| 5,273,884 A | 12/1993 | Gale et al. |
| 5,405,832 A | 4/1995 | Potempa |
| 5,474,904 A | 12/1995 | Potempa et al. |
| 5,545,820 A | 8/1996 | Gatehouse et al. |
| 5,585,349 A | 12/1996 | Potempa |
| 5,783,179 A | 7/1998 | Nestor, Jr. et al. |
| 5,874,238 A | 2/1999 | Potempa et al. |
| 5,951,976 A | 9/1999 | Segal |
| 6,057,295 A | 5/2000 | Caretto et al. |
| 6,117,977 A | 9/2000 | Lasky et al. |
| 6,225,046 B1 | 5/2001 | Vesey et al. |
| 6,376,473 B1 | 4/2002 | Audonnet et al. |
| 6,471,968 B1 | 10/2002 | Baker et al. |
| 6,503,761 B1 | 1/2003 | Koenig et al. |
| 6,528,618 B1 | 3/2003 | Fridkin et al. |
| 6,528,624 B1 | 3/2003 | Idusogie et al. |
| 6,562,784 B1 | 5/2003 | Thiel et al. |
| 6,703,219 B1 | 3/2004 | Potempa et al. |
| 6,733,753 B2 | 5/2004 | Boone et al. |
| 6,846,649 B1 | 1/2005 | Thiel et al. |
| 6,900,292 B2 | 5/2005 | Sun et al. |
| 7,182,945 B2 | 2/2007 | Fridkin et al. |
| 7,202,207 B2 | 4/2007 | Thiel et al. |
| 7,211,396 B2 | 5/2007 | Uttenthal |

(Continued)

FOREIGN PATENT DOCUMENTS

| | | |
|---|---|---|
| EP | 0375736 B1 | 5/1998 |
| EP | 0861667 A2 | 8/2001 |

(Continued)

OTHER PUBLICATIONS

Casey et al (Infect. Immun., 76:1298-1304, 2008).*
Barnum et al., "Comparative Studies on the Binding Specificities of C-Reactive Protein (CRP) and HOPC 8", Annals of the New York Academy of Sciences 389:431-434 (1982).
Culley et al., "C-reactive protein binds to phosphorylated carbohydrates", Glycobiology 10(1):59-65 (2000).
Dumont et al., "Monomeric Fc Fusions: Impact on Pharmacokinetic and Biological Activity of Protein Therapeutics", Biodrugs 20(3):151-160 (2006).

(Continued)

*Primary Examiner* — Brian Gangle
(74) *Attorney, Agent, or Firm* — Nixon Peabody LLP; David S. Resnick; Ravinderjit Braich

(57) ABSTRACT

Described herein are engineered microbe-targeting molecules, microbe-targeting articles, kits comprising the same, and uses thereof. Such microbe-targeting molecules, microbe-targeting articles, or the kits comprising the same can bind or capture of a microbe or microbial matter thereof, and can thus be used in various applications, such as diagnosis or treatment of an infection caused by microbes in a subject or any environmental surface.

5 Claims, 8 Drawing Sheets

Specification includes a Sequence Listing.

(56) References Cited

U.S. PATENT DOCUMENTS

| | | |
|---|---|---|
| 7,226,429 B2 | 6/2007 | Tullis |
| 7,439,224 B2 | 10/2008 | Thiel et al. |
| 7,462,596 B2 | 12/2008 | Larsen et al. |
| 7,566,694 B2 | 7/2009 | Rider |
| 7,629,440 B2 | 12/2009 | Segal et al. |
| 7,695,937 B2 | 4/2010 | Baum |
| 7,763,436 B2 | 7/2010 | Das et al. |
| 8,013,120 B2 | 9/2011 | Du Clos et al. |
| 8,080,245 B2 | 12/2011 | Visintin et al. |
| 8,084,275 B2 | 12/2011 | Hirai et al. |
| 8,088,596 B2 | 1/2012 | Zeng et al. |
| 8,415,118 B2 | 4/2013 | Huang et al. |
| 8,598,324 B2 | 12/2013 | Rider |
| 9,150,631 B2 | 10/2015 | Super et al. |
| 9,644,021 B2 | 5/2017 | Wang et al. |
| 2003/0162248 A1 | 8/2003 | Wakamiya |
| 2003/0166878 A1 | 9/2003 | Nishiya et al. |
| 2003/0180814 A1 | 9/2003 | Hodges et al. |
| 2004/0018611 A1 | 1/2004 | Ward et al. |
| 2004/0229212 A1 | 11/2004 | Thiel et al. |
| 2005/0014932 A1 | 1/2005 | Imboden et al. |
| 2005/0037949 A1 | 2/2005 | O'Brien et al. |
| 2006/0040362 A1 | 2/2006 | Wakamiya |
| 2006/0104978 A1 | 5/2006 | Geijtenbeek et al. |
| 2006/0177879 A1 | 8/2006 | Mayes et al. |
| 2006/0188963 A1 | 8/2006 | Kongerslev et al. |
| 2006/0251582 A1 | 11/2006 | Keppler et al. |
| 2007/0031819 A1 | 2/2007 | Koschwanez et al. |
| 2007/0049532 A1 | 3/2007 | Feige et al. |
| 2007/0072247 A1 | 3/2007 | Wong et al. |
| 2007/0122850 A1 | 5/2007 | Teng |
| 2007/0184463 A1 | 8/2007 | Molho et al. |
| 2007/0224640 A1 | 9/2007 | Caldwell et al. |
| 2007/0231833 A1 | 10/2007 | Arcidiacono et al. |
| 2007/0269818 A1 | 11/2007 | Savage |
| 2008/0014576 A1 | 1/2008 | Jovanovich et al. |
| 2008/0056949 A1 | 3/2008 | Lee et al. |
| 2008/0108120 A1 | 5/2008 | Cho et al. |
| 2008/0156736 A1 | 7/2008 | Hirai et al. |
| 2008/0182793 A1 | 7/2008 | Baum et al. |
| 2008/0193965 A1 | 8/2008 | Zeng et al. |
| 2008/0260738 A1 | 10/2008 | Moore |
| 2008/0300188 A1 | 12/2008 | Yang et al. |
| 2009/0078614 A1 | 3/2009 | Varghese et al. |
| 2009/0175797 A1 | 7/2009 | Warren et al. |
| 2009/0181041 A1 | 7/2009 | Holgersson et al. |
| 2009/0220932 A1 | 9/2009 | Ingber et al. |
| 2009/0252729 A1 | 10/2009 | Farrington et al. |
| 2009/0269843 A1 | 10/2009 | Blume et al. |
| 2009/0297516 A1 | 12/2009 | Mayo et al. |
| 2010/0044232 A1 | 2/2010 | Lin et al. |
| 2010/0055675 A1 | 3/2010 | Kumamoto et al. |
| 2010/0266558 A1 | 10/2010 | Zipori |
| 2010/0323342 A1 | 12/2010 | Gomez et al. |
| 2010/0323429 A1 | 12/2010 | Hu et al. |
| 2010/0331240 A1 | 12/2010 | Michelow et al. |
| 2011/0027267 A1 | 2/2011 | Kyneb et al. |
| 2011/0053145 A1 | 3/2011 | Takakura et al. |
| 2011/0053250 A1 | 3/2011 | Takakura et al. |
| 2011/0159000 A1 | 6/2011 | Silverman |
| 2011/0183398 A1 | 7/2011 | Dasaratha et al. |
| 2011/0281792 A1 | 11/2011 | Zion et al. |
| 2012/0100140 A1 | 4/2012 | Reyes et al. |
| 2012/0164628 A1 | 6/2012 | Duffin et al. |
| 2013/0029428 A1 | 1/2013 | Kim et al. |
| 2013/0035283 A1 | 2/2013 | Super et al. |
| 2013/0072445 A9 | 3/2013 | Du Clos et al. |
| 2013/0212717 A1 | 8/2013 | Kiyokawa et al. |
| 2014/0227723 A1 | 8/2014 | Ingber et al. |
| 2014/0249087 A1 | 9/2014 | Warren et al. |
| 2015/0173883 A1 | 6/2015 | Ingber et al. |
| 2018/0125998 A1 | 5/2018 | Macielag et al. |

FOREIGN PATENT DOCUMENTS

| | | |
|---|---|---|
| EP | 0915970 B1 | 9/2004 |
| EP | 1862541 A1 | 12/2007 |
| EP | 1812459 B1 | 3/2011 |
| JP | S5418198 A | 2/1979 |
| JP | 2006517512 A | 7/2006 |
| JP | 2008515389 A | 5/2008 |
| JP | 2010122205 A | 6/2010 |
| JP | 2010268800 A | 12/2010 |
| WO | 2000006603 A1 | 2/2000 |
| WO | 2001003737 A1 | 1/2001 |
| WO | 2002032292 A2 | 4/2002 |
| WO | 2003014150 A2 | 2/2003 |
| WO | 2003054164 A2 | 7/2003 |
| WO | 2004018698 A2 | 3/2004 |
| WO | 2005092925 A2 | 10/2005 |
| WO | 2006018428 A2 | 2/2006 |
| WO | 2006044650 A2 | 4/2006 |
| WO | 2007/001332 A2 | 1/2007 |
| WO | 2007044642 A2 | 4/2007 |
| WO | 2007111496 A1 | 10/2007 |
| WO | 2008130618 A1 | 10/2008 |
| WO | 2009/040048 A2 | 4/2009 |
| WO | 2009062195 A2 | 5/2009 |
| WO | 2009119722 A1 | 10/2009 |
| WO | 2009126346 A2 | 10/2009 |
| WO | 2011/090954 A2 | 7/2011 |
| WO | 2011084749 A1 | 7/2011 |
| WO | 2011091037 A1 | 7/2011 |
| WO | 2011/103144 A1 | 8/2011 |
| WO | 2012019178 A2 | 2/2012 |
| WO | 2012050874 A2 | 4/2012 |
| WO | 2012100099 A2 | 7/2012 |
| WO | 2012135834 A2 | 10/2012 |
| WO | 2012142515 A2 | 10/2012 |
| WO | 2013/012924 A2 | 1/2013 |
| WO | 2013/130875 A1 | 9/2013 |
| WO | 2014/144325 A1 | 9/2014 |
| WO | 2014/190040 A1 | 11/2014 |
| WO | 2014/190229 A1 | 11/2014 |
| WO | 2015/009734 A2 | 1/2015 |
| WO | 2015/095604 A2 | 6/2015 |

OTHER PUBLICATIONS

Hohenester E., "Tackling the Legs of Mannan-Binding Lectin", Structure 19:1538-1540 (2011).

Huang et al., "Integrated microfluidic system for rapid screening of CRP aptamers utilizing systematic evolution of ligands by exponential enrichment (SELEX)", Biosensors and Bioelectronics 25:1761-1766 (2010).

Lee et al., "Carbohydrate-binding properties of human neo-CRP and its relationship to phosphorylcholine-binding site", Glycobiology 13(1):11-21 (2003).

Mold et al., "Binding of Human C-Reactive Protein to Bacteria", Infection and Immunity 38(1):392-395 (1982).

Presanis et al., "Biochemistry and genetics of mannan-binding lectin (MBL)", Biochemical Society Transactions 31(4):748-752 (2003).

Szalai A., "The biological functions of C-reactive protein", Vascular Pharmacology 39:105-107 (2002).

Ying et al., "Soluble Monomeric IgG1 Fc", The Journal of Biological Chemistry 287(23):19399-19408 (2012).

Zhavnerko et al., "Oriented Immobilization of C-Reactive Protein on Solid Surface for Biosensor Applications", Frontiers of Multifunctional Integrated Nanosystems 95-108 (2004).

Agrawal et al., "C-Reactive Protein Mutant That Does Not Bind to Phosphocholine and Pneumococcal C-Polysaccharide", J. Immunol. 169(6):3217-3222 (2002).

Shoulders et al., "Collagen structure and stability." Annual Review of Biochemistry 78(1):929-958 (2009).

Hwang et al., "The Pepper Mannose-Binding Lectin Gene CaMBL1 Is Required to Regulate Cell Death and Defense Responses to Microbial Pathogens", Plant Physiology 155: 447-463 (2011).

(56) References Cited

OTHER PUBLICATIONS

Idusogie et al., "Engineered Antibodies with Increased Activity to Recruit Complement", The Journal of Immunology 166:2571-2575 (2001).
Ilyas et al., "High glucose disrupts oligosaccharide recognition function via competitive inhibition: a potential mechanism for immune dysregulation in diabetes mellitus", Immunobiology 216(1-2): 126-131 (2011).
Invivo Gen Insight, "IgG-Fc Engineering for Therapeutic Use", (2006). (4 pages).
Jack et al., "Mannose-binding lectin: targeting the microbial world for complement attack and opsonophagocytosis", Immunological Reviews 180:86-99 (2001).
Jarva et al., "*Streptococcus pneumoniae* Evades Complement Attack and Opsonophagocytosis by Expressing the pspC Locus-Encoded Hic Protein That Binds to Short Consensus Repeats 8-11 of Factor H", The Journal of Immunology 168:1886-1894 (2002).
Johnson et al. "Iron metabolism and the innate immune response to infection." Microbes and infection / Insitut Pasteur 14:207 (2012).
Kang et al., "The human macrophage mannose receptor directs *Mycobacterium tuberculosis* lipoarabinomanan-mediated phagosome biogenesis", The Journal of Experimental Medicine 202(7):987-999 (2005).
Keen et al., "Interrelationship Between pH and Surface Growth of Nitrobacter", Soil Biology and Biochemistry 19(6):665-672 (1987).
Kehres, "A kinetic model for binding protein-mediated arabinose transport", Protein Science 1:1661-1665 (1992).
Kjaer et al., "M-ficolin binds selectively to the capsular polysaccharides of *Streptococcus pneumoniae* serotypes 19B and 19C and of a *Streptococcus mitis* strain", Infect Immun 81(2) 452-459 (2013).
Krarup et al., "Simultaneous Activation of Complement and Coagulation by MBL-Associated Serine Protease 2", PLoS One 2(7):e623 (2007). (8 pages).
Li et al. "GlycoMine: a machine learning-based approach for predicting N-, C- and O-linked glycosylation in the human proteome," Bioinformatics, vol. 31, Issue 9,pp. 1411-1419 (2015).
Li et al. "GlycoMinestruct: a new bioinformatics tool for highly accurate mapping of the human N-linked and O-linked glycoproteomes by incorporating structural features," Scientific Reports vol. 6, Article No. 34595 (2016).
Lin et al. "Synergistic inflammation is induced by blood degradation products with microbial Toll-like receptor agonists and is blocked by hemopexin." The Journal of Infectious Diseases 202:624 (2010).
Linehan et al., "Endogenous ligands of carbohydrate recognition domains of the mannose receptor in murine macrophages, endothelial cells and secretory cells; potential relevance to inflammation and immunity", European Journal of Immunology 31:1857-1866 (2001).
Lo et al., "High level expression and secretion of Fc-X fusion proteins in mammalian cells", Protein Engineering 11(6):495-500 (1998).
Loosdrecht et al., "Influence of Interfaces on Microbial Activity", Microbiological Reviews 54(1):75-87 (1990).
Mantuano et al., "The hemopexin domain of matrix metalloproteinase-9 activates cell signaling and promotes migration of schwann cells by binding to low-density lipoprotein receptor-related protein.", The Journal of Neuroscience 28(45):11571-11582 (2008).
Matsushita et al., "Activation of the Classical Complement Pathway by Mannose-binding Protein in Association with a Novel C1s-like Serine Protease", Journal of Experimental Medicine 176(6):1497-1502 (1992).
Mauk et al. "An alternative view of the proposed alternative activities of hemopexin." Protein Science. 20:791 (2011).
Michelow et al., "A Novel L-ficolin/Mannose-binding Lectin Chimeric Molecule with Enhanced Activity against Ebola Virus", The Journal of Biological Chemistry 285(32):24729-24739 (2010).
Nadesalingam et al., "Mannose-Binding Lectin Recognizes Peptidoglycan via the N-acetyl Glucosamine Moiety, and Inhibits Ligand-Induced Proinflammatory Effect and Promotes Chemokine Production by Macrophages", The Journal of Immunology 175:1785-1794 (2005).
Nakamura et al., "Characterization of the interaction between serum mannan-binding protein and nucleic acid ligands", Journal of Leukocyte Biology 86:737-748 (2009).
Neth et al., "Ehancement of Complement Activation and Opsonophagocytosis by Complexes of Mannose-Binding Lectin with Mannose-Binding Lectin-Associated Serine Protease After Binding to *Staphylococcus aureus*", The Journal of Immunology 169:4430-4436 (2002).
Neth et al., "Mannose-Binding Lectin Binds to a Range of Clinically Relevant Microorganisms and Promotes Complement Deposition", Infection and Immunity 68(2):688-693 (2000).
Nisnevitch et al., "The solid phase in affinity chromatography: strategies for antibody attachment", Journal of Biochemical and Biophysical Methods 49:467-480 (2001).
Ogden et al., "C1q and Mannose Binding Lectin Engagement of Cell Surface Calreticulin and CD91 Initiates Macropinocytosis and Uptake of Apoptotic Cells", The Journal of Experimental Medicine 194(6):781-795 (2001).
Perham, "Domains, Motifs, and Linkers in 2-Oxo Acid Dehydrogenase Multienzyme Complexes: A Paradigm in the Design of a Multifunction Protein", Biochemistry 30(35):8501-8512 (1991).
Product Datasheet, "Human Mannan Binding Lectin peptide (237-248) (Carboxyterminal end) ab45655". Downloaded from the world wide web from abcam.com/Human-Mannan-Binding-Lectin-peptide-237-248-Carboxyterminal-end-ab45655.html on May 14, 2015.
Rouhandeh et al., "Surface membrane redistribution and stabilization of concanavalin A-specific receptors following Yaba tumor poxvirus infection." Biochimica et Biophysica Acta (BBA)-Biomembranes 600(2):301-312 (1980).
Rutishauser et al., "Amino Acid Sequence of the Fc Region of a Human γG Immunoglobulin", Biochemistry 61:1414-1421 (1968).
Safarik et al., "The application of magnetic separations in applied microbiology", Journal of Applied Bacteriology 78:575-585 (1995).
Schmidt, "Fusion proteins as biopharmaceuticals—Applications and challenges", Current Opinion in Drug Discovery & Development 12(2):284-295 (2009).
Sheriff et al., "Human mannose-binding protein carbohydrate recognition domain trimerizes through a triple alpha-helical coiled-coil", Nat Struct Biol 1(11) 789-794 (1994).
Shields et al., "High Resolution Mapping of the Binding Site on Human IgG1 for FcγRI, FcγRII, FcγRIII, and FcRn and Design of IgG1 Variants with Improved Binding to the FcγR", The Journal of Biological Chemistry 276(9):6591-6604 (2001).
Sibille et al., "Comparison of serological tests for the diagnosis of feline immunodeficiency virus infection of cats", Veterinary Microbiology 45:259-267 (1995).
Sprong et al., "Mannose-Binding Lectin Is a Critical Factor in Systemic Complement Activation during Meningococcal Septic Shock", Clinical Infectious Diseases 49:1380-1386 (2009).
Steentoft et al. "Precision mapping of the human O-GalNAc glycoproteome through SimpleCell technology," EMBO J. May 15;32(10):1478-88. (2013).
Steurer et al., "Ex Vivo Coating of Islet Cell Allografts with Murine CTLA4/Fc Promotes Graft Tolerance", The Journal of Immunology 155:1165-1174 (1995).
Stuart et al., "Mannose-Binding Lectin-Deficient Mice Display Defective Apoptotic Cell Clearance but No Autoimmune Phenotype", The Journal of Immunology 174:3220-3226 (2005).
Takahashi et al., "Mannose-binding lectin and its associated proteases (MASPs) mediate coagulation and its deficiency is a risk factor in developing complications from infection, including disseminated intravascular coagulation", Immunobiology 216(1-2):96-102 (2011).
Terai et al., "Relationship between gene polymorphisms of mannose-binding lectin (MBL) and two molecular forms of MBL", European Journal of Immunology 33:2755-2763 (2003).
Thiel et al., "A second serine protease associated with mannan-binding lectin that activates complement", Nature 386:506-510 (1997).

(56) References Cited

OTHER PUBLICATIONS

Vaccaro et al., "Engineering the Fc region of immunoglobulin G to modulate in vivo antibody levels", Nature Biotechnology 23(10):1283-1288 (2005).
Ward et al., "Characterization of Humanized Antibodies Secreted by Aspergillus niger", Applied and Environmental Microbiology 70(5):2567-2576 (2004).
Warwick et al., "Use of Quantitative 16S Ribosomal DNA Detection for Diagnosis of Central Vascular Catheter-Associated Bacterial Infection", Journal of Clinical Microbiology 42(4):1402-1408 (2004).
Witus et al., "Identification of Highly Reactive Sequences for PLP-Mediated Bioconjugation Using a Combinatorial Peptide Library", Journal of the American Chemical Society 132:16812-16817 (2010).
Wong et al., "Bioinspired self-repairing slippery surfaces with pressure-stable omniphobicity", Nature 477:443-447 (2011).
Wriggers et al., "Control of Protein Functional Dynamics by Peptide Linkers", Biopolymers (Peptide Science) 80:736-746 (2005).
Frakking et al., "Safety and phamacokinetics of plasma-derived mannose-binding lectin (MBL) substitution in children with chemotherapy-induced neutropaenia", European Journal of Cancer 45(4): 505-512 (2009).
Furukawa et al. "Identification of a novel mechanism of action of bovine IgG antibodies specific for *Staphylococcus aureus*" Vet Res. 49(1): 22 (2018).
Garred et al., "Mannose-binding lectin and its genetic variants", Genes and Immunity 7(2): 85-94 (2006).
Gouin et al., "Multimeric Lactoside "Click Clusters" as Tools to Investigate the Effect of Linker Length in Specific Interactions with Peanut Lectin, Galectin-1, and -3", ChemBioChem 11(10): 1430-1442 (2010).
Grogl et al., "Leishmania braziliensis: Protein, Carbohydrate, and Antigen Differences between Log Phase and Stationary Phase Promastigotes in Vitro", Experimental Parasitology 63(3): 352-359 (1987).
Hinton et al., "Engineered Human IgG Antibodies with Longer Serum Half-lives in Primates", The Journal of Biological Chemistry 279(8): 6213-6216 (2004).
Holmskov et al., "Affinity and kinetic analysis of the bovine plasma C-type lectin collectin-43 (CL-43) interacting with mannan", FEBS Letters 393(2-3): 314-316 (1996).
Huang et al., "Porcine DC-SIGN: Molecular cloning, gene structure, tissue distribution and binding characteristics", Developmental and Comparative Immunology 33(4): 464-480 (2009).
Jones et al. "Immunisation with ID83 fusion protein induces antigen-specific cell mediated and humoral immune responses in cattle." Vaccine. Oct. 25;31(45): 5250-5 (2013).
Xia et al., "Combined microfluidic-micromagnetic separation of living cells in continuous flow", Biomed Microdevices 8: 299-308 (2006).
Ye et al., "Surface display of a glucose binding protein", Journal of Molecular Catalysis B: Enzymatic 28(4-6): 201-206 (2004).
Yung et al., "Micromagnetic-microfluidic blood cleansing device", Lab on a Chip 9(9): 1171-1177 (2009).
Zettner et al., "Principles of competitive binding assays (saturation analysis). 1. Equilibrium techniques", Clin Chem 19(7): 699-705 (1973).
Zettner et al., "Principles of competitive binding assays (saturation analyses). II. Sequential saturation", Clin Chem 20(1): 5-14 (1974).
Bossola et al., "Circulating Bacterial-Derived DNA Fragments and Markers of Inflammation in Chronic Hemodialysis Patients", Clinical Journal of the American Society of Nephrology 4(2): 379-385 (2009).
Arakawa et al., "Elution of antibodies from a Protein-A column by aqueous arginine solutions", Protein Expression and Purification 36(2): 244-248 (2004).
Armour et al., "Recombinant human IgG molecules lacking Fcγ receptor I binding and monocyte triggering activities", European Journal of Immunology 29(8): 2613-2624 (1999).
Ashkenazi et al., "Immunoadhesins as research tools and therapeutic agents", Current Opinion in Immunology 9(2): 195-200 (1997).
Azevedo et al., "Horseradish peroxidase: a valuable tool in biotechnology," Biotechnology Annual Review 9: 199-247 (2003).
Bangs Laboratories, Inc., "Protein Coated Microspheres", Tech. Note #51 (1997) (4 pages).
Bayston et al., "Bacterial endotoxin and current concepts in the diagnosis and treatment of endotoxaemia", Journal of Medical Microbiology 31(2): 73-83 (1990).
Brooks et al., "Expression and secretion of ficolin β by porcine neutrophils", Biochimica et Biophysica Acta 1624 (1-3): 36-45 (2003).
Brouwer et al., "Mannose-Binding Lectin (MBL) Facilitates Opsonophagocytosis of Yeasts but Not of Bacteria despite MBL Binding", The Journal of Immunology 180(6): 4124-4132 (2008).
Castle et al., "The binding of 125I-labeled concanavalin A to the cell surface of rabbit peritoneal polymorphonuclear leucocytes." Biochemical Medicine 28(1): 1-15 (1982).
Chamow et al., "Immunoadhesins: principles and applications", Trends Biotechnology 14(2): 52-60 (1996).
Chang et al., "Crystallization and Preliminary X-ray Analysis of a Trimeric Form of Human Mannose Binding Protein", Journal of Molecular Biology 241(1): 125-127 (1994).
Chen et al., "Fabrication of an Oriented Fc-Fused Lectin Microarray through Boronate Formation", Angewandte Chemie International Edition 47(45): 8627-8630 (2008).
Choma et al. "Design of a Heme-Binding Four-Helix Bundle" 116: 856-865 (1994).
Chuang et al., "Computational prediction of N-linked glycosylation incorporating structural properties and patterns," Bioinformatics. Sep. 1; 28(17): 2249-2255 (2012).
Cooper., "A generic pathogen caputre technology for sepsis diagnosis", retrieved from http://hdl.handle.net/1721.1/83966 (2013).
Czajkowsky et al., "Fc-fusion proteins: new developments and future perspectives", EMBO Mol Med., 4(10): 1015-1028 (2012).
Feng et al., "Identification of carbohydrates on the surface membrane of pathogenic and nonpathogenic piscine haemoflagellates, *Cryptobia salmositica, C. bullocki* and *C. catostomi* (Kinetoplastida)." Diseases of Aquatic Organisms 32(3): 201-209 (1998).
Foster, "Immune Evasion by Staphylococci", Nature 3(12): 948-958 (2005).
Fox et al., "Single amino acid substitutions on the surface of *Escherichia coli* maltose-binding protein can have a profound impact on the solubility of fusion proteins", Protein Science 10(3): 622-630 (2001).

* cited by examiner

CRP CAPTURE/DETECTION OF GRAM POSITIVE BACTERIA

CROSS REFERENCE TO RELATED APPLICATIONS

This application is a 371 National Phase Entry of International Patent Application No. PCT/US2014/071293 filed on Dec. 18, 2014 which claims benefit under 35 U.S.C. § 119(e) of U.S. Provisional Patent Application Ser. No. 61/917,705 filed on Dec. 18, 2013, the content of which are incorporated herein by reference in their entirety.

GOVERNMENT SUPPORT

This invention was made with government support under grant no. N66001-11-1-4180 awarded by Defense Advanced Research Projects Agency (DARPA). The government has certain rights in the invention.

SEQUENCE LISTING

The sequence listing of the present application has been submitted electronically via EFS-Web as an ASCII formatted sequence listing with a file name "002806-08011-PCT_SL", creation date of Jun. 15, 2016 and a size of 88,383 bytes. The sequence listing submitted via EFS-Web is part of the specification and is herein incorporated by reference in its entirety.

TECHNICAL FIELD

Described herein relates generally to molecules, products, kits and methods for detecting and/or removing microbes in a sample or a target area, including bodily fluids such as blood and tissues of a subject, food, water, and environmental surfaces.

BACKGROUND

Sepsis is a major cause of morbidity and mortality in humans and other animals. In the United States, sepsis is the second leading cause of death in intensive care units among patients with non-traumatic illnesses. It is also the leading cause of death in young livestock, affecting 7.5-29% of neonatal calves, and is a common medical problem in neonatal foals. Despite the major advances of the past several decades in the treatment of serious infections, the incidence and mortality due to sepsis continues to rise.

Sepsis results from the systemic invasion of microorganisms into blood and can present two distinct problems. First, the growth of the microorganisms can directly damage tissues, organs, and vascular function. Second, toxic components of the microorganisms can lead to rapid systemic inflammatory responses that can quickly damage vital organs and lead to circulatory collapse (i.e., septic shock) and, often times, death.

There are three major types of sepsis characterized by the type of infecting organism. For example, gram-negative sepsis is the most frequently isolated (with a case fatality rate of about 35%). The majority of these infections are caused by *Escherichia coli, Klebsiella pneumoniae* and *Pseudomonas aeruginosa*. Gram-positive pathogens such as the Staphylococci and Streptococci are the second major cause of sepsis. The third major group includes fungi, with fungal infections causing a relatively small percentage of sepsis cases, but with a high mortality rate; these types of infections also have a higher incidence in immunocomprised patients.

Many patients with septicemia or suspected septicemia exhibit a rapid decline over a 24-48 hour period. It has been reported that patients with septic shock require adapted treatment in less than 6 hours in order to benefit from antimicrobial therapy. Thus, rapid and reliable diagnostic and treatment methods are essential for effective patient care. Unfortunately, a confirmed diagnosis as to the type of infection, e.g., sepsis, traditionally requires microbiological analysis involving inoculation of blood cultures, incubation for 18-24 hours, plating the causative microorganism on solid media, another incubation period, and final identification 1-2 days later. Even with immediate and aggressive treatment, some patients can develop multiple organ dysfunction syndrome and eventually death. Hence, there remains a strong need for improved techniques for diagnosis and treatment of patients with infectious diseases, blood-borne infections, sepsis, or systemic inflammatory response syndrome. The ability to rapidly detect infectious pathogens in food, water, and/or environmental surfaces would also have great value for preventing infections and sepsis in the population.

SUMMARY

Embodiments described herein are based on, at least in part, engineering a microbe-targeting molecule or a microbe-binding molecule. The terms "microbe-targeting molecule" and "microbe-binding molecule." The engineered microbe-targeting molecules described herein provide a valuable building block for various applications including, but not limited to, diagnosis or treatment of diseases caused by microbes or pathogens, removal of microbes or pathogens from a sample, including bodily fluids and tissues of a subject, foods, water, or an environmental surface; and development of targeted drug delivery devices.

Generally, the microbe-targeting moleculecomprise at least one first domain comprising at least a portion of a C-reactive protein (CRP) and at least one second domain. The first and second domains are conjugated together via a linker. In some embodiments, the second domain can be selected from the group consisting of Fc region of an immunoglobulin; microbe-binding domain of a microbe-binding protein, wherein the microbe-binding protein is not CRP; neck region of a lectin; a detectable label; domain for conjugation to surface of a carrier scaffold; at least a portion of a C-reactive protein; and any combinations thereof.

The engineered microbe-targeting molecules described herein can be used as soluble proteins, e.g., in therapeutic compositions, or be immobilized to a carrier scaffold for various applications ranging from diagnosis and/or treatment of a microbial infection or disease, to microbe-clearing compositions or devices, to drug delivery. A carrier scaffold comprising a microbe-targeting molecule conjugated therewith is also referred to as a microbe-targeting article herein.

The microbe-targeting molecules can be used to capture, detect, or remove microbes or pathogens in a sample, e.g., blood and tissues. Accordingly, the microbe-targeting molecules disclosed herein can be used to in assays for detecting the presence or absence of, and/or differentiating between, different microbes or pathogens in a test sample or environmental surfaces. Detection assay can comprise an enzyme-linked immunosorbent assay (ELISA), fluorescent linked immunosorbent assay (FLISA), immunofluorescent microscopy, fluorescence in situ hybridization (FISH), electrochemical sensor assay, or any other radiological, chemical, enzymatic or optical detection assays. Further, the engineered microbe-targeting molecules disclosed herein can be formulated as an antibiotic or antiseptic for use in various applications, e.g., wound dressings, alone or in combination with other wound dressing protocols, e.g., silver nanoparticles and other wound treatment.

The disclosure also provides kits and assays for detecting the presence or absence of microbes, and/or differentiating between, different microbes or pathogens in a test sample or an environmental surface. Such kits can be used for analysis, e.g., by an enzyme-linked immunosorbent assay (ELISA), fluorescent linked immunosorbent assay (FLISA), immunofluorescent microscopy, fluorescence in situ hybridization (FISH), or any other radiological, chemical, enzymatic or optical detection assays. In some embodiments, the kits and assays described herein can be adapted for antibiotic susceptibility tests, e.g., to determine susceptibility of a microbe in a test sample to one or more antibiotics, regardless of whether the identity of the microbe is known or not.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

DETAILED DESCRIPTION OF THE INVENTION

Figure 1:
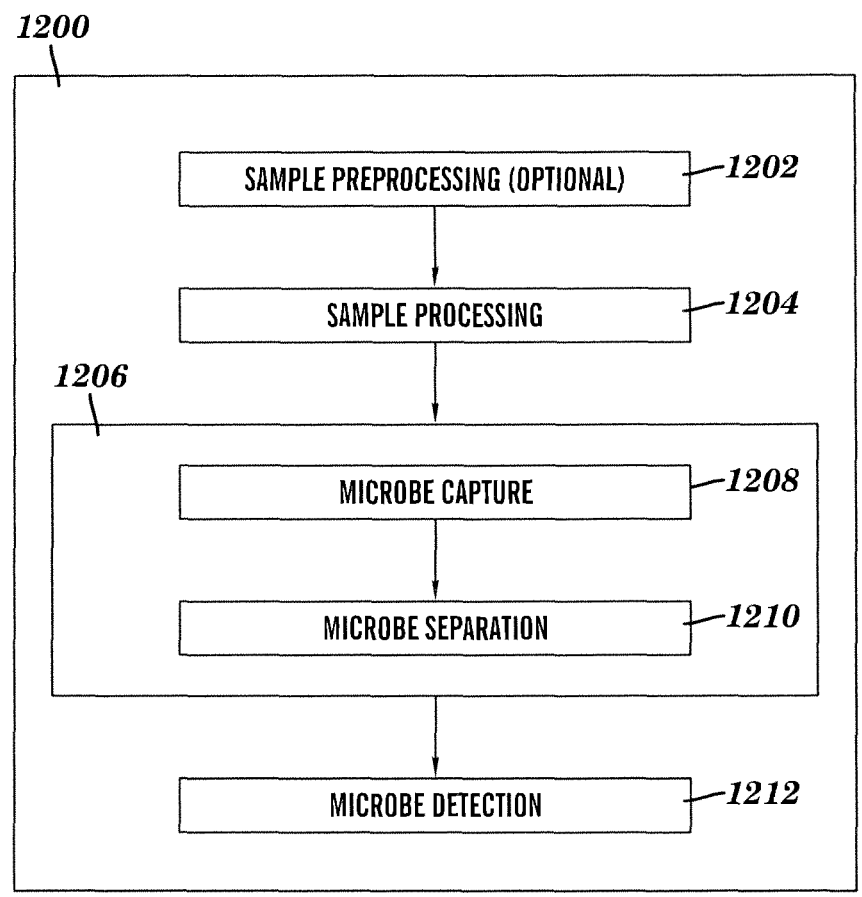
FIG. 1 is a schematic of an exemplary microbial capture/detection process or diagnosis process.
Figure 2:
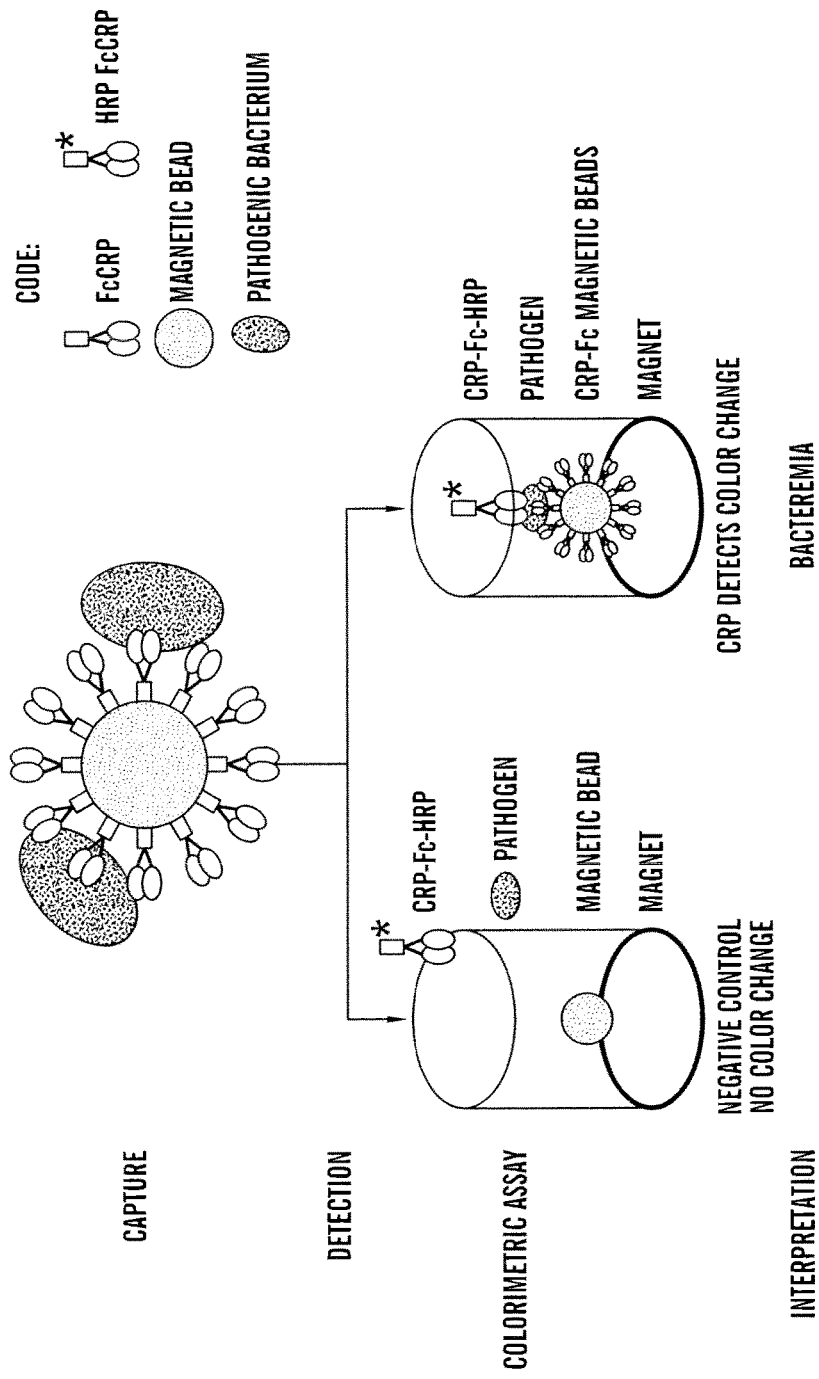
FIG. 2 is a schematic diagram of an exemplary ELISA assay comprising engineered microbe-targeting magnetic microbeads according to one or more embodiments. The ELISA assay can be used for any diagnostic applications, e.g., for sepsis tests.
Figure 3:
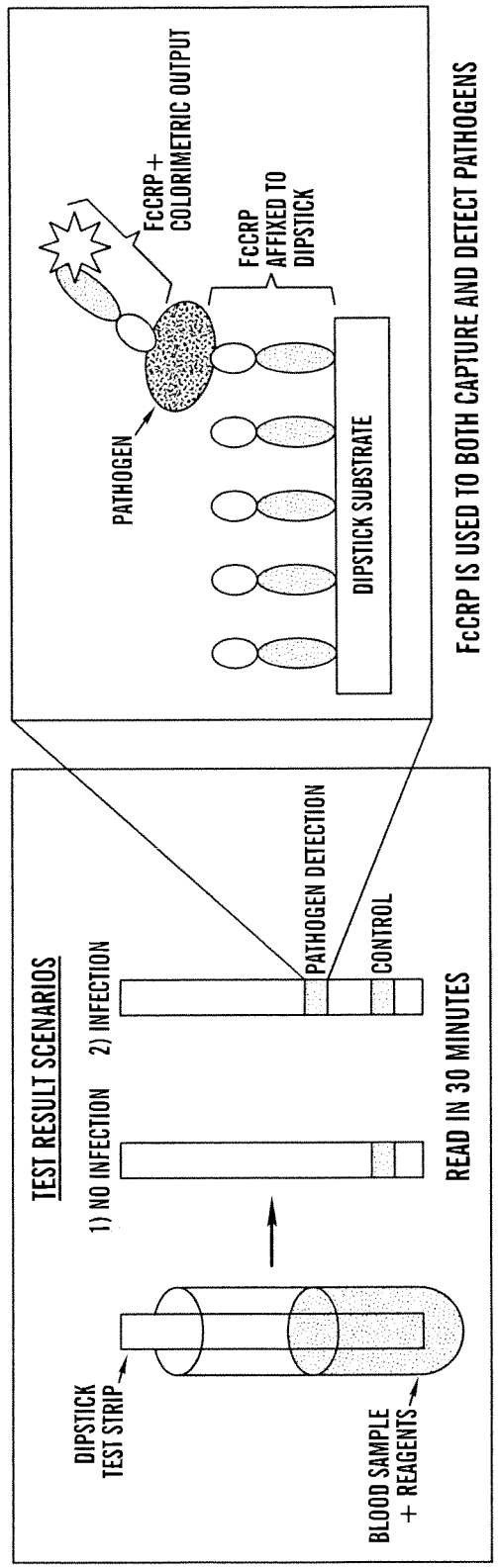
FIG. 3 is a schematic diagram showing one or more embodiments of a dipstick assay for microbial detection. The microbe-targeting molecule can be attached to a membrane (for example Biodyne membrane). The membrane can be mixed with a test sample (e.g., blood sample), washed, incubated with a desired detecting or lableling molecule (e.g., enzyme-linked microbe-targeting molecule or specific antibody for certain microbes, e.g., bacteria or fungus), washed and added with a readout reagent for colorimetric development. The dipstick assay can be performed manually or modified for automation.
Figure 4:
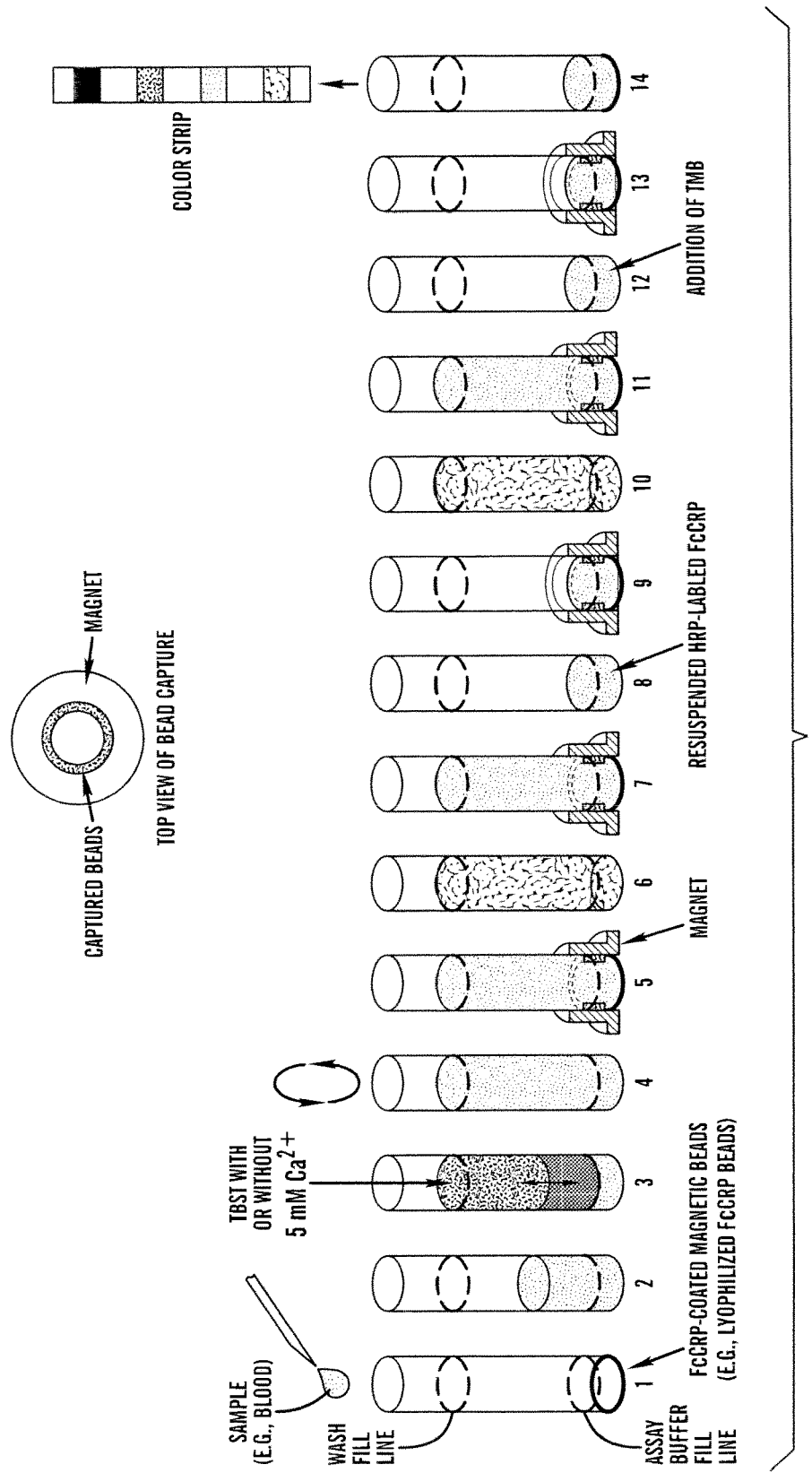
FIG. 4 is a schematic diagram showing one or more embodiments of an ELISA-based test for microbial detection. A test sample (e.g., blood sample) can be added into a single tube (e.g., a blood collection container such as EDTA VACUTAINER®) containing lyophilized microbe-targeting molecule coated magnetic particles. The ELISA-based test can be performed manually or modified for automation. In some embodiments, the single-tube based ELISA assay can be used to detect microbes or pathogens.

Described herein are microbe-targeting molecules, compositions comprising the same, processes or assays, and kits for detecting the presence or absence of a microbe in a test sample. The microbe-targeting molecules disclosed herein can also be used for separating microbes from a test sample in vivo, in situ or in vitro. Generally, the microbe-targeting molecules disclosed herein can bind with or capture at least one microbe. The microbe can be an intact or whole microbe or any matter or component that is derived, originated or secreted from a microbe. Any matter or component that is derived, originated or secreted from a microbe is also referred to as "microbial matter" herein. Thus, the microbe-targeting molecules disclosed herein can bind/capture an intact or whole microbe or microbial matter derived, originated or secreted from the microbe. Exemplary microbial matter that can bind to the microbe-targeting molecule can include, but is not limited to, a cell wall component, an outer membrane, a plasma membrane, a ribosome, a microbial capsule, a pili or flagella, any fragments of the aforementioned microbial components, any nucleic acid (e.g., DNA, including 16S ribosomal DNA, and RNA) derived from a microbe, microbial endotoxin (e.g., lipopolysaccharide), and the like. In addition, microbial matter can encompass non-viable microbial matter that can cause an adverse effect (e.g., toxicity) to a host or an environment. The terms "microbe-binding molecule(s)" and "microbe-targeting molecule(s)" are used interchangeably herein.

Various aspects disclosed herein are based on inventors' discovery that C-reactive protein (CRP) can bind with gram-positive microbe and can be used for capturing/detecting microbes. To the inventors' knowledge, this is the first use of CRP as a pathogen captured/detector and is different from the current use of CRP as a biomarker. While the prior art uses CRP as a biomarker, the inventors have discovered inter alia that CRP can used to capture/detect microbes. Further, CRP binds gram positive organisms (such as Strep agalactiae (AKA GBS and Strep pneumonia) that bind poorly with currently known engineered microbe-binding molecules. Gram positive organisms like are responsible for lung and URTI infections. Accordingly, the molecules, compositions, assays, and methods disclosed herein can be used in diagnosis, imagining and treatment of infections with gram-positive microbes.

In accordance with the various embodiments described herein, the microbe-targeting molecules comprise at least one first domain comprising at least a portion of a C-reactive protein (CRP) and at least one second domain. The first and second domains are conjugated together via a linker.

It is noted that the first domain and second domain in the microbe-targeting molecule can be present in any order. For example, the first domain can be first followed by the second domain, or the second domain can be first followed by the first domain.

Without limitations, the first domain can comprise the full length CRP or a fragment thereof retaining microbe binding activity. In addition to the CRP amino acid sequence, the first domain can further comprise one or more amino acids (e.g., one, two, three, four, five, six, seven, eight, nine, ten, or more) amino acids on the N- or C-terminus of the CRP sequence. Generally, the first domain can have an amino acid sequence of about 10 to about 300 amino acid residues. In some embodiments, the first domain can have an amino acid sequence of about 50 to about 250 amino acid residues. In some embodiments, the microbe surface-binding domain can have an amino acid sequence of at least about 5, at least about 10, at least about 15, at least about 20, at least about 30, at least about 40, at least about 50, at least about 60, at least about 70, at least about 80, at least about 90, at least about 100 amino acid residues or more. For any known sequences of CRP one of skill in the art can determine the optimum length of amino acid sequence for retaining microbe-binding activity.

Without limitations, the CRP can be from any source available to one of skill in the art. For example, the CRP can be from a mammalian source. For example, the CRP can be human CRP (NCBI Reference Sequence: NP_000558.2, SEQ ID NO: 1) or mouse CRP (NCBI Reference Sequence: NP_031794.3, SEQ ID NO: 2). In some embodiments, the first domain comprises an amino acid sequence comprising amino acids 19-224 of the human. In some embodiments, the first domain comprises the amino acid sequence SEQ ID NO: 3 or SEQ ID No: 4. In some embodiments, the first domain comprises amino acid sequence SEQ ID NO: 39.

Modifications to the first domain, e.g., by conservative substitution, are also within the scope described herein. In some embodiments, the CRP or a fragment thereof used in the microbe-targeting molecules described herein can be a wild-type molecule or a recombinant molecule.

In some embodiments, 100% of the first domain can be used to bind to microbes or pathogens. In other embodiments, the first domain can comprise additional regions that are not capable of binding to a microbe, but can have other characteristics or perform other functions, e.g., to provide flexibility to the first domain when interacting with microbes or pathogens. In some embodiments, the first domain can comprise a peptidomimetic that mimics CRP or a fragment thereof that can bind to the surface of a microbe or pathogen, or microbial matter.

The second domina can be selected to provide a desired function or property to the microbe-binding molecules disclosed herein. For example, the second domain can be selected or configured according to a specific need or use of the microbe-binding molecule. By way of example only, in some embodiments, second domain can be selected or configured to have a sufficient length and flexibility such that it can allow for the first domain to orient in a desired orientation with respect to a microbe. In some embodiments, the second domain can be selected or configured to allow multimerization of at least two engineered microbe-targeting molecules (e.g., to from a di-, tri-, tetra-, penta-, hexa- or higher multimeric complex) while retaining biological activity (e.g., microbe-binding activity). In some embodiments, the second domain can be selected or configured to inteact with the linker to allow multimerization of at least two engineered microbe-targeting molecules (e.g., to from a di-, tri-, tetra-, penta-, hexa- or higher multimeric complex) while retaining microbe-binding activity.

In some embodiments, the second domain can be selected or configured to facilitate expression and purification of the engineered microbe-targeting molecule described herein. In some embodiments, the second domain can be selected or configured to provide a recognition site for a protease or a nuclease. In addition, the second domain can be non-reactive with the functional components of the engineered molecule described herein. For example, minimal hydrophobic or charged character to react with the first domain.

In some embodiments, the second domain can include at least a portion of an immunoglobulin, e.g., IgA, IgD, IgE, IgG and IgM including their subclasses (e.g., IgG1), or a modified molecule or recombinant thereof. In some embodiments, the second domain can comprise a portion of fragment crystallization (Fc) region of an immunoglobulin or a modified version thereof. In such embodiments, the portion of the Fc region that can be comprised in the second domain can comprise at least one region selected from the group consisting of a hinge region, a CH2 region, a CH3 region, and any combinations thereof. By way of example, in some embodiments, a CH2 region can be excluded from the portion of the Fc region as the second domain. In one embodiment, Fc region comprised in the second domain comprises a hinge region, a CH2 domain and a CH3 domain.

In some embodiments, the Fc region comprised in the second domain can be can be used to facilitate expression and purification of the engineered microbe-targeting molecules described herein. The N terminal Fc has been shown to improve expression levels, protein folding and secretion of the fusion partner. In addition, the Fc has a staphylococcal Protein A binding site, which can be used for one-step purification protein A affinity chromatography. See Lo K M et al. (1998) *Protein Eng.* 11: 495-500. Further, the Protein A binding site can be used to facilitate binding of Protein A-expressing or Protein G-expressing microbes in the absence of calcium ions. Such binding capability can be used to develop methods for distinguishing protein A-expressing microbes (e.g., *S. aureus*) from non-protein A-expressing or non-protein G-expressing microbes (e.g., *E. coli*) present in a test sample, and various embodiments of such methods will be described in detail later. Further, such Fc regions have a molecule weight above a renal threshold of about 45 kDa, thus reducing the possibility of engineered microbe-targeting molecules being removed by glomerular filtration. Additionally, the Fc region can allow dimerization of two engineered microbe-targeting molecules to form a multimeric complexe, such as a dimer.

In some embodiments, the second domain comprises the amino acid sequence SEQ ID NO: 5, 6, 7 or 42.

In some embodiments, where the second domain comprises a Fc region or a fragment thereof, the Fc region or a fragment thereof can comprise at least one mutation, e.g., to modify the performance of the engineered microbe-targeting molecules. For example, in some embodiments, a half-life of the engineered microbe-targeting molecules described herein can be increased, e.g., by mutating an amino acid lysine (K) at the residue 232 of SEQ ID NO. 5, 6, or 7 to alanine (A). Other mutations, e.g., located at the interface between the CH2 and CH3 domains shown in Hinton et al (2004) *J Biol Chem.* 279:6213-6216 and Vaccaro C. et al. (2005) *Nat Biotechnol.* 23: 1283-1288, can be also used to increase the half-life of the IgG1 and thus the engineered microbe-targeting molecules.

In some embodiments, the second domain can comprise a microbe-binding domain (or a fragment thereof retaining microbe binding activity) from a microbe-binding protein. In some embodiments, the second domain comprises a microbe-binding domain (or a fragment thereof retaining microbe binding activity) from microbe-binding protein that is not CRP. The terms "microbe binding domain" and "microbe surface-binding domain" are used interchangeably herein and refer to any molecule or a fragment thereof that can specifically bind to the surface of a microbe or pathogen, e.g., any component present on a surface of a microbe or pathogen, or any matter or component/fragment that is derived, originated or secreted from a microbe or pathogen. Molecules that can be used in the microbe surface-binding domain can include, for example, but are not limited to, peptides, polypeptides, proteins, peptidomimetics, antibodies, antibody fragments (e.g., antigen binding fragments of antibodies), carbohydrate-binding protein, e.g., a lectin, glycoproteins, glycoprotein-binding molecules, amino acids, carbohydrates (including mono-, di-, tri- and poly-saccharides), lipids, steroids, hormones, lipid-binding molecules, cofactors, nucleosides, nucleotides, nucleic acids (e.g., DNA or RNA, analogues and derivatives of nucleic acids, or aptamers), peptidoglycan, lipopolysaccharide, small molecules, and any combinations thereof.

In some embodiments, the microbe surface-binding domain can comprise a peptidomimetic that mimics a molecule or a fragment thereof that can specifically bind to the surface of a microbe or pathogen, or microbial matter. For example, a microbe surface-binding domain can comprise a peptidomimetic that mimics a carbohydrate recognition domain or a fragment thereof, e.g., carbohydrate recognition domain of MBL or a fragment thereof.

In some embodiments, the microbe surface-binding domain can be a carbohydrate recognition domain or a fragment thereof of carbohydrate binding protein. The term "carbohydrate recognition domain" as used herein refers to a region, at least a portion of which, can bind to carbohydrates on a surface of microbes or pathogens. In some embodiments, the second domain can comprise at least about 50% of the full length CRD, including at least about 60%, at least about 70%, at least about 80%, at least about 90% or higher, capable of binding to carbohydrates on a microbe surface. In some embodiments, 100% of the carbohydrate recognition domain can be used to bind to microbes or pathogens. In other embodiments, the carbohydrate recognition domain can comprise additional regions that are not capable of carbohydrate binding, but can have other characteristics or perform other functions, e.g., to provide flexibility to the carbohydrate recognition domain when interacting with microbes or pathogens.

Exemplary carbohydrate-binding proteins include, but are not limited to, lectin, collectin, ficolin, mannose-binding lectin (MBL), maltose-binding protein, arabinose-binding protein, and glucose-binding protein. Additional carbohydrate-binding proteins that can be included in the microbe surface-binding domain described herein can include, but are not limited to, lectins or agglutinins that are derived from a plant, e.g., *Galanthus nivalis* agglutinin (GNA) from the *Galanthus* (snowdrop) plant, and peanut lectin. In some embodiments, pentraxin family members (e.g., C-reactive protein) can also be used as a carbohydrate-binding protein. Pentraxin family members can generally bind capsulated microbes. Without limitation, the carbohydrate-binding proteins can be wild-type, recombinant or a fusion protein. The respective carbohydrate recognition domains for such carbohydrate-binding proteins are known in the art, and can be modified for various embodiments of the engineered microbe-targeting molecules described herein.

Any art-recognized recombinant carbohydrate-binding proteins or carbohydrate recognition domains can be used in the engineered microbe-targeting molecules. For example, recombinant mannose-binding lectins, e.g., but not limited to, the ones disclosed in the U.S. Pat. Nos. 5,270,199; 6,846,649; U.S. Patent Application No. US 2004/0229212; and PCT Application No. WO 2011/090954, filed Jan. 19, 2011, the contents of all of which are incorporated herein by reference, can be used in constructing the microbe-targeting molecules described herein.

In some embodiments, the CRD is from an MBL, a member of the collectin family of proteins. A native MBL is a multimeric structure (e.g., about 650 kDa) composed of subunits, each of which contains three identical polypeptide chains. Each MBL polypeptide chain (containing 248 amino acid residues in length with a signal sequence: SEQ ID NO.8) comprises a N-terminal cysteine rich region, a collagen-like region, a neck region, and a carbohydrate recognition domain (CRD). The sequence of each region has been identified and is well known in the art. SEQ ID NO. 8 is the full-length amino acid sequence of MBL without a signal sequence. In some embodiments, the signal sequence corresponds to amino acids 1-20 of SEQ ID NO 8, i.e. SEQ ID NO: 10.

The full-length amino acid sequence of carbohydrate recognition domain (CRD) of MBL is shown in SEQ ID NO. 11. In some embodiments, the carbohydrate recognition domain of the engineered MBL molecule can comprise a fragment of SEQ ID NO. 11. Exemplary amino acid sequences of such fragments include, but are not limited to, ND (SEQ ID NO. 12), EZN (SEQ ID NO. 13: where Z is any amino acid, e.g., P), NEGEPNNAGS (SEQ ID NO. 14) or a fragment thereof comprising EPN, GSDEDCVLL (SEQ ID NO. 15) or a fragment thereof comprising E, and LLLKNGQWNDVPCST (SEQ ID NO.16) or a fragment thereof comprising ND. Modifications to such CRD fragments, e.g., by conservative substitution, are also within the scope described herein. In some embodiments, the MBL or a fragment thereof used in the the engineered microbe-targeting molecules described herein can be a wild-type molecule or a recombinant molecule.

In some circumstances, complement or coagulation activation induced by a carbohydrate-binding protein or a fragment thereof can be undesirable depending on various applications, e.g., in vivo administration for treatment of sepsis. In such embodiments, the additional portion of the carbohydrate-binding protein can exclude at least one of complement and coagulation activation regions. By way of example, when the carbohydrate-binding protein is mannose-binding lectin or a fragment thereof, the mannose-binding lectin or a fragment thereof can exclude at least one of the complement and coagulation activation regions located on the collagen-like region. In such embodiments, the mannose-binding lectin or a fragment thereof can exclude at least about one amino acid residue, including at least about two amino acid residues, at least about three amino acid residues, at least about four amino acid residues, at least about five amino acid residues, at least about six amino acid residues, at least about seven amino acid residues, at least about eight amino acid residues, at least about nine amino acid residues, at least about ten amino acid residues or more, around amino acid residue K55 or L56 of SEQ ID NO. 9. Exemplary amino sequences comprising K55 or L56 of SEQ ID NO. 8 that can be excluded from the second domain of the microbe-binding molecule include, but are not limited to, EPGQGLRGLQGPPGKLGPPGN-PGPSGS (SEQ ID NO. 17), GKLG (SEQ ID NO. 18), GPPGKLGPPGN (SEQ ID NO. 19), RGLQGPPGKL (SEQ ID NO. 20), GKLGPPGNPGPSGS (SEQ ID NO. 21), GLRGLQGPPGKLGPPGNPGP (SEQ ID NO. 22), or any fragments thereof.

In some embodiments, the additional portion of the carbohydrate-binding proteins can activate the complement system. In alternative embodiments, the additional portion of the carbohydrate-binding protein cannot activate the complement system. In some embodiments, the additional portion of the carbohydrate-binding protein can be selected, configured, or modified such that it does not activate the complement system.

In some embodiments, the second domain comprises an amino acid sequence selected from the group consisting of SEQ ID NO: 8, 9, 11, 12, or 23-27.

In some embodiments, the second domain can comprise a neck region or a frgament thereof from a lectin. By neck region of a lection is meant the portion of the lection than connects the CRD to rest of the molecule. Without wishing to be bound by theory, the neck region can provide flexibility and proper orientation to the first domain for binding to a microbe surface. When the microbe-binding molecule disclosed herein comprises second domain comprising a neck region and an additional second domain, the neck region can be located between the first domain and the additional second domain, i.e., the neck region can act as a linker for linking the first domain and the additional second domain. In some embodiments, the second domain can comprise one or more (e.g., one, two, three, four, fiv, six, seven, eight, nine, ten, or more) additional amino acids on the N- or C-terminus of the neck region. In some embodiments, the neck region comprises the amino acid sequence

PDGDSSLAASERKALQTEMARIKKWLTFSLGKQ, (SEQ ID NO: 28)

APDGDSSLAASERKALQTEMARIKKWLTFSLGKQ, (SEQ ID NO: 29)

PDGDSSLAASERKALQTEMARIKKWLTFSLG, (SEQ ID NO: 30)
or

APDGDSSLAASERKALQTEMARIKKWLTFSLG. (SEQ ID NO: 31)

In some embodiments, the second domain can comprise a detectable label. As used herein, the term "detectable label" refers to a composition capable of producing a detectable signal indicative of the presence of a target. Detectable labels include any composition detectable by spectroscopic, photochemical, biochemical, immunochemical, electrical, optical or chemical means. Suitable labels include fluorescent molecules, radioisotopes, nucleotide chromophores, enzymes, substrates, chemiluminescent moieties, bioluminescent moieties, and the like. As such, a label is any composition detectable by spectroscopic, photochemical, biochemical, immunochemical, electrical, optical or chemical means needed for the methods and devices described herein.

In some embodiments, the detectable label can be an imaging agent or contrast agent. As used herein, the term "imaging agent" refers to an element or functional group in a molecule that allows for the detection, imaging, and/or monitoring of the presence and/or progression of a condition(s), pathological disorder(s), and/or disease(s). The imaging agent can be an echogenic substance (either liquid or gas), non-metallic isotope, an optical reporter, a boron neutron absorber, a paramagnetic metal ion, a ferromagnetic metal, a gamma-emitting radioisotope, a positron-emitting radioisotope, or an x-ray absorber. As used herein the term "contrast agent" refers to any molecule that changes the optical properties of tissue or organ containing the molecule. Optical properties that can be changed include, but are not limited to, absorbance, reflectance, fluorescence, birefringence, optical scattering and the like. In some embodiments, the detectable labels also encompass any imaging agent (e.g., but not limited to, a bubble, a liposome, a sphere, a contrast agent, or any detectable label described herein) that can facilitate imaging or visualization of a tissue or an organ in a subject, e.g., for diagnosis of an infection.

Suitable optical reporters include, but are not limited to, fluorescent reporters and chemiluminescent groups. A wide variety of fluorescent reporter dyes are known in the art. Typically, the fluorophore is an aromatic or heteroaromatic compound and can be a pyrene, anthracene, naphthalene, acridine, stilbene, indole, benzindole, oxazole, thiazole, benzothiazole, cyanine, carbocyanine, salicylate, anthranilate, coumarin, fluorescein, rhodamine or other like compound.

Exemplary fluorophores include, but are not limited to, 1,5 IAEDANS; 1,8-ANS; 4-Methylumbelliferone; 5-carboxy-2,7-dichlorofluorescein; 5-Carboxyfluorescein (5-FAM); 5-Carboxynapthofluorescein (pH 10); 5-Carboxytetramethylrhodamine (5-TAMRA); 5-FAM (5-Carboxyfluorescein); 5-Hydroxy Tryptamine (HAT); 5-ROX (carboxy-X-rhodamine); 5-TAMRA (5-Carboxytetramethylrhodamine); 6-Carboxyrhodamine 6G; 6-CR 6G; 6-JOE; 7-Amino-4-methylcoumarin; 7-Aminoactinomycin D (7-AAD); 7-Hydroxy-4-methylcoumarin; 9-Amino-6-chloro-2-methoxyacridine; ABQ; Acid Fuchsin; ACMA (9-Amino-6-chloro-2-methoxyacridine); Acridine Orange; Acridine Red; Acridine Yellow; Acriflavin; Acriflavin Feulgen SITSA; Aequorin (Photoprotein); ALEXA FLUOR 350™ (7-Amino-4-methyl-6-sulfocoumarin-3-acetic acid); Fluor ALEXA FLUOR 430™; ALEXA FLUOR 488™; ALEXA FLUOR 532™; ALEXA FLUOR 546™; ALEXA FLUOR 568™; ALEXA FLUOR 594™; ALEXA FLUOR 633™; ALEXA FLUOR 647™; ALEXA FLUOR 660™; ALEXA FLUOR 680™; Alizarin Complexon; Alizarin Red; Allophycocyanin (APC); AMC, AMCA-S; AMCA (Aminomethylcoumarin); AMCA-X; Aminoactinomycin D; Aminocoumarin; Anilin Blue; Anthrocyl stearate; APC-Cy7; APTS; ASTRAZON Brilliant Red 4G (basic red 14); ASTRAZON Orange R (2-[2-(1-Methyl-2-phenyl-1H-indol-3-yl)ethenyl]-1,3,3-trimethyl-3H-indoliumchloride); ASTRAZON Red 6B (basic violet 7); ASTRAZON Yellow 7 GLL; Atabrine; ATTO-TAG™ CBQCA; ATTO-TAG™ FQ; Auramine; Aurophosphine G; Aurophosphine; BAO 9 (Bisaminophenyloxadiazole); BCECF (high pH); BCECF (low pH); Berberine Sulphate; Beta Lactamase; BFP blue shifted GFP (Y66H); BG-647; Bimane; Bisbenzamide; BLANCOPHOR FFG(7-diethylamino-4-methylcoumarin); BLANCOPHOR SV; BOBO™-1; BOBO™-3; BODIPY 492/515; BODIPY 493/503 (4,4-Difluoro-1,3,5,7,8-Pentamethyl-4-Bora-3a,4a-Diaza-s-Indacene); BODIPY 500/510; BODIPY 505/515 (4,4-Difluoro-1,3,5,7-Tetramethyl-4-Bora-3a,4a-Diaza-s-Indacene); BODIPY 530/550; BODIPY 542/563; BODIPY 558/568; BODIPY 564/570; BODIPY 576/589; BODIPY 581/591; BODIPY 630/650-X; BODIPY 650/665-X; BODIPY 665/676; BODIPY Fl; BODIPY FL ATP; BODIPY Fl-Ceramide; BODIPY R6G SE; BODIPY TMR; BODIPY TMR-X conjugate; BODIPY TMR-X, SE; BODIPY TR; BODIPY TR ATP; BODIPY TR-X SE; BO-PRO™-1; BO-PRO™-3; Brilliant Sulphoflavin FF; Calcein; Calcein Blue; Calcium Crimson™; Calcium Green; Calcium Green-1 $Ca^{2+}$ Dye; Calcium Green-2 $Ca^{2+}$; Calcium Green-5N $Ca^{2+}$; Calcium Green-C18 $Ca^{2+}$; Calcium Orange; Calcofluor White; Carboxy-X-rhodamine (5-ROX); Cascade Blue™; Cascade Yellow; Catecholamine; CFDA; CFP—Cyan Fluorescent Protein; Chlorophyll; Chromomycin A; Chromomycin A; CMFDA; Coelenterazine; Coelenterazine cp; Coelenterazine f; Coelenterazine fcp; Coelenterazine h; Coelenterazine hcp; Coelenterazine ip; Coelenterazine 0; Coumarin Phalloidin; CPM Methylcoumarin; CTC; Cy2™; Cy3.1 8; Cy3.5™; Cy3™; Cy5.1 8; Cy5.5™; Cy5™; Cy7™; Cyan GFP; cyclic AMP Fluorosensor (FiCRhR); d2; Dabcyl; Dansyl; Dansyl Amine; Dansyl Cadaverine; Dansyl Chloride; Dansyl DHPE; Dansyl fluoride; DAPI; Dapoxyl; Dapoxyl 2; Dapoxyl 3; DCFDA; DCFH (Dichlorodihydrofluorescein Diacetate); DDAO; DHR (Dihydorhodamine 123); Di-4-ANEPPS; Di-8-ANEPPS (non-ratio); DiA (4-Di-16-ASP); DIDS; Dihydorhodamine 123 (DHR); DiO (DiOC18(3)); DiR; DiR (DiIC18(7)); Dopamine; DsRed; DTAF; DY-630-NHS; DY-635-NHS; EBFP; ECFP; EGFP; ELF 97; Eosin; Erythrosin; Erythrosin ITC; Ethidium homodimer-1 (EthD-1); Euchrysin; Europium (III) chloride; Europium; EYFP; Fast Blue; FDA; Feulgen (Pararosaniline); FITC; FL-645; Flazo Orange; Fluo-3; Fluo-4; Fluorescein Diacetate; Fluoro-Emerald; Fluoro-Gold (Hydroxystilbamidine); Fluor-Ruby; FluorX; FM 1-43™; FM 4-46; Fura Red™ (high pH); Fura-2, high calcium; Fura-2, low calcium; Genacryl Brilliant Red B; Genacryl Brilliant Yellow 10GF; Genacryl Pink 3G; Genacryl Yellow SGF; GFP (S65T); GFP red shifted (rsGFP); GFP wild type, non-UV excitation (wtGFP); GFP wild type, UV excitation (wtGFP); GFPuv; Gloxalic Acid; Granular Blue; Haematoporphyrin; Hoechst 33258; Hoechst 33342; Hoechst 34580; HPTS; Hydroxycoumarin; Hydroxystilbamidine (FluoroGold); Hydroxytryptamine; Indodicarbocyanine (DiD); Indotricarbocyanine (DiR); Intrawhite Cf; JC-1; JO-JO-1; JO-PRO-1; LaserPro; Laurodan; LDS 751; Leucophor PAF; Leucophor SF; Leucophor WS; Lissamine Rhodamine; Lissamine Rhodamine B; LOLO-1; LO-PRO-1; Lucifer Yellow; Mag Green; Magdala Red (Phloxin B); Magnesium Green; Magnesium Orange; Malachite Green; Marina Blue; Maxilon Brilliant Flavin 10 GFF; Maxilon Brilliant Flavin 8 GFF; Merocyanin; Methoxycoumarin; Mitotracker Green FM; Mitotracker Orange; Mitotracker Red; Mitramycin; Monobromobimane; Monobromobimane (mBBr-GSH); Monochlorobimane; MPS (Methyl Green Pyronine Stilbene); NBD; NBD Amine; Nile Red; Nitrobenzoxadidole; Noradrenaline; Nuclear Fast Red; Nuclear Yellow; Nylosan Brilliant Iavin EBG; Oregon Green™; Oregon Green 488-X; Oregon Green™ 488; Oregon Green™ 500; Oregon Green™ 514; Pacific Blue; Pararosaniline (Feulgen); PE-Cy5; PE-Cy7; PerCP; PerCP-Cy5.5; PE-TexasRed (Red 613); Phloxin B (Magdala Red); Phorwite AR; Phorwite BKL; Phorwite Rev; Phorwite RPA; Phosphine 3R; PhotoResist; Phycoerythrin B [PE]; Phycoerythrin R [PE]; PKH26; PKH67; PMIA; Pontochrome Blue Black; POPO-1; POPO-3; PO-PRO-1; PO-PRO-3; Primuline; Procion Yellow; Propidium Iodid (PI); PyMPO; Pyrene; Pyronine; Pyronine B; Pyrozal Brilliant Flavin 7GF; QSY 7; Quinacrine Mustard; Resorufin; RH 414; Rhod-2; Rhodamine; Rhodamine 110; Rhodamine 123; Rhodamine 5 GLD; Rhodamine 6G; Rhodamine B 540; Rhodamine B 200; Rhodamine B extra; Rhodamine BB; Rhodamine BG; Rhodamine Green; Rhodamine Phallicidine; Rhodamine Phalloidine; Rhodamine Red; Rhodamine WT; Rose Bengal; R-phycoerythrin (PE); red shifted GFP (rsGFP, S65T); S65A; S65C; S65L; S65T; Sapphire GFP; Serotonin; Sevron Brilliant Red 2B; Sevron Brilliant Red 4G; Sevron Brilliant Red B; Sevron Orange; Sevron Yellow L; sgBFP™; sgBFP™ (super glow BFP); sgGFP™; sgGFP™ (super glow GFP); SITS; SITS (Primuline); SITS (Stilbene Isothiosulphonic Acid); SPQ (6-methoxy-N-(3-sulfopropyl)-quinolinium); Stilbene; Sulphorhodamine B can C; Sulphorhodamine G Extra; Tetracycline; Tetramethylrhodamine; Texas Red™; Texas Red-X™ conjugate; Thiadicarbocyanine (DiSC3); Thiazine Red R; Thiazole Orange; Thioflavin 5; Thioflavin S; Thioflavin TCN; Thiolyte; Thiozole Orange; Tinopol CBS (Calcofluor White); TMR; TO-PRO-1; TO-PRO-3; TO-PRO-5; TOTO-1; TOTO-3; TriColor (PE-Cy5); TRITC (TetramethylRodamineIsoThioCyanate); True Blue; Tru-Red; Ultralite; Uranine B; Uvitex SFC; wt GFP; WW 781; XL665; X-Rhodamine; XRITC; Xylene Orange; Y66F; Y66H; Y66W; Yellow GFP; YFP; YO-PRO-1; YO-PRO-3; YOYO-1; and YOYO-3. Many suitable forms of these fluorescent compounds are available and can be used.

Other exemplary detectable labels include luminescent and bioluminescent markers (e.g., biotin, luciferase (e.g., bacterial, firefly, click beetle and the like), luciferin, and aequorin), radiolabels (e.g., 3H, 125I, 35S, 14C, or 32P), enzymes (e.g., galactosidases, glucorinidases, phosphatases (e.g., alkaline phosphatase), peroxidases (e.g., horseradish peroxidase), and cholinesterases), and calorimetric labels such as colloidal gold or colored glass or plastic (e.g., polystyrene, polypropylene, and latex) beads. Patents teaching the use of such labels include U.S. Pat. Nos. 3,817,837, 3,850,752, 3,939,350, 3,996,345, 4,277,437, 4,275,149, and 4,366,241, each of which is incorporated herein by reference.

Suitable echogenic gases include, but are not limited to, a sulfur hexafluoride or perfluorocarbon gas, such as perfluoromethane, perfluoroethane, perfluoropropane, perfluorobutane, perfluorocyclobutane, perfluropentane, or perfluorohexane. Suitable non-metallic isotopes include, but are not limited to, $^{11}C$, $^{14}C$, $^{13}N$, $^{18}F$, $^{123}I$, $^{124}I$, and $^{125}I$. Suitable radioisotopes include, but are not limited to, $^{99}mTc$, $^{95}Tc$, $^{111}In$, $^{62}Cu$, Ga, $^{68}Ga$, and $^{153}Gd$. Suitable paramagnetic metal ions include, but are not limited to, Gd(III), Dy(III), Fe(III), and Mn(II). Suitable X-ray absorbers include, but are not limited to, Re, Sm, Ho, Lu, Pm, Y, Bi, Pd, Gd, La, Au, Au, Yb, Dy, Cu, Rh, Ag, and Ir.

In some embodiments, the radionuclide is bound to a chelating agent or chelating agent-linker attached to the microbe-targeting molecule. Suitable radionuclides for direct conjugation include, without limitation, $^{18}F$, $^{124}I$, $^{125}I$, $^{131}I$, and mixtures thereof. Suitable radionuclides for use with a chelating agent include, without limitation, $^{47}Sc$, $^{46}Cu$, $^{67}Cu$, $^{89}Sr$, $^{86}Y$, $^{87}Y$, $^{90}Y$, $^{105}Rh$, $^{111}Ag$, $^{111}In$, $^{117}mSn$, $^{149}Pm$, $^{153}Sm$, $^{166}Ho$, $^{177}Lu$, $^{186}Re$, $^{188}Re$, $^{211}At$, $^{212}Bi$, and mixtures thereof. Suitable chelating agents include, but are not limited to, DOTA, BAD, TETA, DTPA, EDTA, NTA, HDTA, their phosphonate analogs, and mixtures thereof. One of skill in the art will be familiar with methods for attaching radionuclides, chelating agents, and chelating agent-linkers to molecules such as the microbe-targeting molecules and carrier scaffolds disclosed herein.

Means of detecting such labels are well known to those of skill in the art. Thus, for example, radiolabels can be detected using photographic film or scintillation counters, fluorescent markers can be detected using a photo-detector to detect emitted light. Enzymatic labels are typically detected by providing the enzyme with an enzyme substrate and detecting the reaction product produced by the action of the enzyme on the enzyme substrate, and calorimetric labels can be detected by visualizing the colored label. Exemplary methods for in vivo detection or imaging of detectable labels include, but are not limied to, radiography, magnetic resonance imaging (MRI), Positron emission tomography (PET), Single-photon emission computed tomography (SPECT, or less commonly, SPET), Scintigraphy, ultrasound, CAT scan, photoacoustic imaging, thermography, linear tomography, poly tomography, zonography, orthopantomography (OPT or OPG), and computed Tomography (CT) or Computed Axial Tomography (CAT scan).

In some embodiments, the detectable label can include an enzyme. Exemplary enzymes for use as detectable labels include, but are not limited to, horseradish peroxidase (HRP), alkaline phosphastase (AP), or any combinations thereof.

In some embodiments, the detectable can include a microbial enzyme substrate conjugated to a detectable agent. For example, the detectable agent can be any moiety that, when cleaved from a microbial enzyme substrate by the enzyme possessed or secreted by the microbe, forms a detectable moiety but that is not detectable in its conjugated state. The microbial enzyme substrate is a substrate specific for one or more types of microbes to be detected, and it can be selected depending upon what enzymes the microbe possesses or secretes. See, e.g., International Patent Application: WO 2011/103144 for the use of such detectable label in detection of microbes, the content of which is incorporated herein by reference.

In some embodiments, the detectable label is a fluorophore or a quantum dot. Without wishing to be bound by a theory, using a fluorescent reagent can reduce signal-to-noise in the imaging/readout, thus maintaining sensitivity. Accordingly, in some embodiments, prior to detection, the microbes isolated from or remained bound on the microbe-targeting substrate can be stained with at least one stain, e.g., at least one fluorescent staining reagent comprising a microbe-binding molecule, wherein the microbe-binding molecule comprises a fluorophore or a quantum dot. Examples of fluorescent stains include, but are not limited to, any microbe-targeting element (e.g., microbe-specific antibodies or any microbe-binding proteins or peptides or oligonucleotides) typically conjugated with a fluorophore or quantum dot, and any fluorescent stains used for detection as described herein. In some embodiments, the detectable label is a gold particle.

In some embodiments, the detectable label can be configured to include a "smart label", which is undetectable when conjugated to the microbe-binding molecules, but produces a color change when released from the engineered molecules in the presence of a microbe enzyme. Thus, when a microbe binds to the engineered microbe-binding molecules, the microbe releases enzymes that release the detectable label from the engineered molecules. An observation of a color change indicates presence of the microbe in the sample.

In some embodiments, the detectable label can be a chromogenic or fluorogenic microbe enzyme substrate so that when a microbe binds to the engineered microbe-targeting molecule, the enzyme that the microbe releases can interact with the detectable label to induce a color change. Examples of such microbe enzyme substrate can include, but are not limited to, indoxyl butyrate, indoxyl glucoside, esculin, magneta glucoside, red-β-glucuronide, 2-methoxy-4-(2-nitrovinyl) phenyl β-D-glu-copyranoside, 2-methoxy-4-(2-nitrovinyl) phenyl β-D-cetamindo-2-deoxyglucopyranoside, and any other art-recognized microbe enzyme substrates. Such embodiments can act as an indicator for the presence of a microbe or pathogen.

In some embodiments, the second domain can comprise a functional group for conjugating the first domain to another molecule, a composition, a physical substrate, and the like. For example, the second domain can comprise a functional group for covalently linking the first domain with another molecule molecule, a composition, a physical substrate, or the like. Some exemplary functional groups for conjugation include, but are not limited to, an amino group, a N-substituted amino group, a carboxyl group, a carbonyl group, an acid anhydride group, an aldehyde group, a hydroxyl group, an epoxy group, a thiol, a disulfide group, an alkenyl group, a hydrazine group, a hydrazide group, a semicarbazide group, a thiosemicarbazide group, one partner of a binding pair, an amide group, an aryl group, an ester group, an ether group, a glycidyl group, a halo group, a hydride group, an isocyanate group, an urea group, an urethane group, and any combinations thereof.

In some embodiments, the microbe-binding molecule disclosed herein can be immobilized on a carrier scaffold for a variety of applications or purposes. For example, when the affinity of a single microbe surface-binding domain for a target molecule is relatively low, and such binding is generally driven by avidity and multivalency, multivalency of the engineered microbe-targeting molecules disclosed herein can be effectively increased by attachment of a plurality of the engineered microbe-targeting molecules to a carrier scaffold, such as a solid substrate at a high density, which can be varied to provide optimal functionality. Alternatively, the engineered microbe-targeting molecules can be immobilized on a carrier scaffold for easy handling during usage, e.g., for isolation, observation or microscopic imaging.

The attachment of the engineered microbe-binding molecule disclosed herein to a surface of the carrier scaffold can be performed with multiple approaches, for example, by direct cross-linking the engineered microbe-binding molecule to the carrier scaffold surface; cross-linking the engineered microbe-binding molecule to the carrier scaffold surface via a nucleic acid matrix (e.g., DNA matrix or DNA/oligonucleotide origami structures) for orientation and concentration to increase detection sensitivity; cross-linking the microbe-binding molecule to the carrier scaffold surface via a dendrimer-like structure (e.g., PEG/Chitin-structure) to increase detection sensitivity; attracting microbe-binding molecule coated magnetic microbeads to the carrier scaffold surface with a focused magnetic field gradient applied to the scarrier scaffold surface, attaching an engineered microbe-binding molecule to a carrier scaffold via biotin-avidin or biotin-avidin-like interaction, or any other art-recognized methods.

Without limitations, any conjugation chemistry known in the art for conjugating two molecules or different parts of a composition together can be used for conjugating at least one engineered microbe-targeting molecule to a carrier scaffold. Exemplary coupling molecules and/or functional groups for conjugating at least one engineered microbe-targeting molecule to a substrate include, but are not limited to, a polyethylene glycol (PEG, $NH_2$-$PEG_x$-COOH which can have a PEG spacer arm of various lengths X, where $1<X<100$, e.g., PEG-2K, PEG-5K, PEG-10K, PEG-12K, PEG-15K, PEG-20K, PEG-40K, and the like), maleimide conjugation agent, PASylation, HESylation, Bis(sulfosuccinimidyl) suberate conjugation agent, DNA conjugation agent, peptide conjugation agent, silane conjugation agent, polysaccharide conjugation agent, hydrolyzable conjugation agent, and any combinations thereof.

For engineered microbe-targeting molecules to be immobilized on or conjugated to a carrier scaffold, the microbe-targeting molecules described herein can further comprise at least one (e.g., one, two, three, four, five, six, seven, eight, nine, ten, eleven, twelve, thirteen, fourteen, fifteen, sixteen, seventeen, eighteen, nineteen, twenty or more) second domain, e.g., adapted for orienting the first domain away from the carrier scaffold surface. In some embodiments, the carrier scaffold surface can be functionalized with a coupling molecule to facilitate the conjugation of engineered microbe-targeting molecule to the solid surface.

Accordingly, in some embodiments, the second domain can be selected or configured to provide one or more functional groups for conjugating the microbe-binding domain with a carrier scaffold or a deteactable label. A domain adapted for conjugating the microbe-binding molecule to a carrier scaffold is also referred to as a "conjugation domain" herein. As used herein, the term "conjugation domain" refers to any molecule or portion thereof that facilitates the conjugation of the engineered molecules described herein to a carrier scaffold.

In some embodiments, length of the conjugation domain can vary from 1 amino acid residue to about 10 amino acid residues, or about 2 amino acid residues to about 5 amino acid residues. Determination of an appropriate amino acid sequence of the oconjugatio domain for binding with different carrier scaffolds is well within one of skill in the art. For example, according to one or more embodiments, the conjugation domain can comprise an amino acid sequence of AKT (SEQ ID NO: 32), which provides a single biotinylation site for subsequent binding to streptavidin. Preferably the AKT is at the terminus or near the terminus (e.g., within less than 10 amino acids from the terminus) of the microbe-binding molecule. In some embodiments, the conjugation domain comprises a functional group for conjugating or linking the microbe-binding molecule to the carrier scaffold. Some exemplary functional groups for conjugation include, but are not limited to, an amino group, a N-substituted amino group, a carboxyl group, a carbonyl group, an acid anhydride group, an aldehyde group, a hydroxyl group, an epoxy group, a thiol, a disulfide group, an alkenyl group, a hydrazine group, a hydrazide group, a semicarbazide group, a thiosemicarbazide group, one partner of a binding pair, an amide group, an aryl group, an ester group, an ether group, a glycidyl group, a halo group, a hydride group, an isocyanate group, an urea group, an urethane group, and any combinations thereof.

Activation agents can be used to activate the components to be conjugated together. Without limitations, any process and/or reagent known in the art for conjugation activation can be used. Exemplary activation methods or reagents include, but are not limited to, 1-Ethyl-3-[3-dimethylaminopropyl]carbodiimide hydrochloride (EDC or EDAC), hydroxybenzotriazole (HOBT), N-Hydroxysuccinimide (NHS), 2-(1H-7-Azabenzotriazol-1-yl)-1,1,3,3-tetramethyl uronium hexafluorophosphate methanaminium (HATU), silanization, surface activation through plasma treatment, and the like.

In some embodiments, the conjugation domain can comprise at least one amino group that can be non-covalently or covalently coupled with functional groups on the carrier scaffold. For example, the primary amines of the amino acid residues (e.g., lysine or cysteine residues) can be used to conjugate the microbe-binding molecule with the carrier scaffold. In some embodiments, the amino group at the N-terminus of the microbe-binding molecule can be used for conjugating the microbe-binding molecule with the carrier scaffold.

Without limitations, the engineered microbe-targeting molecule can be conjugated to the carrier-scaffold through covalent or non-covalent interactions or any combination of covalent and non-covalent interactions. Further, conjugation can be accomplished any of method known to those of skill in the art. For example, covalent immobilization can be accomplished through, for example, silane coupling. See, e.g., Weetall, 15 *Adv. Mol. Cell Bio.* 161 (2008); Weetall, 44 *Meths. Enzymol.* 134 (1976). The covalent interaction between the engineered microbe-targeting molecule and/or coupling molecule and the surface can also be mediated by other art-recognized chemical reactions, such as NHS reaction or a conjugation agent. The non-covalent interaction between the engineered microbe-targeting molecule and/or coupling molecule and the surface can be formed based on ionic interactions, van der Waals interactions, dipole-dipole interactions, hydrogen bonds, electrostatic interactions, and/or shape recognition interactions.

Without limitations, conjugation can include either a stable or a labile (e.g. cleavable) bond or conjugation agent. Exemplary conjugations include, but are not limited to, covalent bond, amide bond, additions to carbon-carbon multiple bonds, azide alkyne Huisgen cycloaddition, Diels-Alder reaction, disulfide linkage, ester bond, Michael additions, silane bond, urethane, nucleophilic ring opening reactions: epoxides, non-aldol carbonyl chemistry, cycloaddition reactions: 1,3-dipolar cycloaddition, temperature sensitive, radiation (IR, near-IR, UV) sensitive bond or conjugation agent, pH-sensitive bond or conjugation agent, non-covalent bonds (e.g., ionic charge complex formation, hydrogen bonding, pi-pi interactions, hist guest interactions, such as cyclodextrin/adamantly host guest interaction) and the like.

In some embodiments, the microbe-targeting molecule can be conjugated to the carrier-scaffold with a linker. In some embodiments, the the microbe-targeting molecule can be conjugated to the carrier-scaffold with a linking group selected from the group consisting of a direct bond, an atom such as oxygen or sulfur, C(O), C(O)O, OC(O)O, C(O)NH, NHC(O)O, NH, SS, SO, $SO_2$, $SO_3$, and $SO_2NH$.

In some embodiments, the engineered microbe-targeting molecule can be conjugated to the carrier scaffold by a coupling molecule pair. The terms "coupling molecule pair" and "coupling pair" as used interchangeably herein refer to the first and second molecules that specifically bind to each other. One member of the binding pair is conjugated with the carrier scaffold while the second member is conjugated with the microbe-targeting molecule. As used herein, the phrase "first and second molecules that specifically bind to each other" refers to binding of the first member of the coupling pair to the second member of the coupling pair with greater affinity and specificity than to other molecules. Exemplary coupling molecule pairs include, without limitations, any haptenic or antigenic compound in combination with a corresponding antibody or binding portion or fragment thereof (e.g., digoxigenin and anti-digoxigenin; mouse immunoglobulin and goat antimouse immunoglobulin) and nonimmunological binding pairs (e.g., biotin-avidin, biotin-streptavidin), hormone (e.g., thyroxine and cortisol-hormone binding protein), receptor-receptor agonist, receptor-receptor antagonist (e.g., acetylcholine receptor-acetylcholine or an analog thereof), IgG-protein A, lectin-carbohydrate, enzyme-enzyme cofactor, enzyme-enzyme inhibitor, and complementary oligonucleotide pairs capable of forming nucleic acid duplexes). The coupling molecule pair can also include a first molecule that is negatively charged and a second molecule that is positively charged.

One example of using coupling pair conjugation is the biotin-avidin or biotin-streptavidin conjugation. In this approach, one of the members of molecules to be conjugated together (e.g., the engineered microbe-targeting molecule or the carrier scaffold) is biotinylated and the other is conjugated with avidin or streptavidin. Many commercial kits are available for biotinylating molecules, such as proteins. For example, an aminooxy-biotin (AOB) can be used to covalently attach biotin to a molecule with an aldehyde or ketone group. In some embodiments, AOB is attached to the engineered microbe-targeting molecule. Further, as described elsewhere herein, an AKT sequence on the N-terminal of the engineered microbe-targeting molecule can allow the engineered microbe-targeting molecule to be biotinylated at a single site and further conjugated to the streptavidin-coated solid surface. Moreover, the microbe-binding molecule can be coupled to a biotin acceptor peptide, for example, the AviTag or Acceptor Peptide (referred to as AP; Chen et al., 2 *Nat. Methods* 99 (2005)). The Acceptor Peptide sequence allows site-specific biotinylation by the *E. coli* enzyme biotin ligase (BirA; Id.). Thus, in some embodiments, the conjugation domain comprises an amino acid sequence of a biotin acceptor peptide.

Another non-limiting example of using conjugation with a coupling molecule pair is the biotin-sandwich method. See, e.g., Davis et al., 103 *PNAS* 8155 (2006). In this approach, the two molecules to be conjugated together are biotinylated and then conjugated together using tetravalent streptavidin. Another example for conjugation would be to use PLP—mediated bioconjugation. See, e.g., Witus et al., 132 *JACS* 16812 (2010). Still another example of using coupling pair conjugation is double-stranded nucleic acid conjugation.

In this approach, one of the members of molecules to be conjugated together is conjugated with a first strand of the double-stranded nucleic acid and the other is conjugated with the second strand of the double-stranded nucleic acid. Nucleic acids can include, without limitation, defined sequence segments and sequences comprising nucleotides, ribonucleotides, deoxyribonucleotides, nucleotide analogs, modified nucleotides and nucleotides comprising backbone modifications, branchpoints and nonnucleotide residues, groups or bridges.

The carrier scaffold can also be functionalized to include a functional group for conjugating with the microbe-binding molecule. In some embodiments, the carrier scaffold can be functionalized to include a coupling molecule, or a functional fragment thereof, that is capable of selectively binding with an engineered microbe-targeting molecule described herein, As used herein, the term "coupling molecule" refers to any molecule or any functional group that is capable of selectively binding with an engineered microbe surface-binding domain described herein. Representative examples of coupling molecules include, but are not limited to, antibodies, antigens, lectins, proteins, peptides, nucleic acids (DNA, RNA, PNA and nucleic acids that are mixtures thereof or that include nucleotide derivatives or analogs); receptor molecules, such as the insulin receptor; ligands for receptors (e.g., insulin for the insulin receptor); and biological, chemical or other molecules that have affinity for another molecule.

In some embodiments, the coupling molecule is an aptamer. As used herein, the term "aptamer" means a single-stranded, partially single-stranded, partially double-stranded or double-stranded nucleotide sequence capable of specifically recognizing a selected non-oligonucleotide molecule or group of molecules by a mechanism other than Watson-Crick base pairing or triplex formation. Aptamers can include, without limitation, defined sequence segments and sequences comprising nucleotides, ribonucleotides, deoxyribonucleotides, nucleotide analogs, modified nucleotides and nucleotides comprising backbone modifications, branchpoints and nonnucleotide residues, groups or bridges. Methods for selecting aptamers for binding to a molecule are widely known in the art and easily accessible to one of ordinary skill in the art. The aptamers can be of any length, e.g., from about 1 nucleotide to about 100 nucleotides, from about 5 nucleotides to about 50 nucleotides, or from about 10 nucleotides to about 25 nucleotides.

In some embodiments, the second domain comprises a therapeutic agent. For example, the second domain can comprise an anti-microbial agent. Therapeutic agents are described herein below. Any method available to the skilled artisan for conjugating a therapeutic agent to a peptide can be used for conjugating the therapeutic agent to the first domain. For example, functional groups or methods used for conjugating the microbe-targeting molecule to a carrier scaffold can also be used for conjugating the microbe-targeting molecule to a therapeutic agent. This can be beneficial for delvierying or concentrating a therapeutic agent (e.g., an anti-microbial agent) at a nidus of infection.

The first and second domains of the microbe-targeting molecule are linked together by a linker. Further, the microbe-targeting molecule can be conjugated to a carrier scaffold via linker. Accordingly, as used in this disclosre, the term "linker" means a moiety that connects two parts of a compound or molecule. Linkers typically comprise a direct bond or an atom such as oxygen or sulfur, a unit such as $NR^1$, C(O), C(O)O, OC(O)O, C(O)NH, NHC(O)O, NH, SS, SO, $SO_2$, $SO_3$, and $SO_2NH$, or a chain of atoms, such as substituted or unsubstituted alkyl, substituted or unsubstituted alkenyl, substituted or unsubstituted alkynyl, arylalkyl, arylalkenyl, arylalkynyl, heteroarylalkyl, heteroarylalkenyl, heteroarylalkynyl, heterocyclylalkyl, heterocyclylalkenyl, heterocyclylalkynyl, aryl, heteroaryl, heterocyclyl, cycloalkyl, cycloalkenyl, alkylarylalkyl, alkylarylalkenyl, alkylarylalkynyl, alkenylarylalkyl, alkenylarylalkenyl, alkenylarylalkynyl, alkynylarylalkyl, alkynylarylalkenyl, alkynylarylalkynyl, alkylheteroarylalkyl, alkylheteroarylalkenyl, alkylheteroarylalkynyl, alkenylheteroarylalkyl, alkenylheteroarylalkenyl, alkenylheteroarylalkynyl, alkynylheteroarylalkyl, alkynylheteroarylalkenyl, alkynylheteroarylalkynyl, alkylheterocyclylalkyl, alkylheterocyclylalkenyl, alkylhererocyclylalkynyl, alkenylheterocyclylalkyl, alkenylheterocyclylalkenyl, alkenylheterocyclylalkynyl, alkynylheterocyclylalkyl, alkynylheterocyclylalkenyl, alkynylheterocyclylalkynyl, alkylaryl, alkenylaryl, alkynylaryl, alkylheteroaryl, alkenylheteroaryl, alkynylhereroaryl, where one or more methylenes can be interrupted or terminated by O, S, S(O), $SO_2$, NH, $C(O)N(R^1)_2$, C(O), cleavable linking group, substituted or unsubstituted aryl, substituted or unsubstituted heteroaryl, substituted or unsubstituted heterocyclic; where $R^1$ is hydrogen, acyl, aliphatic or substituted aliphatic. In some embodiments, the linker can be a non-covalent association (e.g., by non-covalent interactins) of the two parts of a molecule being conjugated together. Some exemplary non-covalent on ionic interactions, van der Waals interactions, dipole-dipole interactions, hydrogen bonds, electrostatic interactions, and/or shape recognition interactions.

In some embodiments, the linker can comprise at least one cleavable linking group. A cleavable linking group is one which is sufficiently stable under one set of conditions, but which is cleaved under a different set of conditions to release the two parts the linker is holding together. In some embodiments, the cleavable linking group is cleaved at least 10 times or more, e.g., at least 100 times faster under a first reference condition (which can, e.g., be selected to mimic or represent a microbe-infected condition, such as a microbe-infected tissue or body fluid, or a microbial biofilm occurring in an environment) than under a second reference condition (which can, e.g., be selected to mimic or represent non-infected conditions, e.g., found in the non-infected blood or serum, or in an non-infected environment).

Cleavable linking groups are susceptible to cleavage agents, e.g., hydrolysis, pH, redox potential or the presence of degradative molecules. Generally, cleavage agents are more prevalent or found at higher levels or activities at a site of interest (e.g. a microbial infection) than in non-infected area. Examples of such degradative agents include: redox agents which are selected for particular substrates or which have no substrate specificity, including, e.g., oxidative or reductive enzymes or reductive agents such as mercaptans, present in cells, that can degrade a redox cleavable linking group by reduction; esterases; amidases; endosomes or agents that can create an acidic environment, e.g., those that result in a pH of five or lower; enzymes that can hydrolyze or degrade an acid cleavable linking group by acting as a general acid, peptidases (which can be substrate specific) and proteases, and phosphatases.

A linker can include a cleavable linking group that is cleavable by a particular enzyme. The type of cleavable linking group incorporated into a linker can depend on the cell, organ, or tissue to be targeted. In some embodiments, cleavable linking group is cleaved at least 1.25, 1.5, 1.75, 2, 3, 4, 5, 10, 25, 50, or 100 times faster under a first reference condition (or under in vitro conditions selected to mimic a microbe-infected condition, such as a microbe-infected tissue or body fluid, or a microbial biofilm occurring in an environment or on a working surface) than under a second reference condition (or under in vitro conditions selected to mimic non-infected conditions, e.g., found in the non-infected blood or serum, or in an non-infected environment). In some embodiments, the cleavable linking group is cleaved by less than 90%, 80%, 70%, 60%, 50%, 40%, 30%, 20%, 10%, 5%, or 1% in the non-infected conditions, e.g., found in the non-infected blood or serum, or in an non-infected environment, as compared to a microbe-infected condition, such as a microbe-infected tissue or body fluid, or a microbial biofilm occurring in an environment or on a working surface.

Exemplary cleavable linking groups include, but are not limited to, hydrolyzable linkers, redox cleavable linking groups (e.g., —S—S— and —C(R)$_2$—S—S—, wherein R is H or $C_1$-$C_6$ alkyl and at least one R is $C_1$-$C_6$ alkyl such as $CH_3$ or $CH_2CH_3$); phosphate-based cleavable linking groups (e.g., —O—P(O)(OR)—O—, —O—P(S)(OR)—O—, —O—P(S)(SR)—O—, —S—P(O)(OR)—O—, —O—P(O)(OR)—S—, —S—P(O)(OR)—S—, —O—P(S)(ORk)-S—, —S—P(S)(OR)—O—, —O—P(O)(R)—O—, —O—P(S)(R)—O—, —S—P(O)(R)—O—, —S—P(S)(R)—O—, —S—P(O)(R)—S—, —O—P(S)(R)—S—, —O—P(O)(OH)—O—, —O—P(S)(OH)—O—, —O—P(S)(SH)—O—, —S—P(O)(OH)—O—, —O—P(O)(OH)—S—, —S—P(O)(OH)—S—, —O—P(S)(OH)—S—, —S—P(S)(OH)—O—, —O—P(O)(H)—O—, —O—P(S)(H)—O—, —S—P(O)(H)—O—, —S—P(S)(H)—O—, —S—P(O)(H)—S—, and —O—P(S)(H)—S—, wherein R is optionally substituted linear or branched $C_1$-$C_{10}$ alkyl); acid celavable linking groups (e.g., hydrazones, esters, and esters of amino acids, —C=NN— and —OC(O)—); ester-based cleavable linking groups (e.g., —C(O)O—); peptide-based cleavable linking groups, (e.g., linking groups that are cleaved by enzymes such as peptidases and proteases in cells, e.g., —NHCHR$^A$C(O)NHCHR$^B$C(O)—, where R$^A$ and R$^B$ are the R groups of the two adjacent amino acids). A peptide based cleavable linking group comprises two or more amino acids. In some embodiments, the peptide-based cleavage linkage comprises the amino acid sequence that is the substrate for a peptidase or a protease. In some embodiments, an acid cleavable linking group is cleavable in an acidic environment with a pH of about 6.5 or lower (e.g., about 6.5, 6.0, 5.5, 5.0, or lower), or by agents such as enzymes that can act as a general acid.

Without limitations, the linker can be selected to provide a desired function or property to the microbe-binding molecules disclosed herein. For example, the linker can be selected or configured according to a specific need or use of the microbe-binding molecule. By way of example only, in some embodiments, linker can be selected or configured to have a sufficient length and flexibility such that it can allow for the first domain to orient in a desired orientation with respect to a microbe. In some embodiments, the linker can be selected or configured to allow multimerization of at least two engineered microbe-targeting molecules (e.g., to from a di-, tri-, tetra-, penta-, hexa- or higher multimeric complex) while retaining biological activity (e.g., microbe-binding activity). In some embodiments, the linker can be selected or configured to inteact with the second domain to allow multimerization of at least two engineered microbe-targeting molecules (e.g., to from a di-, tri-, tetra-, penta-, hexa- or higher multimeric complex) while retaining microbe-binding activity.

In some embodiments, the linker can be selected or configured to facilitate expression and purification of the engineered microbe-targeting molecule described herein. In some embodiments, the linker can be selected or configured to provide a recognition site for a protease or a nuclease. In addition, the linker can be non-reactive with the functional components of the engineered molecule described herein. For example, minimal hydrophobic or charged character to react with the first domain or second domain. In some embodiments, the linker can be part of the first domain or second domain.

In some embodiments, the linekr can be a peptide or a nucleic acid. In some embodiments, the peptide linker can vary from about 1 to about 1000 amino acids long, from about 10 to about 500 amino acids long, from about 30 to about 300 amino acids long, or from about 50 to about 150 amino acids long. In some embodiments, the peptidyl linker is from about 1 amino acid to about 20 amino acids long. In some embodiments, the nucleic acid linker can vary from about 1 to about 1000 nucleotides long, from about 10 to about 500 nucleotides long, from about 30 to about 300 nucleotides, or from about 50 to about 150 nucleotides. Longer or shorter linker sequences can be also used for the engineered microbe-targeting molecules described herein.

The peptidyl linker can be configured to have a sequence comprising at least one of the amino acids selected from the group consisting of glycine (Gly), serine (Ser), asparagine (Asn), threonine (Thr), methionine (Met) or alanine (Ala). Such amino acids are generally used to provide flexibility of a linker. However, in some embodiments, other uncharged polar amino acids (e.g., Gln, Cys or Tyr), nonpolar amino acids (e.g., Val, Leu, Ile, Pro, Phe, and Trp). In alternative embodiments, polar amino acids can be added to modulate the flexibility of a linker. One of skill in the art can control flexibility of a linker by varying the types and numbers of residues in the linker. See, e.g., Perham, 30 *Biochem.* 8501 (1991); Wriggers et al., 80 *Biopolymers* 736 (2005).

In some embodiments, the peptidyl linker can comprise form 1 to about 25 amino acids, i.e., one, two, three, four, five, six, seven, egiht, nine, ten, eleven, twelve, thirteen, fourteen, fifteen, sixteen, seventeen, eighteen, nineteen, twenty, twenty-one, twenty-two, twenty-three, twenty-four, or twenty-five amino acids. In some embodiments, the peptidyl linker linking the first and second domain comprises the amino acid sequence HHHHHH (SEQ ID NO: 39).

In some embodiments, when the second domain comprises a Fc region, the linker linking the first and the second domain is not a bond or a peptide.

In some embodiments, the linker is a bond.

In some embodiments, the linker conjugating a microbe-targeting molecule to a carrier scaffold is a polyethylene glycol. Exemplary PEGs for use as linkers include, but are not limited to, PEG-2K, PEG-5K, PEG-10K, PEG-12K, PEG-15K, PEG-20K, PEG-40K, and the like.

In some embodiments, the linker can be albumin, transferrin or a fragment thereof. Without limitations, such linkers can be used to extend the plasma half-life of the engineered microbe-targeting molecules. Thus, engineered microbe-targeting molecules can be useful for in vivo administration. See Schmidt S R (2009) *Curr Opin Drug Discov Devel.* 12: 284. In some embodiments, the linker can be a physical substrate, e.g., microparticles or magnetic microbes.

The linker between the first domain and the second domain can provide sufficient distance between the first and the second domain to allow the first domain to interact with the microbes. Accordingly, the distance between the first domain and the second domain can range from about 50 angstroms to about 5000 angstroms, from about 100 angstroms to about 2500 angstroms, or from about 200 angstroms to about 1000 angstroms.

The linkers can be of any shape. For example, the linker can be linear, folded, branched. In some embodiments, the linker can adopt the shape of a carrier scaffold. In some embodiments, the linkers can be linear. In some embodiments, the linkers can be folded. In some embodiments, the linkers can be branched. For branched linkers, each branch of a microbe surface-binding domain can comprise at least one microbe surface-binding domain. In other embodiments, the linker adopts the shape of the physical substrate.

In some embodiments, the linker can further comprise a detectable label. In some embodiments, the detectable label can be a chromogenic or fluorogenic microbe enzyme substrate so that when a microbe binds to the engineered microbe-targeting molecule, the enzyme that the microbe releases can interact with the detectable label to induce a color change. Examples of such microbe enzyme substrate can include, but are not limited to, indoxyl butyrate, indoxyl glucoside, esculin, magneta glucoside, red-β-glucuronide, 2-methoxy-4-(2-nitrovinyl) phenyl β-D-glu-copyranoside, 2-methoxy-4-(2-nitrovinyl) phenyl β-D-cetamindo-2-de-oxyglucopyranoside, and any other art-recognized microbe enzyme substrates. Such embodiments can act as an indicator for the presence of a microbe or pathogen.

The first and second domains can be arranged in any desired orientation in the engineered microbe-targeting molecule. For example, N-terminus of the first domain can be linked to the C-terminus of the second domain or C-terminus of the first domain can be linked to the N-terminus of the second domain. It is understood that linking between the first and second domain is via the linker.

Further, as disclosed herein, an engineered microbe-targeting molecule can comprise at least one microbe surface-binding domain, including at least two, at least three, at least four, at least five, at least six, at least seven, at least eight, at least nine, at least ten or more microbe surface-binding domains. When more than two first or second domains are present, such domains can all be the same, all different, or some same and some different.

In some embodiments, the engineered microbe-targeting molecule disclosed herein comprises two or more first domains and one second domain. In such molecules, one first domain can be linked to the second domain and the other first domains can be linked to the first domain linked to the second domain. Alternatively, two first domains can be linked to the second domain and other first domains can be linked to one or both of the two first domains linked to the second domain.

In some embodiments, the engineered microbe-targeting molecule disclosed herein comprises two or more second domains and one first domain. In such molecules, one second domain can be linked to the first domain and the other second domains can be linked to the second domain linked to the first domain. Alternatively, two second domains can be linked to the first domain and other second domains can be linked to one or both of the two second domains linked to the first domain.

In some embodiments, the engineered mincrobe-targeting molecule is in the form of a multimeric compelex comprising at least two (e.g., two, three, four, five, six, sevem, eight, nine, ten, or more) engineered microbe-targeting molecules. Accordingly, the multimeric compelex can be a di-, tri-, tetra-, penta-, hexa- or higher multimeric complex. In one embodiment, the engineered mincrobe-targeting molecule is in the form of pentameric complex. Without limitations, the multimeric complex can be formed by interactions between a second domain or linker of a first molecule with a second domain or a linker of the second molecule. Such interactions can comprise covalent linking or non-covlalent linking. The microbe-targeting molecules in the multimeric complex can all be the same, all different, or some same and some different.

In some embodiments, the second domain comprises an amino acid sequence selected from the group consistijng of SEQ ID NOs: 5-9, 11, 12, 23-32, 39, and any combinaitons thereof.

General methods of preparing any embodiments of the engineered microbe-targeting molecules are known in the art (Ashkenazi, A. and S. M. Chamow (1997), "Immunoadhesins as research tools and therapeutic agents," Curr. Opin. Immunol. 9(2): 195-200, Chamow, S. M. and A. Ashkenazi (1996). "Immunoadhesins: principles and applications," Trends Biotechnol. 14(2):52-60). In one example, an engineered microbe-targeting molecule can be made by cloning into an expression vector such as Fc-X vector as discussed in Lo et al. (1998) 11:495.

While the exemplary sequences provided herein are derived from a human species, amino acid sequences for same or functionally equivalent domains from other species such as mice, rats, porcine, bovine, feline, and canine are known in the art and within the scope described herein. Furhter, a skill artisan can readily modify the identified sequences to modulate their orientation or binding performance, e.g., by theoretical modeling or in vitro binding experiments. In addition, based on the crystal structure of the native sequences, peptidomimetics that can effectively mimic at least a fragment of a given domain can be also used as a first or second domain of the engineered microbe-targeting molecule described herein. One of skill in the art can readily determine such peptidomimetic structure without undue experimentations, using any methods known in the art and the known crystal structure.

In another strategy of directed evolution, the protein of interest is subjected to random mutagenesis and the resulting proteins are screened for desired qualities. This is a particularly useful technology for affinity maturation of phage display antibodies, where the antibody complementary determining regions (CDRs) are mutated by saturation mutagenesis and successful variants of the six CDRs are shuffled together to form the highest affinity antibodies.

The directed evolution paradigm can be applied to any domain described herein to select variants with a desired property, such as pecific binding to, e.g., but not limited to, yeast, gram-positive bacteria, gram-negative, coagulase negative, and aerobic bacteria. For this to work, however, the pattern and nature of the target sugars or related surface features on these target microorganisms can differ between the classes or species.

Derivatives with a particular specificity can be isolated, e.g., by the following approach, which is a standard phage display strategy: First, express a set of variants from a phagemid vector; then bind this library to a target of interest and perform one or two rounds of selection; and then perform a round of negative selection against a related target, taking those phagemids that fail to bind. These cycles of positive and negative selection are then repeated until a population of phages that generally bind to the target and do not bind to the non-target is generated. This method can be applied to any pair of microbial strains against which differential binding is desired, such as bacteria that are resistant and sensitive to a given antibiotic. This positive/negative enrichment strategy can also be used with an antibody-phage display library, which is an even more standard way to isolate such specific binders.

The inventors have also discovered inter alia that expression of peptides containing a portion of a c-reactive protein can be increased by modifying the nucleic acid encoding the c-reactive protein. Accordingly, provided herein are nucleic acid sequences for the expression of CRP containing peptides that are expressed in an higher amount relative to expression from a wild-type nucleic acid encoding CRP, such as from SEQ ID NO: 52. In some embodiments, the CRP is expressed from a nucleic acid sequence comprising SEQ ID NO: 45, 46, 47, 48, 49, 50, 51 or any combinations thereof.

In some embodiments, the nucleic acid sequence described herein is expressed in a recombinant expression vector or plasmid. As used herein, the term "vector" refers to a polynucleotide sequence suitable for transferring transgenes into a host cell. The term "vector" includes plasmids, mini-chromosomes, phage, naked DNA and the like. See, for example, U.S. Pat. Nos. 4,980,285; 5,631,150; 5,707,828; 5,759,828; 5,888,783 and, 5,919,670, and, Sambrook et al, *Molecular Cloning: A Laboratory Manual,* 2nd Ed., Cold Spring Harbor Press (1989). One type of vector is a "plasmid," which refers to a circular double stranded DNA loop into which additional DNA segments are ligated. Another type of vector is a viral vector, wherein additional DNA segments are ligated into the viral genome. Certain vectors are capable of autonomous replication in a host cell into which they are introduced (e.g., bacterial vectors having a bacterial origin of replication and episomal mammalian vectors). Moreover, certain vectors are capable of directing the expression of genes to which they are operatively linked. Such vectors are referred to herein as "expression vectors". In general, expression vectors of utility in recombinant DNA techniques are often in the form of plasmids. In the present specification, "plasmid" and "vector" is used interchangeably as the plasmid is the most commonly used form of vector. However, the invention is intended to include such other forms of expression vectors, such as viral vectors (e.g., replication defective retroviruses, adenoviruses and adeno-associated viruses), which serve equivalent functions.

A cloning vector is one which is able to replicate autonomously or integrated in the genome in a host cell, and which is further characterized by one or more endonuclease restriction sites at which the vector may be cut in a determinable fashion and into which a desired DNA sequence can be ligated such that the new recombinant vector retains its ability to replicate in the host cell. In the case of plasmids, replication of the desired sequence can occur many times as the plasmid increases in copy number within the host cell such as a host bacterium or just a single time per host before the host reproduces by mitosis. In the case of phage, replication can occur actively during a lytic phase or passively during a lysogenic phase.

An expression vector is one into which a desired DNA sequence can be inserted by restriction and ligation such that it is operably joined to regulatory sequences and can be expressed as an RNA transcript. Vectors can further contain one or more marker sequences suitable for use in the identification of cells which have or have not been transformed or transformed or transfected with the vector. Markers include, for example, genes encoding proteins which increase or decrease either resistance or sensitivity to antibiotics or other compounds, genes which encode enzymes whose activities are detectable by standard assays known in the art (e.g., β-galactosidase, luciferase or alkaline phosphatase), and genes which visibly affect the phenotype of transformed or transfected cells, hosts, colonies or plaques (e.g., green fluorescent protein). In certain embodiments, the vectors used herein are capable of autonomous replication and expression of the structural gene products present in the DNA segments to which they are operably joined.

As used herein, a coding sequence and regulatory sequences are said to be "operably" joined when they are covalently linked in such a way as to place the expression or transcription of the coding sequence under the influence or control of the regulatory sequences. If it is desired that the coding sequences be translated into a functional protein, two DNA sequences are said to be operably joined if induction of a promoter in the 5' regulatory sequences results in the transcription of the coding sequence and if the nature of the linkage between the two DNA sequences does not (1) result in the introduction of a frame-shift mutation, (2) interfere with the ability of the promoter region to direct the transcription of the coding sequences, or (3) interfere with the ability of the corresponding RNA transcript to be translated into a protein. Thus, a promoter region would be operably joined to a coding sequence if the promoter region were capable of effecting transcription of that DNA sequence such that the resulting transcript can be translated into the desired protein or polypeptide.

When the nucleic acid molecule that encodes any of the nucleic acids described herein is expressed in a cell, a variety of transcription control sequences (e.g., promoter/enhancer sequences) can be used to direct its expression. The promoter can be a native promoter, i.e., the promoter of the gene in its endogenous context, which provides normal regulation of expression of the gene. In some embodiments the promoter can be constitutive, i.e., the promoter is unregulated allowing for continual transcription of its associated gene. A variety of conditional promoters also can be used, such as promoters controlled by the presence or absence of a molecule.

The precise nature of the regulatory sequences needed for gene expression can vary between species or cell types, but in general can include, as necessary, 5' non-transcribed and 5' non-translated sequences involved with the initiation of transcription and translation respectively, such as a TATA box, capping sequence, CAAT sequence, and the like. In particular, such 5' non-transcribed regulatory sequences will include a promoter region which includes a promoter sequence for transcriptional control of the operably joined gene. Regulatory sequences can also include enhancer sequences or upstream activator sequences as desired. The vectors of the invention may optionally include 5' leader or signal sequences. The choice and design of an appropriate vector is within the ability and discretion of one of ordinary skill in the art.

Expression vectors containing all the necessary elements for expression are commercially available and known to those skilled in the art. See, e.g., Sambrook et al., *Molecular Cloning: A Laboratory Manual*, Second Edition, Cold Spring Harbor Laboratory Press, 1989. Cells are genetically engineered by the introduction into the cells of heterologous DNA (RNA). That heterologous DNA (RNA) is placed under operable control of transcriptional elements to permit the expression of the heterologous DNA in the host cell.

A nucleic acid molecule that encodes the enzyme of the claimed invention can be introduced into a cell or cells using methods and techniques that are standard in the art. For example, nucleic acid molecules can be introduced by standard protocols such as transformation including chemical transformation and electroporation, transduction, particle bombardment, etc. Expressing the nucleic acid molecule encoding the enzymes of the claimed invention also may be accomplished by integrating the nucleic acid molecule into the genome.

Various aspects described herein related to a method, which comprises recombinantly expressing in a cell one or more nucleic acids disclosed herein. Some aspects provided herein are directed to cell culture medium or supernatant collected from culturing a cell expressing one or more nucleic acids described herein. Other aspects provided herein are directed to a method, comprising culturing in cell culture medium a cell expressing one or more nucleic acids described herein.

Without wishing to be bound by a theory, microbe-binding molecules comprising at least a portion of the CRP or or modified versions thereof can act as broad-spectrum pathogen binding molecules. Accordingly, microbes and/or microbial matter present in a test sample can be captured or detected using microbe-targeting molecules disclosed herein without identifying the microbe. Since CRP is shown to be bind preferentially to gram-positive microbes, the molecules, articles, methods, and assyas disclosed herein are particularly useful for capturing, detecting, or clearing gram-positive microbes.

The engineered microbe-targeting molecules can contain sequences from the same species or from different species. For example, an interspecies hybrid microbe-targeting molecule can have one of the first domain or second domins from a murine species and the other from a human. The engineered microbe-targeting molecules described herein can also include those that are made entirely from murine-derived sequences or fully human.

In some embodiments, the microbe-targeting molecule disclosed herein comprises an amino acid sequence selected from the group consisting of SEQ ID NOs: 32-38, 40, 41, 43, and 44.

Figure 6:
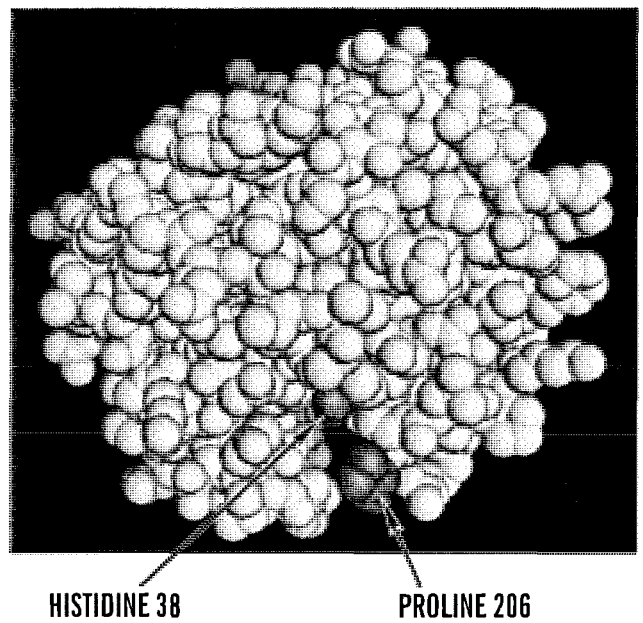
FIG. 6 is a schematic representation showing C-terminus of microbe-targeting molecule (CRP-X-Fc, X is a linker) according to an embodiment of the invention blocks histadine 38 of the CRP.
Figure 7:
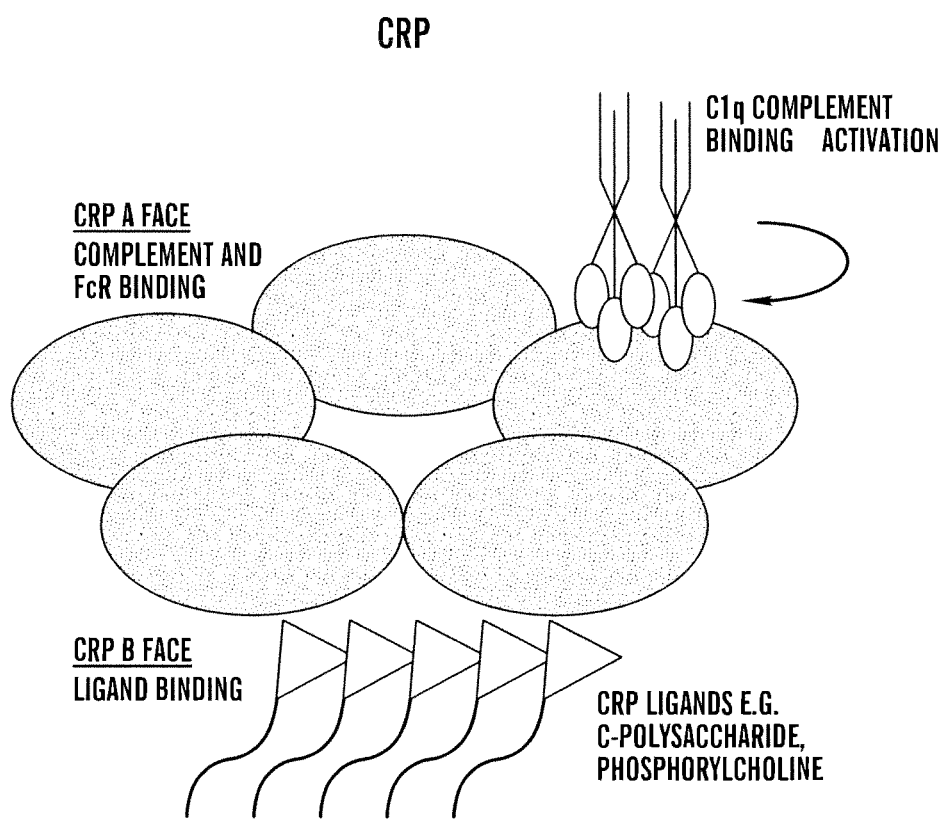
FIG. 7 is a schematic representation showing C1q component binding and complement activation is on A face of CRP and CRP ligand binding, e.g., microbe binding, is on B face of CRP.
Figure 8:
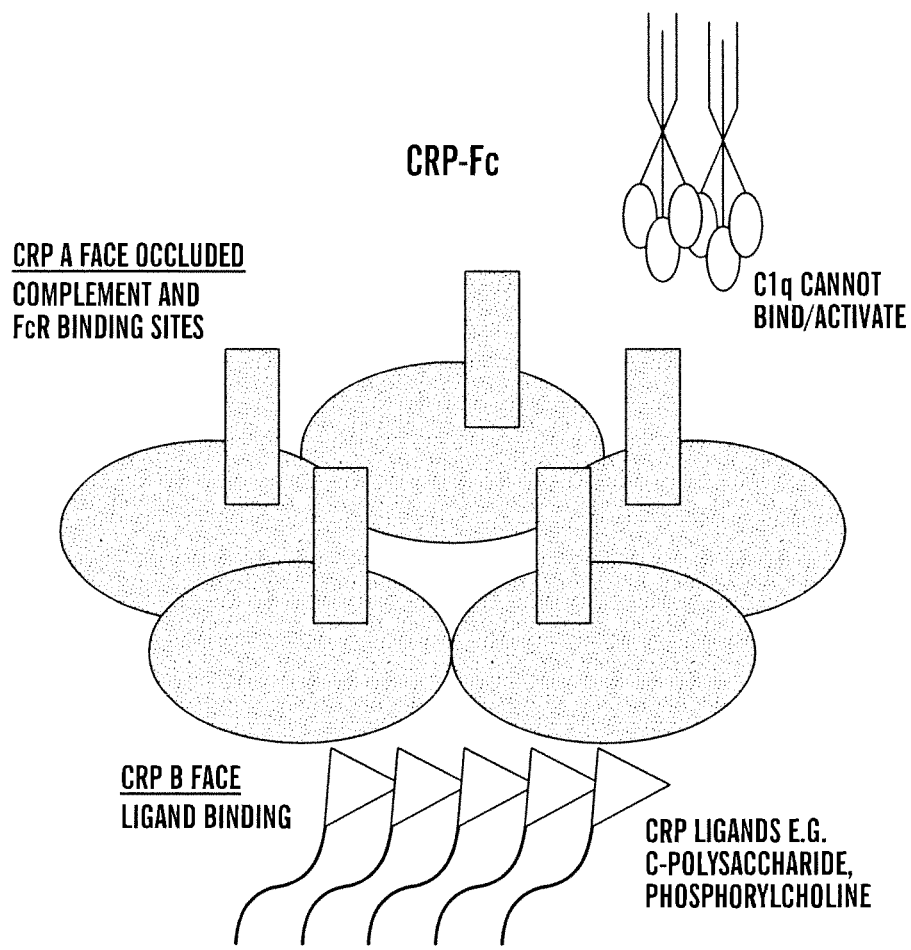
FIG. 8 is a schematic representation showing Fc in CRP-Fc is bound to A face of CRP thereby inhibiting C1q binding and complement activation.

The inventors have discievored inter alia that in microbe-targeting molecules of formula CRP-X-Fc, where X is a linker, Fc is oriented on the complement binding face of the CRP pentamer, thereby providing steric hindrance to complement binding. See FIGS. 7 and 8. Histidine 38 is a critical residue for C1q binding and complement activation. The C-terminus (proline 206) lies very close (<0.6 nm) to this residue and 1nm from other critical residues tyrosine 175 and aspartate 112. The presence of the CH2 domain from an immunoglobulin Fc directly fused to the C-terminus can physically preclude binding of C1q interacting with histidine 38 and therefore stop binding. When folded, both the C and N termini of CRP are located on the complement binding. See FIG. 6.

Without wishing to be bound by a theory, the Fc in the CRP-X-Fc microbe-targeting molecule directes the complement binding face of the CRP towards the substrate when the inmicrobe-targeting molecule is conjugated to a subsstre. This can provide a second steric hindrance mechanism to reduce complement binding.

Conjugation of Engineered Microbe-Targeting Molecules to a Carrier Scaffold

The engineered microbe-targeting molecules can be immobilized or conjugated on any substrate for various applications and/or purposes. For example, when the affinity of a single microbe surface-binding domain for a target molecule (e.g., a carbohydrate recognition domain for a sugar/carbohydrate molecule) is relatively low, and such binding is generally driven by avidity and multivalency, multivalency of such engineered microbe-targeting molecules can be effectively increased by attachment of a plurality of the engineered microbe-targeting molecules (e.g., each with one or two or more carbohydrate recognition domains) to a solid substrate (e.g., a nanometer- or micrometer-sized bead) at a high density, which can be varied to provide optimal functionality. Alternatively, the engineered microbe-targeting molecules can be immobilized on a solid substrate for easy handling during usage, e.g., for isolation, observation or microscopic imaging.

Accordingly, a further aspect provided herein is an article or product for targeting or binding microbes comprising at least one, including at least two, at least three, at least four, at least five, at least ten, at least 25, at least 50, at least 100, at least 250, at least 500, or more engineered microbe-targeting molecules conjugated to a carrier scaffold or a surface thereof. The "carrier scaffold" is also referred to as a "carrier substrate" herein. In some embodiments, surface of the carrier scaffold can be coated with the microbe-targeting molecule disclosed herein. As used herein, the term "article" refers to any distinct physical microscale or macroscale object. An article comprising a microbe-targeting molecule conjugated to a carrier scaffold is also referred to as a "microbe-binding article" or a "microbe-targeting article" herein.

Without limitations, the carrier scaffold can be selected from a wide variety of materials and in a variety of formats. For example, the carrier scaffold can be utilized in the form of beads or particles (including nanoparticles, microparticles, polymer microbeads, magnetic microbeads, and the like), filters, fibers, screens, mesh, tubes, hollow fibers, scaffolds, plates, channels, gold particles, magnetic materials, planar shapes (such as a rectangular strip or a circular disk, or a curved surface such as a stick), other substrates commonly utilized in assay formats, and any combinations thereof.

Examples of carrier scaffolds include, but are not limited to, nucleic acid scaffolds, protein scaffolds, lipid scaffolds, dendrimers, microparticles or microbeads, nanotubes, microtiter plates, medical apparatuses (e.g., needles or catheters) or implants, dipsticks or test strips, microchips, filtration devices or membranes, membranses, diagnostic strips, hollow-fiber reactors, microfluidic devices, living cells and biological tissues or organs, extracorporeal devices, mixing elements (e.g., spiral mixers), and the like. In some embodiments, the carrier scaffold can be in the form of a continuous roll on which the test area(s) and optionally reference area(s) are present in the form of continuous lines or a series of spots.

The carrier scaffold can be made of any material, including, but not limited to, metal, metal alloy, polymer, plastic, paper, glass, fabric, packaging material, biological material such as cells, tissues, hydrogels, proteins, peptides, nucleic acids, and any combinations thereof.

In some embodiments, the microbe-targeting articles disclosed herin can be used to catpture, detect, or remove microbe contaminants from any source or in any fluid, e.g., a biological fluid (e.g., blood sample), environmental fluid or surface (e.g., wastewater, building or machine surface), or an edible substance or fluid (e.g., food, water). In some embodiments where the fluid is blood, after removal of the microbe/pathogen from the blood collected from a subject with the microbe-targeting magnetic microbeads, the blood can be circulated back to the same subject as a therapeutic intervention. In some embodiments, the microbe-targeting articles disclosed herein can be used in diagnostics as a means of collecting potential pathogens for identification; not only in the diagnosis of disease, but in the identification of water- or food-borne pathogens, particulates or other contaminants. Alternatively, the carrier scaffold can comprise a hollow-fiber reactor or any other blood filtration membrane or flow device (e.g., a simple dialysis tube, spiral mixer or static mixer) or other resins, fibers, or sheets to selective bind and sequester the biological pathogens.

The microbe-binding articles disclosed herein also can be used as point-of-care diagnostic tools for microbe or pathogen detection. By way of example only, a microbe-binding article can be brought into contact with a test sample (e.g., a blood sample) from a patient or a subject, and incubated for a period of time, e.g., at least about 15 seconds, at least about 30 seconds, at least about 1 min, at least about 2 mins, at least about 5 mins, at least about 10 mins, at least about 15 mins, at least about 30 mins, at least about 1 hour or more. In some embodiments, the incubated dipstick or test strip can then be incubated in a blocking agent (e.g., BSA, normal serum, casesin, non-fat dry milk, and/or any commercially-available blocking agents to minimize non-specific binding). Depending on different embodiments of the engineered microbe-targeting molecules, in some embodiments, the microbe-binding dipstick or test strip after contact with a test sample (e.g., a blood sample) can be further contacted with at least one additional agent to facilitate detection of pathogen, and/or to increase specificity of the pathogen detection. For example, some embodiments of the dipstick or test strip after contact with a test sample (e.g., a blood sample) can be further contacted with a detectable label that is conjugated to a molecule that binds to a microbe and/or microbial matter. Examples of such molecules can include, but are not limited to, one or more embodiments of the engineered microbe-targeting molecule described herein, an antibody specific for the microbes or pathogens to be detected, a protein, a peptide, a carbohydrate or a nucleic acid that is recognized by the microbes or pathogens to be detected, and any combinations thereof.

In some embodiments, the readout of the microbe-binding article can be performed in a system or device, e.g., a portable device. The system or device can display a signal indicating the presence or the absence of a microbial infection in a test sample, and/or the extent of the microbial infection.

The particular format or material of the carrier scaffold depends on the particular use or application, for example, the separation/detection methods employed in an assay application. In some embodiments, the format or material of the carrier scaffold can be chosen or modified to maximize signal-to-noise ratios, e.g., to minimize background binding or for ease of separation of reagents and cost. For example, carrier scaffold can be treated or modified with surface chemistry to minimize chemical agglutination and non-specific binding. In some embodiments, at least a portion of the caarier scaffold surface that is in contact with a test sample can be treated to become less adhesive to any molecules (including microbes, if any) present in a test sample. By way of example only, the carrier scaffold surface in contact with a test sample can be silanized or coated with a polymer such that the surface is inert to the molecules present in the test sample, including but not limited to, cells or fragments thereof (including blood cells and blood components), proteins, nucleic acids, peptides, small molecules, therapeutic agents, microbes, microorganisms and any combinations thereof. In other embodiments, a carrier scaffold surface can be treated with an omniphobic layer, which can allow binding of a microbe by the engineered microbe-targeting molecule without a subsequent hydrophobic binding between the microbe and the carrier scaffold surface. See, e.g., Wong T S et al., "Bioinspired self-repairing slippery surfaces with pressure-stable omniphobicity." (2011) Nature 477 (7365): 443-447, and International Application No.: PCT/US12/21928, the content of which is incorporated herein by reference, for methods to produce a slippery carrier scaffold surface. Accordingly, non-specific binding of molecules from the test sample (including microbes and/or microbial matter) to a substrate surface can be reduced, thus increasing the sensitivity of the microbial detection.

In some embodiments, the carrier scaffd can be fabricated from or coated with a biocompatible material. As used herein, the term "biocompatible material" refers to any material that does not deteriorate appreciably and does not induce a significant immune response or deleterious tissue reaction, e.g., toxic reaction or significant irritation, over time when implanted into or placed adjacent to the biological tissue of a subject, or induce blood clotting or coagulation when it comes in contact with blood. Suitable biocompatible materials include, for example, derivatives and copolymers of polyimides, poly(ethylene glycol), polyvinyl alcohol, polyethyleneimine, and polyvinylamine, polyacrylates, polyamides, polyesters, polycarbonates, and polystyrenes. In some embodiments, biocompatible materials can include metals, such as titanium and stainless steel, or any biocompatible metal used in medical implants. In some embodiments, biocompatible materials can include paper substrate, e.g., as a carrier scaffold for a diagnostic strip. In some embodiments, biocompatible materials can include peptides or nucleic acid molecules, e.g., a nucleic acid scaffold such as a 2-D DNA sheet or 3-D DNA scaffold.

Additional material that can be used to fabricate or coat a carrier scaffold include, without limitations, polydimethylsiloxane, polyimide, polyethylene terephthalate, polymethylmethacrylate, polyurethane, polyvinylchloride, polystyrene polysulfone, polycarbonate, polymethylpentene, polypropylene, polyvinylidine fluoride, polysilicon, polytetrafluoroethylene, polysulfone, acrylonitrile butadiene styrene, polyacrylonitrile, polybutadiene, poly(butylene terephthalate), poly(ether sulfone), poly(ether ether ketones), poly(ethylene glycol), styrene-acrylonitrile resin, poly(trimethylene terephthalate), polyvinyl butyral, polyvinylidenedifluoride, poly(vinyl pyrrolidone), and any combination thereof.

In some embodiments, the carrier scaffd can be fabricated from or coated with a biodegradable material. As used herein, the term "biodegradable" refers to the ability of a composition to erode or degrade in vivo to form smaller chemical fragments. Degradation can occur, for example, by enzymatic, chemical or physical processes. Non-limiting examples of biodegradable polymers that can be used in aspects provided herein include poly(lactide)s, poly(glycolide)s, poly(lactic acid)s, poly(glycolic acid)s, poly (lactide-co-glycolide), polyanhydrides, polyorthoesters, polycaprolactone, polyesteramides, polycarbonate, polycyanoacrylate, polyurethanes, polyacrylate, blends and copolymers thereof.

Other additional biodegradable polymers include biodegradable polyetherester copolymers. Generally speaking, the polyetherester copolymers are amphiphilic block copolymers that include hydrophilic (for example, a polyalkylene glycol, such as polyethylene glycol) and hydrophobic blocks (for example, polyethylene terephthalate). An exemplary block copolymer is, but is not limited to, poly(ethylene glycol)-based and poly(butylene terephthalate)-based blocks (PEG/PBT polymer). PEG/PBT polymers are commercially available from OctoPlus Inc, under the trade designation PolyActive™. Non-limiting examples of biodegradable copolymers or multiblock copolymers include the ones described in U.S. Pat. Nos. 5,980,948 and 5,252,701, the contents of which are incorporated herein by reference.

Other biodegradable polymer materials include biodegradable terephthalate copolymers that include a phosphorus-containing linkage. Polymers having phosphoester linkages, called poly(phosphates), poly(phosphonates) and poly(phosphites), are known in the art. See, for example, Penczek et al., *Handbook of Polymer Synthesis*, Chapter 17: "Phosphorus-Containing Polymers," 1077-1 132 (Hans R. Kricheldorf ed., 1992), as well as U.S. Pat. Nos. 6,153,212; 6,485,737; 6,322,797; 6,600,010; 6,419,709; 6,419,709; 6,485,737; 6,153,212; 6,322,797 and 6,600,010, the contents of which are incorporated herein by reference.

Biodegradable polyhydric alcohol esters can also be used as a material of a carrier scaffold (e.g., a microparticle) (See U.S. Pat. No. 6,592,895, which is incorporated herein by reference). In some embodiments, the biodegradable polymer can be a three-dimensional crosslinked polymer network containing hydrophobic and hydrophilic components which forms a hydrogel with a crosslinked polymer structure, such as the one described in U.S. Pat. No. 6,583,219. In yet further embodiments, the biodegradable polymer can comprise a polymer based upon α-amino acids (such as elastomeric copolyester amides or copolyester urethanes, as described in U.S. Pat. No. 6,503,538, which is incorporated herein by reference).

In some embodiments, the carrier scaffold can comprise a paper, nitrocellulose, glass, plastic, polymer, membrane material, nylon, and any combinations thereof. This is useful for using the article as a test strip of a dipstick.

As used herein, by the "coating" or "coated" is generally meant a layer of molecules or material formed on an outermost or exposed layer of a surface. With respect to a coating of engineered microbe-targeting molecules on a carrier scaffold, the term "coating" or "coated" refers to a layer of engineered microbe-targeting molecules formed on an outermost or exposed layer of a carrier scaffold surface. In some embodiments, the carrier scaffold surface can encompass an outer surface or an inner surface, e.g., with respect to a hollow structure. For example, the inner surface of a needle or catheter can be coated with the engineered microbe-targeting molecules described herein. This can be useful for removing any potential microbe contaminants from a fluid before administering the fluid to a subject.

The amount of the engineered microbe-targeting molecules conjugated to or coating on a carrier scaffold can vary with a number of factors such as a surface area, conjugation/coating density, types of engineered microbe-targeting molecules, and/or binding performance. A skilled artisan can determine the optimum density of engineered microbe-targeting molecules on a carrier scaffold using any methods known in the art. By way of example only, for magnetic microparticles as a carrier scaffold (as discussed in detail later), the amount of the engineered microbe-targeting molecules used for conjugating to or coating magnetic microbparticles can vary from about 1 wt % to about 30 wt %, or from about 5 wt % to about 20 wt %. In some embodiments, the amount of the engineered microbe-targeting molecules used for conjugating to or coating magnetic microparticles can be higher or lower, depending on a specific need. However, it should be noted that if the amount of the engineered microbe-targeting molecules used for conjugating to or coating the magnetic microparticcles is too low, the magnetic microparticles can show a lower binding performance with a pathogen/microbe. On the contrary, if the amount of the engineered microbe-targeting molecules used for conjugating to or coating the magnetic microparticles is too high, the dense layer of the engineered microbe-targeting molecules can exert an adverse influence on the magnetic properties of the magnetic microbeads, which in turn can degrade the efficiency of separating the magnetic microbeads from a fluid utilizing the magnetic field gradient.

In some embodiments, the carrier scaffold can further comprise at least one area adapted for use as a reference area. By way of example only, the reference area can be adapted for use as a positive control, negative contrl, a reference, or any combination thereof. In some embodiments, the carrier scaffold can further comprise at least two areas, wherein one area is adapted for a positive control and the second area is adapated for a negative control.

In some embodiments, the carrier scaffold can further comprise at least one reference area or control area for comparison with a readout signal determined from the test area. The reference area generally excludes the engineered microbe-targeting molecules, e.g., to account for any background signal. In some embodiments, the reference area can include one or more known amounts of the detectable label that the engineered microbe-targeting molecules in the test area encompass. In such embodiments, the reference area can be used for calibration such that the amount of microbes in a test sample can be estimated or quantified.

In some embodiments, the carrier scaffold further at least one second microbe-targeting molecule, wherein the second microbe-targeting molecule comprises at least one first domain wherein the CRP domain is replaced by a microbe-binding domain of microbe-binding domain protein which is not CRP. Thus, the second microbe-targeting molecule comprises at least one first domain comprising at least a portion of a microbe-binding domain of a microbe-binding protein, wherein the microbe-binding protein is not a CRP; a second domain, as described in this disclosure; and a linker conjugating the first and the second domains. Microbe-binding domains that do not comprise CRP are described elsewhere in the disclosure. Exemplary second microbe-targeting molecules are described, for example, in PCT Application No. PCT/US2011/021603 filed Jan. 19, 2011 and No. PCT/

US2012/047201, filed Jul. 18, 2012, and U.S. Provisional Application No. 61/691,983 filed Aug. 22, 2012, contents of all of which are incorporated herein by reference in their entireties. In some embodiments, the second microbe-targeting molecule comprises an amino acid sequence selected from the group consisting of SEQ ID NOs: 8, 9, 11, 12, and 23-27.

In some embodiments, the carrier scaffold can further comprise a detectable lable. The detetable lable can be seprate from the microbe-targeting molecules conjugated with the carrier scaffold or linked to the the microbe-targeting molecules conjugated with the carrier scaffold.

Microbe-Targeting Microparticles:

In some embodiments, the carrier scaffold is a microparticle. Accordingly, some embodiments described herein provide a microbe-targeting microparticle comprising at least one engineered microbe-targeting molecule on its surface. The term "microparticle" as used herein refers to a particle having a particle size of about 0.001 μm to about 1000 μm, about 0.005 μm to about 50 μm, about 0.01 μm to about 25 μm, about 0.05 μm to about 10 μm, or about 0.05 μm to about 5 μm. In one embodiment, the microparticle has a particle size of about 0.05 μm to about 1 μm. In one embodiment, the microparticle is about 0.09 μm—about 0.2 μm in size.

In some embodiments, the microparticle can range in size from 1 nm to 1 mm, about 2.5 nm to about 500 μm, or about 5 nm to about 250 μm in size. In some embodiments, microparticle can be about 5 nm to about 100 μm in size. In some embodiments, microparticle can be about 0.01 μm to about 10 μm in size. In some embodiments, the micrparticle can be about 0.05 μm to about 5 μm in size. In some embodiments, the micrparticle can be about 0.08 μm to about 1 μm in size. In one embodiment, the micrparticle can be about 10 nm to about 10 μm in size. In some embodiments, the the micrparticle can be about 1 nm to about 1000 nm, from about 10 nm to about 500 nm, from about 25 nm to about 300 nm, from about 40 nm to about 250 nm, or from about 50 nm to about 200 nm. In one embodiment, the micrparticle can be about 50 nm to about 200 nm.

It will be understood by one of ordinary skill in the art that microparticles usually exhibit a distribution of particle sizes around the indicated "size." Unless otherwise stated, the term "size" as used herein refers to the mode of a size distribution of microparticles, i.e., the value that occurs most frequently in the size distribution. Methods for measuring the microparticle size are known to a skilled artisan, e.g., by dynamic light scattering (such as photocorrelation spectroscopy, laser diffraction, low-angle laser light scattering (LALLS), and medium-angle laser light scattering (MALLS)), light obscuration methods (such as Coulter analysis method), or other techniques (such as rheology, and light or electron microscopy).

Without limitations, the microparticle can be of any shape. Thus, the microparticle can be, but is not limited to, spherical, rod, elliptical, cylindrical, disc, and the like. In some embodiments, the term "microparticle" as used herein can encompass a microsphere. The term "microsphere" as used herein refers to a microparticle having a substantially spherical form. A substantially spherical microparticle is a microparticle with a difference between the smallest radii and the largest radii generally not greater than about 40% of the smaller radii, and more typically less than about 30%, or less than 20%.

In some embodiments, the micrparticcles having a substantially spherical shape and defined surface chemistry can be used to minimize chemical agglutination and non-specific binding.

In one embodiment, the term "microparticle" as used herein encompasses a microcapsule. The term "microcapsule" as used herein refers to a microscopic capsule that contains an active ingredient, e.g., a therapeutic agent or an imagining agent. Accordingly, in some embodiments, the microparticles comprising on their surface engineered microbe-targeting molecules can encapsulate at least one active ingredient therein, e.g., a therapeutic agent to treat an infection, and be used as a cell-targeted drug delivery device. In such embodiments, the microparticles can comprise biocompatible polymers as described herein. In some embodiments, the microparticles can further comprise biodegradable polymers, e.g., for releasing the encapsulated drugs.

In general, any biocompatible material well known in the art for fabrication of microparticles can be used in embodiments of the microparticle described herein. Accordingly, a microparticle comprising a lipidic microparticle core is also within the scope described herein. An exemplary lipidic microparticle core is, but is not limited to, a liposome. A liposome is generally defined as a particle comprising one or more lipid bilayers enclosing an interior, e.g., an aqueous interior. In one embodiment, a liposome can be a vesicle formed by a bilayer lipid membrane. Methods for the preparation of liposomes are well described in the art, e.g., Szoka and Papahadjopoulos (1980) *Ann. Rev. Biophys. Bioeng.* 9: 467, Deamer and Uster (1983) Pp. 27-51 In: *Liposomes*, ed. M. J. Ostro, Marcel Dekker, New York.

Microbe-Targeting Magnetic Microparticles:

In some embodiments, the microparticle is a magnetic microparticle. Thus, in some embodiments, provided herein is a "microbe-targeting magnetic microparticle" wherein a magnetic microparticle comprising on its surface at least one engineered microbe-targeting molecule. Without limitations, such microbe-targeting magnetic microparticles can be used to separate microbes or pathogens from a test sample, e.g., but not limited to, any fluid, including a biological fluid such as blood. In some embodiments, the microbe-targeting magnetic microparticle can be used to remove living microbes or pathogens. Using magnetic microparticles as a substrate can be advantageous because the microbe-bound magnetic microparticles can be easily separated from a sample fluid using a magnetic field gradient, be examined for the presence of the microbe, and/or be used to transfer the collected microbes to conventional pathogen culture and sensitivity testing assays. Thus, in some embodiments, the microbe-targeting magnetic microparticles can be used to catpture, detect, or remove microbe contaminants from any source or in any fluid, e.g., a biological fluid (e.g., blood sample), environmental fluid or surface (e.g., wastewater, building or machine surface), or an edible substance or fluid (e.g., food, water). In some embodiments where the fluid is blood, after removal of the microbe/pathogen from the blood collected from a subject with the microbe-targeting magnetic microbeads, the blood can be circulated back to the same subject as a therapeutic intervention. In some embodiments, the microbe-targeting magnetic microbeads can be used in diagnostics as a means of collecting potential pathogens for identification; not only in the diagnosis of disease, but in the identification of water- or food-borne pathogens, particulates or other contaminants. Alternatively, the solid substrate can comprise a hollow-fiber reactor or any other blood filtration membrane or flow device (e.g., a simple dialysis tube, spiral mixer or static mixer) or other resins, fibers, or sheets to selective bind and sequester the biological pathogens.

Magnetic microparticles can be manipulated using magnetic field or magnetic field gradient. Such particles commonly consist of magnetic elements such as iron, nickel and cobalt and their oxide compounds. Magnetic microparticles are well-known and methods for their preparation have been described in the art. See, e.g., U.S. Pat. Nos. 6,878,445; 5,543,158; 5,578,325; 6,676,729; 6,045,925; and 7,462,446; and U.S. Patent Publications No. 2005/0025971; No. 2005/0200438; No. 2005/0201941; No. 2005/0271745; No. 2006/0228551; No. 2006/0233712; No. 2007/01666232; and No. 2007/0264199, the contents of which are incorporated herein by reference.

Magnetic microparticles are also widely and commercially available, with or without functional groups capable of conjugation with the microbe-atrgeting molecules disclosed herein. Magnetic microparticles functionalized with various functional groups, e.g., amino groups, carboxylic acid groups, epoxy groups, tosyl groups, or silica-like groups, are also widely and commercially available. Suitable magnetic microparticles are commercially available such as from AdemTech, Miltenyi, PerSeptive Diagnostics, Inc. (Cambridge, Mass.); Invitrogen Corp. (Carlsbad, Calif.); Cortex Biochem Inc. (San Leandro, Calif.); and Bangs Laboratories (Fishers, Ind.). In particular embodiments, magnetic microparticles that can be used herein can be any DYNABEADS® magnetic microbeads (Invitrogen Inc.), depending on the substrate surface chemistry.

Microbe-Targeting Cells:

In some embodiments, the carrier scaffold to which the engineered microbe-targeting molecule binds can be a living cell, or a biological tissue or organ. For example, the living cells can be associated with an immune response, and such cells include, but are not limited to, a phagocyte (macrophage, neutrophil, and dendritic cell), mast cell, eosinophil, basophil, and/or natural killer cell. Alternatively, the living cell can be the cell of biological tissues or organs of the immune system, such as spleen, lymph nodes, lymphatic vessels, tonsils, thymus, bone marrow, Peyer's patches, connective tissues, mucous membranes, the reticuloendothelial system, etc. In some embodiments, the surface to which the engineered microbe-targeting molecules bind can also be the extracellular matrix of one or more of these tissues or organs.

Microbe-Binding Microtiter Plates:

In some embodiments, the bottom surface of microtiter wells can be coated with the engineered microbe-targeting molecules described herein, e.g., for detecting and/or determining the amount of microbes in a sample. After microbes or pathogens in the sample binding to the engineered microbe-targeting molecules bound to the microwell surface, the rest of the sample can be removed. Detectable molecules that can also bind to microbes or pathogens (e.g., an engineered microbe-targeting molecule conjugated to a detectable molecule as described herein) can then be added to the microwells with microbes/pathogens for detection of microbes/pathogens. Various signal detection methods for determining the amount of proteins, e.g., using enzyme-linked immunosorbent assay (ELISA), with different detectable molecules have been well established in the art, and those signal detection methods can also be employed herein to facilitate detection of the signal induced by microbes/pathogens binding on the engineered microbe-targeting molecules.

Microbe-Binding Dipsticks/Test Strips:

In some embodiments, the carrier scaffold having the microbe-targeting molecule conjugated thereon can be in the form of a dipstick and/or a test strip for capture, detection, or clearance of microbes or pathogens. For example, a dipstick and/or a test strip can include at least one test area containing one or more engineered microbe-targeting molecules described herein. The dipstick and/or a test strip can be in any shape and/or in any format, e.g., a planar shape such as a rectangular strip or a circular disk, or a curved surface such as a stick. Alternatively, a continuous roll can be utilized, rather than discrete test strips, on which the test area(s) and optionally reference area(s) are present in the form of continuous lines or a series of spots. In some embodiments, the microbe-binding dipsticks or test strips described herein can be used as point-of-care diagnostic tools for microbe or pathogen detection.

In some embodiments, the carrier scaffold in the form of a dipstick or a test strip can be made of any material, including, without limitations, paper, nitrocellulose, glass, plastic, polymer, membrane material, nylon, and any combinations thereof. In one embodiment, the carrier scaffold in the form of a dipstick or a test strip can include paper. In one embodiment, the carrier scaffold in the form of a dipstick or a test strip can include nylon.

In some embodiments, the dipstick or a test strip can further comprise at least one reference area or control area for comparison with a readout signal determined from the test area. The reference area generally excludes the engineered microbe-targeting molecules, e.g., to account for any background signal. In some embodiments, the reference area can include one or more known amounts of the detectable label that the engineered microbe-targeting molecules in the test area encompass. In such embodiments, the reference area can be used for calibration such that the amount of microbes in a test sample can be estimated or quantified.

In some embodiments, the dipstick/test strip can further comprise a detectable label as described herein. The detectable lable can be linked to the microbe-targeting molecule conjugated with the dipstick/test strip or separate from the microbe-targeting molecule conjugated with the dipstick/test strip.

In one embodiment, about 1 µg to about 100 µg microbe-binding molecules can be coated on or attached to a dipstick or membrane surface. In another embodiment, about 3 µg to about 60 µg microbe-binding molecules can be coated on or attached to a dipstick or membrane surface. In some embodiments, about 0.1 mg/mL to about 50 mg/mL, about 0.5 mg/mL to about 40 mg/mL, about 1 mg/mL to about 30 mg/mL, about 5 mg/mL to about 20 mg/mL microbe-binding molecules can be coated on or attached to a dipstick or membrane surface. In one embodiment, about 11.5 mg/mL microbe-binding molecules can be coated on or attached to a dipstick or membrane surface.

Exemplary Process for Capture/Detection of a Microbe or Microbial Matter in a Test Sample An exemplary process for detecting a microbe and/or microbial matter in a test sample is described herein. As shown in FIG. 1, the process 1200 comprises the optional step 1202 (preprocessing of the sample), step 1204 (processing of the sample), step 1206 comprising 1208 (microbe capture) and 1210 (microbe separation), and 1212 (microbe detection). While these are discussed as discrete processes, one or more of the preprocessing, processing, capture, microbe separation, and detection can be performed in a microfluidic device. Use of a microfluidic device can automate the analysis process and/or allow analysis of multiple samples at the same time. One of skill in the art is well aware of methods in the art for collecting, handling and processing biological fluids which can be used in the practice of the present disclosure. The process described herein can allow sample analysis at in short time periods. For example, the process can be completed in less than 6 hours, less than 5 hours, less than 4 hours, less than 3 hours, less than 2 hours, less than 1 hour, less than 30 minutes. In some embodiments, presence and identity of a microbe in the sample can be done within 10 minutes to 60 minutes of starting the process.

In some embodiments, the sample can be a biological fluid, e.g., blood, plasma, serum, lactation products, amniotic fluids, sputum, saliva, urine, semen, cerebrospinal fluid, bronchial aspirate, perspiration, mucus, liquefied stool sample, synovial fluid, lymphatic fluid, tears, tracheal aspirate, and any mixtures thereof. For example, the sample can be a whole blood sample obtained from a subject.

The process described herein can be utilized to detect the presence of a microbe in a sample of any given volume. In some embodiments, sample volume is about 0.25 ml to about 50 ml, about 0.5 ml to about 25 ml, about 1ml to about 15 ml, about 2 ml to about 10 ml. In some embodiments, sample volume is about 5 ml. In one embodiment, sample volume is about 5 ml abut 10 ml.

1202 (Sample Preprocessing):

It can be necessary or desired that a test sample, such as whole blood, be preprocessed prior to microbe detection as described herein, e.g., with a preprocessing reagent. Even in cases where pretreatment is not necessary, preprocessing can be optionally done for mere convenience (e.g., as part of a regimen on a commercial platform). A preprocessing reagent can be any reagent appropriate for use with the assays or processes described herein.

The sample preprocessing step generally comprises adding one or more reagent to the sample. This preprocessing can serve a number of different purposes, including, but not limited to, hemolyzing blood cells, dilution of sample, etc. The preprocessing reagents can be present in the sample container before sample is added to the sample container or the preprocessing reagents can be added to a sample already present in the sample container. When the sample is a biological fluid, the sample container can be a VACUTAINER®, e.g., a heparinized VACUTAINER®.

The preprocessing reagents include, but are not limited to, surfactants and detergents, salts, cell lysing reagents, anticoagulants, degradative enzymes (e.g., proteases, lipases, nucleases, lipase, collagenase, cellulases, amylases and the like), and solvents, such as buffer solutions. In some embodiments, a preprocessing reagent is a surfactant or a detergent. In one embodiment, the preprocessing reagent is TRITON X100 (2-[4-(2,4,4-trimethylpentan-2-yl)phenoxy] ethanol).

Amount of preprocessing reagent to be added can depend on a number of factors. Generally, the preprocessing reagent is added to a final concentration of about 0.1 mM to about 10 mM. If a liquid, the preprocessing reagent can be added so as to dilute the sample at least 5%, at least 10%, at least 20%, at least 30%, at least 40%, at least 50%, at least 60%, at least 60%, at least 80%, at least 90%, at least 1-fold, at least 2-fold, at least 3-fold, or at least 5-fold.

After addition of the preprocessing reagent, the reagent can be mixed into the sample. This can be simply accomplished by agitating the sample, e.g., shaking or vortexing the sample and/or moving the sample around, if it is in a microfluidic device.

After addition of the preprocessing reagent, the sample mixture can be incubated for a period of time. For example, the sample mixture can be incubated for at least one minute, at least two minutes, at least three minutes, at least four minutes, at least five minutes, at least ten minutes, at least fifteen minutes, at least thirty minutes, at least forty-five minutes, or at least one hour. In some embodiments, incubation is for about 5 seconds to about 60 seconds. In some embodiments, incubation is for about 10 to about 20 minutes. In one embodiment, incubation is for about 15 minutes. In some embodiments, there is no incubation and the sample mixture is used directly in the sample processing step.

Without limitations, incubation can be at any appropriate temperature. For example, the incubation can be at room temperature (about 16° C. to about 30° C.), a cold temperature (about 16° C. or lower, e.g., from about −4° C. to about 16° C.), or an elevated temperature (about 30° C. or hihgher, e.g., about 25° C. to about 95° C.). In some embodiments, the sample is incubated for about fifteen minutes at room temperature.

1204 (Sample Processing):

After the optional preprocessing step, the sample can be optionally processed by adding one or more processing reagents to the sample. These processing reagents can serve to lyse cells, degrade unwanted molecules present in the sample and/or dilute sample for further processing. These processing reagents include, but are not limited to, surfactants and detergents, salts, cell lysing reagents, anticoagulants, degradative enzymes (e.g., proteases, lipases, nucleases, lipase, collagenase, cellulases, amylases and the like), and solvents, such as buffer solutions. Amount of the processing reagent to be added can depend on the particular sample to be analyzed, the time required for the sample analysis, identity of the microbe to be detected or the amount of microbe present in the sample to be analyzed.

It is not necessary, but if one or more reagents are to be added they can present in a mixture (e.g., in a solution, "processing buffer") in the appropriate concentrations. Amount of the various components of the processing buffer can vary depending upon the sample, microbe to be detected, concentration of the microbe in the sample, or time limitation for analysis.

Generally, addition of the processing buffer can increase the volume of the sample by 5%, 10%, 15%, 20%, 25%, 30%, 35%, 40%, 45%, 50%, or more. In some embodiments, about 50 μl to about 5000 μl of the processing buffer are added for each ml of the sample. In some embodiments, about 100 μl to about 250 μl of the processing buffer are added for each ml of the sample. In one embodiment, about 800 μl of the processing buffer are added for each 200 μl of the sample.

In some embodiments, a detergent or surfactant comprises about 5% to about 20% of the processing buffer volume. In some embodiment, a detergent or surfactant comprises about 5% to about 15% of the processing buffer volume. In one embodiment, a detergent or surfactant comprises about 10% of the processing buffer volume.

Exemplary surfactants and detergents include, but are not limited to, sulfates, such as, ammonium lauryl sulfate, sodium dodecyl sulfate (SDS), and sodium lauryl ether sulfate (SLES) sodium myreth sulfate; sulfonates, such as, dioctyl sodium sulfosuccinate (Docusates), perfluorooctanesulfonate (PFOS), perfluorobutanesulfonate, alkyl benzene sulfonates, and 3-[(3-Cholamidopropyl)dimethylammonio]-1-propanesulfonate (CHAPS); 3-[(3-cholamidopropyl)dimethylammonio]-2-hydroxy-1-propanesulfonate (CHAPSO); phosphates, such as alkyl aryl ether phosphate and alkyl ether phosphate; carboxylates, such as fatty acid salts, sodium stearate, sodium lauroyl sarcosinate, perfluorononanoate, and perfluorooctanoate (PFOA or PFO); octenidine dihydrochloride; alkyltrimethylammonium salts, such as cetyl trimethylammonium bromide (CTAB) and cetyl trimethylammonium chloride (CTAC); cetylpyridinium chloride (CPC); polyethoxylated tallow amine (POEA); benzalkonium chloride (BAC); benzethonium chloride (BZT); 5-Bromo-5-nitro-1,3-dioxane; dimethyldioctadecylammonium chloride; dioctadecyldimethylammonium bromide (DODAB); sultaines, such as cocamidopropyl hydroxysultaine; cetyl alcohol; stearyl alcohol; cetostearyl alcohol (consisting predominantly of cetyl and stearyl alcohols); oleyl alcohol; polyoxyethylene glycol alkyl ethers (Brij) such as, octaethylene glycol monododecyl ether and pentaethylene glycol monododecyl ether; polyoxypropylene glycol alkyl ethers; glucoside alkyl ethers, such as decyl glucoside, lauryl glucoside and octyl glucoside; polyoxyethylene glycol octylphenol ethers, such as TRITON X-100 (2-[4-(2,4,4-trimethylpentan-2-yl)phenoxy] ethanol); polyoxyethylene glycol alkylphenol ethers, such as Nonoxynol-9; glycerol alkyl esters, such as glyceryl laurate; polyoxyethylene glycol sorbitan alkyl esters, such as Polysorbate 20 (Polyoxyethylene (20) sorbitan monolaurate), Polysorbate 40 (Polyoxyethylene (20) sorbitan monopalmitate), Polysorbate 60 (Polyoxyethylene (20) sorbitan monostearate), and Polysorbate 80 (Polyoxyethylene (20) sorbitan monooleate); cocamide ME; cocamide DEA; dodecyldimethylamine oxide; poloxamers; DOC; nonyl phenoxypolyethoxylethanol NP-40 (Tergitol-type NP-40); octyl phenoxypolyethoxylethanol (Noidet P-40); cetyltrimethylammonium bromide; and any mixtures thereof.

In some embodiments, one ml of the processing buffer can comprise about 0.1 U to about 100 U of a degradative enzyme. In some embodiments, one ml of the processing buffer comprises about 5 U to about 50 U of a degradative enzyme. In one embodiment, one ml of the processing buffer comprises about 10 U of a degradative enzyme. Enzyme unit (U) is an art known term for the amount of a particular enzyme that catalyzes the conversion of 1 μmol of substrate per minute.

In some embodiments, one ml of the processing buffer can comprise about 1 μg to about 10 μg of an anti-coagulant. In some embodiment, one ml of the processing buffer can comprise about 1 μg to about 5 μg of an anti-coagulant. In one embodiment, one ml of the processing buffer comprises about 4.6 μg of an anti-coagulant.

In some embodiments, one ml of the processing buffer can comprise about 1 mg to about 10 mg of anti-coagulant. In some embodiment, one ml of the processing buffer can comprise about 1 mg to about 5 mg of anti-coagulant. In one embodiment, one ml of the processing buffer comprises about 4.6 mg of anti-coagulant.

Exemplary anti-coagulants include, but are not limited to, heparin, heparin substitutes, salicylic acid, D-phenylalanyl-L-prolyl-L-arginine chloromethyl ketone (PPACK), Hirudin, Ancrod (snake venom, Vipronax), tissue plasminogen activator (tPA), urokinase, streptokinase, plasmin, prothrombopenic anticoagulants, platelet phosphodiesterase inhibitors, dextrans, thrombin antagonists/inhibitors, ethylene diamine tetraacetic acid (EDTA), acid citrate dextrose (ACD), sodium citrate, citrate phosphate dextrose (CPD), sodium fluoride, sodium oxalate, potassium oxalate, lithium oxalate, sodium iodoacetate, lithium iodoacetate and mixtures thereof.

Suitable heparinic anticoagulants include heparins or active fragments and fractions thereof from natural, synthetic, or biosynthetic sources. Examples of heparin and heparin substitutes include, but are not limited to, heparin calcium, such as calciparin; heparin low-molecular weight, such as enoxaparin and lovenox; heparin sodium, such as heparin, lipo-hepin, liquaemin sodium, and panheprin; heparin sodium dihydroergotamine mesylate; lithium heparin; and ammonium heparin.

Suitable prothrombopenic anticoagulants include, but are not limited to, anisindione, dicumarol, warfarin sodium, and the like.

Examples of phosphodiesterase inhibitors suitable for use herein include, but are not limited to, anagrelide, dipyridamole, pentoxifyllin, and theophylline.

Suitable dextrans include, but are not limited to, dextran70, such as HYSKON™ (CooperSurgical, Inc., Shelton, Conn., U.S.A.) and MACRODEX™ (Pharmalink, Inc., Upplands Vasby, Sweden), and dextran 75, such as GENTRAN™ 75 (Baxter Healthcare Corporation).

Suitable thrombin antagonists include, but are not limited to, hirudin, bivalirudin, lepirudin, desirudin, argatroban, melagatran, ximelagatran and dabigatran.

As used herein, anticoagulants can also include factor Xa inhibitors, factor IIa inhibitors, and mixtures thereof. Various direct factor Xa inhibitors are known in the art including, those described in Hirsh and Weitz, *Lancet,* 93:203-241, (1999); Nagahara et al. *Drugs of the Future,* 20: 564-566, (1995); Pinto et al, 44: 566-578, (2001); Pruitt et al, *Biorg. Med. Chem. Lett.,* 10: 685-689, (2000); Quan et al, *J. Med. Chem.* 42: 2752-2759, (1999); Sato et al, *Eur. J. Pharmacol,* 347: 231-236, (1998); Wong et al, *J. Pharmacol. Exp. Therapy,* 292:351-357, (2000). Exemplary factor Xa inhibitors include, but are not limited to, DX-9065a, RPR-120844, BX-807834 and SEL series Xa inhibitors. DX-9065a is a synthetic, non-peptide, propanoic acid derivative, 571 D selective factor Xa inhibitor. It directly inhibits factor Xa in a competitive manner with an inhibition constant in the nanomolar range. See for example, Herbert et al, *J. Pharmacol. Exp. Ther.* 276:1030-1038 (1996) and Nagahara et al, *Eur. J. Med. Chem.* 30(suppl):140s-143s (1995). As a non-peptide, synthetic factor Xa inhibitor, RPR-120844 (Rhone-Poulenc Rorer), is one of a series of novel inhibitors which incorporate 3-(S)-amino-2-pyrrolidinone as a central template. The SEL series of novel factor Xa inhibitors (SEL1915, SEL-2219, SEL-2489, SEL-2711: Selectide) are pentapeptides based on L-amino acids produced by combinatorial chemistry. They are highly selective for factor Xa and potency in the pM range.

Factor IIa inhibitors include DUP714, hirulog, hirudin, melgatran and combinations thereof. Melagatran, the active form of pro-drug ximelagatran as described in Hirsh and Weitz, *Lancet,* 93:203-241, (1999) and Fareed et al. *Current Opinion in Cardiovascular, pulmonary and renal investigational drugs,* 1:40-55, (1999).

Generally, salt concentration of the processing buffer can range from about 10 mM to about 100 mM. In some embodiments, the processing buffer comprises a salt at a concentration of about 25 mM to about 75 mM. In some embodiment, the processing buffer comprises a salt at a concentration of about 45 mM to about 55 mM. In one embodiment, the processing buffer comprises a salt at a concentration of about 43 mM to about 45 mM.

The processing buffer can be made in any suitable buffer solution known the skilled artisan. Such buffer solutions include, but are not limited to, TBS, PBS, BIS-TRIS, BIS-TRIS Propane, HEPES, HEPES Sodium Salt, MES, MES Sodium Salt, MOPS, MOPS Sodium Salt, Sodium Chloride, Ammonium acetate solution, Ammonium formate solution, Ammonium phosphate monobasic solution, Ammonium tartrate dibasic solution, BICINE buffer Solution, Bicarbonate buffer solution, Citrate Concentrated Solution, Formic acid solution, Imidazole buffer Solution, MES solution, Magnesium acetate solution, Magnesium formate solution, Potassium acetate solution, Potassium acetate solution, Potassium acetate solution, Potassium citrate tribasic solution, Potassium formate solution, Potassium phosphate dibasic solution, Potassium phosphate dibasic solution, Potassium sodium tartrate solution, Propionic acid solution, STE buffer solution, STET buffer solution, Sodium acetate solution, Sodium formate solution, Sodium phosphate dibasic solution, Sodium phosphate monobasic solution, Sodium tartrate dibasic solution, TNT buffer solution, TRIS Glycine buffer solution, TRIS acetate-EDTA buffer solution, Triethylammonium phosphate solution, Trimethylammonium acetate solution, Trimethylammonium phosphate solution, Tris-EDTA buffer solution, TRIZMA® Base, and TRIZMA® HCL. Alternatively, the processing buffer can be made in water.

In some embodiments, the processing buffer comprises a mixture of Trirton-X, DNAse I, human plasmin, $CaCl_2$ and Tween-20. In one embodiment, the processing buffer consists of a mixture of Trirton-X, DNAse I, human plasmin, $CaCl_2$ and Tween-20 in a TBS buffer.

In one embodiment, one ml of the processing buffer comprises 100 µl of TRITON X100 (2-[4-(2,4,4-trimethylpentan-2-yl)phenoxy]ethanol), 10 µl of DNAse (1U/1 µl), 10µl of human plasmin at 4.6 mg/ml and 870 µl of a mixture of TBS, 0.1% Tween-20 and 50 mM $CaCl_2$.

Reagents and treatments for processing blood before assaying are also well known in the art, e.g., as used for assays on Abbott TDx, AxSYM®, and ARCHITECT® analyzers (Abbott Laboratories), as described in the literature (see, e.g., Yatscoff et al., Abbott TDx Monoclonal Antibody Assay Evaluated for Measuring Cyclosporine in Whole Blood, Clin. Chem. 36: 1969-1973 (1990), and Wallemacq et al., Evaluation of the New AxSYM Cyclosporine Assay: Comparison with TDx Monoclonal Whole Blood and EMIT Cyclosporine Assays, Clin. Chem. 45: 432-435 (1999)), and/or as commercially available. Additionally, pretreatment can be done as described in Abbott's U.S. Pat. No. 5,135,875, European Pat. Pub. No. 0 471 293, and U.S. Pat. App. Pub. No. 2008/0020401, content of all of which is incorporated herein by reference. It is to be understood that one or more of these known reagents and/or treatments can be used in addition to or alternatively to the sample treatment described herein.

In some embodiments, after addition of the processing buffer, the sample comprises 1% TRITON X (2-[4-(2,4,4-trimethylpentan-2-yl)phenoxy]ethanol), 10U of DNase, 4.6 mg/ml of plasmin, 5 mM Calcium, 0.01% of Tween 20, 2.5 mM of Tris, 150 mM of NaCl and 0.2 mM of KCl in addition to the components already present in the sample.

After addition of the processing buffer, the sample can undergo mixing. This can be simply accomplished by agitating the sample, e.g., shaking or vortexing the sample and/or moving the sample around, if it is in a microfluidic device. In some embodiments where the microbe-targeting article is in the form of a dipstick or a membrane, the microbe-targeting dipstick or membrane can be dipped in a volume of a test sample and gently agitated with a rocking motion.

After addition of the processing reagents, the sample can be incubated for a period of time, e.g., for at least one minute, at least two minutes, at least three minutes, at least four minutes, at least five minutes, at least ten minutes, at least fifteen minutes, at least thirty minutes, at least forty-five minutes, or at least one hour. Such incubation can be at any appropriate temperature, e.g., room-temperature (e.g., about 16° C. to about 30° C.), a cold temperature (e.g. about 0° C. to about 16° C.), or an elevated temperature (e.g., about 30° C. to about 95° C.). In some embodiments, the sample is incubated for about fifteen minutes at room temperature.

1206 (1208 (Microbe Capture) and 1210 (Microbe Separation)):

After processing of the sample, the sample can be subjected to a microbe capture process. During the microbe capture process, a microbe-targeting article added into a test sample can capture one or more microbes present in the test sample. In some embodiments, the microbe capture process can be repeated and/or performed for a sufficient amount of time to allow for concentrating and/or cleaning up the test sample before microbe detection. Thus, microbe capture and separation process described herein can be used for concentrating and/or cleaning up a sample before analysis for a target component in the sample.

In some embodiments, the microbe capture process can comprise mixing a microbe-targeting article with the test sample. In some embodiments, the microbe-targeting article can be already present in the processing buffer. Amount of the microbe-targeting article added to the sample can be dependent on a number of different factors, such as, number of microbe-targeting molecules on each article, size of the article, shape of the article, binding affinity of the microbe-targeting molecule to the microbe, and concentration of the microbe in the sample. Additionally, amount of the microbe-targeting articles in the sample can be adjusted to optimize the capture of microbes. In some embodiments, amount of microbe-targeting articles in the sample is such that one micrbobe-targeting article binds with one microbe. However, each microbe can be bound to more than one micrbobe-targeting article. This can reduce cross-linking of multiple microbes together which can lead to coagulation and/or precipitation of such cross-linked microbes from the sample.

Generally, the total amount of the microbe-binding molecules contacted with the test sample can range from about 0.01 µg to about 1 mg, about 0.1 µg to about 500 µg, about 0.5 µg to about 250 µg, about 1 µg to about 100 µg, or about 3 µg to about 60 µg. In some embodiments, the total amount of the microbe-binding molecules contacted with the test sample can range from about 500 µg to about 1000 mg, about 1 mg to about 750 mg, about 5 mg to about 500 mg, about 10 mg to about 250 mg, or about 25 mg to about 100 mg.

In some embodiments, a plurality of microbe-targeting articles can be contacted with a test sample. The plurality of microbe-targeting articles can comprise at least two subsets (e.g., 2, 3, 4, 5, or more subsets), wherein each subset of microbe-targeting articles have a pre-determined dimension. In some embodiments, the plurality of microbe-targeting articles can comprise a first subset of the microbe-targeting articles and a second subset of microbe-targeting articles. In such embodiments, the first subset of the microbe-targeting articles each has a first pre-determined dimension; and the second subset of the microbe-targeting articles each has a second pre-determined dimension. Additionally, each subset of the microbe-targeting articles can comprise on their surfaces substantially the same density or different densities of the microbe-binding molecules described herein.

Different subsets of the plurality of the microbe-targeting articles can be brought into contact with a test sample in any manner. For example, in some embodiments, the plurality of the microbe-targeting articles can be provided as a single mixture comprising at least two subsets of the microbe-targeting articles to be added into a test sample. In some embodiments, in order to distinguish among different subsets of the microbe-targeting articles, the microbe-targeting articles in each subset can have a distinct detection label. For example, the microbe-targeting articles in each subset can have a distinct-fluorescent label that can be sorted afterward, for example, by flow cytometry.

In other embodiments, the plurality of the microbe-targeting articles can be brought into contact with a test sample in a sequential manner. For example, a test sample can be contacted with a first subset of the microbe-targeting articles, followed by a contact with at least one more subsets of the microbe-targeting articles. The previous subset of the microbe-targeting articles can be removed from the test sample before addition of another subset of the microbe-targeting articles into the test sample.

By way of example only, when the microbe-targeting article is a microbe-targeting molecule coated microparticle (also referred to as a coated-microparticle), generally, about 100 to about $10^9$ microparticles can be contacted with each ml of the sample. In some embodiments, about $10^4$ to about $5 \times 10^6$ coated-microparticless can be contacted with each ml of sample.

As discussed above, in some embodiments, a plurality of microbe-targeting articles can be contacted with a test sample. Accordingly, in some embodiments, a plurality of coated-microparticles can be contacted with a test sample. The plurality of coated-microparticles can comprise at least two subsets (e.g., 2, 3, 4, 5, or more subsets), wherein each subset of coated-microparticles have a pre-determined dimension. In some embodiments, the plurality of coated-microparticles can comprise a first subset of the coated-microparticles and a second subset of the coated-microparticles. In such embodiments, the first subset of the coated-microparticles each has a first pre-determined dimension; and the second subset of the coated-microparticles each has a second pre-determined dimension. The pre-determined dimension of a coated-microparticle depends, in part, on the dimension of a microparticle described herein to which the engineered microbe-binding molecules are conjugated. For example, in some embodiments, tthe microparticle can have a size of about 10 nm to 10 μm, about 20 nm to about 5 μm, about 40 nm to about 1 μm, about 50 nm to about 500 nm, or about 50 nm to about 200 nm. Additionally, each subset of the coated-microparticles can comprise on their surfaces substantially the same density or different densities of the microbe-targeting molecules disclosed herein.

Different subsets of the plurality of the coated-microbeads can be brought into contact with a test sample in any manner. For example, in some embodiments, the plurality of the coated-microbeads can be provided as a single mixture comprising at least two subsets of the coated-microbeads to be added into a test sample. In some embodiments, in order to distinguish among different subsets of the coated-microbeads, the coated-microbeads in each subset can have a distinct detection label, e.g., a distinctly-fluorescent label that can be sorted afterward, for example, by flow cytometry.

In some embodiments, the coated-microparticles can be present in the processing buffer. In one embodiment, one ml of the processing buffer comprises 100 μl of TRITON X100 (2-[4-(2,4 4-trimethylpentan-2-yl)phenoxy]ethanol), 10 μl of a solution comprising about 25 million coated-microparticles, 10 μl of DNAse (1U/1 μl), 10 μl of human plasmin at 4.6 mg/ml and 870 μl of a mixture of TBS, 0.1% Tween-20. In some embodiments, the processing buffer can include a calcium salt, e.g., $CaCl_2$) (e.g., ~50 mM $CaCl_2$)). In some embodiments, the processing or capture buffer can include no calcium salt, e.g., $CaCl_2$).

After addition of the microbe-targeting articles, the microbe-targeting articles can be mixed in the sample to allow microbes to bind with the microbe-targeting molecules. This can be simply accomplished by agitating the sample, e.g., shaking or vortexing the sample and/or moving the sample around in a microfluidic device. In some embodiments where the microbe-targeting article is in a form of a dipstick or a membrane, the microbe-targeting dipstick or membrane can be dipped in a volume of a test sample and gently agitated with a rocking motion.

The volume of the test sample required for contacting the microbe-targeting article can vary with, e.g., the selection of the microbe-targeting article (e.g., microbeads, fibers, filters, filters, fibers, screens, mesh, tubes, hollow fibers), the concentration of microbes present in the test sample, the platform used to carry out the assay (e.g., a microfluidic device, a blood collection tube, a microtiter plate, or like). For example, if the assay is perfrmed in a microfluidic device, the test sample volume used to perform the assay can range from about 1 μL to about 500 μL, from about 5 μL to about 250 μL, or from about 10 μL to about 100 μL. In some embodiments, if the assay is performed in a test tube, the test sample volume can range from about 0.05 mL to about 50 mL, from about 0.25 ml to about 50 ml, about 0.5 ml to about 25 ml, about 1 ml to about 15 ml, or about 2 ml to about 10 ml. In some embodiments, the test sample volume used to perform the assay described herein can be about 1 mL to about 5 ml. In one embodiment, the test sample volume used to perform the assay described herein is about 5 ml to about 10 mL.

After contacting the test sample with the microbe-targeting mlecules (e.g., with a microbe-targeting article), the sample mixture can be incubated for a period of time to allow the microbe of interest to bind onto the microbe-targeting molceules on the microbe-targeting article. Such incubation can be fr any desired period of time to allow sufficient number of microbes t bind to the microbe-targeting molecules. Forexample, the incubation can be for at least one minute, at least two minutes, at least three minutes, at least four minutes, at least five minutes, at least ten minutes, at least fifteen minutes, at least about twenty minutes, at least thirty minutes, at least forty-five minutes, or at least one hour. In one embodiment, the sample mixture can be incubated for a period of about 10-20 minutes. Further, such incubation can be performed at any appropriate temperature, e.g., room-temperature (e.g., about 16° C. to about 30° C.), a cold temperature (e.g. about 0° C. to about 16° C.), or an elevated temperature (e.g., about 30° C. to about 95° C.). In some embodiments, the incubation can be performed at a temperature ranging from about room temperature to about 37° C. In some embodiments, the sample can be incubated for about 10 mins to about 20 mins at room temperature. In some embodiments, the sample is incubated for about fifteen minutes at room temperature.

To prevent or reduce agglutination (or non-specific binding) during separation of the microbes from the sample, additional reagents can be added to the sample mixture. Such reagents are also referred to as blocking reagents herein. For example, these blocking reagents can comprise a ligand of the affinity molecules on the coated-microbeads. Addition of such blocking reagents can reduce agglutination by binding with any empty ligand binding sites on the affinity molecules. Accordingly, when microbe-targeting magnetic microbeads are used for capturing the microbes, the blocking reagent can be a carbohydrate, such as mannose. Amount of additional reagent can depend on the amount of microbeads added to the sample. Generally, about the reagent is added to a final concentration of about 0.1 mM to about 10 mM. The amount of the blocking agent required can vary, at least partly, with the amount and/or surface area of the microbe-targeting substrate that is in contact with a test sample. In some embodiments, the blocking reagent can be added to a final concentration of about 0.1% (w/v) to about 10% (w/v), about 0.5% (w/v) to about 7.5% (w/v), or about 1% (w/v) to about 5% (w/v). In some embodiments, about 1% casein can be used as a blocking agent in the assay described herein.

After addition of the blocking reagent, the sample mixture can be incubated for a period of time to allow the blocking reagent to bind to with the microbe-targeting molecules, e.g., for at least one minute, at least two minutes, at least three minutes, at least four minutes, at least five minutes, at least ten minutes, at least fifteen minutes, at least thirty minutes, at least forty-five minutes, or at least one hour. Such incubation can be at any appropriate temperature, e.g., room-temperature (e.g., about 16° C. to about 30° C.), a cold temperature (e.g. about 0° C. to about 16° C.), or an elevated temperature (e.g., about 30° C. to about 95° C.). In some embodiments, the sample is incubated for about fifteen minutes at room temperature. In some embodiments, incubation is for about 5 seconds to about 60 seconds. In some embodiments, the incubation can be performed at a temperature ranging from about room temperature to about 37° C. In some embodiments, the sample is incubated for about fifteen minutes at room temperature.

To prevent or reduce non-specific binding during the contact between a microbe-targeting substrate and a test sample, in some embodiments, the microbe-targeting article (e.g., coated-microparticles) or the test sample can be pre-treated with a blocking agent that does not react with microbes, before contacting each other. Exemplary blcking agents include, but are not limited t, casein, normal serum, BSA, non-fat dry milk powder and any art-recognized block agent. Optionally, microbe-targeting article after blocking can be washed with any art-recognized buffer to remove any leftover blocking agent. The number of wash steps can range from 1 to many, e.g., 1, 2, 3, 4, 5, 6, 7, 8, 9, 10 or more wash steps. In one embodiment, the microbe-targeting substrate after blocking can be washed with a buffer, e.g., TBST, for about at least 1-3 times.

After incubation, the microbe-targeting article can then be analyzed, as described below, for the presence or absence of a bound microbe. In some embodiments, the test sample can be subjected to a second microbe capturing/detection assay. The second microbe capturing/detection assay can be carried out using a second microbe-targeting molecule which does not comprises CRP or a fragment thereof. For example, the second microbe-targeting molecule comprises at least one first domain comprising at least a portion of a microbe-binding domain of a microbe-binding protein, wherein the microbe-binding protein is not a CRP; a second domain, as described in this disclosure; and a linker conjugating the first and the second domains. Microbe-binding domains that do not comprise CRP are described elsewhere in the disclosure. Exemplary second microbe-targeting molecules are described, for example, in PCT Application No. PCT/US2011/021603 filed Jan. 19, 2011 and No. PCT/US2012/047201, filed Jul. 18, 2012, and U.S. Provisional Application No. 61/691,983 filed Aug. 22, 2012, contents of all of whihc are incorporated herein by reference in their entireties. In some embodiments, the second microbe-targeting molecule comprises an amino acid sequence selected from the group consisting of SEQ ID NOs: 8, 9, 11, 12, and 23-27.

Exemplary Optional Modifications to 1208 (Microbe Capture):

In accordance with one aspect described herein, the test sample can be contacted with a microbe-targeting molecule in the presence of a chelating agent. Without wishing to be bound by theory, the addition of a chelating agent to a test sample and/or processing buffer can reduce the likelihood of any protein A- and protein G-negative microbe, but not protein A- or protein G-expressing microbe in the test sample, to bind with at least one microbe-binding molecule. Accordingly, detection of any microbes bound on the microbe-targeting substrate described herein in the presence of a chelating agent can determine the presence or absence of a protein A- or protein G-expressing microbe in a test sample.

The chelating agent can be added into the processing buffer comprising the test sample. The amount of the chelating agent is sufficient to chelate free calcium ions and thus prevent or reduce calcium-dependent carbohydrate recognition domain binding (e.g., mannose-binding lectin) with a microbe. The amount of the chelating agent needed to prevent or reduce calcium-dependent carbohydrate recognition domain binding (e.g., mannose-binding lectin) with a microbe can depend on, e.g., the concentration of free calcium ions present in a test sample and optionally a capture buffer, e.g., used to dilute a chelating agent and/or a test sample. Thus, in some embodiments, the concentration of the chelating agent can be higher than the total concentration of free calcium ions present in the combined solution of a test sample and a capture buffer. For example, in some embodiments, the concentration of the chelating agent can be at least about 30% higher, including at least about 40%, at least about 50%, at least about 60%, at least about 70%, at least about 80%, at least about 90%, at least about 95%, at least about 98%, up to and including 100%, or any percent between about 30% and about 100%, higher than the total concentration of free calcium ions present in the combined solution of a test sample and a capture buffer. In other embodiments, the concentration of the chelating agent can be at least about 1.5-fold, at least about 2-fold, at least about 3-fold, at least about 4-fold, at least about 5-fold, at least about 6-fold, at least about 7-fold, at least about 8-fold, at least about 9-fold, at least about 10-fold, at least about 15-fold, at least about 20-fold, at least about 30-fold, at least about 40-fold, at least about 50-fold, at least about 75-fold, at least about 100-fold or more, higher than the total concentration of free calcium ions present in the combined solution of a test sample and a capture buffer. In one embodiment, the concentration of the chelating agent can be at least about 5-fold to about 50-fold, or at least about 7-fold to about 25-fold, higher than the total concentration of free calcium ions present in the combined solution of a test sample and a capture buffer.

In some embodiments, the concentration of a chelating agent present in the test sample and optionally a processing or capture buffer, e.g., used to dilute the chelating agent or the test sample, can range from about 0.1 mM to about 1 M, about 10 mM to about 500 mM, about 20 mM to about 250 mM, or about 25 mM to about 125 mM. In one embodiment, the concentration of a chelating agent present in the test sample and optionally a capture buffer can be about 25 mM to about 125 mM.

In some embodiments, the concentration of a chelating agent present in the test sample containing the microbe-targeting substrate can be sufficient to reduce the likelihood of a protein A- and protein G-negative microbe, if present in the test sample, to bind with at least one microbe-binding molecule. For example, the concentration of a chelating agent present in the test sample with the microbe-targeting substrate can be sufficient to reduce the number of protein A- and protein G-negative microbes, if present in the test sample, to bind with at least one microbe-binding molecule, by at least about 30%, at least about 40%, at least about 50%, at least about 60%, at least about 70%, at least 80% or higher, as compared to the number of protein A- and protein G-negative microbes bound on the microbe binding molecules in the absence of the chelating agent. In some embodiments, the concentration of a chelating agent present in the test sample with the microbe-targeting substrate can be sufficient to reduce the number of protein A- and protein G-negative microbes, if present in the test sample, to bind with at least one microbe-binding molecule, by at least about 85%, at least about 90%, at least about 95%, at least about 98%, at least about 99%, up to and including 100%, or any values between about 85% and about 100%, as compared to the number of protein A- and protein G-negative microbes bound on the microbe-binding molecules in the absence of the chelating agent.

The protein A-expressing and protein G-expressing microbes can generally bind to microbe-binding molecules via two independent (but additive) mechanisms: Fc-mediated binding and microbe surface-binding domain mediated binding. Without wishing to be bound by theory, while the protein A-expressing and protein G-expressing microbes can still be captured on the microbe-targeting mlceules in the presence of a chelating agent, the presence of free calcium ions can further increase the number of protein A-expressing and protein G-expressing microbes bound to the microbe-targeting molecules, because the overall binding in the presence of calcium ions can be almost twice as strong as in the absence of calcium ions.

Accordingly, in some embodiments, the concentration of a chelating agent present in the test sample containing the microbe-targeting articles can reduce the number of protein A-expressing microbes or protein G-expressing microbes bound onto the microbe-targeting substrate, but such effect as compared to that on the protein A- and protein G-negative microbes is much smaller, e.g., at least about 30% smaller, at least about 40% smaller, at least about 50%, at least about 60% smaller, at least about 70% smaller, or at least about 80% smaller.

In some embodiments, the concentration of a chelating agent used in the assay described herein can be high enough to prevent at least about 80% or higher, including at least about 90%, at least about 95%, up to and including 100%, of the protein A- and protein G-negative microbes from binding to be microbe-targeting substrate, but low enough to allow at least about 30% or higher, including at least about 40%, at least about 50%, at least about 60%, at least about 70% or higher, of the protein A-expressing microbes or protein G-expressing microbes to bind with the microbe-targeting substrate. In one embodiment, the concentration of a chelating agent used in the assay described herein can be high enough to prevent at least about 90% or higher, of the protein A- and protein G-negative microbes, if any present in the test sample, from binding to be microbe-targeting substrate, but low enough to allow at least about 50% of the protein A-expressing microbes or protein G-expressing microbes, if any present in the test sample, to bind with the microbe-targeting substrate.

Examples of calcium ion-chelating agents can include, but are not limited to, 1,2-bis(2-aminophenoxy)ethane-N,N, N',N'-tetraacetic acid, ethylenediaminetetraacetic acid (EDTA); ethylene glycol-bis(2-aminoethylether)-N,N,N',N'- tetraacetic acid; ethylene glycol-bis(β-aminoethyl ether)-N, N,N',N'-tetraacetic acid (EGTA), 1,2-bis(o-aminophenoxy) ethane-N,N,N',N'-tetraacetic acid (BAPTA), a buffer containing citrate, N,N-Bis(2-(bis-(carboxymethyl)amino) ethyl)-glycine (DTPA), nitrilo-2,2',2"-triacetic acid (NTA), a buffer that precipitates a calcium ion from the test sample, including, e.g., a phosphate buffer, a carbonate buffer and a bicarbonate buffer, a low pH buffer (e.g., a pH buffer less than pH 7 or less than pH 6), citric acids and its salts, gluconic acid and its salts, alkali metal pyrophosphates, alkali metal polyphosphates, sodium hexametaphosphate, triethylene tetramine, diethylene triamine, o-phenanthroline, oxalic acid and any combinations thereof.

The chelating agent can be directly added to the test sample or prepared in a processing or capture buffer, which is then added to the test sample in contact with the microbe-targeting substrate. The processing or capture buffer can be any buffered solutions, e.g., with a pH ranging from about 6 to about 10. In some embodiments, the processing or capture buffer can include, but is not limited to, a tris-buffered saline, a phosphate buffered saline or a combination thereof. In some embodiments, the processing or capture buffer can include a surfactant, e.g., to prevent non-specific binding of a microbe to a microbe-surface-binding domain of the microbe-targeting substrate, and/or to saturate non-specific binding sites, if any, present in the microbe-targeting substrate. A surfactant or detergent, e.g., as described earlier, can be dissolved in a buffered solution in any amount, e.g., ranging from about 0.001% (v/v) to about 5% (v/v), from about 0.01% (v/v) to about 2.5% (v/v), or from about 0.05% (v/v) to about 1% (v/v). In some embodiments, the surfactant added to the processing or capture buffer can include Tween 80 or polysorbate 80 at a concentration of about 0.01% to about 0.1%. In one embodiment, the surfactant added to the processing or capture buffer can include Tween 80 or polysorbates 80 at a concentration of about 0.05%.

After incubation, the microbe-targeting article can then be analyzed, as described below, for the presence or absence of a bound microbe. In the absence of a microbe-targeting article-bound microbe, in some embodiments, the previous volume of the test sample or a new fresh volume of the test sample can be contacted with a fresh microbe-targeting substrate in the presence of free calcium ions, e.g., to determine the presence or absence of protein A- and protein G-negative microbes. In some embodiments, the free calcium ions can be produced adding a sufficient amount of calcium salts in the test sample. If there has been a chelating agent present in the test sample, a higher amount of calcium salts is generally needed in order to obtain free calcium ions.

As used herein, the term "free calcium ions" refers to calcium ions that are not complexed with any molecule or compound, e.g., a chelating agent, which can hinder its reaction with other molecules or ions to mediate binding of carbohydrate patterns on a microbial cell surface to a microbe surface-binding domain (e.g., MBL) of the engineered microbe-binding molecule. Accordingly, in some embodiments, free calcium ions can be present in the absence of chelating agent. In some embodiments, free calcium ions can be present in a solution comprising a chelating agent and calcium ions. In some embodiments, the amount of calcium ions present in the solution is at least about 30% more than an amount sufficient to interact with substantially all the chelating agent molecules present in the solution to form chelate complexes. For example, in some embodiments, in order to obtain free calcium ions, the amount of calcium ions present in the solution can be at least about 30%, including at least about 40%, at least about 50%, at least about 60%, at least about 70%, at least about 80%, at least about 90%, at least about 95%, at least about 98%, up to and including 100% and any percent between 30% and 100%, more than an amount sufficient to interact with substantially all the chelating agent molecules present in the solution to form chelate complexes. In some embodiments, in order to obtain free calcium ions, the amount of calcium ions present in the solution can be at least about 1-fold, at least about 2-fold, at least about 3-fold, at least about 4-fold, at least about 5-fold, at least about 6-fold, at least about 7-fold, at least about 8-fold, at least about 9-fold, at least about 10-fold, at least about 15-fold, at least about 20-fold, at least about 25-fold, at least about 50-fold, at least about 100-fold, at least about 500-fold, at least about 1000-fold, more than an amount sufficient to interact with substantially all the chelating agent molecules present in the solution to form chelate complexes. In some embodiments, free calcium ions can be present in a solution when the concentration of calcium ions in the solution is at least about 1.5-fold, at least about 2-fold, at least about 3-fold, at least about 4-fold, at least about 5-fold, at least about 6-fold, at least about 7-fold, at least about 8-fold, at least about 9-fold, at least about 10-fold, at least about 20-fold, or higher than the concentration of a chelating agent present in the same solution.

In some embodiments, calcium ions can be obtained from a water-soluble calcium salt. By the term "water-soluble calcium salt" is meant a calcium salt which has significant solubility in water at room temperature, for example at least 1 gram per 100 ml water, at least 10 grams per 100 ml water, or at least 25 grams per 100 ml water or higher. Examples of calcium salts include, without limitations, calcium chloride, calcium fluoride, calcium bromide, calcium iodide, calcium nitrate, calcium citrate, calcium formate, calcium acetate, calcium gluconate, calcium ascorbate, calcium lactate, calcium glycinate and mixtures thereof. In some embodiments, calcium chloride can be used as a source of calcium ions.

Free calcium ions can be present at a concentration or an amount sufficient to mediate binding of calcium-dependent carbohydrate recognition domain with a microbe surface. In some embodiments, free calcium ions can be present at a concentration of at least about 1 µM, at least about 10 µM, at least about 25 µM, at least about 50 µM, at least about 100 µM, at least about 250 µM, at least about 500 µM, or at least about 1 mM or higher. In some embodiments, the free calcium ions can be present at a concentration of at least about 1 mM, at least about 2.5 mM, at least about 5 mM, at least about 10 mM, at least about 25 mM, at least about 50 mM, at least about 75 mM, at least about 100 mM or higher. In other embodiments, the free calcium ions can be present at a concentration of at least about 100 mM, at least about 150 mM, at least about 200 mM, at least about 300 mM, at least about 400 mM, at least about 500 mM, at least about 600 mM, at least about 700 mM, at least about 800 mM, at least about 900 mM, at least about 1 M or higher. In one embodiment, the free calcium ions can be present at a concentration of about 1 mM to about 10 mM. In one embodiment, the free calcium ions can be present at a concentration of at least about 5 mM.

While a chelating agent can be added during an initial capture of a microbe on a microbe-targeting substrate, the chelating agent can also be first excluded to allow the initial capture of any microbe, including protein A- and protein G-negative microbes, on a microbe-targeting substrate in the presence of free calcium ions, but added after the capture to remove any captured protein A- or protein G-negative microbes from the microbe-targeting substrate.

Accordingly, in some embodiments, the microbe capture can comprise (i) contacting at least a first volume of a test sample with a microbe-targeting substrate described herein in the presence of free calcium ions, and (ii) contacting the microbe-binding molecule of the microbe-targeting substrate described herein, upon the contact with the test sample, with a solution comprising a chelating agent.

When the microbe-targeting substrate is contacted with a test sample in the presence of free calcium ions as described herein, microbes that primarily depend on calcium-dependent MBL-mediated binding such as protein A- and protein G-negative microbes, e.g., *E. coli* can bind to the microbe-target substrate, in addition to microbes associated with Fc-mediated binding such as protein A-expressing microbes (e.g., *S. aureus*), and protein G-expressing microbes.

To elute off or remove from the microbe-targeting substrate the captured microbes that primarily depend on calcium-dependent MBL-mediated binding such as protein A- and protein G-negative microbes, e.g., *E. coli*, the microbe-binding molecules on the microbe-targeting substrates can be contacted with a solution comprising a sufficient amount of a chelating agent as described herein. The solution comprising the chelating agent can be same as a capture buffer described above. In such embodiments, the microbe-targeting substrate can be incubated with the solution comprising a chelating agent for a period of time to allow microbes that primarily bind to microbe-binding molecules via calcium-dependent MBL-mediated binding to elute off the microbe-targeting substrate, e.g., incubation for at least one minute, at least two minutes, at least three minutes, at least four minutes, at least five minutes, at least ten minutes, at least fifteen minutes, at least thirty minutes, at least forty-five minutes, or at least one hour. Such incubation can be performed at any appropriate temperature, e.g., room-temperature (e.g., about 16° C. to about 30° C.), a cold temperature (e.g. about 0° C. to about 16° C.), or an elevated temperature (e.g., about 30° C. to about 95° C.). In some embodiments, the microbe-targeting substrate can be incubated with the solution comprising a chelating agent for at least about 5 mins to about 15 mins at room temperature.

In these embodiments, the concentration of a chelating agent used in the assay described herein is sufficient to elute off or remove from the microbe-targeting substrate at least about 30% of the bound protein A- and protein G-negative microbes (e.g., *E. coli*). For example, the concentration of a chelating agent used in the assay described herein is sufficient to elute off or remove from the microbe-targeting substrate at least about 30% of the bound protein A- and protein G-negative microbes (e.g., *E. coli*), including at least about 40%, at least about 50%, at least about 60%, at least about 70%, at least 80% or higher, of the bound protein A- and protein G-negative microbes (e.g., *E. coli*). In some embodiments, the concentration of a chelating agent used in the assay described herein is sufficient to elute off or remove from the microbe-targeting substrate at least about 85% of the bound protein A- and protein G-negative microbes (e.g., *E. coli*), including at least about 85%, at least about 90%, at least about 95%, at least about 98%, up to and including 100%, or any values between about 85% and about 100%, of the bound protein A- and protein G-negative microbes (e.g., *E. coli*).

As noted above, the protein A-expressing and protein G-expressing microbes can bind to microbe-binding molecules via Fc-mediated and calcium ion-dependent MBL-mediated binding. Without wishing to be bound by theory, the concentration of a chelating agent used in the assay described herein can also elute off or remove at least a portion of the protein A-expressing and/or protein G-expressing microbes from the microbe-targeting substrate. For example, the concentration of a chelating agent used to elute off or remove protein A- and protein G-negative microbes from the microbe-targeting substrate can be sufficient to elute off or remove no more than 60%, no more than 50%, no more than 40%, no more than 30%, no more than 20%, no more than 10% or lower, of the bound protein A-expressing or protein G-expressing microbes. In some embodiments, the concentration of a chelating agent used to elute off or remove from the microbe-targeting substrate at least about 80% or more, including at least about 90% or more, of the bound protein A- and protein G-negative microbes can be sufficient to elute off or remove no more than 50%, or more than 40% of the bound protein A-expressing and/or protein G-expressing microbes.

As a person having ordinary skill in the art can appreciate, the assay described herein can further comprise isolating the microbe-targeting substrate from the test sample, e.g., as described below, before contacting microbe-binding molecules on its substrate surface with the solution comprising the chelating agent described herein.

1210 (Microbe Separation from Sample):

The sample mixture can be then subjected to a microbe separation process. In some embodiments, because microbes are bound with one or more magnetic microparticles, a magnet can be employed to separate the bound microbes from the test sample. The skilled artisan is well aware of methods for carrying out magnetic separations. Generally, a magnetic field gradient can be applied to direct the capture of magnetic microbeads. Optionally, the bound microbe can be washed with a buffer to remove any leftover sample and unbound components. Number of wash steps can range from 1 to many, e.g., 1, 2, 3, 4, 5, 6, 7, 8, 9, 10 or more wash steps. Without wishing to be bound by a theory, capture and separation of the bound microbes from the sample can concentrate the microbes and also remove components, which can interfere with the assay or process, from the test sample.

The magnetic field source can be any magnet device positioned to generate the magnetic field gradient that is used to pull the captured microbe out from the sample. An electromagnetic controller can be used to control and adjust the magnetic field and gradients thereof, and to control the migration, separation and orientation of the magnetically bound microbes. The magnetic field gradient can be generated by a permanent magnet or by an electromagnetic signal generator. The electromagnetic signal generator can include an electromagnet or electrically-polarizable element, or at least one permanent magnet. The magnetic field gradient can be produced at least in part according to a pre-programmed pattern. The magnetic field gradient can have a defined magnetic field strength and/or spatial orientation. In some embodiments, the magnetic field gradient has a defined magnetic field strength. The term "magnetic field gradient" as used herein refers to a variation in the magnetic field with respect to position. By way of example only, a one-dimensional magnetic field gradient is a variation in the magnetic field with respect to one direction, while a two-dimensional magnetic field gradient is a variation in the magnetic field with respect to two directions.

As used herein, the term "magnetic field" refers to magnetic influences which create a local magnetic flux that flows through a composition and can refer to field amplitude, squared-amplitude, or time-averaged squared-amplitude. It is to be understood that magnetic field can be a direct-current (DC) magnetic field or alternating-current (AC) magnetic field. The magnetic field strength can range from about 0.00001 Tesla per meter (T/m) to about $10^5$ T/m. In some embodiments, the magnetic field strength can range from about 0.0001 T/m to about $10^4$ T/m. In some other embodiments, the magnetic field strength can range from about 0.001 T/m to about $10^3$ T/m.

In some embodiments, microbe capture and/or microbe-targeting substrate separation can be performed by a rapid microbe diagnostic assay or device as described in Int. Pat. App. No. WO 2011/091037, filed Jan. 19, 2011, the content of which is incorporated herein by reference. A rapid microbe diagnostic device as described in Int. Pat. App. No. WO 2011/091037, filed Jan. 19, 2011, can be modified to replace the capture chamber or capture and visualization chamber with an s-shaped flow path. A magnet can then be used to capture bound microbe against the flow path wall; separating the bound microbe from rest of the sample.

In some embodiments, microbe capture and/or separation is by a device or method as described in U.S. Pat. App. Pub. No. 2009/0220932, No. 2009/007861, No. 2010/0044232, No. 2007/0184463, No. 2004/0018611, No. 2008/0056949, No. 2008/0014576, No. 2007/0031819, No. 2008/0108120, and No. 2010/0323342, the contents of which are all incorporated herein by reference.

In some embodiments, microbe capture, separation, or detection is by a device or method as described in PCT Application No. PCT/US2013/028409, filed Feb. 28, 2013, No. PCT/US2012/031864, filed Feb. 4, 2012, and No. PCT/US2011/021718 filed Jan. 19, 2011; U.S. patent application Ser. No. 13/918,193 filed Jun. 14, 2013; and U.S. Prov. App. No. No. 61/788,570 filed Mar. 15, 2013, No. 61/772,436 filed Mar. 4, 2013, No. 61/772,360 filed Mar. 4, 2013, and No. 61/673,071 filed Jul. 18, 2013, the contents of which are all incorporated herein by reference.

Without limitations, if a microbe-targeting substrate does not possess a magnetic property, isolation of a microbe-targeting substrate (e.g., particles, posts, fibers, dipsticks, membrane, filters, capillary tubes, etc.) from the test sample can be carried out by non-magnetic means, e.g., centrifugation, and filtration. In some embodiments where the microbe-targeting substrate is in a form a dipstick or membrane, the microbe-targeting dipstick or membrane can be simply removed from the test sample, where microbes, if any, in the test sample, remained bound to the engineered microbe-binding molecules conjugated to the dipstick or membrane substrate.

Optionally, the microbe-targeting substrate after isolated from the test sample or processing buffer can be washed with a buffer (e.g., TBST) to remove any residues of test sample, solution comprising the chelating agent or any unbound microbes. The number of wash steps can range from 1 to many, e.g., 1, 2, 3, 4, 5, 6, 7, 8, 9, 10 or more wash steps. In one embodiments, the microbe-targeting substrate after isolated from the solution comprising the chelating agent and/or the test sample can be washed with a buffer (e.g., TBST) for about at least 1-3 times.

1212 (Microbe Detection/Analysis):

A detection component, device or system can be used to detect and/or analyze the presence of the separated microbe, for example, by spectroscopy, electrochemical detection, polynucleotide detection, fluorescence anisotropy, fluorescence resonance energy transfer, electron transfer, enzyme assay, magnetism, electrical conductivity, isoelectric focusing, chromatography, immunoprecipitation, immunoseparation, aptamer binding, filtration, electrophoresis, use of a CCD camera, immunoassay, ELISA, Gram staining, immunostaining, microscopy, immunofluorescence, western blot, polymerase chain reaction (PCR), RT-PCR, fluorescence in situ hybridization, sequencing, mass spectroscopy, or substantially any combination thereof. The separated microbe can remain bound on the microbe-targeting substrate during detection and/or analysis, or be isolated form the microbe-targeting substrate prior to detection and/or analysis.

In some embodiments, labeling molecules that can bind with the microbe can also be used to label the microbes for detection. As used herein, a "labeling molecule" refers to a molecule that comprises a detectable label and can bind with a target microbe. Labeling molecules can include, but are not limited to, an engineered microbe-targeting molecule disclosed herein, wheat germ agglutinin, lectins, antibodies (e.g., gram-negative antibodies or gram-positive antibodies, antibiotics to specific microbial strains or species), antigen binding fragments of antibodies, aptamers, ligands (agonists or antagonists) of cell-surface receptors and the like. The labeling molecule can also be a non-specific labeling molecule that non-specifically stains all viable cells in a sample.

Any method known in the art for detecting the particular label can be used for detection. Exemplary methods include, but are not limited to, spectrometry, fluorometry, microscopy imaging, immunoassay, and the like. While the microbe capture step can specifically capture microbes, it can be beneficial to use a labeling molecule that can enhance this specificity. If imaging, e.g., microscopic imaging, is to be used for detecting the label, the staining can be done either prior to or after the microbes have been laid out for microscopic imaging. Additionally, imaging analysis can be performed via automated image acquisition and analysis.

For optical detection, including fluorescent detection, more than one stain or dye can be used to enhance the detection or identification of the microbe. For example, a first dye or stain can be used that can bind with a genus of microbes, and a second dye or strain can be used that can bind with a specific microbe. Colocalization of the two dyes then provides enhanced detection or identification of the microbe by reducing false positive detection of microbes.

In some embodiments, microscopic imaging can be used to detect signals from label on the labeling agent. Generally, the microbes in the subsample are stained with a staining reagent and one or more images taken from which an artisan can easily count the number of cells present in a field of view.

In particular embodiments, microbe can be detected through use of one or more enzyme assays, e.g., enzyme-linked assay (ELISA). Numerous enzyme assays can be used to provide for detection. Examples of such enzyme assays include, but are not limited to, beta-galactosidase assays, peroxidase assays, catalase assays, alkaline phosphatase assays, and the like. In some embodiments, enzyme assays can be configured such that an enzyme will catalyze a reaction involving an enzyme substrate that produces a fluorescent product. Enzymes and fluorescent enzyme substrates are known and are commercially available (e.g., Sigma-Aldrich, St. Louis, Mo.). In some embodiments, enzyme assays can be configured as binding assays that provide for detection of microbe. For example, in some embodiments, a labeling molecule can be conjugated with an enzyme for use in the enzyme assay. An enzyme substrate can then be introduced to the one or more immobilized enzymes such that the enzymes are able to catalyze a reaction involving the enzyme substrate to produce a detectable signal.

In some embodiments, an enzyme-linked assay (ELISA) can be used to detect signals from the labeling molecule. In ELISA, the labeling molecule can comprise an enzyme as the detectable label. Each labeling molecule can comprise one or more (e.g., 1, 2, 3, 4, 5, 6, 7, 8, 9, 10 or more) enzymes. Additionally, each labeling molecule can comprise one or more (e.g., 1, 2, 3, 4, 5, 6, 7, 8, 9, 10 or more) sites for binding with a microbe. Without wishing to be bound by a theory, presence of multimeric probe molecules can enhance ELISA signal.

For ELISA, any labeling molecule conjugated to an enzyme can be used. Exemplary labeling molecule include those comprising the microbe-binding molecules comprising detectable labels, wheat germ agglutinin, lectins, antibodies (e.g., gram-negative antibodies or gram-positive antibodies), antigen binding fragments of antibodies, aptamers, ligands (agonists or antagonists) of cell-surface receptors and the like. In some embodiments, the labeling molecule can be a microbe-targeting molecule disclosed herein, wherein the microbe-targeting molecule comprises a detectable label. In some embodiments, the labeling molecule can be a microbe-targeting molecule as described, for example, in PCT Application No. PCT/US2011/021603 filed Jan. 19, 2011 and No. PCT/US2012/047201, filed Jul. 18, 2012, and U.S. Provisional Application No. 61/691,983 filed Aug. 22, 2012, contents of all of whihc are incorporated herein by reference in their entireties.

Similarly, a variety of enzymes can be used, with either colorimetric or fluorogenic substrates. In some embodiments, the reporter-enzyme produces a calorimetric change which can be measured as light absorption at a particular wavelength. Exemplary enzymes include, but are not limited to, beta-galactosidases, peroxidases, catalases, alkaline phosphatases, and the like. In some embodiments, the enzyme is a horseradish peroxidase (HRP) or an alkaline peroxidase (AP).

A microbe-binding molecule and the detectable label can be linked to each other by a linker. In some embodiments, the linker between the microbe-binding molecule and the detectable label an amide bond. In some embodiments, the linker between the microbe-binding molecule and the detectable label is a disulfide (S-S) bond. When the microbe-binding molecule is a peptide, polypeptide or a protein, the detectable label can be linked at the N-terminus, the C-terminus, or at an internal position of the microbe-binding molecule. Similarly, when the detectable label is an enzyme, the enzyme can be linked by its N-terminus, C-terminus, or an internal position.

In one embodiment, the ELISA probe molecule can comprise a microbe-targeting molecule comprising a CRP (or a portion there of) inked to HRP or AP. Conjugation of HRP or AP to peptides, proteins, and antibodies are known in the art. In one embodiment, the construct can be generated by direct coupling of the enzyme to the microbe-targeting molecule using a commercially-available conjugation kit.

In some embodiments, the microbes isolated from or remained bound on the microbe-targeting substrate can be incubated with the enzyme labeled microbe-binding molecules for a period of time, e.g., at least about 5 mins, at least about 10 mins, at least about 15 mins, at least about 20 mins, at least about 25 mins, at least about 30 mins. The typical concentrations of enzyme-labeled molecules used in the ELISA assay can range from about 1:500 to about 1:20,000 dilutions. In one embodiment, the concentration of enzyme-labeled microbe-binding molecules can be about 1:1000 to about 1:10000 dilutions.

Following incubation with the ELISA probe molecules, the sample can be washed with a wash buffer one or more (e.g., 1, 2, 3, 4, 5 or more) times to remove any unbound probes. An appropriate substrate for the enzyme (e.g., HRP or AP) can be added to develop the assay. Chromogenic substrates for the enzymes (e.g., HRP or AP) are known to one of skill in the art. A skilled artisan can select appropriate chromogenic substrates for the enzyme, e.g., TMB substrate for the HRP enzyme, or BCIP/NBT for the AP enzyme. In some embodiments, the wash buffer used after incubation with an ELISA probe molecule can contain calcium ions at a concentration of about at least about 0.01 mM, at least about 0.05 mM, at least about 0.1 mM, at least about 0.5 mM, at least about 1 mM, at least about 2.5 mM, at least about 5 mM, at least about 10 mM, at least about 20 mM, at least about 30 mM, at least about 40 mM, at least about 50 mM or more. In alternative embodiments, the wash buffer used after incubation with an ELISA probe molecule can contain no calcium ions. In some embodiments, the wash buffer used after incubation with an ELISA probe molecule can contain a chelating agent. A wash buffer can be any art-recognized buffer used for washing between incubations with antibodies and/or labeling molecules. An exemplary wash buffer can include, but is not limited to, TBST.

In some embodiments, without wishing to be bound by theory, it can be desirable to use a wash buffer without a surfactant or a detergent for the last wash before addition of a chromogenic substrate, because a surfactant or detergent may have adverse effect to the enzymatic reaction with a chromogenic substrate.

One advantage of the ELISA-based approach is that the microbe-targeting article does not need to be dispersed or dissociated from the microbe before binding the secondary reagents. This is in contrast to microscopic techniques, in which excess residual solid substrate may obscure the microbe during imaging. Furthermore, the optical readout components for ELISA are likely cheaper than in the microscopy case, and there is no need for focusing or for demanding that the sample be on the same focal plane. A further advantage of the ELISA-based approach is that it can take advantage of commercially available laboratory equipment. In particular, when the solid substrate is magnetic, magnetic separation can be automated using the KINGFISHER® system, the brief culture can be performed using an airlift fermenter, and the colorimetric/fluorescent readout can be attained using a standard plate reader.

Further amplification of the ELISA signal can be obtained by multimerizing the recognition molecule (e.g., the microbe-binding molecule) or by multimerizing the detection enzyme (HRP, etc.). For instance, phage expression can be used to yield multimerized microbe-targeting mlecules and provide a scaffold to increase the concentration of enzyme, either through direct coupling of enzyme to the phage particles or using an enzyme conjugated antibody.

In some embodiments, microbe can be detected through use of immunoassay. Numerous types of detection methods may be used in combination with immunoassay based methods.

In some embodiments, detection of microbes in a sample can also be carried out using light microscopy with phase contrast imaging based on the characteristic size (5 um diameter), shape (spherical to elliptical) and refractile characteristics of target components such as microbes that are distinct from all normal blood cells. Greater specificity can be obtained using optical imaging with fluorescent or cytochemical stains that are specific for all microbes or specific subclasses (e.g. calcofluor (1 µM to 100 µM) for chitin in fungi, fluorescent antibodies directed against fungal surface molecules, gram stains, acid-fast stains, fluorescent microbe-targeting molecules, etc. . . . .

Microbe detection can also be carried out using an epifluorescent microscope to identify the characteristic size (5 um diameter), shape (spherical to elliptical) and staining characteristics of microbes. For example, fungi stain differently from all normal blood cells, strongly binding calcofluor (1 µM to 100 µM) and having a rigid ellipsoid shape not found in any other normal blood cells.

In some embodiments, a microbe can be detected through use of spectroscopy. Numerous types of spectroscopic methods can be used. Examples of such methods include, but are not limited to, ultraviolet spectroscopy, visible light spectroscopy, infrared spectroscopy, x-ray spectroscopy, fluorescence spectroscopy, mass spectroscopy, plasmon resonance (e.g., Cherif et al., $Clinical\ Chemistry$, 52:255-262 (2006) and U.S. Pat. No. 7,030,989; herein incorporated by reference), nuclear magnetic resonance spectroscopy, Raman spectroscopy, fluorescence quenching, fluorescence resonance energy transfer, intrinsic fluorescence, ligand fluorescence, and the like.

In some embodiments, a microbe can be detected through use of fluorescence anisotropy. Fluorescence anisotropy is based on measuring the steady state polarization of sample fluorescence imaged in a confocal arrangement. A linearly polarized laser excitation source preferentially excites fluorescent target molecules with transition moments aligned parallel to the incident polarization vector. The resultant fluorescence is collected and directed into two channels that measure the intensity of the fluorescence polarized both parallel and perpendicular to that of the excitation beam. With these two measurements, the fluorescence anisotropy, r, can be determined from the equation: r=(Intensity parallel−Intensity perpendicular)/(Intensity parallel+2(Intensity perpendicular)) where the I terms indicate intensity measurements parallel and perpendicular to the incident polarization. Fluorescence anisotropy detection of fluorescent molecules has been described. Accordingly, fluorescence anisotropy can be coupled to numerous fluorescent labels as have been described herein and as have been described in the art.

In some embodiments, microbe can be detected through use of fluorescence resonance energy transfer (FRET). Fluorescence resonance energy transfer refers to an energy transfer mechanism between two fluorescent molecules. A fluorescent donor is excited at its fluorescence excitation wavelength. This excited state is then nonradiatively transferred to a second molecule, the fluorescent acceptor. Fluorescence resonance energy transfer may be used within numerous configurations to detect captured microbe. For example, in some embodiments, a first labeling molecule can be labeled with a fluorescent donor and second labeling molecule can be labeled with a fluorescent acceptor. Accordingly, such labeled first and second labeling molecules can be used within competition assays to detect the presence and/or concentration of microbe in a sample. Numerous combinations of fluorescent donors and fluorescent acceptors can be used for detection.

In some embodiments, a microbe can be detected through use of polynucleotide analysis. Examples of such methods include, but are not limited to, those based on polynucleotide hybridization, polynucleotide ligation, polynucleotide amplification, polynucleotide degradation, and the like. Methods that utilize intercalation dyes, fluorescence resonance energy transfer, capacitive deoxyribonucleic acid detection, and nucleic acid amplification have been described, for example, in U.S. Pat. Nos. 7,118,910 and 6,960,437; herein incorporated by reference). Such methods can be adapted to provide for detection of one or more microbe nucleic acids. In some embodiments, fluorescence quenching, molecular beacons, electron transfer, electrical conductivity, and the like can be used to analyze polynucleotide interaction. Such methods are known and have been described, for example, in Jarvius, *DNA Tools and Microfluidic Systems for Molecular Analysis*, Digital Comprehensive Summaries of Uppsala Dissertations from the Faculty of Medicine 161, ACTA UNIVERSITATIS UPSALIENSIS UPPSALA 2006, ISBN: 91-554-6616-8; Singh-Zocchi et al, *Proc. Natl. Acad. Sci*, 100:7605-7610 (2003); Wang et al. *Anal. Chem*, 75:3941-3945 (2003); and Fan et al, *Proc. Natl. Acad. Sci*, 100:9134-9137 (2003) and in U.S. Pat. Nos. 6,958,216; 5,093,268; and 6,090,545, the content of all of which is incorporated herein by reference. In some embodiments, the polynucleotide analysis is by polymerase chain reaction (PCR). The fundamentals of PCR are well-known to the skilled artisan, see, e.g. McPherson, et al., *PCR, A Practical Approach*, IRL Press, Oxford, Eng. (1991), hereby incorporated by reference.

In some embodiments, a metabolic assay is used to determine the relative number of microbes in a sample compared to a control. As will be apparent to one of ordinary skill in the art any metabolic indicator that can be associated with cells can be used, such as but not limited to, turbidity, fluorescent dyes, and redox indicators such as, but not limited to, Alamar Blue, MTT, XTT, MTS, and WST. Metabolic indicators can be components inherent to the cells or components added to the environment of the cells. In some embodiments, changes in or the state of the metabolic indicator can result in alteration of ability of the media containing the sample to absorb or reflect particular wavelengths of radiation.

Exemplary metabolic assays include, but are not limited to, ATP Luminescence, reactive oxygen species (ROS) assays, Resazurin assays, Luminol, MTT-metabolic assays, and the like. Further, as one of skill in the art is well aware, kits and methods for carrying out metabolic assays are commercially available. For example, 2-(N-(7-Nitrobenz-2-oxa-1,3-diazol-4-yl)Amino)-2-Deoxyglucose (2-NBDG), ATP Determination Kit, AMPLEX® Red Galactose/Galactose Oxidase Assay Kit, AMPLEX® Red Glucose/Glucose Oxidase Assay Kit, AMPLEX® Red Glutamic Acid/Glutamate Oxidase Assay Kit, AMPLEX® Red Hydrogen Peroxide/Peroxidase Assay Kit, AMPLEX® Red Monoamine Oxidase Assay Kit, AMPLEX® Red Neuraminidase (Sialidase) Assay Kit, AMPLEX® Red Phosphatidylcholine-Specific Phospholipase C Assay Kit, AMPLEX® Red Sphingomyelinase Assay kit, AMPLEX® Red Uric Acid/Uricase Assay Kit, AMPLEX® Red Xanthine/Xanthine Oxidase Assay Kit, THIOLTRACKER™ Violet (Glutathione Detection Reagent), THIOLTRACKER™ Violet (Glutathione Detection Reagent), and VYBRANT® Cell Metabolic Assay Kit from Invitrogen; Adenosine 5'-triphospahte (ATP) Luminescence Assay Kit (ENLITEN® from Promega; ATPLITE™ from PerkinElmer Life Sciences; ATP Bioluminescence Assay kit HS II from Boehringer Mannheim, Germany; Adenosine 5'-triphosphate (ATP) Luminescence Assay Kit from EMD Millipore; Reactive Oxygen Species (ROS) Assays from Cell BioLabs, Inc.; Cellular Reactive Oxygen Species Detection Assay Kit from ABCAM®; hROS Detection Kit from Cell Technology, Inc.; and ABTS Antioxidant Assay Kit, ORAC Antioxidant Assay Kit, OxiSelect HORAC Activity Assay Kit, OxiSelect In vitro ROS/RNS Assay Kit (Green Fluorescence), OxiSelect Intracellular ROS Assay Kit (Green Fluorescence), OxiSelect ORAC Activity Assay Kit, OxiSelect Total Antioxidant Capacity (TAC) Assay Kit, and Total Antioxidant Capacity Assay Kit from BioCat.

In some embodiments, microbes isolated from or remained bound on microbe-targeting article can be labeled with nucleic acid barcodes for subsequent detection and/or multiplexing detection. Nucleic acid barcoding methods for detection of one or more analytes in a sample are well known in the art.

In other embodiments, the captured microbe can be analyzed and/or detected in the capture chamber or capture and visualization chamber of a rapid microbe diagnostic device described in the Int. Pat. App. No. Int. Pat. App. No. WO 2011/091037, filed Jan. 19, 2011. Alternatively, the captured microbe can be recovered (i.e., removed) and analyzed and/or detected.

In some embodiments, the captured microbe is recovered and analyzed and/or detected using a particle on membrane assay as described in U.S. Pat. No. 7,781,226, content of which is incorporated herein by reference. A particle on membrane assay as described in U.S. Pat. No. 7,781,226 can be operably linked with a rapid microbe diagnostic device of the Int. Pat. App. No. Int. Pat. App. No. WO 2011/091037 to reduce the number of sample handling steps, automate the process and/or integrate the capture, separation and analysis/detection steps into a microfluidic device.

In some embodiments, microbe capture, separation and analysis can be done using a hybrid microfluidic SPR and molecular imagining device as described in U.S. Pat. App. Pub. No. US 2011/0039280.

In some embodiments, the microbe capture, separation and analysis using the microbe-targeting molecules disclosed herein can be done by an assay or device described, for example, in PCT Application No. PCT/US2011/021603 filed Jan. 19, 2011, No. PCT/US2012/047201 filed Jul. 18, 2012, and No. PCT/US2013/028409 filed Feb. 28, 2013, and US Provisional Application No. 61/788,570 filed Mar. 15, 2013, No. 61/772,436 filed Mar. 4, 2013, No. 61/673,071 filed Jul. 18, 2013, and No. 61/772,360 filed Mar. 4, 2013, contents of all of which are incorporated herein by reference.

In some embodiments, the processes or assays described herein can detect the presence or absence of a microbe and/or identify a microbe in a test sample in less than 24 hours, less than 12 hours, less than 10 hours, less than 8 hours, less than 6 hours, less than 4 hours, less than 3 hours, less than 2 hours, less than 1 hour, or lower. In some embodiments, the processes or assays described herein can detect the presence or absence of a microbe and/or identify a microbe in a test sample in less than 6 hours, less than 4 hours, less than 3 hours, less than 2 hours, less than 1 hour, or lower.

Optional Additional Analyses or Treatment—Culturing:

In some embodiments of any aspects described herein, the assay or process can further comprise culturing any microbe bound on the microbe-targeting article (e.g., microbe-targeting microparticles) for a period of time. In such embodiments, the microbe bound on the microbe-targeting article can expand in population by at least about 10% after culturing for a period of time.

In some embodiments, the microbe bound on the microbe-targeting article (e.g., microbe-targeting microparticle) can be cultured for a period of time, e.g., at least about 15 mins, at least about 30 mins, at least about 1 hour, at least about 2 hours, at least about 3 hours, at least about 6 hours, at least about 9 hours, at least about 12 hours, at least about 18 hours, at least about 24 hours or longer. In some embodiments, the microbe bound on the microbe-targeting article can be cultured for at least about 30 mins to at least about 3 hours.

In some embodiments, the number of microbes bound on the microbe-targeting article after culturing for a certain period of time can be increased or expanded by at least about 30%, at least about 40%, at least about 50%, at least about 60%, at least about 70%, at least about 80%, at least about 90%, at least about 100%, as compared to the number of the microbes originally bound on the microbe-targeting article. In some embodiments, the number of microbes bound on the microbe-targeting article after culturing for a certain period of time can be increased or expanded by at least about 1.5-fold, at least about 2-fold, at least about 3-fold, at least about 4-fold, at least about 5-fold, at least about 10-fold, at least about 50-fold, at least about 100-fold, at least about 500-fold, at least about 1000-fold, at least about 10000-fold, at least about 100000-fold, as compared to the number of the microbes originally bound on the microbe-targeting article.

In some embodiments, the microbes bound on the microbe-targeting articles can be cultured on a microbe-compatible culture medium, e.g., plated on an agar plate or cultured in LB broth. One of skill in the art will readily recognize microbial culture techniques, including, but not limited to, the use of incubators and/or equipment used to provide a gentle agitation, e.g., rotator platforms, and shakers, if necessary, e.g., to prevent the cells from aggregation without subjecting them to a significant shear stress and provide aerial agitation.

The microbes can remain bound on the microbe-article during detection or additional analyses described herein or they can be detached, eluted off or removed from a microbe-targeting article prior to detection or additional analyses described herein. In some embodiments where the bound microbes are desired to be detached, eluted off or removed from a microbe-targeting article, the microbe-binding molecules of the microbe-targeting article can be further contacted with a low pH buffer, e.g., a pH buffer less than 6, less than 5, less than 4, less than 3, less than 2, less than 1 or lower. In some embodiments, a low pH buffer that does not cause precipitation of a chelating agent, if present, can be used. In one embodiment, a low pH buffer can be arginine. In another embodiment, a low pH buffer can be pyrophosphate.

In some embodiments of any aspects described herein, the microbe-binding molecules of the microbe-targeting article can be further contacted with a low pH buffer and a chelating agent. In some embodiments, the contact of the microbe-binding molecules of the microbe-targeting article with the low pH buffer and the chelating agent can be concurrent or sequentially. In one embodiment, the microbe-binding molecules of the microbe-targeting substrate can be further contacted with arginine (e.g., 2 M) with EDTA or EGTA at pH 4.4.

The isolated microbes can then be used for analyses described earlier or additional treatment, e.g., expansion in culture, antibiotic sensitivity testing, sequencing and/or DNA or RNA analysis.

Optional Additional Analyses or Treatment-Antibiotic Sensitivity or Susceptibility Testing:

In some embodiments of any aspects described herein, the process or assay described herein can further comprise subjecting the microbes bound on the microbe-targeting article or the expanded cultures of microbes isolated from the microbe-targeting article to one or more antibiotics. The response of the microbe to an antibiotic can then be evaluated with any known methods in the art, e.g., by measuring the viability of microbes. Thus, an appropriate antibiotic can be identified for treatment of an infection caused by a microbe, even though the specific species of the microbe bound onto the microbe-targeting substrate is initially unknown. Additional details for use of engineered microbe-targeting molecules described herein in antibiotic sensitivity testings can be found, e.g., in U.S. Prov. App. Nos. 61/604,878 filed Feb. 29, 2012 and 61/647,860 filed May 16, 2012, and PCT Application No. PCT/US2013/028409 filed Feb. 28, 2013, content of all of which is incorporated herein by reference in their entireties.

Any processes or steps described herein can be performed by a module or device. While these are discussed as discrete processes, one or more of the processes or steps described herein can be combined into one system for carrying out the assays of any aspects described herein.

Exemplary Embodiments of Methods for Diagnosing or Locating a Microbial Infection or Contamination In general, embodiments of the assays or processes of any aspects described herein can be used to detect the presence or absence of a microbe or microbial matter in a test sample or in situ (e.g., where the microbe actually resides, e.g., in a water reservoir or on a working surface). For example, in some embodiments, a test sample, e.g., obtained from a subject or an environmental source, or an environmental surface can be contacted with engineered microbe-binding molecules or engineered microbe-binding articles described herein, such that any microbes, if present, in the test sample or environmental surface can be captured by the engineerd microbe-binding molecules or engineered microbe-binding articles e.g., using any embodiments of the exemplary process described above. In some embodiments, the captured microbes bound on the engineered microbe-binding molecules or microbe-binding articles can then be subjected to different analyses as described above, e.g., for identifying a microbe genus or species such as by immunoassay (e.g., using antibodies to a specific microbe), mass spectrometry, PCR, etc. In alternative embodiments where the engineered microbe-binding molecules comprise an imaging agent (e.g., a bubble, a liposome, a sphere, a diagnostic contrast agent or a detectable label described herein), the binding of the microbes to the engineered microbe-binding molecules can be detected in situ for identification of localized microbial infection or contamination, and also allow localized treatment of the infection or contamination.

In some embodiments, the assays or processes described herein can be used to diagnose or locate a microbial infection in situ in a subject. For example, engineered microbe-targeting microbeads comprising an imaging agent (e.g., the engineered microbe-targeting microbeads can be linked to an imaging agent, e.g., a bubble, a liposome, a sphere, a diagnostic contrast agent or a detectable label described herein) can be administered to a subject, either systemically (e.g., by injection), or locally. In such embodiments, the engineered microbe-targeting microbeads comprising an imaging agent can be used to identify and/or localize pockets of localized microbial infection (e.g., in a tissue) in the subject and optionally allow localized treatment of the microbial infection, which is described in the section "Exemplary Compositions and Methods for Treating and/or Preventing a Microbial Infection" below.

For example, there is a strong need for more rapid and/or effective diagnostic methods for distinguishing gram-positive microbe from gram-negative microbes, which can permit physicians to initiate an appropriate drug therapy early on, rather than starting with a sub-optimal or a completely ineffective antibiotic. A delay in treatment of a microbial infection can significantly affect the treatment outcome, and can be sometimes fatal.

Thus, in some embodiments, the assays or processes described herein can be used to distinguish a protein gram-positive microbe from gram-negative microbe in a test sample.

Accordingly, exemplary methods of determining the presence or absence of a gram-possitive microbe nfection in a subject are also provided herein. For example, the method can comprise contacting at least a first volume or portion of a test sample with a microbe-targeting molecule or article described herein and detecting binding of a microbe.

In some embodiments, the method can further comprise contacting at least a second volume or portion of the test sample with at least one second microbe-targeting molecule r a carrier scaffold conjugated to the same, wherein the second microbe-targeting molecule comprises at least one first domain wherein the CRP domain is replaced by a microbe-binding domain of microbe-binding domain protein which is not CRP. Thus, the second microbe-targeting molecule comprises at least one first domain comprising at least a portion of a microbe-binding domain of a microbe-binding protein, wherein the microbe-binding protein is not a CRP; a second domain, as described in this disclosure; and a linker conjugating the first and the second domains. Microbe-binding domains that do not comprise CRP are described elsewhere in the disclosure. Exemplary second microbe-targeting molecules are described, for example, in PCT Application No. PCT/US2011/021603 filed Jan. 19, 2011 and No. PCT/US2012/047201, filed Jul. 18, 2012, and U.S. Provisional Application No. 61/691,983 filed Aug. 22, 2012, contents of all of whihc are incorporated herein by reference in their entireties. In some embodiments, the second microbe-targeting molecule comprises an amino acid sequence selected from the group consisting of SEQ ID NOs: 8, 9, 11, 12, and 23-27.

Generally, detecton of binding with the CRP comprising microbe-targeting molecules but not with the second second microbe-targeting molecule can be indicative of presence of a gram-positive microbe in the sample. Detection of binding with the second second microbe-targeting molecule but not with the CRP comprising microbe-targeting molecules can be indicative of presence of a gram-negative microbe in the sample. Detection of binding with the the CRP comprising microbe-targeting molecules and the second second microbe-targeting molecule but not with the CRP comprising microbe-targeting molecules can be indicative of presence of a gram-negative microbe in the sample or both a gram-negative microbe and a gram-positive microbe in the sample.

In some embodiments, the method can further comprise administering or prescribing to the subject an antimicrobial agent when the subject is detected with an infection. Some exemplary antimicrobial agents include, but are not limited to, penicillin, methicillin, nafcillin, oxacillin, cloxacillin, dicloxacillin, flucloxacillin, vancomycin, and any combinations thereof.

Without wishing to be bound by theory, some embodiments of the engineered microbe-binding molecules can be used to opsonize a microbe, which is then cleared out by an innate immune response. In some embodiments, the microbe-targeting molecules can be a more potent opsonin of a microbe. Accordingly, in some embodiments, when the subject is diagnosed with a microbial infection using the methods described herein, the subject can be administered or prescribed with a composition comprising at least one engineered microbe-binding molecule described herein. Without limitations, the methods of any aspects described herein can be used to diagnose a microbe that is resistant to at least one, at least two, at least three, at least four or more antibiotics.

In some embodiment, the assay disclosed herein can be performed using a "dipstick" format. By way of example only, a microbe-binding dipstick or test strip can be brought into contact with a test sample (e.g., a blood sample) from a patient or a subject, and incubated for a period of time, e.g., at least about 15 seconds, at least about 30 seconds, at least about 1 min, at least about 2 mins, at least about 5 mins, at least about 10 mins, at least about 15 mins, at least about 30 mins, at least about 1 hour or more. In some embodiments, the incubated dipstick or test strip can then be incubated in a blocking agent (e.g., BSA, normal serum, casesin, non-fat dry milk, and/or any commercially-available blocking agents to minimize non-specific binding). Depending on different embodiments of the engineered microbe-targeting molecules, in some embodiments, the microbe-binding dipstick or test strip after contact with a test sample (e.g., a blood sample) can be further contacted with at least one additional agent to facilitate detection of pathogen, and/or to increase specificity of the pathogen detection. For example, some embodiments of the dipstick or test strip after contact with a test sample (e.g., a blood sample) can be further contacted with a detectable label that is conjugated to a molecule that binds to a microbe and/or microbial matter. Examples of such molecules can include, but are not limited to, one or more embodiments of the engineered microbe-targeting molecule described herein, an antibody specific for the microbes or pathogens to be detected, a protein, a peptide, a carbohydrate or a nucleic acid that is recognized by the microbes or pathogens to be detected, and any combinations thereof.

In some embodiments, the readout of the microbe-binding dipsticks and/or test strips can be performed in a system or device, e.g., a portable device. The system or device can display a signal indicating the presence or the absence of a microbial infection in a test sample, and/or the extent of the microbial infection.

In one embodiment, the assay can be used for detecting or imaging a nidus of infection in vivo. For example, a subject can be administered a microbe-targeting molecule disclsoed herein, wherein the microbe-targeting molecule comprises a detectable label; and scanning the subject using diagnostic imaging. Without limitations, the diagnostic imaging is selected from the group consisting of radiography, magnetic resonance imaging (MRI), Positron emission tomography (PET), Single-photon emission computed tomography (SPECT, or less commonly, SPET), Scintigraphy, ultrasound, CAT scan, photoacoustic imaging, thermography, linear tomography, poly tomography, zonography, orthopantomography (OPT or OPG), computed Tomography (CT) or Computed Axial Tomography (CAT scan), and any combinations thereof.

Exemplary Compositions and Methods for Treating and/or Preventing a Microbial Infection The binding of microbes to engineered microbe-targeting molecules can facilitate isolation and removal of microbes and/or microbial matter from an infected area. Accordingly, another aspect provided herein relate to compositions for treating and/or preventing a microbial infection or microbial contamination comprising one or more engineered microbe-targeting molecules or microbe-targeting substrates (e.g., microbe-targeting magnetic microbeads) described herein.

In some embodiments, the composition can further comprise at least one second microbe-targeting molecule, wherein the second microbe-targeting molecule comprises at least one first domain wherein the CRP domain is replaced by a microbe-binding domain of microbe-binding domain protein which is not CRP. Thus, the second microbe-targeting molecule comprises at least one first domain comprising at least a portion of a microbe-binding domain of a microbe-binding protein, wherein the microbe-binding protein is not a CRP; a second domain, as described in this disclosure; and a linker conjugating the first and the second domains. Microbe-binding domains that do not comprise CRP are described elsewhere in the disclosure. Exemplary second microbe-targeting molecules are described, for example, in PCT Application No. PCT/US2011/021603 filed Jan. 19, 2011 and No. PCT/US2012/047201, filed Jul. 18, 2012, and U.S. Provisional Application No. 61/691,983 filed Aug. 22, 2012, contents of all of whihc are incorporated herein by reference in their entireties. In some embodiments, the second microbe-targeting molecule comprises an amino acid sequence selected from the group consisting of SEQ ID NOs: 8, 9, 11, 12, and 23-27

In some embodiments, the composition can be formulated for treating and/or preventing a microbial infection or a microbial contamination present in an environmental surface. The term "environmental surface" as used herein refers to any surface and/or body of an environment or an object. The environmental object can be a non-living object or a living object, e.g., a botanical plant. Examples of an environmental surface can include, but is not limited to, a medical device, an implantable device, a surface in a hospital or clinic (e.g., an operating room or an intensive-care unit), a machine or working surface for manufacturing or processing food or pharmaceutical products (e.g., drugs, therapeutic agents or imaging agents), a cell culture, a water treatment plant, a water reservoir and a botanical plant.

In some embodiments, the composition can be formulated for treating and/or preventing microbial infection in a body fluid of a subject, e.g., blood. While in some embodiments, the engineered microbe-targeting molecules of the composition described herein can capture microbes and/or microbial matter in a circulating body fluid, e.g., blood, in other embodiments, the engineered microbe-targeting molecules can opsonize a microbe and/or microbial matter such that the microbe and/or microbial matter can be recognized by an innate immune system for clearance.

Alternatively, the engineered microbe-targeting molecules can localize a microbe and can thus prevent it from spreading, e.g., deeper into a wound. In particular, the inventors have demonstrated that *S. aureus* can strongly bind to some embodiments of the engineered microbe-targeting molecules (e.g., microbe-binding magnetic microbeads) due to the presence of both carbohydrate patterns and protein A on its microbial surface capable of independent binding to the engineered microbe-targeting molecules. Thus, in some embodiments, the engineered microbe-targeting molecules can be used to localize a microbe load, which can then be easily removed from an infected area. In some embodiments, the microbead can be labeled for specific imaging of infected sites. For SPECT imaging the tracer radioisotopes typically used such as iodine-123, technetium-99m, xenon-133, thallium-201, and fluorine-18 can be used. Technetium 99m can be used for scintigraphic assay. Iodine-derived or other radioopaque contrast agents can also be incorporated in the beads for radiographic or CT-scan imaging. The use of paramagnetic or superparamagnetic microbeads can be used for magnetic resonance imaging as contrast agents to alter the relaxation times of atoms within a nidus of infection. In another embodiment, the microspheres can be fluorescently dyed and applied to a surgical wound to determine the extension of an infectious process. This can be useful for assisting the surgeon in distinguishing between infected and healthy tissues during debridement surgeries for osteomyelitis, cellulitis or fasciitis.

Accordingly, another aspect provided herein related to compositions for treating and/or preventing a microbial infection in a tissue of a subject. In some embodiments, the composition comprises at least one engineered microbe-targeting molecule as described herein. In some embodiments, the amount of the engineered microbe-targeting molecules and/or microbe-targeting substrates present in the composition is sufficient to reduce the growth and/or spread of the microbe in the tissue of the subject. The phrase "reducing the growth and/or spread of the microbe in the tissue" as used herein refers to reducing the number of colonies of the microbe and/or movement of the microbe in the tissue. In some embodiments, the engineered microbe-targeting molecule can capture and localize a microbe present in a tissue such that the number of colonies of the microbe in the tissue can be reduced by at least about 30%, at least about 40%, at least about 50%, at least about 60%, at least about 70%, at least about 80%, at least about 90%, at least about 95%, at least about 98%, up to and including 100%, as compared to in the absence of the engineered microbe-targeting molecule. In some embodiments, the engineered microbe-targeting molecule can capture and localize a microbe present in a tissue such that the number of colonies of the microbe in the tissue can be reduced by at least about 1.5-fold, at least about 2-fold, at least about 3-fold, at least about 4-fold, at least about 5-fold, at least about 6-fold, at least about 7-fold, at least about 8-fold, at least about 9-fold, at least about 10-fold, at least about 15-fold, at least about 20-fold or more, as compared to in the absence of the engineered microbe-targeting molecules. In one embodiment, the binding of the engineered microbe-targeting molecules with a microbe (e.g., *S. aureus*) reduces the number of colonies by at least about 4-fold to at least about 6-fold (e.g., at least about 5-fold), as compared to in the absence of the engineered microbe-targeting molecules, after a period of at least about 12 hours, at least about 16 hours or at least about 24 hours.

In other embodiments, the engineered microbe-targeting molecule can capture and localize a microbe present in a tissue such that the movement of the microbe within the tissue (e.g., in terms of a distance travelled deeper into the tissue and/or area of spread from the infected site) can be reduced by at least about 30%, at least about 40%, at least about 50%, at least about 60%, at least about 70%, at least about 80%, at least about 90%, at least about 95%, at least about 98%, up to and including 100%, as compared to in the absence of the engineered microbe-targeting molecule. In some embodiments, the engineered microbe-targeting molecule can capture and localize a microbe present in a tissue such that the movement of the microbe within the tissue (e.g., in terms of a distance travelled deeper into the tissue and/or area of spread from the infected site) can be reduced by at least about 1.5-fold, at least about 2-fold, at least about 3-fold, at least about 4-fold, at least about 5-fold, at least about 6-fold, at least about 7-fold, at least about 8-fold, at least about 9-fold, at least about 10-fold, at least about 15-fold, at least about 20-fold or more, as compared to in the absence of the engineered microbe-targeting molecule.

In some embodiments, the composition can further comprise at least one of an antimicrobial agent and a drug delivery vehicle. For example, in some embodiments, the composition can further comprise at least 1, at least 2, at least 3, at least 4, at least 5 or more antimicrobial agents. In some embodiments, the composition can further comprise one or a plurality of (e.g., 2, 3, 4, 5, 6, 7, 8, 9, 10, 20, 30, 40, 50, 60, 70, 80, 90, 100, 500, 1000 or more) delivery vehicles. In some embodiments, the composition can further comprise a combination of at least one (including at least 2, at least 3, at least 4, at least 5 or more) antimicrobial agent and at least one (including 1, 2, 3, 4, 5, 6, 7, 8, 9, 10, 20, 30, 40, 50, 60, 70, 80, 90, 100, 500, 1000 or more) drug delivery vehicle. As used herein, the term "drug delivery vehicle" generally refers to any material that can be used to carry an active agent to a target site. Examples of drug delivery vehicles includes, but are not limited to, a cell, a peptide particle, a polymeric particle, a dendrimer, a vesicle, a liposome, a hydrogel, a nucleic acid scaffold, an aptamer, and any combinations thereof, In some embodiments where a drug delivery vehicle is included, an engineered microbe-targeting molecule and/or an antimicrobial agent can be dispersed within (e.g., encapsulated or embedded in) a drug delivery vehicle and/or coated on a surface of the drug delivery vehicle.

In some embodiments where the composition includes at least one antimicrobial agent, the antimicrobial agent can be present as a separate entity from the engineered microbe-targeting molecule and/or it can be fused with at least one engineered microbe-targeting molecule, e.g., by genetic modification and/or chemical conjugation.

The term "antimicrobial agent" as used herein refers to any entity with antimicrobial activity, i.e. the ability to inhibit or reduce the growth and/or kill a microbe, e.g., by at least about 30%, at least about 40%, at least about 50%, at least about 75%, at least about 90% or more, as compared to in the absence of an antimicrobial agent. An antimicrobial agent can be, for example, but not limited to, a silver nanoparticle, a small molecule, a peptide, a peptidomimetics, an antibody or a fragment thereof, a nucleic acid, an enzyme (e.g., an antimicrobial metalloendopeptidase such as lysostaphin), an aptamer, a drug, an antibiotic, a chemical or any entity that can inhibit the growth and/or kill a microbe. Examples of an antimicrobial peptide that can be included in the composition described herein, include, but are not limited to, mefloquine, venturicidin A, antimycin, myxothiazol, stigmatellin, diuron, iodoacetamide, potassium tellurite hydrate, aDL-vinylglycine, N-ethylmaleimide, L-allyglycine, diaryquinoline, betaine aldehyde chloride, acivcin, psicofuraine, buthionine sulfoximine, diaminopemelic acid, 4-phospho-D-erythronhydroxamic acid, motexafin gadolinium and/or xycitrin or modified versions or analogues thereof.

In some embodiments, an antimicrobial agent included in the composition can be an antibiotic. As used herein, the term "antibiotic" is art recognized and includes antimicrobial agents naturally produced by microorganisms such as bacteria (including *Bacillus* species), actinomycetes (including *Streptomyces*) or fungi that inhibit growth of or destroy other microbes, or genetically-engineered thereof and isolated from such natural source. Substances of similar structure and mode of action can be synthesized chemically, or natural compounds can be modified to produce semi-synthetic antibiotics. Exemplary classes of antibiotics include, but are not limited to, (1) β-lactams, including the penicillins, cephalosporins monobactams, methicillin, and carbapenems; (2) aminoglycosides, e.g., gentamicin, kanamycin, neomycin, tobramycin, netilmycin, paromomycin, and amikacin; (3) tetracyclines, e.g., doxycycline, minocycline, oxytetracycline, tetracycline, and demeclocycline; (4) sulfonamides (e.g., mafenide, sulfacetamide, sulfadiazine and sulfasalazine) and trimethoprim; (5) quinolones, e.g., ciprofloxacin, norfloxacin, and ofloxacin; (6) glycopeptides (e.g., vancomycin, telavancin, teicoplanin); (7) macrolides, which include for example, erythromycin, azithromycin, and clarithromycin; (8) carbapenems (e.g., ertapenem, doripenem, meropenem, and imipenem); (9) cephalosporins (e.g., cefadroxil, cefepime, and ceftobiprole); (10) lincosamides (e.g., clindamycin, and lincomycin); (11) monobactams (e.g., aztreonam); (12) nitrofurans (e.g., furazolidone, and nitrofurantoin); (13) Penicillins (e.g., amoxicillin, and Penicillin G); (14) polypeptides (e.g., bacitracin, colistin, and polymyxin B); and (15) other antibiotics, e.g., ansamycins, polymycins, carbacephem, chloramphenicol, lipopeptide, and drugs against mycobacteria (e.g., the ones causing diseases in mammals, including tuberculosis (*Mycobacterium tuberculosis*) and leprosy (*Mycobacterium leprae*), and any combinations thereof.

Additional exemplary antimicrobial agent can include, but are not limited to, antibacterial agents, antifungal agents, antiprotozoal agents, antiviral agents, and any mixtures thereof.

Exemplary antibacterial agents include, but are not limited to, Acrosoxacin, Amifloxacin, Amoxycillin, Ampicillin, Aspoxicillin, Azidocillin, Azithromycin, Aztreonam, Balofloxacin, lc Benzylpenicillin, Biapenem, Brodimoprim, Cefaclor, Cefadroxil, Cefatrizine, Cefcapene, Cefdinir, Cefetamet, Cefmetazole, Cefprozil, Cefroxadine, Ceftibuten, Cefuroxime, Cephalexin, Cephalonium, Cephaloridine, Cephamandole, Cephazolin, Cephradine, Chlorquinaldol, Chlortetracycline, Ciclacillin, Cinoxacin, Ciprofloxacin, Clarithromycin, Clavulanic Acid, Clindamycin, Clofazimine, Cloxacillin, Danofloxacin, Dapsone, Demeclocycline, Dicloxacillin, Difloxacin, Doxycycline, Enoxacin, Enrofloxacin, Erythromycin, Fleroxacin, Flomoxef, Flucloxacillin, Flumequine, Fosfomycin, Isoniazid, Levofloxacin, Mandelic Acid, Mecillinam, Metronidazole, Minocycline, Mupirocin, Nadifloxacin, Nalidixic Acid, Nifuirtoinol, Nitrofurantoin, Nitroxoline, Norfloxacin, Ofloxacin, Oxytetracycline, Panipenem, Pefloxacin, Phenoxymethylpenicillin, Pipemidic Acid, Piromidic Acid, Pivampicillin, Pivmecillinam, Prulifloxacin, Rufloxacin, Sparfloxacin, Sulbactam, Sulfabenzamide, Sulfacytine, Sulfametopyrazine, Sulphacetamide, Sulphadiazine, Sulphadimidine, Sulphamethizole, Sulphamethoxazole, Sulphanilamide, Sulphasomidine, Sulphathiazole, Temafioxacin, Tetracycline, Tetroxoprim, Tinidazole, Tosufloxacin, Trimethoprim, and phramceutically acceptable salts or esters thereof.

Exemplary antifungal agents include, but are not limited to, Bifonazole, Butoconazole, Chlordantoin, Chlorphenesin, Ciclopirox Olamine, Clotrimazole, Eberconazole, Econazole, Fluconazole, Flutrimazole, Isoconazole, Itraconazole, Ketoconazole, Miconazole, Nifuroxime, Tioconazole, Terconazole, Undecenoic Acid, and pharmaceutically acceptable salts or esters thereof.

Exemplary antiprotozoal agents include, but are not limited to, Acetarsol, Azanidazole, Chloroquine, Metronidazole, Nifuratel, Nimorazole, Omidazole, Propenidazole, Secnidazole, Sineflngin, Tenonitrozole, Temidazole, Tinidazole, and pharmaceutically acceptable salts or esters thereof.

Exemplary antiviral agents include, but are not limited to, Acyclovir, Brivudine, Cidofovir, Curcumin, Desciclovir, 1-Docosanol, Edoxudine, gQ Fameyclovir, Fiacitabine, Ibacitabine, Imiquimod, Lamivudine, Penciclovir, Valacyclovir, Valganciclovir, and pharmaceutically acceptable salts or esters thereof.

In some embodiments, the antimicrobial agent can include silver present in any form, e.g., a nanoparticle, a colloid, a suspension, powder, and any combinations thereof.

In some embodiments, the composition can be used to treat and/or prevent an infection caused by any microbe described herein. In one embodiment, the composition can be used to treat and/or prevent an infection caused by S. aureus.

In some embodiments, the composition can be used to treat and/or prevent an infection caused by a microbe that is resistant to at least one, at least two, at least three, at least four or more antimicrobial agents described herein. In one embodiment, the composition can be used to treat and/or prevent an infection caused by a microbe that is resistant to at least one, at least two, at least three, at least four or more antibiotics described herein. For example, in one embodiment, the composition can be used to treat and/or prevent an infection caused by methicillin-resistant S. aureus. In another embodiment, the composition can be used to treat and/or prevent an infection caused by vancomycin-resistant S. aureus.

Exemplary Antimicrobial Applications and/or Products:

The compositions described herein can be formulated or configured for different applications and/or products such antimicrobial products. In some embodiments, the composition described herein can be formulated as pharmaceutical compositions as described below, e.g., for therapeutic treatment as an antibiotic or antiseptic.

Wound Dressings:

In some embodiments, the composition described herein can be formulated for topical application, e.g., in wounds, lesions or abscesses. By way of example only, in some embodiments, a plurality of engineered microbe-targeting molecules can be blended with, attached to or coated on a wound dressing, for example, but not limited to, a bandage, an adhesive, a gauze, a film, a gel, foam, hydrocolloid, alginate, hydrogel, paste (e.g., polysaccharide paste), a spray, a granule and a bead.

In some embodiments, the wound dressing can include an additional antimicrobial agent described herein and/or an antiseptic chemical, e.g., boracic lint and/or medicinal castor oil.

In one embodiment, a plurality of engineered microbe-targeting molecules (e.g., microbe-targeting microparticles or microbe-targeting magnetic microbeads) can be attached or coated onto a wound dressing such as a bandage or an adhesive. When such wound dressing is applied to a wound or a lesion, any microbe (e.g., S. aureus) and/or microbial matter present in the wound or lesion can bind and localized to the wound dressing. Thus, regular replacement of the wound dressing can remove the microbe from the wound or lesion and thus prevent the microbe from moving deeper into the wound or lesion for further infection.

In one embodiment, a plurality of engineered microbe-targeting molecules (e.g., microbe-targeting microparticles or microbe-targeting magnetic microbeads) can be formulated into a wound dressing spray, which can be handy and used anywhere, e.g., during a transportation on an emergency vehicle. When the wound dressing spray containing the microbe-targeting magnetic microbeads, the microbe-targeting magnetic microbeads with bound microbes (e.g., S. aureus) can be removed from the wound with a magnetic field gradient before re-application of the spray.

Debridement Fluids or Sprays:

In some embodiments, the composition described herein can be formulated as part of a debridement fluid (optionally with suspended particulates that are abrasive to a lesion area). In some embodiments, the composition described herein can be formulated as part of a debridement spray. As used herein, the term "debridement" generally refers to complete or partial removal of a subject's dead, damaged, and/or infected tissue to improve the healing potential of the remaining healthy and/or non-infected tissue. By way of example only, a plurality of engineered microbe-targeting molecules (e.g., microbe-targeting microparticles or magnetic microbeads) can be suspended in a debridement fluid or spray, e.g., for use in an orthopedic procedure. The debridement fluid or spray containing the engineered microbe-targeting molecules can be applied to a lesion, an abscess or a wound, where the engineered microbe-targeting microparticles or magnetic microbeads can capture a microbe (e.g., S. aureus) and/or microbial matter from the lesion, abscess or wound. The debridement fluid or spray can then be removed from the applied site by vacuum, or suction. In some embodiments, the debridement fluid or spray containing the engineered microbe-targeting magnetic microbeads can be also removed from the applied site by exposing the applied site to a magnetic field gradient, which can pull or attract the applied microbe-targeting magnetic microbeads out from the applied site.

Medical Device Coating:

In some embodiments, the composition described herein can be coated on a surface of a medical device, e.g., a fluid delivery device such as hollow fibers, tubing or a spiral mixer in an extracorporeal device, or an implantable device such as an indwelling catheter, chip or scaffold. By way of example only, a plurality of engineered microbe-targeting molecules can be coated or conjugated to a surface of a fluid delivery device such that when a fluid (e.g., blood) flows through the fluid delivery device coated with engineered microbe-targeting molecules, any microbe (e.g., S. aureus) and/or microbial matter present in the fluid (e.g., blood) can be extracted therefrom, thus reducing the chance of a microbial infection. In another embodiment, a plurality of engineered microbe-targeting molecules coated on a medical device can comprise a detectable label, e.g., a "smart label" described herein, which can provide a detectable signal when any microbe (e.g., S. aureus) binds to a surface of the medical device, indicating that the medical device has been contaminated and/or infected, and thus is not appropriate for use or implantation.

The disclosure further provides methods for removing a microbe and/or microbial matter from a target area comprising contacting the target area with at least one composition described herein. As removal of a microbe and/or microbial matter from an infected area can treat and/or prevent a microbial infection or microbial contamination, provided herein also include methods for treating and/or preventing a microbial infection or microbial contamination in a target area. An exemplary method comprises contacting the target area with a composition comprising the engineered microbe-targeting molecule disclosed herein. The target area can be anywhere, e.g., an environmental surface or in a body of a subject (e.g., body fluid, and/or tissue). In some embodiments, the method comprises contacting the tissue of the subject with any embodiments of the composition described herein. In some embodiments, the tissue can have an open wound, a lesion or an abscess.

In one embodiment, the composition can be formulated for use as a wound dressing described herein.

As the engineered microbe-targeting molecules can localize a microbe (e.g., S. aureus) for easier removal of the microbe from the tissue, in some embodiments, the method can further comprise replacing the previously-applied composition in contact with the tissue with a fresh composition after a period of time. For example, depending on the condition of the microbial infection and/or specific compositions, the previously-applied composition can be replaced every 1 hour, every 2 hours, every 3 hours, every 4 hours, every 5 hours, every 6 hours, every 8 hours, every 10 hours, every 12 hours, every 16 hours, every 24 hours or longer.

In some embodiments, the method can further comprise administering an additional treatment to the tissue. Exemplary additional treatments can include, but are not limited to, a negative-pressure treatment, a vacuum-assisted debridement, administration of an antimicrobial agent, or any combinations thereof.

Without limitations, the compositions and/or methods of any aspects described herein can be used to treat and/or prevent a microbial infection or contamination in vitro, in situ or in vivo. In some embodiments, the compositions and/or methods of any aspects described herein can be used to treat and/or prevent a microbal infection or contamination in a fluid or on any surface, including, but not limited to, a tissue surface, a solid substrate surface, e.g., a medical device surface, an environmental surface, or food.

Additionally, in some embodiments where the composition comprises at least one engineered microbe-targeting molecule conjugated to a detectable label described herein or an imaging agent, can be used to image an infection in situ, e.g., in a subject or on an environmental surface.

The disclosure also provides a method for delivering or concentrating an anti-microbial agent at a nidus of infection. Generally, the nidus is contacted with a composition of comprising at least one microbe-targeting molecule disclosed herein and an anti-microbial agent. The microbial agent can be covalently or non-covalently linked with the microbe-targeting molecule. In some embodiments, the anti-microbial agent can be encompassed in a particle covalently or non-covalently lined with the microbe-targeting molecule.

In some embodiments, the composition further comprises at least one second microbe-targeting molecule, wherein the second microbe-targeting molecule comprises at least one first domain wherein the CRP domain is replaced by a microbe-binding domain of microbe-binding domain protein which is not CRP. Thus, the second microbe-targeting molecule comprises at least one first domain comprising at least a portion of a microbe-binding domain of a microbe-binding protein, wherein the microbe-binding protein is not a CRP; a second domain, as described in this disclosure; and a linker conjugating the first and the second domains. Microbe-binding domains that do not comprise CRP are described elsewhere in the disclosure. Exemplary second microbe-targeting molecules are described, for example, in PCT Application No. PCT/US2011/021603 filed Jan. 19, 2011 and No. PCT/US2012/047201, filed Jul. 18, 2012, and U.S. Provisional Application No. 61/691,983 filed Aug. 22, 2012, contents of all of whihc are incorporated herein by reference in their entireties. In some embodiments, the second microbe-targeting molecule comprises an amino acid sequence selected from the group consisting of SEQ ID NOs: 8, 9, 11, 12, and 23-27.

Pharmaceutical Compositions

Some embodiments of the engineered microbe-targeting molecules can be used for therapeutic purposes. For administration to a subject in need thereof, engineered microbe-targeting molecules described herein can be provided in pharmaceutically acceptable compositions. Accordingly, in yet another aspect, provided herein is a pharmaceutical composition comprising at least one engineered microbe-targeting molecule described herein, and a pharmaceutically acceptable carrier.

When the engineered microbe-targeting molecules are used as therapeutics in vivo, the second domain or the linker can be further modified to modulate the effector function such as antibody-dependent cellular cytotoxicity (ADCC) and complement-dependent cytotoxicity (CDC). By way of example only, the Fc region for use as a second domain can mediate ADCC and CDC. In ADCC, the Fc region can generally bind to Fc receptors on the surface of immune effector cells such as natural killers and macrophages, leading to the phagocytosis or lysis of a targeted cell. In CDC, the Fc region can generally trigger the complement cascade at the cell surface to kill the targeted cell. Accordingly, modulating effector functions can be achieved by engineering the Fc region to either increase or decrease their binding to the Fc receptors on the surface of the immune effector cells or the complement factors. For example, numerous mutations within a Fc region for modulating ADCC and CDC are well known to a skilled artisan, e.g., see Armour K L. et al. (1999) *Eur J Immmunol* 29: 2613-2624; Shields R L. et al. (2001) *J Biol Chem.* 276: 6591-6604; Idusogie E E. et al. (2001) *J Immunol.* 166: 2571-2575; Idusogie E E. et al. (2000) *J Immunol.* 155: 1165-1174; and Steurer W. et al. (1995) *J Immunol.* 155: 1165-1674. In one embodiment, the amino acid asparagine (N) at the residue 82 of the SEQ ID NO. 6 can be mutated to aspartic acid (D), e.g., to remove the glycosylation of Fc and thus, in turn, reduce ADCC and CDC functions.

In some embodiments, the pharmaceutical composition further comprises at least one second microbe-targeting molecule, wherein the second microbe-targeting molecule comprises at least one first domain wherein the CRP domain is replaced by a microbe-binding domain of microbe-binding domain protein which is not CRP. Thus, the second microbe-targeting molecule comprises at least one first domain comprising at least a portion of a microbe-binding domain of a microbe-binding protein, wherein the microbe-binding protein is not a CRP; a second domain, as described in this disclosure; and a linker conjugating the first and the second domains. Microbe-binding domains that do not comprise CRP are described elsewhere in the disclosure. Exemplary second microbe-targeting molecules are described, for example, in PCT Application No. PCT/US2011/021603 filed Jan. 19, 2011 and No. PCT/US2012/047201, filed Jul. 18, 2012, and U.S. Provisional Application No. 61/691,983 filed Aug. 22, 2012, contents of all of whihc are incorporated herein by reference in their entireties. In some embodiments, the second microbe-targeting molecule comprises an amino acid sequence selected from the group consisting of SEQ ID NOs: 8, 9, 11, 12, and 23-27.

Depending on the selected administration route, the compositions or preparations can be in any form, e.g., a tablet, a lozenge, a suspension, a free-flowing powder, an aerosol, and a capsule. The term "pharmaceutically acceptable," as used herein, refers to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

As used herein, the term "pharmaceutically acceptable carrier" refers to a pharmaceutically-acceptable material, composition or vehicle for administration of an active agent described herein. Pharmaceutically acceptable carriers include any and all solvents, dispersion media, coatings, antibacterial and antifungal agents, isotonic and absorption delaying agents, and the like which are compatible with the activity of the active agent and are physiologically acceptable to the subject. Some examples of materials which can serve as pharmaceutically-acceptable carriers include: (i) sugars, such as lactose, glucose and sucrose; (ii) starches, such as corn starch and potato starch; (iii) cellulose, and its derivatives, such as sodium carboxymethyl cellulose, methylcellulose, ethyl cellulose, microcrystalline cellulose and cellulose acetate; (iv) powdered tragacanth; (v) malt; (vi) gelatin; (vii) lubricating agents, such as magnesium stearate, sodium lauryl sulfate and talc; (viii) excipients, such as cocoa butter and suppository waxes; (ix) oils, such as peanut oil, cottonseed oil, safflower oil, sesame oil, olive oil, corn oil and soybean oil; (x) glycols, such as propylene glycol; (xi) polyols, such as glycerin, sorbitol, mannitol and polyethylene glycol (PEG); (xii) esters, such as ethyl oleate and ethyl laurate; (xiii) agar; (xiv) buffering agents, such as magnesium hydroxide and aluminum hydroxide; (xv) alginic acid; (xvi) pyrogen-free water; (xvii) isotonic saline; (xviii) Ringer's solution; (xix) ethyl alcohol; (xx) pH buffered solutions; (xxi) polyesters, polycarbonates and/or polyanhydrides; (xxii) bulking agents, such as polypeptides and amino acids (xxiii) serum component, such as serum albumin, HDL and LDL; (xxiv) C2-C12 alcohols, such as ethanol; and (xxv) other non-toxic compatible substances employed in pharmaceutical formulations. Wetting agents, coloring agents, release agents, coating agents, sweetening agents, flavoring agents, perfuming agents, preservative and antioxidants can also be present in the formulation. For compositions or preparations described herein to be administered orally, pharmaceutically acceptable carriers include, but are not limited to pharmaceutically acceptable excipients such as inert diluents, disintegrating agents, binding agents, lubricating agents, sweetening agents, flavoring agents, coloring agents and preservatives. Suitable inert diluents include sodium and calcium carbonate, sodium and calcium phosphate, and lactose, while corn starch and alginic acid are suitable disintegrating agents. Binding agents may include starch and gelatin, while the lubricating agent, if present, will generally be magnesium stearate, stearic acid or talc. If desired, the tablets may be coated with a material such as glyceryl monostearate or glyceryl distearate, to delay absorption in the gastrointestinal tract.

Pharmaceutically acceptable carriers can vary in a preparation described herein, depending on the administration route and formulation. The compositions and preparations described herein can be delivered via any administration mode known to a skilled practitioner. For example, the compositions and preparations described herein can be delivered in a systemic manner, via administration routes such as, but not limited to, oral, and parenteral including intravenous, intramuscular, intraperitoneal, intradermal, and subcutaneous. In some embodiments, the compositions and preparations described herein are in a form that is suitable for injection. In other embodiments, the compositions and preparations described herein are formulated for oral administration.

When administering parenterally, a composition and preparation described herein can be generally formulated in a unit dosage injectable form (solution, suspension, emulsion). The compositions and preparations suitable for injection include sterile aqueous solutions or dispersions. The carrier can be a solvent or dispersing medium containing, for example, water, cell culture medium, buffers (e.g., phosphate buffered saline), polyol (for example, glycerol, propylene glycol, liquid polyethylene glycol, and the like), suitable mixtures thereof. In some embodiments, the pharmaceutical carrier can be a buffered solution (e.g. PBS).

An oral composition can be prepared in any orally acceptable dosage form including, but not limited to, tablets, capsules, emulsions and aqueous suspensions, dispersions and solutions. Commonly used carriers for tablets include lactose and corn starch. Lubricating agents, such as magnesium stearate, are also typically added to tablets. For oral administration in a capsule form, useful diluents include lactose and dried corn starch. When aqueous suspensions or emulsions are administered orally, the active ingredient can be suspended or dissolved in an oily phase combined with emulsifying or suspending agents. If desired, certain sweetening, flavoring, or coloring agents can be added. Liquid preparations for oral administration can also be prepared in the form of a dry powder to be reconstituted with a suitable solvent prior to use.

The compositions can also contain auxiliary substances such as wetting or emulsifying agents, pH buffering agents, gelling or viscosity enhancing additives, preservatives, colors, and the like, depending upon the route of administration and the preparation desired. Standard texts, such as "REMINGTON'S PHARMACEUTICAL SCIENCE", 17th edition, 1985, incorporated herein by reference, may be consulted to prepare suitable preparations, without undue experimentation. With respect to compositions described herein, however, any vehicle, diluent, or additive used should have to be biocompatible with the active agents described herein. Those skilled in the art will recognize that the components of the compositions should be selected to be biocompatible with respect to the active agent. This will present no problem to those skilled in chemical and pharmaceutical principles, or problems can be readily avoided by reference to standard texts or by simple experiments (not involving undue experimentation).

In some embodiments, the compositions and preparations described herein can be formulated in an emulsion or a gel. Such gel compositions and preparations can be implanted locally to a diseased tissue region of a subject.

For in vivo administration, the compositions or preparations described herein can be administered with a delivery device, e.g., a syringe. Accordingly, an additional aspect described herein provides for delivery devices comprising at least one chamber with an outlet, wherein the at least one chamber comprises a pre-determined amount of any composition described herein and the outlet provides an exit for the composition enclosed inside the chamber. In some embodiments, a delivery device described herein can further comprise an actuator to control release of the composition through the outlet. Such delivery device can be any device to facilitate the administration of any composition described herein to a subject, e.g., a syringe, a dry powder injector, a nasal spray, a nebulizer, or an implant such as a microchip, e.g., for sustained-release or controlled release of any composition described herein.

In some embodiments of the products described herein, the microbe-targeting microparticles described herein itself can be modified to control its degradation and thus the release of active agents. In some embodiments, the engineered microbe-targeting molecules, microbe-targeting microparticles and/or microbe-targeting cells described herein can be combined with other types of delivery systems available and known to those of ordinary skill in the art. They include, for example, polymer-based systems such as polylactic and/or polyglycolic acids, polyanhydrides, polycaprolactones, copolyoxalates, polyesteramides, polyorthoesters, polyhydroxybutyric acid, and/or combinations thereof. Microcapsules of the foregoing polymers containing drugs are described in, for example, U.S. Pat. No. 5,075,109. Other examples include nonpolymer systems that are lipid-based including sterols such as cholesterol, cholesterol esters, and fatty acids or neukal fats such as mono-, di- and triglycerides; hydrogel release systems; liposome-based systems; phospholipid based—systems; silastic systems; peptide based systems; or partially fused implants. Specific examples include, but are not limited to, erosional systems in which the composition is contained in a form within a matrix (for example, as described in U.S. Pat. Nos. 4,452, 775, 4,675,189, 5,736,152, 4,667,014, 4,748,034 and -29 5,239,660), or diffusional systems in which an active component controls the release rate (for example, as described in U.S. Pat. Nos. 3,832,253, 3,854,480, 5,133,974 and 5,407, 686). The formulation may be as, for example, microspheres, hydrogels, polymeric reservoirs, cholesterol matrices, or polymeric systems. In some embodiments, the system may allow sustained or controlled release of the composition to occur, for example, through control of the diffusion or erosion/degradation rate of the formulation containing the composition. In addition, a pump-based hardware delivery system can be used to deliver one or more embodiments of the compositions or preparations described herein. Use of a long-term sustained release formulations or implants can be particularly suitable for treatment of some infections. Long-term release, as used herein, means that a formulation or an implant is made and arranged to deliver compositions or preparations described herein at a therapeutic level for at least 30 days, or at least 60 days. In some embodiments, the long-term release refers to a formulation or an implant being configured to deliver an active agent at a therapeutic level over several months.

Kits

Kits for capturing, detecting and/or determining the presence or absence of a microbe and/or microbial matter in a sample are also provided herein. In some embodiments, the kit can comprise: (a) one or more containers containing a population of engineered microbe-targeting molecules described herein; and (b) at least one reagent. In these embodiments, a user can generate their own microbe-targeting substrates by conjugating the provided engineered microbe-targeting molecules to their desired substrate, e.g., using any art-recognized conjugation chemistry and/or methods described herein. In such embodiments, the reagent can include, but is not limited to, a coupling agent for conjugation of engineered microbe-targeting molecules to a substrate. In some embodiments, the kit can further comprise one or more substrates (e.g., microbeads such as magnetic microbeads) to which the engineered microbe-targeting molecules described herein are conjugated. In such embodiments, a user can further modify the surface chemistry of the provided substrate prior to conjugation of the engineered microbe-targeting molecules to the substrate.

In other embodiments, the kit can provide microbe-targeting substrates that are ready for use. Accordingly, in these embodiments, the kit can comprise: (a) one or more microbe-targeting substrates described herein; and (b) at least one reagent. In some embodiments, the microbe-targeting substrate can include one or more microbe-binding dipsticks, e.g., as described herein. In other embodiments, the microbe-targeting substrate can include a population of microbe-targeting microbeads (including, but not limited to, polymeric microbeads and magnetic microbeads). In some embodiments, the microbe-targeting substrate can include a population of microbe-targeting magnetic microbeads. The microbe-targeting microbeads or microbe-targeting magnetic microbeads can be provided in one or more separate containers, if desired. In some embodiments, the population of the microbe-targeting microbeads or magnetic microbeads contained in one or more containers can be lyophilized.

In sme embodiments, a kit disclosed herein can further comprise at least one second microbe-targeting molecule or a second microbe-targeting molecule conjugated to a carrier scaffold, wherein the second microbe-targeting molecule comprises at least one first domain wherein the CRP domain is replaced by a microbe-binding domain of microbe-binding domain protein which is not CRP. Thus, the second microbe-targeting molecule comprises at least one first domain comprising at least a portion of a microbe-binding domain of a microbe-binding protein, wherein the microbe-binding protein is not a CRP; a second domain, as described in this disclosure; and a linker conjugating the first and the second domains. Microbe-binding domains that do not comprise CRP are described elsewhere in the disclosure. Exemplary second microbe-targeting molecules are described, for example, in PCT Application No. PCT/US2011/021603 filed Jan. 19, 2011, and No. PCT/US2012/047201, filed Jul. 18, 2012, contents of both of which are incorporated herein by reference in their entireties. In some embodiments, the second microbe-targeting molecule comprises an amino acid sequence selected from the group consisting of SEQ ID NOs: 8, 9, 11, 12, and 23-27

In some embodiments of any aspects of the kits described herein, the population of the microbeads or microbe-targeting microbeads can comprise at least one distinct subset of the microbeads or microbe-targeting microbeads, respectively. For example, each distinct subset of the microbeads or microbe-targeting microbeads can be provided in a separate container. In some embodiments, the distinct subset of the microbeads or microbe-targeting microbeads can have a size. In some embodiments, the distinct subset of microbe-targeting microbeads can comprise on their surfaces a different density of engineered microbe-targeting molecules from the rest of the population. In these embodiments, two or more subsets of the microbe-targeting microbes having different sizes and/or different coating density of the engineered microbe-binding molecules can be used to detect and differentiate microbes of different classes and/or sizes, e.g., employing the methods described herein. In some embodiments, the distinct subset of microbe-targeting substrates, e.g., microbe-targeting microbeads, can comprise a different carbohydrate recognition domain from the others.

In some embodiments of any aspects of the kits described herein, the substrates (e.g., microbeads) or microbe-targeting substrates (e.g., microbe-targeting microbeads) can further comprise a detection label. By way of example only, depending on the choice of detection methods, each distinct subset of the microbeads can comprise a unique detection label or the same detection label. For example, if each distinct subset of the microbe-targeting microbeads is used in a different sampling well, the same detection label can be used on the microbe-targeting microbeads. However, if it is desirable to detect multiple different microbe-targeting microbeads in the same well, it is preferably to have each distinct subset of microbe-targeting microbeads comprising a distinct detection label.

Detectable labels suitable for use in any kits provided herein include any composition detectable by spectroscopic, photochemical, biochemical, immunochemical, electrical, optical or chemical means. Any art-recognized detectable labels or the ones described herein can be included in the kits described herein.

Means of detecting such labels are well known to those of skill in the art and exemplary detection methods are described herein. For example, radiolabels can be detected using photographic film or scintillation counters, fluorescent markers can be detected using a photo-detector to detect emitted light. Enzymatic labels are typically detected by providing the enzyme with an enzyme substrate and detecting the reaction product produced by the action of the enzyme on the enzyme substrate, and calorimetric labels can be detected by visualizing the colored label.

In some embodiments of any aspects described herein, the kits can further comprise one or more containers containing a population of detectable labels, wherein the detectable label is conjugated to a molecule. In some embodiments, at least one of the containers can contain a distinct population of detectable labels.

In some embodiments, at least one of the containers can contain a distinct population of the molecule-detectable label conjugate as described earlier. The distinct population of the molecule-detectable label conjugate can contain a unique molecule with the detectable label same as others, or a conjugate comprising a distinct detectable label (e.g., a unique fluorescent molecule) and a distinct molecule. As each distinct detectable label can identify the associated protein, conjugates comprising a distinct detectable label associated with a distinct molecule can allow detecting in a single sample at least two or more distinct populations of the engineered microbe-targeting substrates (e.g., microbe-targeting magnetic microbeads); for example, each distinct population of the engineered microbe-targeting magnetic microbeads can bind to a distinct genus or species or type/size of a microbe. In alternative embodiments, the molecule-detectable label conjugates in each of the containers can comprise the same detectable label. For example, the detectable label can comprise an enzyme (e.g., horseradish peroxidase or alkaline phosphatase) that produces a color change in the presence of an enzyme substrate. In such embodiments, the kit can further comprise one or more containers containing an enzyme substrate that changes color in the presence of the enzyme.

In one embodiment, the microbe-targeting article provided in the kit can include a dipstick or test strip or membrane containing one or more engineered microbe-targeting molecules, e.g., microbe-binding dipstick or membrane described herein. In this embodiment, the kit can comprise 1, 2, 3, 4, 5, 6, 7, 8, 9, 10, 15, 20, 25, 50, 75, 100, 150, 200 or more microbe-binding dipsticks or test strips described herein. These kits comprising the microbe-binding dipsticks or test strips can be used as a diagnostic or probe for a microbe anywhere, e.g., at home, in clinics or hospitals, on emergency vehicles, in outdoor environments, in food processing plants, and anywhere in need of microbe capture and/or detection.

In some embodiments, each microbe-targeting article described herein, e.g., each microbe-binding dipstick or membrane, can be individually packaged to maintain their sterility. In some embodiments, two or more products (e.g., 2, 3, 4, 5, 6, 7, 8, 9, 10, 15, 20, 25, 50, or more products such as microbe-binding dipsticks or membranes) can be packaged into one single unit. In such embodiments, users can sterilize any unused products after opening, e.g., with UV radiation, high temperature, gamma-radiation, ethylene oxide sterilization or any other known methods that would not significantly affect the activity of the engineered microbe-targeting molecules for microbe detection.

In other embodiments, the microbe-targeting article provided in the kit can include a population of microbe-targeting microparticles. In some embodiments, the microbe-targeting microparticles can be lyophilized.

Depending on the configuration/combination of the molecule-detectable label conjugates provided in the kit, different populations of the microbe-targeting microparticles can be mixed together with a test sample in a single reaction, or different populations each can be applied separately to different aliquots of the same test sample. After contacting the test sample with the microbe-targeting microbeads or magnetic microbeads, any microbes or pathogens recognized by the microbe-targeting molecules will bind to the microbe-targeting microparticles.

In some embodiments, the kit can further comprise at least one blood collection container or any equivalent sample container or chamber, including at least 1, at least 2, at least 3, at least 4, at least 5, at least 6, at least 7, at least 8, at least 9, at least 10, at least 15, at least 20 blood collection containers or equivalent sample containers or chambers. In some embodiments, the population of the microbe-targeting microbeads or magnetic microbeads can be pre-loaded in at least one blood collection container. In some embodiments, the blood collection container can further comprise an anti-coagulant agent described herein. In some embodiments, a blood sample can be directly added to such blood collection container containing a population of the microbe-targeting articles for carrying out a microbe detection assay, e.g., as described herein. An ordinary artisan will readily appreciate that some embodiments of the microbe-targeting articles (without magnetic properties) described herein can also be applicable for the assay. For example, instead of using a magnet to collect the microbe-targeting magnetic microparticless after contact with a test sample (e.g., a blood sample), the microbe-targeting article (without magnetic properties) can also be collected, e.g., by filtration, centrifugation or any other methods known in the art.

In some embodiments where the kits comprise microbe-targeting magnetic microbeads, the kits can further comprise a magnet adapted for use with the assay for isolation of the microbe-targeting magnetic microbeads from a test sample. For example, if the assay is carried out in a blood collection tube, the magnet can be adapted for use with the blood collection tube, e.g., a magnet can be designed to be a magnet collar surrounding the blood collection tube to immobilize or isolate the microbe-targeting magnetic microbeads from a test sample or an assay buffer.

In any aspects of the kits provided herein, the kits can further comprise a portable readout machine or device, e.g., to determine and display the signal produced from the assay performed with the kit. For example, the readout machine or device can detect a colorimetric signal and/or a fluorescent signal produced from the assay of pathogen detection performed with the kits described herein.

In any aspects of the kits described herein, the kits can further include a reference for comparison with a readout determined from a test sample. An exemplary reference can be a strip or a chart showing different colors corresponding to various extents or degrees of a microbial infection.

Depending on different embodiments of the engineered microbe-targeting molecules and/or products provided in the kits, some embodiments of any aspects of the kits described herein can further comprise an additional agent. For example, in some embodiments where the engineered microbe-targeting molecules present on the substrate are unlabeled, the kit can further comprise one or more containers containing a population of detectable labels described earlier, each of which is conjugated to a targeting agent specific for a microbe, e.g., without limitations, one or more embodiments of an engineered microbe-targeting molecule or a fragment thereof, an antibody specific for at least one microbe (e.g., antibodies specific for Gram-positive microbes such as anti-LTA antibodies, antibodies specific for Gram-negative microbes such as anti-LPS antibodies, or antibodies specific for fungus, and any combinations thereof). The use of an additional targeting agent specific for a microbe conjugated to a detectable label can not only facilitate the detection of microbes or pathogens, but can also increase the specificity of the detection for a microbe or a pathogen.

In any aspects of the kits provided herein, when the detection label includes an enzyme (e.g., horseradish peroxidase, alkaline phosphatase and any others commonly used for colorimetric detection), the kits can further comprise one or more containers containing an enzyme substrate that produces a color change in the presence of the enzyme. One of skill in the art can readily recognize an appropriate enzyme substrate for any art-recognized enzymes used for colorimetric detection. By way of example only, an exemplary substrate for alkaline phosphatase can include BCIP/NBT or PNPP (p-Nitrophenyl Phosphate, Disodium Salt); an exemplary substrate for horseradish peroxidase can include TMB.

In any aspects of the kits provided herein, the at least one reagent can be a wash buffer, a dilution buffer, a stop buffer, e.g., to stop the color development, a buffer solution containing a chelating agent described herein, or any combinations thereof. In one embodiment, at least one of the reagents provided in the kit can include at least one buffered solution containing a chelating agent. The chelating agent can be used to chelate any ions (e.g., divalent ions) present in the test samples or assay buffer, e.g., for inhibiting calcium-dependent binding of certain microbes, but not others, to some embodiments of the microbe-binding molecules described herein. Accordingly, such kit can be used to distinguish one microbe (e.g., *S. aureus*) from another (e.g., *E. coli*) in a test sample, e.g. employing some embodiments of the method described herein.

In any aspects of the kits provided herein, the kits can further comprise at least one microtiter plate, e.g., for performing the reaction and the detection.

In addition to the above mentioned components, any embodiments of the kits described herein can include informational material. The informational material can be descriptive, instructional, marketing or other material that relates to the methods described herein and/or the use of the aggregates for the methods described herein. For example, the informational material can describe methods for using the kits provided herein to perform an assay for pathogen or microbe capture and/or detection. The kit can also include an empty container and/or a delivery device, e.g., which can be used to deliver a test sample to a test container.

The informational material of the kits is not limited in its form. In many cases, the informational material, e.g., instructions, is provided in printed matter, e.g., a printed text, drawing, and/or photograph, e.g., a label or printed sheet. However, the informational material can also be provided in other formats, such as Braille, computer readable material, video recording, or audio recording. In another embodiment, the informational material of the kit is a link or contact information, e.g., a physical address, email address, hyperlink, website, or telephone number, where a user of the kit can obtain substantive information about the formulation and/or its use in the methods described herein. Of course, the informational material can also be provided in any combination of formats.

In some embodiments, the kit can contain separate containers, dividers or compartments for each component and informational material. For example, each different component can be contained in a bottle, vial, or syringe, and the informational material can be contained in a plastic sleeve or packet. In other embodiments, the separate elements of the kit are contained within a single, undivided container. For example, a collection of the magnetic microbeads is contained in a bottle, vial or syringe that has attached thereto the informational material in the form of a label.

In general, the kits described herein can be used to separate, remove, and/or detect a microbe present in a test sample. In some embodiments, the kits can be used to differentiate between different microbe species, classes, and/or sizes, by employing the methods and/or assays described herein. By way of example only, some embodiments of the kits can be used to detect the presence or absence of a gram-positive microbe in a test sample. Accordingly, some embodiments of the kits described herein can be used to detect or determine the presence or absence of at least one gram-positive microbe in a test sample.

In some embodiments, the kits described herein can be used to screen a pharmaceutical product (e.g., a drug, a therapeutic agent, or an imaging agent), or a medical device (including, but not limited to, implantable devices) for the presence or absence of microbial matter (including, but not limited to, endotoxins secreted by a microbe).

Test Sample

In accordance with various embodiments described herein, a test sample or sample, including any fluid or specimen (processed or unprocessed), that is suspected of comprising a microbe and/or microbial matter can be subjected to an assay or method, kit and system described herein. The test sample or fluid can be liquid, supercritical fluid, solutions, suspensions, gases, gels, slurries, and combinations thereof. The test sample or fluid can be aqueous or non-aqueous.

In some embodiments, the test sample can be an aqueous fluid. As used herein, the term "aqueous fluid" refers to any flowable water-containing material that is suspected of comprising a microbe and/or microbial matter.

In some embodiments, the test sample can include a biological fluid obtained from a subject. Exemplary biological fluids obtained from a subject can include, but are not limited to, blood (including whole blood, plasma, cord blood and serum), lactation products (e.g., milk), amniotic fluids, sputum, saliva, urine, semen, cerebrospinal fluid, bronchial aspirate, perspiration, mucus, liquefied feces, synovial fluid, lymphatic fluid, tears, tracheal aspirate, and fractions thereof. In some embodiments, a biological fluid can include a homogenate of a tissue specimen (e.g., biopsy) from a subject.

In some embodiments, the biological fluid sample obtained from a subject, e.g., a mammalian subject such as a human subject or a domestic pet such as a cat or dog, can contain cells from the subject. In other embodiments, the biological fluid sample can contain non-cellular biological material, such as non-cellular fractions of blood, saliva, or urine, which can be used to measure plasma/serum biomarker expression levels.

The biological fluid sample can be freshly collected from a subject or a previously collected sample. In some embodiments, the biological fluid sample used in the assays and/or methods described herein can be collected from a subject no more than 24 hours, no more than 12 hours, no more than 6 hours, no more than 3 hours, no more than 2 hours, no more than 1 hour, no more than 30 mins or shorter.

In some embodiments, the biological fluid sample or any fluid sample described herein can be treated with a chemical and/or biological reagent described herein prior to use with the assays and/or methods described herein. In some embodiments, at least one of the chemical and/or biological reagents can be present in the sample container before a fluid sample is added to the sample container. For example, blood can be collected into a blood collection tube such as VACU-TAINER®, which has already contained heparin. Examples of the chemical and/or biological reagents can include, without limitations, surfactants and detergents, salts, cell lysing reagents, anticoagulants, degradative enzymes (e.g., proteases, lipases, nucleases, collagenases, cellulases, amylases), and solvents such as buffer solutions.

In some embodiments, the test sample can include a fluid or specimen obtained from an environmental source, e.g., but not limited to, water supplies (including wastewater), ponds, rivers, reservoirs, swimming pools, soils, food processing and/or packaging plants, agricultural places, hydrocultures (including hydroponic food farms), pharmaceutical manufacturing plants, animal colony facilities, and any combinations thereof.

In some embodiments, the test sample can include a fluid (e.g., culture medium) from a biological culture. Examples of a fluid (e.g., culture medium) obtained from a biological culture includes the one obtained from culturing or fermentation, for example, of single- or multi-cell organisms, including prokaryotes (e.g., bacteria) and eukaryotes (e.g., animal cells, plant cells, yeasts, fungi), and including fractions thereof. In some embodiments, the test sample can include a fluid from a blood culture. In some embodiments, the culture medium can be obtained from any source, e.g., without limitations, research laboratories, pharmaceutical manufacturing plants, hydrocultures (e.g., hydroponic food farms), diagnostic testing facilities, clinical settings, and any combinations thereof.

In some embodiments, the test sample can include a media or reagent solution used in a laboratory or clinical setting, such as for biomedical and molecular biology applications. As used herein, the term "media" refers to a medium for maintaining a tissue, an organism, or a cell population, or refers to a medium for culturing a tissue, an organism, or a cell population, which contains nutrients that maintain viability of the tissue, organism, or cell population, and support proliferation and growth.

As used herein, the term "reagent" refers to any solution used in a laboratory or clinical setting for biomedical and molecular biology applications. Reagents include, but are not limited to, saline solutions, PBS solutions, buffered solutions, such as phosphate buffers, EDTA, Tris solutions, and any combinations thereof. Reagent solutions can be used to create other reagent solutions. For example, Tris solutions and EDTA solutions are combined in specific ratios to create "TE" reagents for use in molecular biology applications.

In some embodiments, the test sample can be a non-biological fluid. As used herein, the term "non-biological fluid" refers to any fluid that is not a biological fluid as the term is defined herein. Exemplary non-biological fluids include, but are not limited to, water, salt water, brine, buffered solutions, saline solutions, sugar solutions, carbohydrate solutions, lipid solutions, nucleic acid solutions, hydrocarbons (e.g. liquid hydrocarbons), acids, gasoline, petroleum, liquefied samples (e.g., liquefied samples), and mixtures thereof.

Exemplary Microbes or Pathogens

As used herein, the term "microbes" or "microbe" generally refers to microorganism(s), including bacteria, fungi, protozoan, archaea, protists, e.g., algae, and a combination thereof. The term "microbes" encompasses both live and dead microbes. The term "microbes" also includes pathogenic microbes or pathogens, e.g., bacteria causing diseases such as plague, tuberculosis and anthrax; protozoa causing diseases such as malaria, sleeping sickness and toxoplasmosis; fungi causing diseases such as ringworm, candidiasis or histoplasmosis; and bacteria causing diseases such as sepsis. In some embodiments, the microbe is a gram-positive microbe.

Microbe-Induced Diseases:

In some other embodiments, the engineered microbe-targeting molecules or artciles, assays, products and kits described herein can be used to detect or bind to gram-positive microbe or associated microbial matter. Some exemplary gram-positive microbes include, but are not limited to, the genera *Aerococcus, Bacillus, Bifdobacterium, Carcina, Clostridium, Corprococcus, Corynebacterium, Deinobacter, Deinococcus, Enterococcus, Erysipelothrix, Eubacterium, Gemella, Lactobacillus, Lactococcus, Leuconostoc, Listeria, Marinococcus, Micrococcus, Pediococcus, Peptococcus, Peptostreptococcus, Planococcus, Propionibacterium, Ruminococcus, Saccharococcus, Salinococcus, Staphylococcus, Staphylococcus, Stomatococcus, Streptococcus, Streptomyces, Trichococcus,* and *Vagococcus*. Some specific gram-positive microbe species include, but are not limited to, *Actinomyces* spp., *Bacillus alkalophilus, Bacillus amyloliquefaciens, Bacillus brevis, Bacillus circulans, Bacillus clausii, Bacillus coagulans, Bacillus firmus, Bacillus lautus, Bacillus lentus, Bacillus licheniformis, Bacillus megaterium, Bacillus pumilus, Bacillus stearothennophilus, Bacillus subtilis, Bacillus thuringiensis, Bifidobacterium* spp., *Clostridium clostridiiforme, Clostridium difficile, Clostridium innocuum, Clostridium perfringens, Clostridium ramosum, Corynebacterium jeikeium, E. lentum, Enterococcus faecalis, Enterococcus faecium, Enterococcus gallinarum, Eubacterium aerofaciens, L. casei, L. plantarum, Lactobacillus acidophilus, Lactococcus lactis, Lactococcus* spp., *Leuconostoc* spp., *Listeria monocytogenes, Moraxella* spp. (including *M. catarrhalis*), *Mycobacterium leprae, Mycobacterium tuberculosis, P. asaccarolyticus, P. magnus, P. micros, P. prevotii, P. productus, Pediococcus, Peptostreptococcus anaerobius, Propionibacterium acnes, Staphylococcus aureus, Staphylococcus aureus* (MRSA), *Staphylococcus epidermidis, Staphylococcus haemolyticus, Staphylococcus hominis, Staphylococcus lugdunensis, Staphylococcus saprophytics, Streptococcus agalactiae, Streptococcus avium, Streptococcus bovis, Streptococcus lactis, Streptococcus mitis, Streptococcus pneumoniae, Streptococcus pyogenes, Streptococcus sangius, Streptococcus viridans*, and *Streptomyces lividans*.

In some embodiments, the engineered microbe-targeting molecules or artcles, products, and kits described herein can bedescribed herein can be used to differentiate a gram-positive microbe from a gram-negative microbe by employing the methods or assays described herein.

One skilled in the art can understand that the engineered microbe-targeting molecules or substrates, products and kits described herein can be used to target any microorganism with a microbe surface-binding domain described herein modified for each microorganism of interest. A skilled artisan can determine the cell-surface proteins or carbohydrates for each microorganism of interest using any microbiology techniques known in the art.

Biofilm:

Accordingly, in some embodiments, the microbe-targeting molecules or substrates, products and kits herein can be used to detect microbes and/or assocatied microbial matter present in a biofilm or to treat equipment surfaces to prevent or inhibit formation of a biofilm. For example, Listeria monocytogenes can form biofilms on a variety of materials used in food processing equipment and other food and non-food contact surfaces (Blackman, J Food Prot 1996; 59:827-31; Frank, J Food Prot 1990; 53:550-4; Krysinski, J Food Prot 1992; 55:246-51; Ronner, J Food Prot 1993; 56:750-8). Biofilms can be broadly defined as microbial cells attached to a surface, and which are embedded in a matrix of extracellular polymeric substances produced by the microorganisms. Biofilms are known to occur in many environments and frequently lead to a wide diversity of undesirable effects. For example, biofilms cause fouling of industrial equipment such as heat exchangers, pipelines, and ship hulls, resulting in reduced heat transfer, energy loss, increased fluid frictional resistance, and accelerated corrosion. Biofilm accumulation on teeth and gums, urinary and intestinal tracts, and implanted medical devices such as catheters and prostheses frequently lead to infections (Characklis W G. Biofilm processes. In: Characklis W G and Marshall K C eds. New York: John Wiley & Sons, 1990: 195-231; Costerton et al., Annu Rev Microbiol 1995; 49:711-45). In some embodiments, the engineered microbe-targeting microparticles, e.g., encapsulating a drug or a chemical for treatment of a biofilm, can be sprayed on contaminated equipment surfaces. The bacteria present in the biofilm bind to the microbe-targeting microparticles, which release the drug to treat the bacteria for targeted drug delivery.

In addition, L. monocytogenes attached to surfaces such as stainless steel and rubber, materials commonly used in food processing environments, can survive for prolonged periods (Helke and Wong, J Food Prot 1994; 57:963-8). This would partially explain their ability to persist in the processing plant. Common sources of L. monocytogenes in processing facilities include equipment, conveyors, product contact surfaces, hand tools, cleaning utensils, floors, drains, walls, and condensate (Tomkin et al., Dairy, Food Environ Sanit 1999; 19:551-62; Welbourn and Williams, Dairy, Food Environ Sanit 1999; 19:399-401). In some embodiments, the engineered microbe-targeting molecules can be configured to include a "smart label", which is undetectable when conjugated to the engineered microbe-targeting molecules, but produces a color change when released from the engineered molecules in the presence of a microbe enzyme. Thus, when a microbe binds to the engineered microbe-targeting molecules, the microbe releases enzymes that release the detectable label from the engineered molecules. An observation of a color change indicates a risk for bacteria contamination on a particular surface, and thus some embodiments of the engineered microbe-targeting molecules and products can be used for early detection of biofilm formation.

Plant Microbes:

In still further embodiments, the engineered microbe-targeting molecules or substrates and products described herein can be used to target plant microbes and/or associated microbial matter. Plant fungi have caused major epidemics with huge societal impacts. Examples of plant fungi include, but are not limited to, Phytophthora infestans, Crinipellis perniciosa, frosty pod (Moniliophthora roreri), oomycete Phytophthora capsici, Mycosphaerella fijiensis, Fusarium Ganoderma spp fungi and Phytophthora. An exemplary plant bacterium includes Burkholderia cepacia. Exemplary plant viruses include, but are not limited to, soybean mosaic virus, bean pod mottle virus, tobacco ring spot virus, barley yellow dwarf virus, wheat spindle streak virus, soil born mosaic virus, wheat streak virus in maize, maize dwarf mosaic virus, maize chlorotic dwarf virus, cucumber mosaic virus, tobacco mosaic virus, alfalfa mosaic virus, potato virus X, potato virus Y, potato leaf roll virus and tomato golden mosaic virus.

Military and Bioterrorism Applications:

In yet other embodiments, the engineered microbe-targeting molecules and product comprising thereof can be used to detect or combat bioterror agents (e.g., B. Anthracis, and smallpox).

In accordance with some embodiments described herein, an engineered microbe-binding molecule or microbe-binding substrate can be modified to bind to any of the microbes, e.g., the ones described herein, including the associated microbial matter (e.g., but not limited to, fragments of cell wall, microbial nucleic acid and endotoxin).

Exemplary embodiments of the various aspects disclosed herein can be described by one or more of the numbered paragraphs:

1. A microbe-targeting molecule comprising:
   a. at least one first domain comprising at least a portion of a c-reactive protein (CRP);
   b. at least one second domain comprising at least a portion of a domain selected from the group consisting of:
      i. Fc region of an immunoglobulin;
      ii. microbe-binding domain of a microbe-binding protein, wherein the microbe-binding protein is not CRP;
      iii. neck region of a lectin;
      iv. a detectable label;
      v. domain for conjugation to surface of a carrier scaffold;
      vi. pattern recognition receptor domain of CRP; and
      vii. any combinations of (i)-(vi); and
   c. a linker conjugating the first and second domains.
2. The microbe-targeting molecule of paragraph 1, wherein the first domain is conjugated to N-terminus of the second domain.
3. The microbe-targeting molecule of paragraph 1, wherein the second domain is conjugated to N-terminus of the first domain.
4. The microbe-targeting molecule of any of paragraphs 1-3, wherein the molecule is a multimeric molecule.
5. The microbe-targeting molecule of paragraph 4, wherein the molecule is a pentamer.
6. The microbe-targeting molecule of paragraph 4 or 5, wherein the multimeric molecule is formed by interactions between the linkers and/or the second domains of different molecules forming the multimeric molecule.
7. The microbe-targeting molecule of any of paragraphs 1-6, wherein the first domain comprises the amino acid sequence selected from SEQ ID NOs: 1-4 and 39.
8. The microbe-targeting molecule of any of paragraphs 1-7, wherein the detectable molecule is selected from the group consisting of biotin, fluorophore, luminescent or bioluminescent marker, a radiolabel, an enzyme, an enzyme substrate, a quantum dot, an imaging agent, a gold particle, and any combinations thereof.
9. The microbe-targeting molecule of paragraph 8, wherein the enzyme is horseradish peroxide or alkaline phosphatase.
10. The microbe-targeting molecule of any of paragraphs 1-9, wherein the immunoglobulin is selected from the group consisting of IgA, IgD, IgE, IgG, and IgM.
11. The microbe-targeting molecule of any of paragraphs 1-11, wherein the Fc region comprises at least one region selected from the group consisting of a hinge region, a CH2 region, a CH3 region, and any combinations thereof.
12. The microbe-targeting molecule of any of paragraphs 1-12, wherein the Fc region comprises at least one mutation.
13. The microbe-targeting molecule of paragraph 13, wherein the mutation is selected to: (i) increase biological half-life of the engineered molecule; (ii) modulate antibody dependent cell-mediated cytotoxicity; and/or (iii) modulate complement dependent cytotoxicity.
14. The microbe-targeting molecule of any of paragraphs 1-13, wherein the Fc region comprises the amino acid sequence SEQ ID NO: 5, 6, 7 or 42.
15. The microbe-targeting molecule of any of paragraphs 1-14, wherein the microbe-binding protein is a carbohydrate binding protein and the microbe-binding domain is a carbohydrate recognition domain (CRD) of the carbohydrate binding protein.
16. The microbe-targeting molecule of paragraph 15, wherein the CRD excludes at least one of complement and coagulation region of the carbohydrate binding protein.
17. The microbe-targeting molecule of paragraph 15 or 16, wherein the CRD is from a lectin or ficolin.
18. The microbe-targeting molecule of any of paragraphs 15-17, wherein the CRD is from a Collectin.
19. The microbe-targeting molecule of any of paragraphs 15-18, wherein the CRD is from a mannose-binding lection (MBL).
20. The microbe-targeting molecule of any of paragraphs 15-19, wherein the CRD comprises the amino acid sequences SEQ ID NO: 8, 9, 11, or 12.
21. The microbe-targeting molecule of any of paragraphs 1-19, wherein the neck region comprises an amino acid sequence from neck region of a lectin.
22. The microbe-targeting molecule of any of paragraphs 1-20, wherein the neck region comprises the amino acid sequence SEQ ID NO: 28, 29, 30, or 31.
23. The microbe-targeting molecule of any of paragraphs 1-21, wherein the second domain comprises at least a portion of Fc region of an immunoglobulin and at least a portion of the neck region of a lectin.
24. The microbe-targeting molecule of paragraph 22, wherein the neck region is between the Fc region and the first domain.
25. The microbe-targeting molecule of any of paragraphs 1-23, wherein the domain for conjugation to surface of a carrier scaffold comprises an amino group, a N-substituted amino group, a carboxyl group, a carbonyl group, an acid anhydride group, an aldehyde group, a hydroxyl group, an epoxy group, a thiol, a disulfide group, an alkenyl group, a hydrazine group, a hydrazide group, a semicarbazide group, a thiosemicarbazide group, one partner of a binding pair, an amide group, an aryl group, an ester group, an ether group, a glycidyl group, a halo group, a hydride group, an isocyanate group, an urea group, an urethane group, and any combinations thereof.
26. The microbe-targeting molecule of any of paragraphs 1-24, wherein the domain for conjugation to surface of the carrier scaffold comprises the N-terminal amino acid sequence AKT (SEQ ID NO: 32).
27. The microbe-targeting molecule of any of paragraphs 1-25, wherein the domain for conjugation to surface of the carrier scaffold is present at a terminus end of the engineered molecule.
28. The microbe-targeting molecule of any of paragraphs 1-26, wherein the second domain comprises an amino acid sequence selected from the group consisting of SEQ ID NOs: 5-12, 23-27, 32, 42, and any combinations thereof.
29. The microbe-targeting molecule of any of paragraphs 1-27, wherein the microbe-targeting molecule comprises an amino acid sequence selected from the group consisting of SEQ ID NOs: 33-38, 40, 41, 43, 44, and any combinations thereof.
30. A pharmaceutical composition comprising a microbe-targeting molecule of any of paragraphs 1-29 and a pharmaceutically acceptable excipient or carrier.
31. An article comprising at least one microbe-targeting molecule of any of paragraphs 1-29 conjugated to a surface of a carrier scaffold.
32. The article of paragraph 31, wherein the carrier scaffold is selected from the group consisting of a nucleic acid scaffold, a protein scaffold, a lipid scaffold, a polymeric scaffold, a dendrimer, a particle or bead, a nanotube, a microtiter plate, a medical apparatus or implant, a microchip, a filtration device, a membrane, a diagnostic strip, a dipstick, an extracorporeal device, a spiral mixer, a hollow-fiber tube, a living cell, a biological tissue or organ, magnetic material, hollow fiber, and any combinations thereof.
33. The article of paragraph 31 or 32, wherein the carrier scaffold is a nano- or micro-particle.
34. The article of any of paragraphs 31-33, wherein the carrier scaffold is a magnetic particle, a florescent particle, a quantum dot, a drug delivery vehicle, a dipstick, a paper strip, a membrane, a hollow fiber tube, or a gold particle.
35. The article of any of paragraphs 31-34, wherein the carrier scaffold further comprises at least one area adapted for use as a reference area.
36. The article of any of paragraphs 31-35, wherein the carrier scaffold is modified or functionalized.
37. The article of any of paragraphs 31-36, wherein the carrier scaffold is treated to reduce or inhibit adhesion of the carrier scaffold to a biological molecule.
38. The article of paragraph 37, wherein the biological molecule is selected from the group consisting of blood cells and components, proteins, nucleic acids, peptides, small molecules, therapeutic agents, cells or fragments thereof, and any combinations thereof.
39. The article of any of paragraphs 31-36, wherein the article further comprises a detection label.
40. The article of paragraph 39, wherein the detection label is separate from the microbe-targeting molecule.
41. The article of any of paragraphs 31-40, wherein the article further comprises at least one second microbe-targeting molecule, wherein the second microbe-targeting molecule comprises:
a. at least one first domain comprising at least a portion of a microbe-binding domain of a microbe-binding protein, wherein the microbe-binding protein is not CRP;

b. at least one second domain comprising at least a portion of a domain selected from the group consisting of:
    i. Fc region of an immunoglobulin;
    ii. neck region of a lectin;
    iii. a detectable label;
    iv. domain for conjugation to surface of a carrier scaffold; and
    v. any combinations of (i)-(iv); and
  c. a linker conjugating the first and second domains.
42. An assay for determining the presence or absence of a microbe in a test sample, the assay comprising:
  (i) contacting a test sample with a microbe-targeting molecule of any of paragraphs 1-29 or an article of any of paragraphs 31-40; and
  (ii) detecting binding of a microbe to the microbe-targeting molecule,
wherein a microbe is present in the test sample if binding is detected.
43. An assay for differentiating a gram positive microbe from a gram negative microbe in a test sample, the assay comprising:
  (i) contacting a test sample with a microbe-targeting molecule of any of paragraphs 1-29 or an article of any of paragraphs 31-40; and
  (ii) detecting binding of a microbe to the microbe-targeting molecule,
wherein the gram positive microbe is selectively bound to the microbe-targeting molecule, thereby differentiating the gram positive microbe from the gram negative microbe in the test sample.
44. The assay of paragraph 42 or 43, wherein said detecting step comprises an enzyme-linked immunosorbent assay (ELISA), a fluorescent linked immunosorbent assay (FLISA), immunofluorescent microscopy, hybridization, fluorescence in situ hybridization (FISH), antibody-based imaging, a radiological detection assay, a chemical detection assay, an enzymatic detection assay, an optical detection assay, an electrochemical assay, cell culture, or any combinations thereof.
45. The assay of any of paragraphs 42-44, wherein said detecting step comprises contacting the sample from step (i) with a microbe-targeting molecule of any of paragraphs 1-29, wherein the microbe-targeting molecule is conjugated with a detectable label.
46. The assay of any of paragraphs 42-45, wherein the microbe-bound microbe-targeting molecule is detectable without prior cell culture.
47. The assay of any of paragraphs 42-46, wherein the contacting step comprises flowing the test sample through a channel, wherein the channel is coated with the microbe-targeting molecules.
48. The assay of any of paragraphs 42-47, wherein the contacting step comprises flowing the test sample and microbe-targeting molecule through a channel.
49. An assay for differentiating a gram positive microbe from a gram negative microbe in a test sample, the assay comprising:
  (i) contacting a first portion of a test sample with a microbe-targeting molecule of any of paragraphs 1-29 or an article of any of paragraphs 31-40 and detecting binding of a microbe to the microbe-targeting molecule or the article; and
  (ii) contacting a second portion of the test sample with a second microbe-targeting molecule or an article comprising at least one second microbe-targeting molecule conjugated to a surface of a carrier scaffold, wherein the second microbe-targeting comprises:
    a. at least one first domain comprising at least a portion of a microbe-binding domain of a microbe-binding protein, wherein the microbe-binding protein is not CRP;
    b. at least one second domain comprising at least a portion of a domain selected from the group consisting of:
      i. Fc region of an immunoglobulin;
      ii. neck region of a lectin;
      iii. a detectable label;
      iv. domain for conjugation to surface of a carrier scaffold; and
      v. any combinations of (i)-(iv); and
    c. a linker conjugating the first and second domains
wherein:
    (a) binding in step (i) and not in step (ii) is indicative of a gram-positive microbe in the sample;
    (b) binding in step (ii) and not in step (i) is indicative of a gram-negative microbe in the sample; and
    (c) binding in both step (i) and step (ii) is indicative of a gram-positive microbe in the sample or both a gram-positive microbe and a gram-negative microbe in the sample.
50. The assay of paragraph 49, wherein said detecting in step (i) or (ii) comprises an enzyme-linked immunosorbent assay (ELISA), a fluorescent linked immunosorbent assay (FLISA), immunofluorescent microscopy, hybridization, fluorescence in situ hybridization (FISH), antibody-based imaging, a radiological detection assay, a chemical detection assay, an enzymatic detection assay, an optical detection assay, an electrochemical assay, cell culture, or any combinations thereof.
51. The assay of paragraph 49 or 50, wherein said detecting in step (i) comprises contacting the sample with a microbe-targeting molecule of any of paragraphs 1-29, wherein the microbe-targeting molecule is conjugated with a detectable label.
52. The assay of any of paragraphs 49-51, wherein said detecting in step (ii) comprises contacting the sample with the second microbe-targeting molecule, wherein the microbe-targeting molecule is conjugated with a detectable label.
53. A kit comprising:
  (i) one or more microbe-targeting molecules of any of paragraphs 1-29 or one or more articles of any of paragraphs 31-40; and
  (ii) a reagent.
54. A kit comprising:
  (i) one or more microbe-targeting molecules of any of paragraphs 1-29 or one or more articles of any of paragraphs 31-40; and
  (ii) one or more second microbe-targeting molecules or an article comprising at least one second microbe-targeting molecule conjugated to a surface of a carrier scaffold, wherein the second microbe-targeting molecules comprise:
    a. at least one first domain comprising at least a portion of a microbe-binding domain of a microbe-binding protein, wherein the microbe-binding protein is not CRP;
    b. at least one second domain comprising at least a portion of a domain selected from the group consisting of:
      i. Fc region of an immunoglobulin;
      ii. neck region of a lectin;
      iii. a detectable label;

iv. domain for conjugation to surface of a carrier scaffold; and
v. any combinations of (i)-(iv); and
c. a linker conjugating the first and second domains.
55. A composition for treating and/or preventing a microbial infection or a microbial contamination, the composition comprising at least one microbe-targeting molecule of any of paragraphs 1-29 or an article of any of paragraphs 31-40.
56. The composition of paragraph 55, further comprising a second microbe-targeting molecule or an article comprising at least one second microbe-targeting molecule conjugated to a surface of a carrier scaffold, wherein the second microbe-targeting molecule comprises:
a. at least one first domain comprising at least a portion of a microbe-binding domain of a microbe-binding protein, wherein the microbe-binding protein is not CRP;
b. at least one second domain comprising at least a portion of a domain selected from the group consisting of:
i. Fc region of an immunoglobulin;
ii. neck region of a lectin;
iii. a detectable label;
iv. domain for conjugation to surface of a carrier scaffold; and
v. any combinations of (i)-(iv); and
c. a linker conjugating the first and second domains.
57. The composition of paragraph 55 or 56, wherein the composition is formulated for treating and/or preventing microbial infection or contamination of a surface.
58. The composition of paragraph 57, wherein the surface is selected from the group consisting of a medical device, an implantable device, hospital or clinic, a machine or working surface for processing food or pharmaceutical products, a cell culture, a water treatment plant, a water reservoir, a botanical plant, and any combinations thereof.
59. The composition of any of paragraphs 55-57, wherein the composition is formulated for treating and/or preventing a microbial infection in a subject.
60. The composition of any of paragraphs 55-58, wherein the composition is formulated for treating and/or preventing a microbial infection in a tissue or a body fluid of a subject.
61. The composition of any of paragraphs 55-59, further comprising an antimicrobial agent.
62. The composition of paragraph 60, wherein the antimicrobial agent is conjugated with the microbe-targeting molecule.
63. The composition of paragraph 60 or 61, further comprising a drug delivery vehicle.
64. The composition of paragraph 62, wherein at least one of the microbe-targeting molecule or the antimicrobial agent is coated on a surface of the drug delivery vehicle.
65. The composition of paragraph 62 or 63, wherein the drug delivery vehicle is selected from the group consisting of a peptide particle, a polymeric particle, a dendrimer, a vesicle, a liposome, a hydrogel, a nucleic acid scaffold, an aptamer, and any combinations thereof.
66. A method of inhibiting, preventing, and/or treating a microbial infection or contamination in a target area, the method comprising contacting the target area with a first composition of any of paragraphs 55-65.
67. A method of removing a microbe or microbial matter thereof from a target area, the method comprising contacting the target area with a first composition of any of paragraphs 55-65.
68. The method of paragraph 66 or 67, wherein the target area comprises an environmental surface.
69. The method of paragraph 68, wherein the environmental surface is selected from the group consisting of a medical device, an implantable device, hospital or clinic, a machine or working surface for processing food or pharmaceutical products, a cell culture, a water treatment plant, a water reservoir, a botanical plant, and any combinations thereof.
70. The method of any of paragraphs 66-69, wherein the target area is a tissue or a body fluid of a subject.
71. The method of paragraph 70, further comprising administering an additional treatment to the tissue.
72. The method of paragraph 71, wherein the additional treatment includes a negative-pressure treatment, a vacuum-assisted debridement, administration of an antimicrobial agent, or any combinations thereof
73. The method of any of paragraphs 66-72, further comprising replacing the first composition in contact with the tissue with a second composition of any of paragraphs 55-65 after a period of time.
74. A method comprising:
administering a therapeutic agent having activity against a gram-positive microbe to a subject in need thereof, wherein the therapeutic agent is selected based on the presence a gram-positive microbe in a test sample from the subject, and wherein the presence or absence of the gram-positive microbe in the sample is determined by the assay of any of paragraphs 42-52.
75. The method of paragraph 74, further comprising performing the assay.
76. A method for detecting or imaging a nidus of infection in vivo, the method comprising:
administering to a subject a microbe-targeting molecule of any of paragraphs 1-X, wherein the microbe-targeting molecule comprises a detectable label; and
scanning the subject using diagnostic imaging.
77. The method of paragraph 76, wherein diagnostic imaging is selected from the group consisting of radiography, magnetic resonance imaging (MRI), Positron emission tomography (PET), Single-photon emission computed tomography (SPECT, or less commonly, SPET), Scintigraphy, ultrasound, CAT scan, photoacoustic imaging, thermography, linear tomography, poly tomography, zonography, orthopantomography (OPT or OPG), computed Tomography (CT) or Computed Axial Tomography (CAT scan), and any combinations thereof.
78. A method of delivering or concentrating an anti-microbial agent at a nidus of infection, the method comprising contacting the nidus of infection with a composition of comprising at least one microbe-targeting molecule of any of paragraphs 1-29 or an article of any of paragraphs 31-40, wherein the composition further comprises an anti-microbial agent.
79. The method of paragraph 78, wherein said nidus of infection is in vivo.
80. The method of paragraph 78 or 79, wherein the composition further comprises a second microbe-targeting molecule or an article comprising at least one second microbe-targeting molecule conjugated to a surface of a carrier scaffold, wherein the second microbe-targeting molecule comprises:
a. at least one first domain comprising at least a portion of a microbe-binding domain of a microbe-binding protein, wherein the microbe-binding protein is not CRP;
b. at least one second domain comprising at least a portion of a domain selected from the group consisting of:
i. Fc region of an immunoglobulin;
ii. neck region of a lectin;

iii. a detectable label;
  iv. domain for conjugation to surface of a carrier scaffold; and
  v. any combinations of (i)-(iv); and
  c. a linker conjugating the first and second domains.
81. The method of any of paragraphs 78-80, wherein the anti-micorbial agent is conjugated with the microbe-targeting molecule.
82. An assay for determining the presence or absence of a microbe in a test sample, the assay comprising:
  (i) contacting a test sample with a c-reactive protein or a portion thereof; and
  (ii) detecting binding of a microbe to the c-reactive protein,
wherein a microbe is present in the test sample if binding is detected.
83. The assay of paragraph 82, wherein the c-reactive protein is wild-type protein.
84. The assay of paragraph 82, wherein the c-reactive protein is a recombinant protein.
85. The assay of any of paragraphs 82-84, wherein the c-reactive protein is conjugated with a carrier scaffold.
86. The assay of any of paragraphs 82-85, wherein said detecting step comprises an enzyme-linked immunosorbent assay (ELISA), a fluorescent linked immunosorbent assay (FLISA), immunofluorescent microscopy, hybridization, fluorescence in situ hybridization (FISH), antibody-based imaging, a radiological detection assay, a chemical detection assay, an enzymatic detection assay, an optical detection assay, an electrochemical assay, cell culture, or any combinations thereof.
87. The assay of any of paragraphs 82-86, wherein said detecting step comprises contacting the sample from step (i) with a c-reactive protein conjugated with a detectable label.
88. A nucleic acid encoding c-reactive protein, wherein the nucleic acid comprises the nucleic acid sequence SEQ ID NO: 45, SEQ ID NO: 46, SEQ ID NO: 47; SEQ ID NO: 48; SEQ ID NO: 49, SEQ ID NO: 50, SEQ ID NO: 51, or any combinations thereof.
89. An expression vector comprising a nucleic acid SEQ ID NO: 45, SEQ ID NO: 46, SEQ ID NO: 47; SEQ ID NO: 48; SEQ ID NO: 49, SEQ ID NO: 50, SEQ ID NO: 51, or any combinations thereof.
90. A method for synthesizing a peptide comprising at least a portion of a CRP, the method comprises experessing a expression vector in a cell, wheiren the expression vector comprises a nucleic acid sequence SEQ ID NO: 45, SEQ ID NO: 46, SEQ ID NO: 47; SEQ ID NO: 48; SEQ ID NO: 49, SEQ ID NO: 50, SEQ ID NO: 51, or any combinations thereof.
91. An assay for determining the presence or absence of a microbe in a test sample, the assay comprising:
  (i) contacting a test sample with c-reactive protein or a microbe binding portion thereof; and
  (ii) detecting binding of a microbe to the c-reactive protein or a microbe binding portion thereof,
wherein a microbe is present in the test sample if binding is detected.
92. The assay of paragraph 91, wherein said detecting step comprises an enzyme-linked immunosorbent assay (ELISA), a fluorescent linked immunosorbent assay (FLISA), immunofluorescent microscopy, hybridization, fluorescence in situ hybridization (FISH), antibody-based imaging, a radiological detection assay, a chemical detection assay, an enzymatic detection assay, an optical detection assay, an electrochemical assay, cell culture, or any combinations thereof.
93. The assay of any of paragraphs 91 or 92, wherein said detecting step comprises contacting the sample from step (i) with a microbe-targeting molecule of any of paragraphs 1-29, wherein the microbe-targeting molecule is conjugated with a detectable label.
94. The assay of any of paragraphs 91-93, wherein the contacting step comprises flowing the test sample through a channel, wherein the channel is coated with the microbe-targeting molecules.
95. The assay of any of paragraphs 91-94, wherein the contacting step comprises flowing the test sample and microbe-targeting molecule through a channel.

Some Selected Definitions

Unless stated otherwise, or implicit from context, the following terms and phrases include the meanings provided below. Unless explicitly stated otherwise, or apparent from context, the terms and phrases below do not exclude the meaning that the term or phrase has acquired in the art to which it pertains. The definitions are provided to aid in describing particular embodiments of the aspects described herein, and are not intended to limit the claimed invention, because the scope of the invention is limited only by the claims. Further, unless otherwise required by context, singular terms shall include pluralities and plural terms shall include the singular.

As used herein the term "comprising" or "comprises" is used in reference to compositions, methods, and respective component(s) thereof, that are essential to the invention, yet open to the inclusion of unspecified elements, whether essential or not.

As used herein the term "consisting essentially of" refers to those elements required for a given embodiment. The term permits the presence of additional elements that do not materially affect the basic and novel or functional characteristic(s) of that embodiment of the invention.

The term "consisting of" refers to compositions, methods, and respective components thereof as described herein, which are exclusive of any element not recited in that description of the embodiment.

Other than in the operating examples, or where otherwise indicated, all numbers expressing quantities of ingredients or reaction conditions used herein should be understood as modified in all instances by the term "about." The term "about" when used in connection with percentages may mean±1%.

The singular terms "a," "an," and "the" include plural referents unless context clearly indicates otherwise. Similarly, the word "or" is intended to include "and" unless the context clearly indicates otherwise. Thus for example, references to "the method" includes one or more methods, and/or steps of the type described herein and/or which will become apparent to those persons skilled in the art upon reading this disclosure and so forth.

Although methods and materials similar or equivalent to those described herein can be used in the practice or testing of this disclosure, suitable methods and materials are described below. The term "comprises" means "includes." The abbreviation, "e.g." is derived from the Latin exempli gratia, and is used herein to indicate a non-limiting example. Thus, the abbreviation "e.g." is synonymous with the term "for example."

The terms "microbe-binding" and "microbe-targeting" as used interchangeably herein refers to an ability of a molecule or composition to bind and/or capture a microbe and/or microbial matter.

The term "FcCRP microparticle" as used herein refers to a microparticle comprising on its surface at least one FcCRP molecule. In some embodiments, the microparticle comprises on its surface a saturating amount of the FcCRP molecules. A microbead can be magnetic or non-magnetic.

The term "FcCRPmagnetic microparticle" as used herein refers to a magnetic microbead comprising on its surface at least one FcCRP molecule. In some embodiments, the magnetic microparricle comprises on its surface a saturating amount of the FcCRP molecules.

The term "antibody" as used herein refers to immunoglobulin molecules and immunologically active portions of immunoglobulin molecules (molecules that contain an antigen binding site which specifically binds an antigen), including monoclonal antibodies (including full length monoclonal antibodies), polyclonal antibodies, multispecific antibodies (for example, bispecific antibodies), chimeric antibodies, humanized antibodies, human antibodies, and single chain antibodies (scFvs).

The term "peptide" refers to a polymer of amino acids, or amino acid analogs, regardless of its size or function. In some embodiments, the term "peptide" refers to small polypeptides, e.g., a polymer of about 15-25 amino acids.

The term "oligonucleotide" as used herein refers to a short nucleic acid polymer, typically with twenty or fewer bases.

As used herein, a "subject" means a human or animal. Usually the animal is a vertebrate such as a primate, rodent, domestic animal or game animal. Primates include chimpanzees, cynomologous monkeys, spider monkeys, and macaques, e.g., Rhesus. Rodents include mice, rats, woodchucks, ferrets, rabbits and hamsters. Domestic and game animals include cows, horses, pigs, deer, bison, buffalo, feline species, e.g., domestic cat, canine species, e.g., dog, fox, wolf, avian species, e.g., chicken, emu, ostrich, and fish, e.g., trout, catfish and salmon. Patient or subject includes any subset of the foregoing, e.g., all of the above, but excluding one or more groups or species such as humans, primates or rodents. In certain embodiments of the aspects described herein, the subject is a mammal, e.g., a primate, e.g., a human. The terms, "patient" and "subject" are used interchangeably herein.

In some embodiments, the subject is a mammal. The mammal can be a human, non-human primate, mouse, rat, dog, cat, horse, or cow, but are not limited to these examples. Mammals other than humans can be advantageously used as subjects that represent animal models of disorders.

A subject can be one who has been previously diagnosed with or identified as suffering from or having a disease or disorder caused by any microbes or pathogens described herein. By way of example only, a subject can be diagnosed with sepsis, inflammatory diseases, or infections.

The term "therapeutic agents" is art-recognized and refers to any chemical moiety that is a biologically, physiologically, or pharmacologically active substance that acts locally or systemically in a subject. Examples of therapeutic agents, also referred to as "drugs", are described in well-known literature references such as the Merck Index, the Physicians Desk Reference, and The Pharmacological Basis of Therapeutics, and they include, without limitation, medicaments; vitamins; mineral supplements; substances used for the treatment, prevention, diagnosis, cure or mitigation of a disease or illness; substances which affect the structure or function of the body; or pro-drugs, which become biologically active or more active after they have been placed in a physiological environment. Various forms of a therapeutic agent may be used which are capable of being released from the subject composition into adjacent tissues or fluids upon administration to a subject. Examples include steroids and esters of steroids (e.g., estrogen, progesterone, testosterone, androsterone, cholesterol, norethindrone, digoxigenin, cholic acid, deoxycholic acid, and chenodeoxycholic acid), boron-containing compounds (e.g., carborane), chemotherapeutic nucleotides, drugs (e.g., antibiotics, antivirals, antifungals), enediynes (e.g., calicheamicins, esperamicins, dynemicin, neocarzinostatin chromophore, and kedarcidin chromophore), heavy metal complexes (e.g., cisplatin), hormone antagonists (e.g., tamoxifen), non-specific (non-antibody) proteins (e.g., sugar oligomers), oligonucleotides (e.g., antisense oligonucleotides that bind to a target nucleic acid sequence (e.g., mRNA sequence)), peptides, proteins, antibodies, photodynamic agents (e.g., rhodamine 123), radionuclides (e.g., I-131, Re-186, Re-188, Y-90, Bi-212, At-211, Sr-89, Ho-166, Sm-153, Cu-67 and Cu-64), toxins (e.g., ricin), and transcription-based pharmaceuticals.

As used here in, the term "peptidomimetic" means a peptide-like molecule that has the activity of the peptide on which it is structurally based. Such peptidomimetics include chemically modified peptides, peptide-like molecules containing non-naturally occurring amino acids, and peptoids, and have an activity such as the cardiac specificity of the peptide upon which the peptidomimetic is derived (see, for example, Goodman and Ro, Peptidomimetics for Drug Design, in "Burger's Medicinal Chemistry and Drug Discovery", Vol. 1 (ed. M. E. Wolff; John Wiley & Sons 1995), pages 803-861).

A variety of peptidomimetics are known in the art and can be encompassed within embodiments described herein including, for example, peptide-like molecules which contain a constrained amino acid, a non-peptide component that mimics peptide secondary structure, or an amide bond isostere. A peptidomimetic that contains a constrained, non-naturally occurring amino acid can include, for example, an α-methylated amino acid; α,α-dialkylglycine or α-aminocycloalkane carboxylic acid; an Nα-Cacyclized amino acid; an Nα-methylated amino acid; αβ- or γ-amino cycloalkane carboxylic acid; an α,β-unsaturated amino acid; β,β-dimethyl or β-methyl amino acid; αβ-substituted-2,3-methano amino acid; an N—Cδ or Cα-δ cyclized amino acid; a substituted proline or another amino acid mimetic. A peptidomimetic which mimics peptide secondary structure can contain, for example, a nonpeptidic β-turn mimic; γ-turn mimic; mimic of β-sheet structure; or mimic of helical structure, each of which is well known in the art. A peptidomimetic also can be a peptide-like molecule which contains, for example, an amide bond isostere such as a retro-inverso modification; reduced amide bond; methylenethioether or methylene-sulfoxide bond; methylene ether bond; ethylene bond; thioamide bond; transolefin or fluoroolefin bond; 1,5-disubstituted tetrazole ring; ketomethylene or fluoroketomethylene bond or another amide isostere. One skilled in the art understands that these and other peptidomimetics are encompassed within the meaning of the term "peptidomimetic" as used herein.

Methods for identifying a peptidomimetic are well known in the art and include, for example, the screening of databases that contain libraries of potential peptidomimetics. For example, the Cambridge Structural Database contains a collection of greater than 300,000 compounds that have known crystal structures (Allen et al., Acta Crystallogr. Section B, 35:2331 (1979)). This structural depository is continually updated as new crystal structures are determined and can be screened for compounds having suitable shapes, for example, the same shape as a peptide described herein, as well as potential geometrical and chemical complementarity to a cognate receptor. Where no crystal structure of a peptide described herein is available, a structure can be generated using, for example, the program CONCORD (Rusinko et al., J. Chem. Inf. Comput. Sci. 29:251 (1989)). Another database, the Available Chemicals Directory (Molecular Design Limited, Informations Systems; San Leandro Calif.), contains about 100,000 compounds that are commercially available and also can be searched to identify potential peptidomimetics of a peptide described herein, for example, having specificity for the microbes.

The terms "homology" as used herein refers to sequence similarity between two peptides or between two nucleic acid molecules. Homology can be determined by comparing a position in each sequence which may be aligned for purposes of comparison. When an equivalent position in the compared sequences is occupied by the same base or amino acid, then the molecules are identical at that position; when the equivalent site occupied by the same or a similar amino acid residue (e.g., similar in steric and/or electronic nature), then the molecules can be referred to as homologous (similar) at that position. Expression as a percentage of homology refers to a function of the number of identical or similar amino acids at positions shared by the compared sequences. A sequence which is "unrelated" or "non-homologous" shares less than 40% identity. Determination of homologs of the genes or peptides described herein may be easily ascertained by the skilled artisan.

The term "conservative substitution," when describing a polypeptide, refers to a change in the amino acid composition of the polypeptide that does not substantially alter the polypeptide's activity, fore examples, a conservative substitution refers to substituting an amino acid residue for a different amino acid residue that has similar chemical properties. Conservative amino acid substitutions include replacement of a leucine with an isoleucine or valine, an aspartate with a glutamate, or a threonine with a serine. "Conservative amino acid substitutions" result from replacing one amino acid with another having similar structural and/or chemical properties, such as the replacement of a leucine with an isoleucine or valine, an aspartate with a glutamate, or a threonine with a serine. Thus, a "conservative substitution" of a particular amino acid sequence refers to substitution of those amino acids that are not critical for polypeptide activity or substitution of amino acids with other amino acids having similar properties (e.g., acidic, basic, positively or negatively charged, polar or non-polar, etc.) such that the substitution of even critical amino acids does not substantially alter activity. Conservative substitution tables providing functionally similar amino acids are well known in the art. For example, the following six groups each contain amino acids that are conservative substitutions for one another: 1) Alanine (A), Serine (S), Threonine (T); 2) Aspartic acid (D), Glutamic acid (E); 3) Asparagine (N), Glutamine (Q); 4) Arginine (R), Lysine (K); 5) Isoleucine (I), Leucine (L), Methionine (M), Valine (V); and 6) Phenylalanine (F), Tyrosine (Y), Tryptophan (W). (See also Creighton, Proteins, W. H. Freeman and Company (1984).) In addition, individual substitutions, deletions or additions that alter, add or delete a single amino acid or a small percentage of amino acids in an encoded sequence are also "conservative substitutions." Insertions or deletions are typically in the range of about 1 to 5 amino acids.

The terms "decrease", "reduced", "reduction", "decrease" or "inhibit" are all used herein generally to mean a decrease by a statistically significant amount. However, for avoidance of doubt, "reduced", "reduction" or "decrease" or "inhibit" means a decrease by at least 10% as compared to a reference level, for example a decrease by at least about 20%, or at least about 30%, or at least about 40%, or at least about 50%, or at least about 60%, or at least about 70%, or at least about 80%, or at least about 90% or up to and including a 100% decrease (e.g. absent level as compared to a reference sample), or any decrease between 10-100% as compared to a reference level.

The terms "increased", "increase" or "enhance" or "activate" are all used herein to generally mean an increase by a statically significant amount; for the avoidance of any doubt, the terms "increased", "increase" or "enhance" or "activate" means an increase of at least 10% as compared to a reference level, for example an increase of at least about 20%, or at least about 30%, or at least about 40%, or at least about 50%, or at least about 60%, or at least about 70%, or at least about 80%, or at least about 90% or up to and including a 100% increase or any increase between 10-100% as compared to a reference level, or at least about a 2-fold, or at least about a 3-fold, or at least about a 4-fold, or at least about a 5-fold or at least about a 10-fold increase, or any increase between 2-fold and 10-fold or greater as compared to a reference level.

The term "statistically significant" or "significantly" refers to statistical significance and generally means at least two standard deviation (2SD) away from a reference level. The term refers to statistical evidence that there is a difference. It is defined as the probability of making a decision to reject the null hypothesis when the null hypothesis is actually true.

As used herein, "genetic elements" refers to defined nucleic acids (generally DNA or RNA) having expressible coding sequences for products such as proteins, apoproteins, or antisense nucleic acid constructs, which can perform or control pathway enzymatic functions. The expressed proteins can function as enzymes, repress or depress enzyme activity, or control expression of enzymes. The nucleic acids encoding these expressible sequences can be either chromosomal, e.g. integrated into a nonhuman organism's chromosome by homologous recombination, transposition, or some other method, or extrachromosomal (episomal), e.g. carried by plasmids, cosmids, etc. Genetic elements include control elements. Many other genetic elements are known in the art. See, for example, U.S. Pat. Nos. 4,980,285; 5,631,150; 5,759,828; 5,888,783 and, 5,919,670.

As used herein, the term "genetic manipulation" refers to the purposeful alteration of polynucleotide sequences either by in vitro techniques, in vivo techniques, or a combination of both in vitro and in vivo techniques. "Genetic manipulation" includes the introduction of heterologous polynucleotide sequences into nonhuman organisms, either into the chromosome or as extrachromosomaily replicating elements, the alteration of chromosomal polynucleotide sequences, the addition and/or replacement of transcriptional and/or translational regulatory signals to chromosomal or plasmid encoded genes, and the introduction of various insertion, deletion and replacement mutations in genes of interest. Methods for in vitro and in vivo genetic manipulations are widely known to those skilled in the art. See, for example, Sambrook et al., *Molecular Cloning: A Laboratory Manual,* 2nd Ed., Cold Spring Harbor Press (1989) and U.S. Pat. Nos. 4,980,285; 5,631,150; 5,759,828; 5,888,783 and, 5,919,670.

As used herein, "operably linked" refers to juxtaposition such that the normal function of the components can be performed. Thus, a coding sequence "operably linked" to control sequences refers to a configuration wherein the coding sequences can be expressed under the control of these sequences. Such control may be direct, that is, a single gene associated with a single promoter, or indirect, as in the case where a polycistronic transcript is expressed from a single promoter. See, for example, U.S. Pat. Nos. 4,980,285; 5,631,150; 5,707,828; 5,759,828; 5,888,783 and, 5,919,670, and Sambrook et al., *Molecular Cloning: A Laboratory Manual,* 2nd Ed., Cold Spring Harbor Press (1989).

As used herein, "over-expression" refers to gene expression. Genes and gene products can be overexpressed. Such gene products include RNAs, proteins and enzymes. On the other hand, "overproduce" refers to cellular products that accumulate, especially cell products that are to be harvested for some specific use. Thus proteins, materials (such as polymers), and metabolites (such as amino acids) are overproduced. Proteins may be either overexpressed (if referring to the control of gene expression) or overproduced (if referring to the accumulation of the proteins). By "over production" of ergothioneine, it is intended that a cell "overproducing" ergothioneine produces more molecules of ergothioneine for each cell under a given set of growth conditions than a similar cell not "over producing" ergothioneine.

As used herein, the term "promoter" has its art-recognized meaning, denoting a portion of a gene containing DNA sequences that provide for the binding of RNA polymerase and initiation of transcription. Promoter sequences are commonly, but not always, found in the 5' non-coding regions of genes. Sequence elements within promoters that function in the initiation of transcription are often characterized by consensus nucleotide sequences. Useful promoters include constitutive and inducible promoters. Many such promoter sequences are known in the art. See, for example, U.S. Pat. Nos. 4,980,285; 5,631,150; 5,707,828; 5,759,828; 5,888,783; 5,919,670, and, Sambrook et al, *Molecular Cloning: A Laboratory Manual,* 2nd Ed., Cold Spring Harbor Press (1989). Other useful promoters include promoters which are neither constitutive nor responsive to a specific (or known) inducer molecule. Such promoters may include those that respond to developmental cues (such as growth phase of the culture or stage of cell differentiation), or environmental cues (such as pH, osmoticum, heat, or cell density). A heterologous promoter is a promoter which is not naturally linked to the gene. Heterologous promoters may be from the same or different species. For example, a heterologous promoter may be a promoter from the same organism as the gene but naturally found linked to a different gene.

As used herein, the term "transgene" when used in reference to polynucleotide sequences, refers to polynucleotide sequences not naturally present in a cell. Thus the term "transgene" includes, for example, the promoter of gene A operably joined to structural gene B, when A and B genes are from the same organism, as well as the case in which a polynucleotide sequence of one species is transferred to a cell of a different species (or strain). The term "transgene" also includes clones of transgenes which have been so modified. See, U.S. Pat. Nos. 4,980,285; 5,631,150; 5,707,828; 5,759,828; 5,888,783 and, 5,919,670.

As used herein, the terms "culture media," and "cell culture media," refers to media that are suitable to support the growth of cells in vitro (i.e., cell cultures). It is not intended that the term be limited to any particular cell culture medium. For example, it is intended that the definition encompass outgrowth as well as maintenance media. Indeed, it is intended that the term encompass any culture medium suitable for the growth of the cell cultures of interest.

As used herein, the term "cell type," refers to any cell, regardless of its source or characteristics.

As used herein, the term "transformed cell lines," refers to cell cultures that have been transformed into continuous cell lines with the characteristics as described herein.

As used herein, the term "transformed nonhuman organisms" includes the primary transformed subject cell and its transformed progeny. The nonhuman organism can be prokaryotic or eukaryotic. Thus "transformants" or "transformed cells" includes the primary subject cell, transformed with the transgene, and cultures derived therefrom, without regard for the number of transfers. It is also understood that all progeny may not be precisely identical in DNA content, due to deliberate or inadvertent mutations and/or modifications. Mutant progeny which have the same functionality as screened for in the originally transformed cell are included. Where distinct designations are intended, it will be clear from the context. See, for example, U.S. Pat. Nos. 4,980, 285; 5,631,150; 5,707,828; 5,759,828; 5,888,783; 5,919, 670, and, Sambrook et al., *Molecular Cloning: A Laboratory Manual,* 2nd ed., 60 Cold Spring Harbor Press (1989).

As used herein, the term "isolated" means altered "by the hand of man" from the natural state. An "isolated" composition or substance is one that has been changed or removed from its original environment, or both. For example, a polynucleotide or a polypeptide naturally present in a cell or living animal is not "isolated," but the same polynucleotide or polypeptide separated from the coexisting materials of its natural state is "isolated," as the term is employed herein.

Although preferred embodiments have been depicted and described in detail herein, it will be apparent to those skilled in the relevant art that various modifications, additions, substitutions, and the like can be made without departing from the spirit of the invention and these are therefore considered to be within the scope of the invention as defined in the claims which follow. Further, to the extent not already indicated, it will be understood by those of ordinary skill in the art that any one of the various embodiments herein described and illustrated may be further modified to incorporate features shown in any of the other embodiments disclosed herein.

It should be understood that this invention is not limited to the particular methodology, protocols, and reagents, etc., described herein and as such canvary. The terminology used herein is for the purpose of describing particular embodiments only, and is not intended to limit the scope of the present invention, which is defined solely by the claims.

As used herein and in the claims, the singular forms include the plural reference and vice versa unless the context clearly indicates otherwise. Other than in the operating examples, or where otherwise indicated, all numbers expressing quantities of ingredients or reaction conditions used herein should be understood as modified in all instances by the term "about."

All patents and other publications identified are expressly incorporated herein by reference for the purpose of describing and disclosing, for example, the methodologies described in such publications that might be used in connection with the present invention. These publications are provided solely for their disclosure prior to the filing date of the present application. Nothing in this regard should be construed as an admission that the inventors are not entitled to antedate such disclosure by virtue of prior invention or for any other reason. All statements as to the date or representation as to the contents of these documents is based on the information available to the applicants and does not constitute any admission as to the correctness of the dates or contents of these documents.

EXAMPLES

The following examples illustrate some embodiments and aspects of the invention. It will be apparent to those skilled in the relevant art that various modifications, additions, substitutions, and the like can be performed without altering the spirit or scope of the invention, and such modifications and variations are encompassed within the scope of the invention as defined in the claims which follow. The following examples do not in any way limit the invention.

Example 1: C-Reactive Protein Capture/Detection of GRAM POSITIVE Bacteria

C-reactive protein (CRP) is an acute inflammation protein originally characterized by its ability to bind to C-polysaccharide from the cell wall of Streptococcus pneumoniae (1). CRP helps bridge the innate and adaptive immune responses primarily through activation of complement, opsonization, and induction of phagocytosis (2). As a two-sided allosteric pentamer, CRP functions by binding to host cell proteins on one side and phosphocholine-containing debris from pathogenic microbes on the other in calcium-dependent zwitterionic interactions (2, 3). Despite CRP's original characterization as a Pattern Recognition Receptor, its primary use in medicine is as a biomarker of systemic inflammation in critically ill patients, as well as a predictor of atherosclerosis (4, 5, 6).

Using the ability of CRP to bind immunologically active components of bacteria, we have developed an assay using CRP as both a capture and detection agent for *Enterococcus faecalis*, *Enterococcus faecium*, and *Streptococcus pneumoniae* and other gram positive bacteria. Using this assay, we have developed a Rapid assay with which we can detect and classify Gram Positive bacteria, even where there is no positive blood culture. This information can be used for optimizing antibiotic treatment.

Using the binding properties of CRP (coupled to superparamagnetic beads) we have developed an assay (CRP-ELISA) that can detect gram positive bacteria (Table 1) from complex media such as blood and can be used as a rapid gram test for infected clinical samples. In addition, the CRP coupled to either superparamagnetic beads or dialysis filters can be used to clear the pathogens from infected blood.

The current panel of pathogens tested to date demonstrate CRP coupled beads are specific to gram positive bacteria. All gram negative bacteria tested are negative for binding. Therefore the use of CRP to capture and detect bacteria (gram positive) can be used as a rapid gram test of infected patient samples.

Figure 5A:
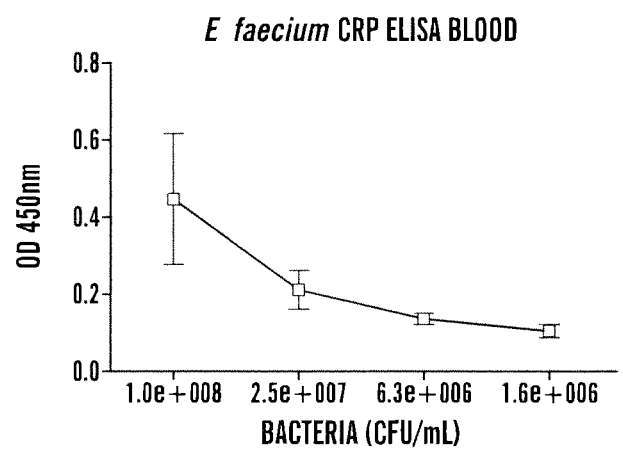
FIG. 5 shows an example of CRP-HRP ELISA: Detection of *Enterococcus faecalis* (A) and NOT *E. coli* (B) from whole blood. *E. faecalis* and *E. coli* were grown to 0.5 McFarlan in RPMI 5% Glucose, serial dilutions made, spiked into whole blood, used for capture and assayed by CRP-HRP ELISA.
Figure 5B:
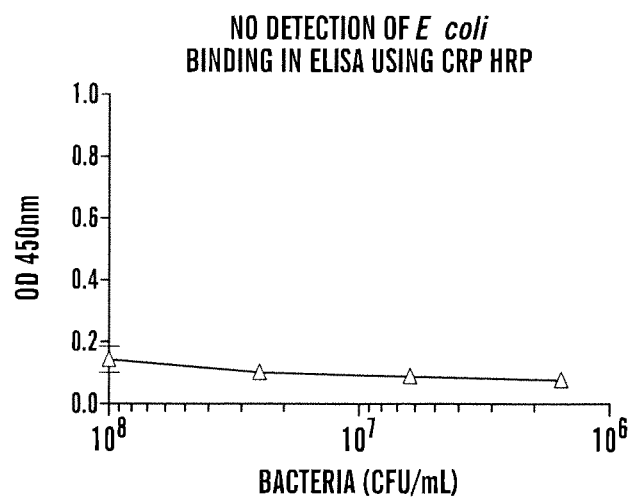

An Exemplary Detection Assay Using the Microbe-Trageting Molecules According to Some Embodiments 1. Bead: CRP is coupled to superparamagnetic beads (example: CRP is biotinylated and coupled to streptavidin coated luM MyONE beads from ThermoFisher).
2. Capture: CRP beads are added to the test sample (example infected blood), mixed (capture step), removed, and washed for assaying. Optimum time and shake speed to be determined.
3. Detection: Bead/pathogen complex is assayed by CRP-HRP ELISA (HRP=horseradish peroxidase) (FIG. 5). Optimum assay conditions to be determined, for example incubation time, CRP-HRP concentration etc.
4. Sample protocol: Bead/pathogen mixes are incubated with CRP-HRP (1:2500 in TBST-$Ca^{++}$ 5 mM 3% BSA) for 20 minutes. Beads are washed 3× in TBST $Ca^{++}$ 5 mM, 1× in TBS $Ca^{++}$ 5 mM and positive capture by beads detected using colorimeteric detection (TMB substrate).

TABLE 1

List of bacteria tested for CRP binding

| | | CRP Capture/Detection |
|---|---|---|
| Acinetobacter | baumannii | Yes |
| Aeromonas | sobria | Yes |
| Burkholderia | cepacia | Yes |
| Citrobacter | freundii | Yes |
| Enterobacter | aerogenes | Yes |
| Enterobacter | cloacae | Yes |
| Enterococcus | faecalis | Yes |
| Enterococcus | faecium | Yes |
| Escherichia | coli | Yes |
| Klebsiella | oxytoca | Yes |
| Klebsiella | pneumoniae | Yes |
| Listeria | monocytogenes | Yes |
| Pseudomonas | aeruginosa | Yes |
| Salmonella | enteriditis | Yes |
| Salmonella | typhimurium | Yes |
| Serratia | marcescens | Yes |
| Staphylococcus | aureus | Yes |
| Staphylococcus | aureus (MRSA) | Yes |
| Staphylococcus | epidermidis | Yes |
| Staphylococcus | lugdunensis | Yes |
| Streptococcus | agalactiae | Yes |
| Streptococcus | Group A | Yes |
| Streptococcus | mitis | Yes |
| Streptococcus | pneumoniae | Yes |
| Streptococcus | pyogenes | Yes |

Capture/binding of clinical isolates was determined by CRP ELISA using 1 μM CRP coated beads and detection by CRP-HRP

REFERENCES

1. Tillet W S, Francis T. Serological reactions in pneumonia with a non-protein somatic fraction of the Pneumococcus. J Exp Med 1930; 52: 561-71.
2. Szalai, A I. The biological functions of C-reactive protein. Vasc Pharm 2002; 39: 105-107.
3. Barnum et al. Comparative studies on the binding specificities of C-reactive Protein and HOPC. Annals of NYAS 1982; 4: 431-434.
4. Tsalik et al. Discriminative value of inflammatory biomarkers of sepsis. J Emerg Med 2012; 43: 1.97-106.
5. Levy M M, et al. 2001 SCCM/ESICM/ACCP/ATS/SIS International Sepsis Definitions Conference. Crit Care Med 2003; 31: 1250-6.
6. Ablij H C, Meinders A E. C-reactive protein: history and revival. EJIM 2002; 13: 412-422.

C-reactive protein's ability to bind to the phosphorylcholine moieties on the surface of pathogenic bacteria may be useful in the diagnosis and characterization of infection and sepsis. Early research demonstrated the importance of C-reactive protein in the innate immune response to microbial infection, but much of contemporary research on C-reactive protein (CRP) has focused on its usefulness as a biomarker of inflammation and predictor of cardiovascular disease.

This study revisits the function of CRP as a binder of immunologically active molecules and its function in innate immune defense. Using CRP-coated magnetic microbeads, intact *Enterococcus faecalis* and *Enterococcus faecium* were bound and removed by magnet from a serum-like buffer solution. The total concentration of bacteria dropped from 10,000 CFU/mL to 1000 CFU/mL, a significant reduction when compared with controls. Using a magnetic bead-based ELISA with CRP as the detection agent, intact Enterococci were detected at concentrations as low as 100 CFU/mL. When run with mechanically fragmented bacterial cells, sensitive detection of Enterocci, Streptococci and Staphylococci was possible. Detection of fragments in buffer has clinical relevance because it mimics the physiologically conditions of infection. Fragments of dead cells far outnumber living bacteria in cases of sepsis. CRP's ability to bind pathogenic bacterial fragments is relevant in the diagnostics for sepsis.

Example 2: Enhanced CRP Expression

Genes for the following proteins were cloned into a mammalian expression vector downstream of a retroviral promoter. This vector was transfected into HEK 293F cells using 293Fectin. Supernatents from the transfected cells was harvested after cell viability dropped below 50% and CRP containing proteins were bound to on immobilized p-Aminophenyl Phosphoryl Choline in the presense of calcium and eluted using an EDTA containing buffer.

TABLE 2

| Name | DNA Sequence (SEQ ID NO:) | Encoded Amino Acid Sequence (SEQ ID NO:) | Design | Rationale | Yield (mg Protein/ L cell culture) |
|---|---|---|---|---|---|
| wtCRP | 52 | 39 | none | wild type cDNA | 0.3 |
| OPTCRP | 45 | 39 | Heuristically optimized sequence | | 35 |
| OptCRPv2b | 46 | 39 | WT sequence with just 4 codons optimized for human bias (Pro25, Arg47, Cys97, Cys36) | Mixes between optimized and wt CRP DNA sequence to identify minimal DNAs needed to achieve high CRP expressions | 0.3 |
| OptCRPv2c | 47 | 39 | WT sequence - all codons able to be improved 2.5 fold in terms of human usage replaced | Mixes between optimized and wt CRP DNA sequence to identify minimal DNAs needed to achieve high CRP expressions | 7 |
| OptCRPv2d | 48 | 39 | 1-97 WT, 98-end optimized sequence | Mixes between optimized and wt CRP DNA sequence to identify minimal DNAs needed to achieve high CRP expressions | 5 |
| OptCRPv2e | 49 | 39 | 1-97 optimized, 98-end WT | Mixes between optimized and wt CRP DNA sequence to identify minimal DNAs needed to achieve high CRP expressions | 14 |
| OptCRPv2F | 50 | 39 | 1-52 & 170-end WT; middle optimized sequence | Mixes between optimized and wt CRP DNA sequence to identify minimal DNAs needed to achieve high CRP expressions | 5 |

TABLE 2-continued

| Name | DNA Sequence (SEQ ID NO:) | Encoded Amino Acid Sequence (SEQ ID NO:) | Design | Rationale | Yield (mg Protein/ L cell culture) |
|---|---|---|---|---|---|
| OptCRPv2g | 51 | 39 | 1-52, 170-end optimized; middle wild-type sequence | Mixes between optimized and wt CRP DNA sequence to identify minimal DNAs needed to achieve high CRP expressions | 14 |

```
HumanCRP (NCBI Reference Sequence: NP_000558.2,
                                                    (SEQ ID NO: 1)
MEKLLCFLVLTSLSHAFGQTDMSRKAFVFPKESDTSYVSLKAPLTKPLKAFTVCLHFYTE

LSSTRGYSIFSYATKRQDNEILIFWSKDIGYSFTVGGSEILFEVPEVTVAPVHICTSWESAS

GIVEFWVDGKPRVRKSLKKGYTVGAEASIILGQEQDSFGGNFEGSQSLVGDIGNVNMWD

FVLSPDEINTIYLGGPFSPNVLNWRALKYEVQGEVFTKPQLWP

MouseCRP (NCBI Reference Sequence: NP_031794.3,
                                                    SEQ ID NO: 2)
MEKLLWCLLIMISFSRTFGHEDMFKKAFVFPKESDTSYVSLEAESKKPLNTFTVCLHFYT

ALSTVRSESVESYATKKNSNDILIEWNKDKQYTEGVGGAEVREMVSEIPEAPTHICASWE

SATGIVEFWIDGKPKVRKSLHKGYTVGPDASIILGQEQDSYGGDFDAKQSLVGDIGDVN

MWDEVLSPEQISTVYVGGTLSPNVLNWRALNYKAQGDVEIKPQLWS

CRP sequence
                                                    (SEQ ID NO: 3)
QTDMSRKAFVFPKESDTSYVSLKAPLTKPLKAFTVCLHFYTELSSTRGYSIFSYATKRQD

NEILIFWSKDIGYSFTVGGSEILFEVPEVTVAPVHICTSWESASGIVEFWVDGKPRVRKSL

KKGYTVGAEASIILGQEQDSFGGNFEGSQSLVGDIGNVNMWDFVLSPDEINTIYLGGPFSP

NVLNWRALKYEVQGEVFTK

CRP Sequence with Cys to Ala modifications-
                                                    (SEQ ID NO: 4)
QTDMSRKAFVFPKESDTSYVSLKAPLTKPLKAFTVALHEYTELSSTRGYSIESYATKRQD

NEILIFWSKDIGYSFTVGGSEILFEVPEVTVAPVHIATSWESASGIVEFWVDGKPRVRKSL

KKGYTVGAEASIILGQEQDSFGGNFEGSQSLVGDIGNVNMWDFVLSPDEINTIYLGGPFSP

NVLNWRALKYEVQGEVFTKPQLWP

Fc Sequence
                                                    (SEQ ID NO: 5)
EPKSSDKTHTCPPCPAPELLGGPSVFLFPPKPKDTLMISRTPEVTCVVVDVSHEDPEVKFN

WYVDGVEVHNAKTKPREEQYNSTYRVVSVLTVLHQDWLNGKEYKCKVSNKALPAPIE

KTISKAKGQPREPQVYTLPPSRDELTKNQVSLTCLVKGFYPSDIAVEWESNGQPENNYKT

TPPVLDSDGSFFLYSKLTVDKSRWQQGNVFSCSVMHEALHNHYTQKSLSLSPGA

Fc Sequence with Asn82Asp modification
                                                    (SEQ ID NO: 6)
EPKSSDKTHTCPPCPAPELLGGPSVFLFPPKPKDTLMISRTPEVTCVVVDVSHEDPEVKFN

WYVDGVEVHNAKTKPREEQYDSTYRVVSVLTVLHQDWLNGKEYKCKVSNKALPAPIE
```

KTISKAKGQPREPQVYTLPPSRDELTKNQVSLTCLVKGFYPSDIAVEWESNGQPENNYKT

TPPVLDSDGSFFLYSKLTVDKSRWQQGNVFSCSVMHEALHNHYTQKSLSLSPG

Fc-neck sequence
(SEQ ID NO: 7)
EPKSSDKTHTCPPCPAPELLGGPSVFLFPPKPKDTLMISRTPEVTCVVVDVSHEDPEVKFN

WYVDGVEVHNAKTKPREEQYDSTYRVVSVLTVLHQDWLNGKEYKCKVSNKALPAPIE

KTISKAKGQPREPQVYTLPPSRDELTKNQVSLTCLVKGFYPSDIAVEWESNGQPENNYKT

TPPVLDSDGSFFLYSKLTVDKSRWQQGNVFSCSVMHEALHNHYTQKSLSLSPGAPDGDS

SLAASERKALQTEMARIKKWLTFSLG

MBL full length (SEQ ID NO: 8):
MSLFPSLPLLLLSMVAASYSETVTCEDAQKTCPAVIACSSPGINGFPGKDGRDGTKGEKG

EPGQGLRGLQGPPGKLGPPGNPGPSGSPGPKGQKGDPGKSPDGDSSLAASERKALQTEM

ARIKKWLTFSLGKQVGNKFFLTNGEIMTFEKVKALCVKFQASVATPRNAAENGAIQNLI

KEEAFLGITDEKTEGQFVDLTGNRLTYTNWNEGEPNNAGSDEDCVLLLKNGQWNDVPC

STSHLAVCEFPI

MBL without the signal sequence
(SEQ ID NO: 9)
ETVTCEDAQKTCPAVIACSSPGINGFPGKDGRDGTKGEKGEPGQGLRGLQGPPGKLGPPG

NPGPSGSPGPKGQKGDPGKSPDGDSSLAASERKALQTEMARIKKWLTFSLGKQVGNKFFL

TNGEIMTFEKVKALCVKFQASVATPRNAAENGAIQNLIKEEAFLGITDEKTEGQFVDLTG

NRLTYTNWNEGEPNNAGSDEDCVLLLKNGQWNDVPCSTSHLAVCEFPI

MBL signal sequence
(SEQ ID NO: 10)
MSLFPSLPLLLLSMVAASYS

Truncated MBL
(SEQ ID NO: 11)
AASERKALQTEMARIKKWLTFSLGKQVGNKFFLTNGEIMTFEKVKALCVKFQASVATPR

NAAENGAIQNLIKEEAFLGITDEKTEGQFVDLTGNRLTYTNWNEGEPNNAGSDEDCVLL

LKNGQWNDVPCSTSHLAVCEFPI

Carbohydrate recognition domain (CRD) of MBL
(SEQ ID NO: 12)
VGNKFFLTNGEIMTFEKVKALCVKFQASVATPRNAAENGAIQNLIKEEAFLGITDEKTEG

QFVDLTGNRLTYTNWNEGEPNNAGSDEDCVLLLKNGQWNDVPCSTSHLAVCEFPI

Neck + Carbohydrate recognition domain of MBL
(SEQ ID NO: 23)
PDGDSSLAASERKALQTEMARIKKWLTFSLGKQVGNKFFLTNGEIMTFEKVKALCVKFQ

ASVATPRNAAENGAIQNLIKEEAFLGITDEKTEGQFVDLTGNRLTYTNWNEGEPNNAGS

DEDCVLLLKNGQWNDVPCSTSHLAVCEFPI

FcMBL.81
(SEQ ID NO: 24)
EPKSSDKTHTCPPCPAPELLGGPSVFLFPPKPKDTLMISRTPEVTCVVVDVSHEDPEVKFN

WYVDGVEVHNAKTKPREEQYNSTYRVVSVLTVLHQDWLNGKEYKCKVSNKALPAPIE

KTISKAKGQPREPQVYTLPPSRDELTKNQVSLTCLVKGFYPSDIAVEWESNGQPENNYKT

TPPVLDSDGSFFLYSKLTVDKSRWQQGNVFSCSVMHEALHNHYTQKSLSLSPGAPDGDS

SLAASERKALQTEMARIKKWLTFSLGKQVGNKFFLTNGEIMTFEKVKALCVKFQASVAT

PRNAAENGAIQNLIKEEAFLGITDEKTEGQFVDLTGNRLTYTNWNEGEPNNAGSDEDCV

LLLKNGQWNDVPCSTSHLAVCEFPI

AKT-FcMBL

-continued

```
                                                  (SEQ ID NO: 25)
AKTEPKSSDKTHTCPPCPAPELLGGPSVFLFPPKPKDTLMISRTPEVTCVVVDVSHEDPEV

KFNWYVDGVEVHNAKTKPREEQYNSTYRVVSVLTVLHQDWLNGKEYKCKVSNKALPA

PIEKTISKAKGQPREPQVYTLPPSRDELTKNQVSLTCLVKGFYPSDIAVEWESNGQPENNY

KTTPPVLDSDGSFFLYSKLTVDKSRWQQGNVFSCSVMHEALHNHYTQKSLSLSPGAPDG

DSSLAASERKALQTEMARIKKWLTFSLGKQVGNKFFLTNGEIMTFEKVKALCVKFQASV

ATPRNAAENGAIQNLIKEEAFLGITDEKTEGQFVDLTGNRLTYTNWNEGEPNNAGSDED

CVLLLKNGQWNDVPCSTSHLAVCEFPI

FcMBL.111
                                                  (SEQ ID NO: 26)
EPKSSDKTHTCPPCPAPELLGGPSVFLFPPKPKDTLMISRTPEVTCVVVDVSHEDPEVKFN

WYVDGVEVHNAKTKPREEQYNSTYRVVSVLTVLHQDWLNGKEYKCKVSNKALPAPIE

KTISKAKGQPREPQVYTLPPSRDELTKNQVSLTCLVKGFYPSDIAVEWESNGQPENNYKT

TPPVLDSDGSFFLYSKLTVDKSRWQQGNVFSCSVMHEALHNHYTQKSLSLSPGATSKQV

GNKFFLTNGEIMTFEKVKALCVKFQASVATPRNAAENGAIQNLIKEEAFLGITDEKTEGQ

FVDLTGNRLTYTNWNEGEPNNAGSDEDCVLLLKNGQWNDVPCSTSHLAVCEFPI

CRD Sequence
                                                  (SEQ ID NO: 27)
KQVGNKFFLTNGEIMTFEKVKALCVKFQASVATPRNAAENGAIQNLIKEEAFLGITDEKT

EGQFVDLTGNRLTYTNWNEGEPNNAGSDEDCVLLLKNGQWNDVPCSTSHLAVCEFPI

FcCRP, where Fc is the Fragment crystallization from IgG and CRP
is thematue form of CRP
                                                  (SEQ ID NO: 33)
EPKSSDKTHTCPPCPAPELLGGPSVFLFPPKPKDTLMISRTPEVTCVVVDVSHEDPEVKFN

WYVDGVEVHNAKTKPREEQYDSTYRVVSVLTVLHQDWLNGKEYKCKVSNKALPAPIE

KTISKAKGQPREPQVYTLPPSRDELTKNQVSLTCLVKGFYPSDIAVEWESNGQPENNYKT

TPPVLDSDGSFFLYSKLTVDKSRWQQGNVFSCSVMHEALHNHYTQKSLSLSPG<linker>Q

TDMSRKAFVFPKESDTSYVSLKAPLTKPLKAFTVCLHEYTELSSTRGYSIFSYATKRQDN

EILIFWSKDIGYSFTVGGSEILFEVPEVTVAPVHICTSWESASGIVEFWVDGKPRVRKSLK

KGYTVGAEASIILGQEQDSFGGNFEGSQSLVGDIGNVNMWDFVLSPDEINTIYLGGPFSPN

VLNWRALKYEVQGEVFTK (<linker>refers of a linker from 0 to 20 amino acids, e.g.,
0, 1, 2, 3, 4, 5, 6, 7, 8, 9, 10, 11, 12, 13, 14, 15, 16, 17,
18, 19 or 20 amino acids, the linker can be encoded in the
expression vector)

FcmCRP, where mCRP refers to a monomeric version of mature CRP
                                                  (SEQ ID NO: 34)
EPKSSDKTHTCPPCPAPELLGGPSVFLFPPKPKDTLMISRTPEVTCVVVDVSHEDPEVKFN

WYVDGVEVHNAKTKPREEQYDSTYRVVSVLTVLHQDWLNGKEYKCKVSNKALPAPIE

KTISKAKGQPREPQVYTLPPSRDELTKNQVSLTCLVKGFYPSDIAVEWESNGQPENNYKT

TPPVLDSDGSFFLYSKLTVDKSRWQQGNVFSCSVMHEALHNHYTQKSLSLSPG<linker>Q

TDMSRKAFVFPKESDTSYVSLKAPLTKPLKAFTVALHFYTELSSTRGYSIFSYATKRQDN

EILIFWSKDIGYSFTVGGSEILFEVPEVTVAPVHIATSWESASGIVEFWVDGKPRVRKSLK

KGYTVGAEASIILGQEQDSFGGNFEGSQSLVGDIGNVNMWDFVLSPDEINTIYLGGPFSPN

VLNWRALKYEVQGEVFTKPQLWP (<linker>refers of a linker from 0 to 20 amino acids, e.g.,
0, 1, 2, 3, 4, 5, 6, 7, 8, 9, 10, 11, 12, 13, 14, 15, 16,
17, 18, 19 or 20 amino acids, the linker can be encoded
in the expression vector)
```

CRP-CRD, where CRD refers to any carbohydrate binding domain
from a C-type lectin, e.g., MBL (SEQ ID NO: 35)
QTDMSRKAFVFPKESDTSYVSLKAPLTKPLKAFTVCLHFYTELSSTRGYSIFSYATKRQD

NEILIFWSKDIGYSFTVGGSEILFEVPEVTVAPVHICTSWESASGIVEFWVDGKPRVRKSL

KKGYTVGAEASIILGQEQDSFGGNFEGSQSLVGDIGNVNMWDFVLSPDEINTIYLGGPFSP

NVLNWRALKYEVQGEVETKPQLWP<linker>KQVGNKFFLTNGEIMTFEKVKALCVKFQ

ASVATPRNAAENGAIQNLIKEEAFLGITDEKTEGQFVDLTGNRLTYTNWNEGEPNNAGS

DEDCVLLLKNGQWNDVPCSTSHLAVCEFPI (<linker>refers of a linker from 0 to 20 amino acids, e.g.,
0, 1, 2, 3, 4, 5, 6, 7, 8, 9, 10, 11, 12, 13, 14, 15, 16,
17, 18, 19 or 20 amino acids, the linker can be encoded
in the expression vector CRD-CRP
(SEQ ID NO: 36)
KQVGNKFFLTNGEIMTFEKVKALCVKFQASVATPRNAAENGAIQNLIKEEAFLGITDEKT

EGQFVDLTGNRLTYTNWNEGEPNNAGSDEDCVLLLKNGQWNDVPCSTSHLAVCEFPI

<linker>QTDMSRKAFVFPKESDTSYVSLKAPLTKPLKAFTVCLHEYTELSSTRGYSIFSYA

TKRQDNEILIFWSKDIGYSFTVGGSEILFEVPEVTVAPVHICTSWESASGIVEFWVDGKPR

VRKSLKKGYTVGAEASIILGQEQDSFGGNFEGSQSLVGDIGNVNMWDFVLSPDEINTIYL

GGPFSPNVLNWRALKYEVQGEVFTKPQLWP (<linker>refers of a linker from 0 to 20 amino acids, e.g.,
0, 1, 2, 3, 4, 5, 6, 7, 8, 9, 10, 11, 12, 13, 14, 15, 16, 17,
18, 19 or 20 amino acids, the linker can be encoded in
the expression vector)

Fc-neck-mCRP, where neck refers to the triple helix neck
from a Collectins, e.g., MBL (SEQ ID NO: 37)
EPKSSDKTHTCPPCPAPELLGGPSVFLFPPKPKDTLMISRTPEVTCVVVDVSHEDPEVKFN

WYVDGVEVHNAKTKPREEQYDSTYRVVSVLTVLHQDWLNGKEYKCKVSNKALPAPIE

KTISKAKGQPREPQVYTLPPSRDELTKNQVSLTCLVKGFYPSDIAVEWESNGQPENNYKT

TPPVLDSDGSFFLYSKLTVDKSRWQQGNVFSCSVMHEALHNHYTQKSLSLSPGAPDGDS

SLAASERKALQTEMARIKKWLTESLG<linker>QTDMSRKAFVFPKESDTSYVSLKAPLTK

PLKAFTVALHFYTELSSTRGYSIFSYATKRQDNEILIEWSKDIGYSFTVGGSEILFEVPEVT

VAPVHIATSWESASGIVEFWVDGKPRVRKSLKKGYTVGAEASIILGQEQDSFGGNFEGSQ

SLVGDIGNVNMWDFVLSPDEINTIYLGGPFSPNVLNWRALKYEVQGEVFTKPQLWP (<linker>refers of a linker from 0 to 20 amino acids,
e.g., 0, 1, 2, 3, 4, 5, 6, 7, 8, 9, 10, 11, 12, 13, 14, 15,
16, 17, 18, 19 or 20 amino acids, the linker can be encoded
in the expression vector)

*AKT-His-CRP*; where AKT is a tri-peptide for site specific
conjugation of the protein and His refers to a histidine
tag for purification (SEQ ID NO: 38)
AKTHHHHHHQTDMSRKAFVFPKESDTSYVSLKAPLTKPLKAFTVCLHFYTELSSTRGYSI

FSYATKRQDNEILIFWSKDIGYSFTVGGSEILFEVPEVTVAPVHICTSWESASGIVEFWVD

GKPRVRKSLKKGYTVGAEASIILGQEQDSFGGNFEGSQSLVGDIGNVNMWDFVLSPDEIN

TIYLGGPFSPNVLNWRALKYEVQGEVFTKPQLWP wtCRP
(SEQ ID NO: 39)
QTDMSRKAFVFPKESDTSYVSLKAPLTKPLKAFTVCLHFYTELSSTRGYSIFSYATKRQD

NEILIFWSKDIGYSFTVGGSEILFEVPEVTVAPVHICTSWESASGIVEFWVDGKPRVRKSL

-continued

KKGYTVGAEASIILGQEQDSFGGNFEGSQSLVGDIGNVNMWDFVLSPDEINTIYLGGPFSP

NVLNWRALKYEVQGEVFTKPQLWP

CRP-Fc; (N297D variant) with/withouta linker
(SEQ ID NO: 40)
QTDMSRKAFVFPKESDTSYVSLKAPLTKPLKAFTVCLHFYTELSSTRGYSIFSYATKRQD

NEILIFWSKDIGYSFTVGGSEILFEVPEVTVAPVHICTSWESASGIVEFWVDGKPRVRKSL

KKGYTVGAEASIILGQEQDSFGGNFEGSQSLVGDIGNVNMWDFVLSPDEINTIYLGGPFSP

NVLNWRALKYEVQGEVFTKPQLWP<linker>EPKSSDKTHTCPPCPAPELLGGPSVFLFPP

KPKDTLMISRTPEVTCVVVDVSHEDPEVKFNWYVDGVEVHNAKTKPREEQYDSTYRVV

SVLTVLHQDWLNGKEYKCKVSNKALPAPIEKTISKAKGQPREPQVYTLPPSRDELTKNQ

VSLTCLVKGFYPSDIAVEWESNGQPENNYKTTPPVLDSDGSFELYSKLTVDKSRWQQGN

VFSCSVMHEALHNHYTQKSLSLSPGA (<linker>refers of a linker from 0 to 20 amino acids, e.g.,
0, 1, 2, 3, 4, 5, 6, 7, 8, 9, 10, 11, 12, 13, 14, 15, 16, 17,
18, 19 or 20 amino acids, the linker can be encoded
in the expression vector)

CRP-Fc; (N297D variant) with a single leucine residue as a linker
(SEQ ID NO: 41)
QTDMSRKAFVFPKESDTSYVSLKAPLTKPLKAFTVCLHFYTELSSTRGYSIFSYATKRQD

NEILIFWSKDIGYSFTVGGSEILFEVPEVTVAPVHICTSWESASGIVEFWVDGKPRVRKSL

KKGYTVGAEASIILGQEQDSFGGNFEGSQSLVGDIGNVNMWDFVLSPDEINTIYLGGPFSP

NVLNWRALKYEVQGEVFTKPQLWPLEPKSSDKTHTCPPCPAPELLGGPSVFLFPPKPKDT

LMISRTPEVTCVVVDVSHEDPEVKFNWYVDGVEVHNAKTKPREEQYDSTYRVVSVLTV

LHQDWLNGKEYKCKVSNKALPAPIEKTISKAKGQPREPQVYTLPPSRDELTKNQVSLTCL

VKGFYPSDIAVEWESNGQPENNYKTTPPVLDSDGSFFLYSKLTVDKSRWQQGNVFSCSV

MHEALHNHYTQKSLSLSPGA

Fc sequence; N297D variant
(SEQ ID NO: 42)
EPKSSDKTHTCPPCPAPELLGGPSVFLFPPKPKDTLMISRTPEVTCVVVDVSHEDPEVKFN

WYVDGVEVHNAKTKPREEQYDSTYRVVSVLTVLHQDWLNGKEYKCKVSNKALPAPIE

KTISKAKGQPREPQVYTLPPSRDELTKNQVSLTCLVKGFYPSDIAVEWESNGQPENNYKT

TPPVLDSDGSFFLYSKLTVDKSRWQQGNVFSCSVMHEALHNHYTQKSLSLSPGA

CRP-Fc; N297 with/without a linker
(SEQ ID NO: 43)
QTDMSRKAFVFPKESDTSYVSLKAPLTKPLKAFTVCLHFYTELSSTRGYSIFSYATKRQD

NEILIFWSKDIGYSFTVGGSEILFEVPEVTVAPVHICTSWESASGIVEFWVDGKPRVRKSL

KKGYTVGAEASIILGQEQDSFGGNFEGSQSLVGDIGNVNMWDFVLSPDEINTIYLGGPFSP

NVLNWRALKYEVQGEVFTKPQLWP<linker>EPKSSDKTHTCPPCPAPELLGGPSVFLFPP

KPKDTLMISRTPEVTCVVVDVSHEDPEVKFNWYVDGVEVHNAKTKPREEQYNSTYRVV

SVLTVLHQDWLNGKEYKCKVSNKALPAPIEKTISKAKGQPREPQVYTLPPSRDELTKNQ

VSLTCLVKGFYPSDIAVEWESNGQPENNYKTTPPVLDSDGSFFLYSKLTVDKSRWQQGN

VFSCSVMHEALHNHYTQKSLSLSPGA (<linker>refers of a linker from 0 to 20 amino acids, e.g.,
0, 1, 2, 3, 4, 5, 6, 7, 8, 9, 10, 11, 12, 13, 14, 15, 16, 17,
18, 19 or 20 amino acids, the linker can be encoded in
the expression vector)

CRP-Fc; N297 no linker
(SEQ ID NO: 44)
QTDMSRKAFVFPKESDTSYVSLKAPLTKPLKAFTVCLHFYTELSSTRGYSIFSYATKRQD

NEILIFWSKDIGYSFTVGGSEILFEVPEVTVAPVHICTSWESASGIVEFWVDGKPRVRKSL

KKGYTVGAEASIILGQEQDSFGGNFEGSQSLVGDIGNVNMWDFVLSPDEINTIYLGGPFSP

NVLNWRALKYEVQGEVFTKPQLWPEPKSSDKTHTCPPCPAPELLGGPSVFLFPPKPKDTL

MISRTPEVTCVVVDVSHEDPEVKFNWYVDGVEVHNAKTKPREEQYNSTYRVVSVLTVL

HQDWLNGKEYKCKVSNKALPAPIEKTISKAKGQPREPQVYTLPPSRDELTKNQVSLTCL

VKGFYPSDIAVEWESNGQPENNYKTTPPVLDSDGSFFLYSKLTVDKSRWQQGNVFSCSV

MHEALHNHYTQKSLSLSPGA cDNA; heuristically optimized sequence
(SEQ ID NO: 45)
CAGACCGATATGAGCCGGAAAGCCTTCGTGTTCCCTAAAGAGAGCGATACCAGCTAT

GTGAGCCTGAAAGCCCCACTGACCAAACCACTGAAGGCCTTCACCGTGTGCCTGCAC

TTTTACACCGAGCTGAGCTCCACACGAGGGTACAGCATCTTTTCCTATGCTACAAAG

AGGCAGGACAACGAAATCCTGATTTTCTGGTCAAAAGATATCGGCTATAGCTTTACT

GTGGGCGGATCCGAGATTCTGTTCGAGGTGCCCGAAGTCACAGTGGCTCCTGTCCAT

ATCTGTACTTCCTGGGAGTCAGCAAGCGGCATTGTCGAATTCTGGGTGGACGGAAAG

CCTAGGGTGAGAAAATCTCTGAAGAAAGGATACACAGTGGGGGCCGAGGCTAGTAT

CATTCTGGGGCAGGAACAGGACTCATTCGGGGGCAACTTTGAAGGCTCCCAGTCTCT

GGTCGGGGATATCGGCAACGTGAACATGTGGGACTTTGTCCTGAGCCCAGATGAGAT

CAATACCATCTACCTGGGAGGGCCCTTCAGCCCTAACGTGCTGAATTGGCGCGCACT

GAAGTATGAGGTCCAGGGCGAAGTGTTTACAAAACCCCAGCTGTGGCCA cDNA; WT sequence with just 4 codons optimized for human bias
(Pro25, Arg47, Cys97, Cys36); CRP v2b
((SEQ ID NO: 46)
*CAGACAGACATGTCGAGGAAGGCTTTTGTGTTTCCCAAAGAGTCGGATACTTCCTATGTAT*

*CCCTCAAAGCACCCTTAACGAAGCCTCTCAAAGCCTTCACTGTGTGCCTCCACTTCTACAC*

*GGAACTGTCCTCGACCAGAGGGTACAGTATTTTCTCGTATGCTACTAAGAGACAAGACAAT*

*GAGATTCTCATATTTTGGTCTAAGGATATAGGATACAGTTTTACAGTGGGTGGGTCTGAAAT*

*ATTATTCGAGGTTCCTGAAGTCACAGTAGCTCCAGTACACATTTGCACAAGCTGGGAGTCC*

*GCCTCAGGGATCGTGGAGTTCTGGGTAGATGGGAAGCCCAGGGTGAGGAAGAGTCTGAA*

*GAAGGGATACACTGTGGGGGCAGAAGCAAGCATCATCTTGGGGCAGGAGCAGGATTCCTT*

*CGGTGGGAACTTTGAAGGAAGCCAGTCCCTGGTGGGAGACATTGGAAATGTGAACATGTG*

*GGACTTTGTGCTGTCACCAGATGAGATTAACACCATCTATCTTGGCGGGCCCTTCAGTCCT*

*AATGTCCTGAACTGGCGGGCACTGAAGTATGAAGTGCAAGGCGAAGTGTTCACCAAACCC*

*CAGCTGTGGCCC* cDNA; WT sequence-all codons able to be improved 2.5 fold in
terms of human usage replaced; CRP v2c
(SEQ ID NO: 47)
CAGACAGACATGAGCAGGAAGGCTTTTGTGTTTCCCAAAGAGAGCGATACTTCCTAT

GTGTCCCTCAAAGCACCCGCTGACCAAGCCTCTCAAAGCCTTCACTGTGTGCCTCCACT

TCTACACCGAACTGTCCAGCACCCGTGGGTACAGTATTTTCAGCTATGCTACTAAGA

GACAGGACAATGAGATTCTCATATTTTGGTCTAAGGATATCGGATACAGTTTTACAG

TGGGTGGGTCTGAAATACTGTTCGAGGTGCCTGAAGTCACAGTGGCTCCAGTACACA

TTTGTACAAGCTGGGAGTCCGCCTCAGGGATCGTGGAGTTCTGGGTGGATGGGAAGC

CCAGGGTGAGGAAGAGTCTGAAGAAGGGATACACTGTGGGGGCAGAAGCAAGCATC

ATCCTGGGGCAGGAGCAGGATTCCTTCGGTGGGAACTTTGAAGGAAGCCAGTCCCTG

GTGGGAGACATTGGAAATGTGAACATGTGGGACTTTGTGCTGTCACCAGATGAGATT

AACACCATCTATCTGGGCGGGCCCTTCAGTCCTAATGTCCTGAACTGGCGGGCACTG

AAGTATGAAGTGCAGGGCGAAGTGTTCACCAAACCCCAGCTGTGGCCC cDNA; 1-97 WT, 98-end optimized sequence; CRP v2d
(SEQ ID NO: 48)
CAGACAGACATGTCGAGGAAGGCTTTTGTGTTTCCCAAAGAGTCGGATACTTCCTAT

GTATCCCTCAAAGCACCGTTAACGAAGCCTCTCAAAGCCTTCACTGTGTGCCTCCACT

TCTACACGGAACTGTCCTCGACCCGTGGGTACAGTATTTTCTCGTATGCTACTAAGAG

ACAAGACAATGAGATTCTCATATTTTGGTCTAAGGATATAGGATACAGTTTTACAGT

GGGTGGGTCTGAAATATTATTCGAGGTTCCTGAAGTCACAGTAGCTCCAGTACACAT

TTGTACTTCCTGGGAGTCAGCAAGCGGCATTGTCGAATTCTGGGTGGACGGAAAGCC

TAGGGTGAGAAAATCTCTGAAGAAAGGATACACAGTGGGGGCCGAGGCTAGTATCA

TTCTGGGGCAGGAACAGGACTCATTCGGGGGCAACTTTGAAGGCTCCCAGTCTCTGG

TCGGGGATATCGGCAACGTGAACATGTGGGACTTTGTCCTGAGCCCAGATGAGATCA

ATACCATCTACCTGGGAGGGCCCTTCAGCCCTAACGTGCTGAATTGGCGCGCACTGA

AGTATGAGGTCCAGGGCGAAGTGTTTACAAAACCCCAGCTGTGGCCA cDNA; 1-97 optimized, 98-end WT; CRP v2e
(SEQ ID NO: 49)
CAGACCGATATGAGCCGGAAAGCCTTCGTGTTCCCTAAAGAGAGCGATACCAGCTAT

GTGAGCCTGAAAGCCCCACTGACCAAACCACTGAAGGCCTTCACCGTGTGCCTGCAC

TTTTACACCGAGCTGAGCTCCACACGAGGGTACAGCATCTTTTCCTATGCTACAAAG

AGGCAGGACAACGAAATCCTGATTTTCTGGTCAAAAGATATCGGCTATAGCTTTACT

GTGGGCGGATCCGAGATTCTGTTCGAGGTGCCCGAAGTCACAGTGGCTCCTGTCCAT

ATCTGTACAAGCTGGGAGTCCGCCTCAGGGATCGTGGAGTTCTGGGTAGATGGGAAG

CCCAGGGTGAGGAAGAGTCTGAAGAAGGGATACACTGTGGGGGCAGAAGCAAGCAT

CATCTTGGGGCAGGAGCAGGATTCCTTCGGTGGGAACTTTGAAGGAAGCCAGTCCCT

GGTGGGAGACATTGGAAATGTGAACATGTGGGACTTTGTGCTGTCACCAGATGAGAT

TAACACCATCTATCTTGGCGGGCCCTTCAGTCCTAATGTCCTGAACTGGCGGGCACTG

AAGTATGAAGTGCAAGGCGAAGTGTTCACCAAACCCCAGCTGTGGCCC cDNA; 1-52 & 170-end WT, middle optimized sequence; CRP v2f
(SEQ ID NO: 50)
CAGACCGATATGAGCCGGAAAGCCTTCGTGTTCCCTAAAGAGAGCGATACCAGCTAT

GTGAGCCTGAAAGCCCCACTGACCAAACCACTGAAGGCCTTCACCGTGTGCCTGCAC

TTTTACACCGAGCTGAGCTCCACACGAGGGTACAGCATCTTTTCGTATGCTACTAAG

AGACAAGACAATGAGATTCTCATATTTTGGTCTAAGGATATAGGATACAGTTTTACA

GTGGGTGGGTCTGAAATATTATTCGAGGTTCCTGAAGTCACAGTAGCTCCAGTACAC

ATTTGTACAAGCTGGGAGTCCGCCTCAGGGATCGTGGAGTTCTGGGTAGATGGGAAG

CCCAGGGTGAGGAAGAGTCTGAAGAAGGGATACACTGTGGGGGCAGAAGCAAGCAT

CATCTTGGGGCAGGAGCAGGATTCCTTCGGTGGGAACTTTGAAGGAAGCCAGTCCCT

GGTGGGAGACATTGGAAATGTGAACATGTGGGACTTTGTGCTGTCACCAGATGAGAT

CAATACCATCTACCTGGGAGGGCCCTTCAGCCCTAACGTGCTGAATTGGCGCGCACT

GAAGTATGAGGTCCAGGGCGAAGTGTTTACAAAACCCCAGCTGTGGCCA cDNA; 1-52, 170-end optimized, middle wild-type sequence; CRP v2g
(SEQ ID NO: 51)
CAGACAGACATGTCGAGGAAGGCTTTTGTGTTTCCCAAAGAGTCGGATACTTCCTAT

GTATCCCTCAAAGCACCGTTAACGAAGCCTCTCAAAGCCTTCACTGTGTGCCTCCACT

TCTACACGGAACTGTCCTCGACCCGTGGGTACAGTATTTTCTCCTATGCTACAAAGAG

GCAGGACAACGAAATCCTGATTTTCTGGTCAAAAGATATCGGCTATAGCTTTACTGT

GGGCGGATCCGAGATTCTGTTCGAGGTGCCCGAAGTCACAGTGGCTCCTGTCCATAT

CTGTACTTCCTGGGAGTCAGCAAGCGGCATTGTCGAATTCTGGGTGGACGGAAAGCC

TAGGGTGAGAAAATCTCTGAAGAAAGGATACACAGTGGGGGCCGAGGCTAGTATCA

TTCTGGGGCAGGAACAGGACTCATTCGGGGGCAACTTTGAAGGCTCCCAGTCTCTGG

TCGGGGATATCGGCAACGTGAACATGTGGACTTTGTCCTGAGCCCAGATGAGATTA

ACACCATCTATCTTGGCGGGCCCTTCAGTCCTAATGTCCTGAACTGGCGGGCACTGA

AGTATGAAGTGCAAGGCGAAGTGTTCACCAAACCCCAGCTGTGGCCC cDNA; wild type
(SEQ ID NO: 52)
CAGACAGACATGTCGAGGAAGGCTTTTGTGTTTCCCAAAGAGTCGGATACTTCCTAT

GTATCCCTCAAAGCACCGTTAACGAAGCCTCTCAAAGCCTTCACTGTGTGCCTCCACT

TCTACACGGAACTGTCCTCGACCCGTGGGTACAGTATTTTCTCGTATGCTACTAAGAG

ACAAGACAATGAGATTCTCATATTTTGGTCTAAGGATATAGGATACAGTTTTACAGT

GGGTGGGTCTGAAATATTATTCGAGGTTCCTGAAGTCACAGTAGCTCCAGTACACAT

TTGTACAAGCTGGGAGTCCGCCTCAGGGATCGTGGAGTTCTGGGTAGATGGGAAGCC

CAGGGTGAGGAAGAGTCTGAAGAAGGGATACACTGTGGGGGCAGAAGCAAGCATCA

TCTTGGGGCAGGAGCAGGATTCCTTCGGTGGGAACTTTGAAGGAAGCCAGTCCCTGG

TGGGAGACATTGGAAATGTGAACATGTGGACTTTGTGCTGTCACCAGATGAGATTA

ACACCATCTATCTTGGCGGGCCCTTCAGTCCTAATGTCCTGAACTGGCGGGCACTGA

AGTATGAAGTGCAAGGCGAAGTGTTCACCAAACCCCAGCTGTGGCCC

---

What is claimed is:

1. An assay for determining the presence or absence of a microbe in a test sample, the assay comprising:
    (i) contacting a test sample with a microbe-targeting molecule; and
    (ii) detecting binding of a microbe to the microbe-targeting molecule, wherein said detecting comprises contacting the sample from (i) with a labeling molecule comprising a detectable label that is conjugated to a c-reactive protein or a microbe binding portion thereof, and
    wherein a microbe is present in the test sample if binding is detected, and
    wherein the microbe-targeting molecule comprises:
        a. at least one first domain comprising at least a portion of a c-reactive protein (CRP);
        b. at least one second domain comprising at least a portion of a domain selected from the group consisting of:
            (i) Fc region of an immunoglobulin;
            (ii) microbe-binding domain of a microbe-binding protein, wherein the microbe-binding protein is not CRP;
            (ii) neck region of a lectin;
            (iv) a detectable label;
            (v) domain for conjugation to surface of a carrier scaffold;
            (vi) pattern recognition receptor domain of CRP; and
            (vii) any combinations of (i)-(vi); and
        a linker conjugating the first and second domains, and wherein the molecule is a multimeric molecule.

2. The assay of claim 1, wherein the multimeric molecule is formed by interactions between the linkers of different molecules forming the multimeric molecule, or the linker and the second domain of different molecules forming the multimeric molecule, or the second domains of different molecules forming the multimeric molecule.

3. An assay for determining the presence or absence of a microbe in a test sample, the assay comprising:
    (i) contacting a test sample with a microbe-targeting molecule; and
    (ii) detecting binding of a microbe to the microbe-targeting molecule, wherein said detecting comprises contacting the sample from (i) with a labeling molecule comprising a detectable label that is conjugated to a c-reactive protein or a microbe binding portion thereof, and
    wherein a microbe is present in the test sample if binding is detected, and wherein the microbe-targeting molecule comprises:
  a. at least one first domain comprising at least a portion of a c-reactive protein (CRP);
  b. at least one second domain comprising at least a portion of a domain selected from the group consisting of:
    (i) Fc region of an immunoglobulin;
    (ii) microbe-binding domain of a microbe-binding protein, wherein the microbe-binding protein is not CRP;
    (ii) neck region of a lectin;
    (iv) a detectable label;
    (v) domain for conjugation to surface of a carrier scaffold;
    (vi) pattern recognition receptor domain of CRP; and
    (vii) any combinations of (i)-(vi); and
  a linker conjugating the first and second domains, and wherein the domain for conjugation to surface of a carrier scaffold comprises an amino group, a N-substituted amino group, a carboxyl group, a carbonyl group, an acid anhydride group, an aldehyde group, a hydroxyl group, an epoxy group, a thiol, a disulfide group, an alkenyl group, a hydrazine group, a hydrazide group, a semicarbazide group, a thiosemicarbazide group, one partner of a binding pair, an amide group, an aryl group, an ester group, an ether group, a glycidyl group, a halo group, a hydride group, an isocyanate group, an urea group, or an urethane group.

4. An assay for determining the presence or absence of a microbe in a test sample, the assay comprising:
  (i) contacting a test sample with a microbe-targeting molecule; and
  (ii) detecting binding of a microbe to the microbe-targeting molecule, wherein said detecting comprises contacting the sample from (i) with a labeling molecule comprising a detectable label that is conjugated to a c-reactive protein or a microbe binding portion thereof, and
wherein a microbe is present in the test sample if binding is detected, and
wherein the microbe-targeting molecule comprises:
  a. at least one first domain comprising at least a portion of a c-reactive protein (CRP);
  b. at least one second domain comprising at least a portion of a domain selected from the group consisting of:
    (i) Fc region of an immunoglobulin;
    (ii) microbe-binding domain of a microbe-binding protein, wherein the microbe-binding protein is not CRP;
    (ii) neck region of a lectin;
    (iv) a detectable label;
    (v) domain for conjugation to surface of a carrier scaffold;
    (vi) pattern recognition receptor domain of CRP; and
    (vii) any combinations of (i)-(vi); and
  a linker conjugating the first and second domains, and wherein the microbe-targeting molecule is conjugated to a surface of a carrier scaffold.

5. The assay of claim 4, wherein the carrier scaffold is selected from the group consisting of a nucleic acid scaffold, a protein scaffold, a lipid scaffold, a polymeric scaffold, a dendrimer, a particle, a bead, a nanotube, a microtiter plate, a medical apparatus or implant, a microchip, a filtration device, a membrane, a diagnostic strip, a dipstick, an extracorporeal device, a spiral mixer, a hollow-fiber tube, a living cell, magnetic material, hollow fiber, and any combinations thereof.

* * * * *

SEQUENCE LISTING

<160> NUMBER OF SEQ ID NOS: 53

<210> SEQ ID NO 1
<211> LENGTH: 224
<212> TYPE: PRT
<213> ORGANISM: Homo sapiens

<400> SEQUENCE: 1

Met Glu Lys Leu Leu Cys Phe Leu Val Leu Thr Ser Leu Ser His Ala
1               5                   10                  15

Phe Gly Gln Thr Asp Met Ser Arg Lys Ala Phe Val Phe Pro Lys Glu
            20                  25                  30

Ser Asp Thr Ser Tyr Val Ser Leu Lys Ala Pro Leu Thr Lys Pro Leu
        35                  40                  45

Lys Ala Phe Thr Val Cys Leu His Phe Tyr Thr Glu Leu Ser Ser Thr
    50                  55                  60

Arg Gly Tyr Ser Ile Phe Ser Tyr Ala Thr Lys Arg Gln Asp Asn Glu
65                  70                  75                  80

Ile Leu Ile Phe Trp Ser Lys Asp Ile Gly Tyr Ser Phe Thr Val Gly
            85                  90                  95

Gly Ser Glu Ile Leu Phe Glu Val Pro Glu Val Thr Val Ala Pro Val
        100                 105                 110

His Ile Cys Thr Ser Trp Glu Ser Ala Ser Gly Ile Val Glu Phe Trp
        115                 120                 125

Val Asp Gly Lys Pro Arg Val Arg Lys Ser Leu Lys Lys Gly Tyr Thr
        130                 135                 140

Val Gly Ala Glu Ala Ser Ile Ile Leu Gly Gln Glu Gln Asp Ser Phe
145                 150                 155                 160

Gly Gly Asn Phe Glu Gly Ser Gln Ser Leu Val Gly Asp Ile Gly Asn
                165                 170                 175

Val Asn Met Trp Asp Phe Val Leu Ser Pro Asp Glu Ile Asn Thr Ile
                180                 185                 190

Tyr Leu Gly Gly Pro Phe Ser Pro Asn Val Leu Asn Trp Arg Ala Leu
                195                 200                 205

Lys Tyr Glu Val Gln Gly Glu Val Phe Thr Lys Pro Gln Leu Trp Pro
        210                 215                 220

<210> SEQ ID NO 2
<211> LENGTH: 225
<212> TYPE: PRT
<213> ORGANISM: Mus musculus

<400> SEQUENCE: 2

Met Glu Lys Leu Leu Trp Cys Leu Leu Ile Met Ile Ser Phe Ser Arg
1               5                   10                  15

Thr Phe Gly His Glu Asp Met Phe Lys Lys Ala Phe Val Phe Pro Lys
                20                  25                  30

Glu Ser Asp Thr Ser Tyr Val Ser Leu Glu Ala Glu Ser Lys Lys Pro
        35                  40                  45

Leu Asn Thr Phe Thr Val Cys Leu His Phe Tyr Thr Ala Leu Ser Thr
    50                  55                  60

Val Arg Ser Phe Ser Val Phe Ser Tyr Ala Thr Lys Lys Asn Ser Asn
65                  70                  75                  80

Asp Ile Leu Ile Phe Trp Asn Lys Asp Lys Gln Tyr Thr Phe Gly Val
                85                  90                  95

Gly Gly Ala Glu Val Arg Phe Met Val Ser Glu Ile Pro Glu Ala Pro
        100                 105                 110

Thr His Ile Cys Ala Ser Trp Glu Ser Ala Thr Gly Ile Val Glu Phe
        115                 120                 125

Trp Ile Asp Gly Lys Pro Lys Val Arg Lys Ser Leu His Lys Gly Tyr
        130                 135                 140

Thr Val Gly Pro Asp Ala Ser Ile Ile Leu Gly Gln Glu Gln Asp Ser
145                 150                 155                 160

Tyr Gly Gly Asp Phe Asp Ala Lys Gln Ser Leu Val Gly Asp Ile Gly
                165                 170                 175

Asp Val Asn Met Trp Asp Phe Val Leu Ser Pro Glu Gln Ile Ser Thr
                180                 185                 190

Val Tyr Val Gly Gly Thr Leu Ser Pro Asn Val Leu Asn Trp Arg Ala
                195                 200                 205

Leu Asn Tyr Lys Ala Gln Gly Asp Val Phe Ile Lys Pro Gln Leu Trp
        210                 215                 220

Ser
225

<210> SEQ ID NO 3
<211> LENGTH: 201
<212> TYPE: PRT
<213> ORGANISM: Homo sapiens

<400> SEQUENCE: 3

```
Gln Thr Asp Met Ser Arg Lys Ala Phe Val Phe Pro Lys Glu Ser Asp
1               5                   10                  15

Thr Ser Tyr Val Ser Leu Lys Ala Pro Leu Thr Lys Pro Leu Lys Ala
            20                  25                  30

Phe Thr Val Cys Leu His Phe Tyr Thr Glu Leu Ser Ser Thr Arg Gly
        35                  40                  45

Tyr Ser Ile Phe Ser Tyr Ala Thr Lys Arg Gln Asp Asn Glu Ile Leu
    50                  55                  60

Ile Phe Trp Ser Lys Asp Ile Gly Tyr Ser Phe Thr Val Gly Gly Ser
65                  70                  75                  80

Glu Ile Leu Phe Glu Val Pro Glu Val Thr Val Ala Pro Val His Ile
                85                  90                  95

Cys Thr Ser Trp Glu Ser Ala Ser Gly Ile Val Glu Phe Trp Val Asp
            100                 105                 110

Gly Lys Pro Arg Val Arg Lys Ser Leu Lys Lys Gly Tyr Thr Val Gly
        115                 120                 125

Ala Glu Ala Ser Ile Ile Leu Gly Gln Glu Gln Asp Ser Phe Gly Gly
    130                 135                 140

Asn Phe Glu Gly Ser Gln Ser Leu Val Gly Asp Ile Gly Asn Val Asn
145                 150                 155                 160

Met Trp Asp Phe Val Leu Ser Pro Asp Glu Ile Asn Thr Ile Tyr Leu
                165                 170                 175

Gly Gly Pro Phe Ser Pro Asn Val Leu Asn Trp Arg Ala Leu Lys Tyr
            180                 185                 190

Glu Val Gln Gly Glu Val Phe Thr Lys
        195                 200
```

<210> SEQ ID NO 4
<211> LENGTH: 206
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 4

```
Gln Thr Asp Met Ser Arg Lys Ala Phe Val Phe Pro Lys Glu Ser Asp
1               5                   10                  15

Thr Ser Tyr Val Ser Leu Lys Ala Pro Leu Thr Lys Pro Leu Lys Ala
            20                  25                  30

Phe Thr Val Ala Leu His Phe Tyr Thr Glu Leu Ser Ser Thr Arg Gly
        35                  40                  45

Tyr Ser Ile Phe Ser Tyr Ala Thr Lys Arg Gln Asp Asn Glu Ile Leu
    50                  55                  60

Ile Phe Trp Ser Lys Asp Ile Gly Tyr Ser Phe Thr Val Gly Gly Ser
65                  70                  75                  80

Glu Ile Leu Phe Glu Val Pro Glu Val Thr Val Ala Pro Val His Ile
                85                  90                  95

Ala Thr Ser Trp Glu Ser Ala Ser Gly Ile Val Glu Phe Trp Val Asp
            100                 105                 110
```

```
Gly Lys Pro Arg Val Arg Lys Ser Leu Lys Lys Gly Tyr Thr Val Gly
        115                 120                 125

Ala Glu Ala Ser Ile Ile Leu Gly Gln Glu Gln Asp Ser Phe Gly Gly
        130                 135                 140

Asn Phe Glu Gly Ser Gln Ser Leu Val Gly Asp Ile Gly Asn Val Asn
145                 150                 155                 160

Met Trp Asp Phe Val Leu Ser Pro Asp Glu Ile Asn Thr Ile Tyr Leu
                165                 170                 175

Gly Gly Pro Phe Ser Pro Asn Val Leu Asn Trp Arg Ala Leu Lys Tyr
                180                 185                 190

Glu Val Gln Gly Glu Val Phe Thr Lys Pro Gln Leu Trp Pro
        195                 200                 205

<210> SEQ ID NO 5
<211> LENGTH: 232
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 5

Glu Pro Lys Ser Ser Asp Lys Thr His Thr Cys Pro Pro Cys Pro Ala
1               5                   10                  15

Pro Glu Leu Leu Gly Gly Pro Ser Val Phe Leu Phe Pro Pro Lys Pro
                20                  25                  30

Lys Asp Thr Leu Met Ile Ser Arg Thr Pro Glu Val Thr Cys Val Val
            35                  40                  45

Val Asp Val Ser His Glu Asp Pro Glu Val Lys Phe Asn Trp Tyr Val
50                  55                  60

Asp Gly Val Glu Val His Asn Ala Lys Thr Lys Pro Arg Glu Glu Gln
65                  70                  75                  80

Tyr Asn Ser Thr Tyr Arg Val Val Ser Val Leu Thr Val Leu His Gln
                85                  90                  95

Asp Trp Leu Asn Gly Lys Glu Tyr Lys Cys Lys Val Ser Asn Lys Ala
            100                 105                 110

Leu Pro Ala Pro Ile Glu Lys Thr Ile Ser Lys Ala Lys Gly Gln Pro
        115                 120                 125

Arg Glu Pro Gln Val Tyr Thr Leu Pro Pro Ser Arg Asp Glu Leu Thr
    130                 135                 140

Lys Asn Gln Val Ser Leu Thr Cys Leu Val Lys Gly Phe Tyr Pro Ser
145                 150                 155                 160

Asp Ile Ala Val Glu Trp Glu Ser Asn Gly Gln Pro Glu Asn Asn Tyr
                165                 170                 175

Lys Thr Thr Pro Pro Val Leu Asp Ser Asp Gly Ser Phe Phe Leu Tyr
            180                 185                 190

Ser Lys Leu Thr Val Asp Lys Ser Arg Trp Gln Gln Gly Asn Val Phe
        195                 200                 205

Ser Cys Ser Val Met His Glu Ala Leu His Asn His Tyr Thr Gln Lys
    210                 215                 220

Ser Leu Ser Leu Ser Pro Gly Ala
225                 230

<210> SEQ ID NO 6
<211> LENGTH: 231
<212> TYPE: PRT
```

```
<213> ORGANISM: Artificial Sequence
<220> FEATURE:
<223> OTHER INFORMATION: Description of Artificial Sequence: Synthetic
      polypeptide

<400> SEQUENCE: 6

Glu Pro Lys Ser Ser Asp Lys Thr His Thr Cys Pro Pro Cys Pro Ala
1               5                   10                  15

Pro Glu Leu Leu Gly Gly Pro Ser Val Phe Leu Phe Pro Pro Lys Pro
            20                  25                  30

Lys Asp Thr Leu Met Ile Ser Arg Thr Pro Glu Val Thr Cys Val Val
        35                  40                  45

Val Asp Val Ser His Glu Asp Pro Glu Val Lys Phe Asn Trp Tyr Val
50                  55                  60

Asp Gly Val Glu Val His Asn Ala Lys Thr Lys Pro Arg Glu Glu Gln
65                  70                  75                  80

Tyr Asp Ser Thr Tyr Arg Val Val Ser Val Leu Thr Val Leu His Gln
                85                  90                  95

Asp Trp Leu Asn Gly Lys Glu Tyr Lys Cys Lys Val Ser Asn Lys Ala
            100                 105                 110

Leu Pro Ala Pro Ile Glu Lys Thr Ile Ser Lys Ala Lys Gly Gln Pro
        115                 120                 125

Arg Glu Pro Gln Val Tyr Thr Leu Pro Pro Ser Arg Asp Glu Leu Thr
130                 135                 140

Lys Asn Gln Val Ser Leu Thr Cys Leu Val Lys Gly Phe Tyr Pro Ser
145                 150                 155                 160

Asp Ile Ala Val Glu Trp Glu Ser Asn Gly Gln Pro Glu Asn Asn Tyr
                165                 170                 175

Lys Thr Thr Pro Pro Val Leu Asp Ser Asp Gly Ser Phe Phe Leu Tyr
            180                 185                 190

Ser Lys Leu Thr Val Asp Lys Ser Arg Trp Gln Gln Gly Asn Val Phe
        195                 200                 205

Ser Cys Ser Val Met His Glu Ala Leu His Asn His Tyr Thr Gln Lys
210                 215                 220

Ser Leu Ser Leu Ser Pro Gly
225                 230

<210> SEQ ID NO 7
<211> LENGTH: 263
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 7

Glu Pro Lys Ser Ser Asp Lys Thr His Thr Cys Pro Pro Cys Pro Ala
1               5                   10                  15

Pro Glu Leu Leu Gly Gly Pro Ser Val Phe Leu Phe Pro Pro Lys Pro
            20                  25                  30

Lys Asp Thr Leu Met Ile Ser Arg Thr Pro Glu Val Thr Cys Val Val
        35                  40                  45

Val Asp Val Ser His Glu Asp Pro Glu Val Lys Phe Asn Trp Tyr Val
50                  55                  60

Asp Gly Val Glu Val His Asn Ala Lys Thr Lys Pro Arg Glu Glu Gln
65                  70                  75                  80

Tyr Asp Ser Thr Tyr Arg Val Val Ser Val Leu Thr Val Leu His Gln
```

```
                  85                  90                  95
Asp Trp Leu Asn Gly Lys Glu Tyr Lys Cys Lys Val Ser Asn Lys Ala
                 100                 105                 110
Leu Pro Ala Pro Ile Glu Lys Thr Ile Ser Lys Ala Lys Gly Gln Pro
             115                 120                 125
Arg Glu Pro Gln Val Tyr Thr Leu Pro Pro Ser Arg Asp Glu Leu Thr
         130                 135                 140
Lys Asn Gln Val Ser Leu Thr Cys Leu Val Lys Gly Phe Tyr Pro Ser
145                 150                 155                 160
Asp Ile Ala Val Glu Trp Glu Ser Asn Gly Gln Pro Glu Asn Asn Tyr
                 165                 170                 175
Lys Thr Thr Pro Pro Val Leu Asp Ser Asp Gly Ser Phe Phe Leu Tyr
             180                 185                 190
Ser Lys Leu Thr Val Asp Lys Ser Arg Trp Gln Gln Gly Asn Val Phe
         195                 200                 205
Ser Cys Ser Val Met His Glu Ala Leu His Asn His Tyr Thr Gln Lys
210                 215                 220
Ser Leu Ser Leu Ser Pro Gly Ala Pro Asp Gly Asp Ser Ser Leu Ala
225                 230                 235                 240
Ala Ser Glu Arg Lys Ala Leu Gln Thr Glu Met Ala Arg Ile Lys Lys
                 245                 250                 255
Trp Leu Thr Phe Ser Leu Gly
             260

<210> SEQ ID NO 8
<211> LENGTH: 248
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 8

Met Ser Leu Phe Pro Ser Leu Pro Leu Leu Leu Ser Met Val Ala
1               5                  10                  15
Ala Ser Tyr Ser Glu Thr Val Thr Cys Glu Asp Ala Gln Lys Thr Cys
             20                  25                  30
Pro Ala Val Ile Ala Cys Ser Ser Pro Gly Ile Asn Gly Phe Pro Gly
         35                  40                  45
Lys Asp Gly Arg Asp Gly Thr Lys Gly Glu Lys Gly Glu Pro Gly Gln
     50                  55                  60
Gly Leu Arg Gly Leu Gln Gly Pro Pro Gly Lys Leu Gly Pro Pro Gly
65                  70                  75                  80
Asn Pro Gly Pro Ser Gly Ser Pro Gly Pro Lys Gly Gln Lys Gly Asp
                 85                  90                  95
Pro Gly Lys Ser Pro Asp Gly Asp Ser Ser Leu Ala Ala Ser Glu Arg
                 100                 105                 110
Lys Ala Leu Gln Thr Glu Met Ala Arg Ile Lys Lys Trp Leu Thr Phe
             115                 120                 125
Ser Leu Gly Lys Gln Val Gly Asn Lys Phe Phe Leu Thr Asn Gly Glu
         130                 135                 140
Ile Met Thr Phe Glu Lys Val Lys Ala Leu Cys Val Lys Phe Gln Ala
145                 150                 155                 160
Ser Val Ala Thr Pro Arg Asn Ala Ala Glu Asn Gly Ala Ile Gln Asn
                 165                 170                 175
```

-continued

```
Leu Ile Lys Glu Glu Ala Phe Leu Gly Ile Thr Asp Glu Lys Thr Glu
            180                 185                 190

Gly Gln Phe Val Asp Leu Thr Gly Asn Arg Leu Thr Tyr Thr Asn Trp
        195                 200                 205

Asn Glu Gly Glu Pro Asn Asn Ala Gly Ser Asp Glu Asp Cys Val Leu
    210                 215                 220

Leu Leu Lys Asn Gly Gln Trp Asn Asp Val Pro Cys Ser Thr Ser His
225                 230                 235                 240

Leu Ala Val Cys Glu Phe Pro Ile
                245
```

<210> SEQ ID NO 9
<211> LENGTH: 228
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 9

```
Glu Thr Val Thr Cys Glu Asp Ala Gln Lys Thr Cys Pro Ala Val Ile
1               5                   10                  15

Ala Cys Ser Ser Pro Gly Ile Asn Gly Phe Pro Gly Lys Asp Gly Arg
            20                  25                  30

Asp Gly Thr Lys Gly Glu Lys Gly Glu Pro Gly Gln Gly Leu Arg Gly
        35                  40                  45

Leu Gln Gly Pro Pro Gly Lys Leu Gly Pro Pro Gly Asn Pro Gly Pro
    50                  55                  60

Ser Gly Ser Pro Gly Pro Lys Gly Gln Lys Gly Asp Pro Gly Lys Ser
65                  70                  75                  80

Pro Asp Gly Asp Ser Ser Leu Ala Ala Ser Glu Arg Lys Ala Leu Gln
                85                  90                  95

Thr Glu Met Ala Arg Ile Lys Lys Trp Leu Thr Phe Ser Leu Gly Lys
            100                 105                 110

Gln Val Gly Asn Lys Phe Phe Leu Thr Asn Gly Glu Ile Met Thr Phe
        115                 120                 125

Glu Lys Val Lys Ala Leu Cys Val Lys Phe Gln Ala Ser Val Ala Thr
    130                 135                 140

Pro Arg Asn Ala Ala Glu Asn Gly Ala Ile Gln Asn Leu Ile Lys Glu
145                 150                 155                 160

Glu Ala Phe Leu Gly Ile Thr Asp Glu Lys Thr Glu Gly Gln Phe Val
                165                 170                 175

Asp Leu Thr Gly Asn Arg Leu Thr Tyr Thr Asn Trp Asn Glu Gly Glu
            180                 185                 190

Pro Asn Asn Ala Gly Ser Asp Glu Asp Cys Val Leu Leu Leu Lys Asn
        195                 200                 205

Gly Gln Trp Asn Asp Val Pro Cys Ser Thr Ser His Leu Ala Val Cys
    210                 215                 220

Glu Phe Pro Ile
225
```

<210> SEQ ID NO 10
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 10

Met Ser Leu Phe Pro Ser Leu Pro Leu Leu Leu Ser Met Val Ala
1               5                   10                  15

Ala Ser Tyr Ser
            20

<210> SEQ ID NO 11
<211> LENGTH: 141
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 11

Ala Ala Ser Glu Arg Lys Ala Leu Gln Thr Glu Met Ala Arg Ile Lys
1               5                   10                  15

Lys Trp Leu Thr Phe Ser Leu Gly Lys Gln Val Gly Asn Lys Phe Phe
            20                  25                  30

Leu Thr Asn Gly Glu Ile Met Thr Phe Glu Lys Val Lys Ala Leu Cys
        35                  40                  45

Val Lys Phe Gln Ala Ser Val Ala Thr Pro Arg Asn Ala Ala Glu Asn
    50                  55                  60

Gly Ala Ile Gln Asn Leu Ile Lys Glu Glu Ala Phe Leu Gly Ile Thr
65                  70                  75                  80

Asp Glu Lys Thr Glu Gly Gln Phe Val Asp Leu Thr Gly Asn Arg Leu
                85                  90                  95

Thr Tyr Thr Asn Trp Asn Glu Gly Glu Pro Asn Asn Ala Gly Ser Asp
            100                 105                 110

Glu Asp Cys Val Leu Leu Leu Lys Asn Gly Gln Trp Asn Asp Val Pro
        115                 120                 125

Cys Ser Thr Ser His Leu Ala Val Cys Glu Phe Pro Ile
    130                 135                 140

<210> SEQ ID NO 12
<211> LENGTH: 115
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 12

Val Gly Asn Lys Phe Phe Leu Thr Asn Gly Glu Ile Met Thr Phe Glu
1               5                   10                  15

Lys Val Lys Ala Leu Cys Val Lys Phe Gln Ala Ser Val Ala Thr Pro
            20                  25                  30

Arg Asn Ala Ala Glu Asn Gly Ala Ile Gln Asn Leu Ile Lys Glu Glu
        35                  40                  45

Ala Phe Leu Gly Ile Thr Asp Glu Lys Thr Glu Gly Gln Phe Val Asp
    50                  55                  60

Leu Thr Gly Asn Arg Leu Thr Tyr Thr Asn Trp Asn Glu Gly Glu Pro
65                  70                  75                  80

Asn Asn Ala Gly Ser Asp Glu Asp Cys Val Leu Leu Leu Lys Asn Gly
                85                  90                  95

Gln Trp Asn Asp Val Pro Cys Ser Thr Ser His Leu Ala Val Cys Glu
            100                 105                 110

```
Phe Pro Ile
        115

<210> SEQ ID NO 13
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Any amino acid

<400> SEQUENCE: 13

Glu Xaa Asn
1

<210> SEQ ID NO 14
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 14

Asn Glu Gly Glu Pro Asn Asn Ala Gly Ser
1               5                   10

<210> SEQ ID NO 15
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 15

Gly Ser Asp Glu Asp Cys Val Leu Leu
1               5

<210> SEQ ID NO 16
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 16

Leu Leu Leu Lys Asn Gly Gln Trp Asn Asp Val Pro Cys Ser Thr
1               5                   10                  15

<210> SEQ ID NO 17
<211> LENGTH: 27
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 17

Glu Pro Gly Gln Gly Leu Arg Gly Leu Gln Gly Pro Pro Gly Lys Leu
1               5                   10                  15

Gly Pro Pro Gly Asn Pro Gly Pro Ser Gly Ser
            20                  25
```

<210> SEQ ID NO 18
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 18

Gly Lys Leu Gly
1

<210> SEQ ID NO 19
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 19

Gly Pro Pro Gly Lys Leu Gly Pro Pro Gly Asn
1               5                   10

<210> SEQ ID NO 20
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 20

Arg Gly Leu Gln Gly Pro Pro Gly Lys Leu
1               5                   10

<210> SEQ ID NO 21
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 21

Gly Lys Leu Gly Pro Pro Gly Asn Pro Gly Pro Ser Gly Ser
1               5                   10

<210> SEQ ID NO 22
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 22

Gly Leu Arg Gly Leu Gln Gly Pro Pro Gly Lys Leu Gly Pro Pro Gly
1               5                   10                  15

Asn Pro Gly Pro
            20

<210> SEQ ID NO 23
<211> LENGTH: 148
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 23

```
Pro Asp Gly Asp Ser Ser Leu Ala Ala Ser Glu Arg Lys Ala Leu Gln
1               5                   10                  15

Thr Glu Met Ala Arg Ile Lys Lys Trp Leu Thr Phe Ser Leu Gly Lys
            20                  25                  30

Gln Val Gly Asn Lys Phe Phe Leu Thr Asn Gly Glu Ile Met Thr Phe
        35                  40                  45

Glu Lys Val Lys Ala Leu Cys Val Lys Phe Gln Ala Ser Val Ala Thr
50                  55                  60

Pro Arg Asn Ala Ala Glu Asn Gly Ala Ile Gln Asn Leu Ile Lys Glu
65                  70                  75                  80

Glu Ala Phe Leu Gly Ile Thr Asp Glu Lys Thr Glu Gly Gln Phe Val
                85                  90                  95

Asp Leu Thr Gly Asn Arg Leu Thr Tyr Thr Asn Trp Asn Glu Gly Glu
            100                 105                 110

Pro Asn Asn Ala Gly Ser Asp Glu Asp Cys Val Leu Leu Leu Lys Asn
        115                 120                 125

Gly Gln Trp Asn Asp Val Pro Cys Ser Thr Ser His Leu Ala Val Cys
130                 135                 140

Glu Phe Pro Ile
145
```

<210> SEQ ID NO 24
<211> LENGTH: 380
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 24

```
Glu Pro Lys Ser Ser Asp Lys Thr His Thr Cys Pro Pro Cys Pro Ala
1               5                   10                  15

Pro Glu Leu Leu Gly Gly Pro Ser Val Phe Leu Phe Pro Pro Lys Pro
            20                  25                  30

Lys Asp Thr Leu Met Ile Ser Arg Thr Pro Glu Val Thr Cys Val Val
        35                  40                  45

Val Asp Val Ser His Glu Asp Pro Glu Val Lys Phe Asn Trp Tyr Val
50                  55                  60

Asp Gly Val Glu Val His Asn Ala Lys Thr Lys Pro Arg Glu Glu Gln
65                  70                  75                  80

Tyr Asn Ser Thr Tyr Arg Val Val Ser Val Leu Thr Val Leu His Gln
                85                  90                  95

Asp Trp Leu Asn Gly Lys Glu Tyr Lys Cys Lys Val Ser Asn Lys Ala
            100                 105                 110

Leu Pro Ala Pro Ile Glu Lys Thr Ile Ser Lys Ala Lys Gly Gln Pro
        115                 120                 125

Arg Glu Pro Gln Val Tyr Thr Leu Pro Pro Ser Arg Asp Glu Leu Thr
130                 135                 140

Lys Asn Gln Val Ser Leu Thr Cys Leu Val Lys Gly Phe Tyr Pro Ser
145                 150                 155                 160

Asp Ile Ala Val Glu Trp Glu Ser Asn Gly Gln Pro Glu Asn Asn Tyr
                165                 170                 175
```

```
Lys Thr Thr Pro Pro Val Leu Asp Ser Asp Gly Ser Phe Phe Leu Tyr
            180                 185                 190

Ser Lys Leu Thr Val Asp Lys Ser Arg Trp Gln Gln Gly Asn Val Phe
        195                 200                 205

Ser Cys Ser Val Met His Glu Ala Leu His Asn His Tyr Thr Gln Lys
    210                 215                 220

Ser Leu Ser Leu Ser Pro Gly Ala Pro Asp Gly Asp Ser Ser Leu Ala
225                 230                 235                 240

Ala Ser Glu Arg Lys Ala Leu Gln Thr Glu Met Ala Arg Ile Lys Lys
                245                 250                 255

Trp Leu Thr Phe Ser Leu Gly Lys Gln Val Gly Asn Lys Phe Phe Leu
            260                 265                 270

Thr Asn Gly Glu Ile Met Thr Phe Glu Lys Val Lys Ala Leu Cys Val
        275                 280                 285

Lys Phe Gln Ala Ser Val Ala Thr Pro Arg Asn Ala Ala Glu Asn Gly
    290                 295                 300

Ala Ile Gln Asn Leu Ile Lys Glu Glu Ala Phe Leu Gly Ile Thr Asp
305                 310                 315                 320

Glu Lys Thr Glu Gly Gln Phe Val Asp Leu Thr Gly Asn Arg Leu Thr
                325                 330                 335

Tyr Thr Asn Trp Asn Glu Gly Glu Pro Asn Asn Ala Gly Ser Asp Glu
            340                 345                 350

Asp Cys Val Leu Leu Leu Lys Asn Gly Gln Trp Asn Asp Val Pro Cys
        355                 360                 365

Ser Thr Ser His Leu Ala Val Cys Glu Phe Pro Ile
    370                 375                 380

<210> SEQ ID NO 25
<211> LENGTH: 383
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 25

Ala Lys Thr Glu Pro Lys Ser Ser Asp Lys Thr His Thr Cys Pro Pro
1               5                   10                  15

Cys Pro Ala Pro Glu Leu Leu Gly Gly Pro Ser Val Phe Leu Phe Pro
            20                  25                  30

Pro Lys Pro Lys Asp Thr Leu Met Ile Ser Arg Thr Pro Glu Val Thr
        35                  40                  45

Cys Val Val Val Asp Val Ser His Glu Asp Pro Glu Val Lys Phe Asn
    50                  55                  60

Trp Tyr Val Asp Gly Val Glu Val His Asn Ala Lys Thr Lys Pro Arg
65                  70                  75                  80

Glu Glu Gln Tyr Asn Ser Thr Tyr Arg Val Val Ser Val Leu Thr Val
                85                  90                  95

Leu His Gln Asp Trp Leu Asn Gly Lys Glu Tyr Lys Cys Lys Val Ser
            100                 105                 110

Asn Lys Ala Leu Pro Ala Pro Ile Glu Lys Thr Ile Ser Lys Ala Lys
        115                 120                 125

Gly Gln Pro Arg Glu Pro Gln Val Tyr Thr Leu Pro Pro Ser Arg Asp
    130                 135                 140

Glu Leu Thr Lys Asn Gln Val Ser Leu Thr Cys Leu Val Lys Gly Phe
```

```
                  145                 150                 155                 160
        Tyr Pro Ser Asp Ile Ala Val Glu Trp Glu Ser Asn Gly Gln Pro Glu
                        165                 170                 175

Asn Asn Tyr Lys Thr Thr Pro Pro Val Leu Asp Ser Asp Gly Ser Phe
                        180                 185                 190

Phe Leu Tyr Ser Lys Leu Thr Val Asp Lys Ser Arg Trp Gln Gln Gly
                        195                 200                 205

Asn Val Phe Ser Cys Ser Val Met His Glu Ala Leu His Asn His Tyr
                        210                 215                 220

Thr Gln Lys Ser Leu Ser Leu Ser Pro Gly Ala Pro Asp Gly Asp Ser
        225                 230                 235                 240

Ser Leu Ala Ala Ser Glu Arg Lys Ala Leu Gln Thr Glu Met Ala Arg
                        245                 250                 255

Ile Lys Lys Trp Leu Thr Phe Ser Leu Gly Lys Gln Val Gly Asn Lys
                        260                 265                 270

Phe Phe Leu Thr Asn Gly Glu Ile Met Thr Phe Glu Lys Val Lys Ala
                        275                 280                 285

Leu Cys Val Lys Phe Gln Ala Ser Val Ala Thr Pro Arg Asn Ala Ala
                        290                 295                 300

Glu Asn Gly Ala Ile Gln Asn Leu Ile Lys Glu Ala Phe Leu Gly
        305                 310                 315                 320

Ile Thr Asp Glu Lys Thr Glu Gly Gln Phe Val Asp Leu Thr Gly Asn
                        325                 330                 335

Arg Leu Thr Tyr Thr Asn Trp Asn Glu Gly Pro Asn Asn Ala Gly
                        340                 345                 350

Ser Asp Glu Asp Cys Val Leu Leu Leu Lys Asn Gly Gln Trp Asn Asp
                        355                 360                 365

Val Pro Cys Ser Thr Ser His Leu Ala Val Cys Glu Phe Pro Ile
                        370                 375                 380

<210> SEQ ID NO 26
<211> LENGTH: 351
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 26

Glu Pro Lys Ser Ser Asp Lys Thr His Thr Cys Pro Pro Cys Pro Ala
        1               5                   10                  15

Pro Glu Leu Leu Gly Gly Pro Ser Val Phe Leu Phe Pro Pro Lys Pro
                        20                  25                  30

Lys Asp Thr Leu Met Ile Ser Arg Thr Pro Glu Val Thr Cys Val Val
                        35                  40                  45

Val Asp Val Ser His Glu Asp Pro Glu Val Lys Phe Asn Trp Tyr Val
                        50                  55                  60

Asp Gly Val Glu Val His Asn Ala Lys Thr Lys Pro Arg Glu Glu Gln
        65                  70                  75                  80

Tyr Asn Ser Thr Tyr Arg Val Val Ser Val Leu Thr Val Leu His Gln
                        85                  90                  95

Asp Trp Leu Asn Gly Lys Glu Tyr Lys Cys Lys Val Ser Asn Lys Ala
                        100                 105                 110

Leu Pro Ala Pro Ile Glu Lys Thr Ile Ser Lys Ala Lys Gly Gln Pro
                        115                 120                 125
```

```
Arg Glu Pro Gln Val Tyr Thr Leu Pro Pro Ser Arg Asp Glu Leu Thr
    130                 135                 140
Lys Asn Gln Val Ser Leu Thr Cys Leu Val Lys Gly Phe Tyr Pro Ser
145                 150                 155                 160
Asp Ile Ala Val Glu Trp Glu Ser Asn Gly Gln Pro Glu Asn Asn Tyr
                165                 170                 175
Lys Thr Thr Pro Pro Val Leu Asp Ser Asp Gly Ser Phe Phe Leu Tyr
            180                 185                 190
Ser Lys Leu Thr Val Asp Lys Ser Arg Trp Gln Gln Gly Asn Val Phe
        195                 200                 205
Ser Cys Ser Val Met His Glu Ala Leu His Asn His Tyr Thr Gln Lys
    210                 215                 220
Ser Leu Ser Leu Ser Pro Gly Ala Thr Ser Lys Gln Val Gly Asn Lys
225                 230                 235                 240
Phe Phe Leu Thr Asn Gly Glu Ile Met Thr Phe Glu Lys Val Lys Ala
                245                 250                 255
Leu Cys Val Lys Phe Gln Ala Ser Val Ala Thr Pro Arg Asn Ala Ala
            260                 265                 270
Glu Asn Gly Ala Ile Gln Asn Leu Ile Lys Glu Glu Ala Phe Leu Gly
        275                 280                 285
Ile Thr Asp Glu Lys Thr Glu Gly Gln Phe Val Asp Leu Thr Gly Asn
    290                 295                 300
Arg Leu Thr Tyr Thr Asn Trp Asn Glu Gly Glu Pro Asn Asn Ala Gly
305                 310                 315                 320
Ser Asp Glu Asp Cys Val Leu Leu Leu Lys Asn Gly Gln Trp Asn Asp
                325                 330                 335
Val Pro Cys Ser Thr Ser His Leu Ala Val Cys Glu Phe Pro Ile
            340                 345                 350

<210> SEQ ID NO 27
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 27

Lys Gln Val Gly Asn Lys Phe Phe Leu Thr Asn Gly Glu Ile Met Thr
1               5                   10                  15
Phe Glu Lys Val Lys Ala Leu Cys Val Lys Phe Gln Ala Ser Val Ala
                20                  25                  30
Thr Pro Arg Asn Ala Ala Glu Asn Gly Ala Ile Gln Asn Leu Ile Lys
            35                  40                  45
Glu Glu Ala Phe Leu Gly Ile Thr Asp Glu Lys Thr Glu Gly Gln Phe
        50                  55                  60
Val Asp Leu Thr Gly Asn Arg Leu Thr Tyr Thr Asn Trp Asn Glu Gly
65                  70                  75                  80
Glu Pro Asn Asn Ala Gly Ser Asp Glu Asp Cys Val Leu Leu Leu Lys
                85                  90                  95
Asn Gly Gln Trp Asn Asp Val Pro Cys Ser Thr Ser His Leu Ala Val
            100                 105                 110
Cys Glu Phe Pro Ile
        115

<210> SEQ ID NO 28
```

```
<211> LENGTH: 33
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 28

Pro Asp Gly Asp Ser Ser Leu Ala Ala Ser Glu Arg Lys Ala Leu Gln
1               5                   10                  15

Thr Glu Met Ala Arg Ile Lys Lys Trp Leu Thr Phe Ser Leu Gly Lys
            20                  25                  30

Gln

<210> SEQ ID NO 29
<211> LENGTH: 34
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 29

Ala Pro Asp Gly Asp Ser Ser Leu Ala Ala Ser Glu Arg Lys Ala Leu
1               5                   10                  15

Gln Thr Glu Met Ala Arg Ile Lys Lys Trp Leu Thr Phe Ser Leu Gly
            20                  25                  30

Lys Gln

<210> SEQ ID NO 30
<211> LENGTH: 31
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 30

Pro Asp Gly Asp Ser Ser Leu Ala Ala Ser Glu Arg Lys Ala Leu Gln
1               5                   10                  15

Thr Glu Met Ala Arg Ile Lys Lys Trp Leu Thr Phe Ser Leu Gly
            20                  25                  30

<210> SEQ ID NO 31
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 31

Ala Pro Asp Gly Asp Ser Ser Leu Ala Ala Ser Glu Arg Lys Ala Leu
1               5                   10                  15

Gln Thr Glu Met Ala Arg Ile Lys Lys Trp Leu Thr Phe Ser Leu Gly
            20                  25                  30

<210> SEQ ID NO 32
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 32

Ala Lys Thr
1

<210> SEQ ID NO 33
<211> LENGTH: 452
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (232)..(251)
<223> OTHER INFORMATION: Any amino acid and this region may encompass 0
      to 20 residues, wherein some positions may be absent

<400> SEQUENCE: 33

Glu Pro Lys Ser Ser Asp Lys Thr His Thr Cys Pro Pro Cys Pro Ala
1               5                   10                  15

Pro Glu Leu Leu Gly Gly Pro Ser Val Phe Leu Phe Pro Pro Lys Pro
            20                  25                  30

Lys Asp Thr Leu Met Ile Ser Arg Thr Pro Glu Val Thr Cys Val Val
        35                  40                  45

Val Asp Val Ser His Glu Asp Pro Glu Val Lys Phe Asn Trp Tyr Val
    50                  55                  60

Asp Gly Val Glu Val His Asn Ala Lys Thr Lys Pro Arg Glu Glu Gln
65                  70                  75                  80

Tyr Asp Ser Thr Tyr Arg Val Val Ser Val Leu Thr Val Leu His Gln
                85                  90                  95

Asp Trp Leu Asn Gly Lys Glu Tyr Lys Cys Lys Val Ser Asn Lys Ala
            100                 105                 110

Leu Pro Ala Pro Ile Glu Lys Thr Ile Ser Lys Ala Lys Gly Gln Pro
        115                 120                 125

Arg Glu Pro Gln Val Tyr Thr Leu Pro Pro Ser Arg Asp Glu Leu Thr
    130                 135                 140

Lys Asn Gln Val Ser Leu Thr Cys Leu Val Lys Gly Phe Tyr Pro Ser
145                 150                 155                 160

Asp Ile Ala Val Glu Trp Glu Ser Asn Gly Gln Pro Glu Asn Asn Tyr
                165                 170                 175

Lys Thr Thr Pro Pro Val Leu Asp Ser Asp Gly Ser Phe Phe Leu Tyr
            180                 185                 190

Ser Lys Leu Thr Val Asp Lys Ser Arg Trp Gln Gln Gly Asn Val Phe
        195                 200                 205

Ser Cys Ser Val Met His Glu Ala Leu His Asn His Tyr Thr Gln Lys
    210                 215                 220

Ser Leu Ser Leu Ser Pro Gly Xaa Xaa Xaa Xaa Xaa Xaa Xaa Xaa Xaa
225                 230                 235                 240

Xaa Xaa Xaa Xaa Xaa Xaa Xaa Xaa Xaa Xaa Xaa Gln Thr Asp Met Ser
                245                 250                 255

Arg Lys Ala Phe Val Phe Pro Lys Glu Ser Asp Thr Ser Tyr Val Ser
            260                 265                 270

Leu Lys Ala Pro Leu Thr Lys Pro Leu Lys Ala Phe Thr Val Cys Leu
        275                 280                 285

His Phe Tyr Thr Glu Leu Ser Ser Thr Arg Gly Tyr Ser Ile Phe Ser
    290                 295                 300

Tyr Ala Thr Lys Arg Gln Asp Asn Glu Ile Leu Ile Phe Trp Ser Lys
```

```
305                 310                 315                 320

Asp Ile Gly Tyr Ser Phe Thr Val Gly Gly Ser Glu Ile Leu Phe Glu
                325                 330                 335

Val Pro Glu Val Thr Val Ala Pro Val His Ile Cys Thr Ser Trp Glu
            340                 345                 350

Ser Ala Ser Gly Ile Val Glu Phe Trp Val Asp Gly Lys Pro Arg Val
            355                 360                 365

Arg Lys Ser Leu Lys Lys Gly Tyr Thr Val Gly Ala Glu Ala Ser Ile
        370                 375                 380

Ile Leu Gly Gln Glu Gln Asp Ser Phe Gly Gly Asn Phe Glu Gly Ser
385                 390                 395                 400

Gln Ser Leu Val Gly Asp Ile Gly Asn Val Asn Met Trp Asp Phe Val
            405                 410                 415

Leu Ser Pro Asp Glu Ile Asn Thr Ile Tyr Leu Gly Gly Pro Phe Ser
            420                 425                 430

Pro Asn Val Leu Asn Trp Arg Ala Leu Lys Tyr Glu Val Gln Gly Glu
        435                 440                 445

Val Phe Thr Lys
    450

<210> SEQ ID NO 34
<211> LENGTH: 457
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (232)..(251)
<223> OTHER INFORMATION: Any amino acid and this region may encompass 0
      to 20 residues, wherein some positions may be absent

<400> SEQUENCE: 34

Glu Pro Lys Ser Ser Asp Lys Thr His Thr Cys Pro Pro Cys Pro Ala
1               5                   10                  15

Pro Glu Leu Leu Gly Gly Pro Ser Val Phe Leu Phe Pro Pro Lys Pro
            20                  25                  30

Lys Asp Thr Leu Met Ile Ser Arg Thr Pro Glu Val Thr Cys Val Val
        35                  40                  45

Val Asp Val Ser His Glu Asp Pro Glu Val Lys Phe Asn Trp Tyr Val
    50                  55                  60

Asp Gly Val Glu Val His Asn Ala Lys Thr Lys Pro Arg Glu Glu Gln
65                  70                  75                  80

Tyr Asp Ser Thr Tyr Arg Val Val Ser Val Leu Thr Val Leu His Gln
                85                  90                  95

Asp Trp Leu Asn Gly Lys Glu Tyr Lys Cys Lys Val Ser Asn Lys Ala
            100                 105                 110

Leu Pro Ala Pro Ile Glu Lys Thr Ile Ser Lys Ala Lys Gly Gln Pro
        115                 120                 125

Arg Glu Pro Gln Val Tyr Thr Leu Pro Pro Ser Arg Asp Glu Leu Thr
    130                 135                 140

Lys Asn Gln Val Ser Leu Thr Cys Leu Val Lys Gly Phe Tyr Pro Ser
145                 150                 155                 160

Asp Ile Ala Val Glu Trp Glu Ser Asn Gly Gln Pro Glu Asn Asn Tyr
                165                 170                 175

Lys Thr Thr Pro Pro Val Leu Asp Ser Asp Gly Ser Phe Phe Leu Tyr
```

```
                180                 185                 190
Ser Lys Leu Thr Val Asp Lys Ser Arg Trp Gln Gln Gly Asn Val Phe
            195                 200                 205

Ser Cys Ser Val Met His Glu Ala Leu His Asn His Tyr Thr Gln Lys
        210                 215                 220

Ser Leu Ser Leu Ser Pro Gly Xaa Xaa Xaa Xaa Xaa Xaa Xaa Xaa Xaa
225                 230                 235                 240

Xaa Xaa Xaa Xaa Xaa Xaa Xaa Xaa Xaa Xaa Gln Thr Asp Met Ser
                245                 250                 255

Arg Lys Ala Phe Val Phe Pro Lys Glu Ser Asp Thr Ser Tyr Val Ser
            260                 265                 270

Leu Lys Ala Pro Leu Thr Lys Pro Leu Lys Ala Phe Thr Val Ala Leu
        275                 280                 285

His Phe Tyr Thr Glu Leu Ser Ser Thr Arg Gly Tyr Ser Ile Phe Ser
        290                 295                 300

Tyr Ala Thr Lys Arg Gln Asp Asn Glu Ile Leu Ile Phe Trp Ser Lys
305                 310                 315                 320

Asp Ile Gly Tyr Ser Phe Thr Val Gly Gly Ser Glu Ile Leu Phe Glu
                325                 330                 335

Val Pro Glu Val Thr Val Ala Pro Val His Ile Ala Thr Ser Trp Glu
            340                 345                 350

Ser Ala Ser Gly Ile Val Glu Phe Trp Val Asp Gly Lys Pro Arg Val
        355                 360                 365

Arg Lys Ser Leu Lys Lys Gly Tyr Thr Val Gly Ala Glu Ala Ser Ile
        370                 375                 380

Ile Leu Gly Gln Glu Gln Asp Ser Phe Gly Gly Asn Phe Glu Gly Ser
385                 390                 395                 400

Gln Ser Leu Val Gly Asp Ile Gly Asn Val Asn Met Trp Asp Phe Val
                405                 410                 415

Leu Ser Pro Asp Glu Ile Asn Thr Ile Tyr Leu Gly Gly Pro Phe Ser
            420                 425                 430

Pro Asn Val Leu Asn Trp Arg Ala Leu Lys Tyr Glu Val Gln Gly Glu
        435                 440                 445

Val Phe Thr Lys Pro Gln Leu Trp Pro
        450                 455

<210> SEQ ID NO 35
<211> LENGTH: 343
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (207)..(226)
<223> OTHER INFORMATION: Any amino acid and this region may encompass 0
      to 20 residues, wherein some positions may be absent

<400> SEQUENCE: 35

Gln Thr Asp Met Ser Arg Lys Ala Phe Val Phe Pro Lys Glu Ser Asp
1               5                   10                  15

Thr Ser Tyr Val Ser Leu Lys Ala Pro Leu Thr Lys Pro Leu Lys Ala
                20                  25                  30

Phe Thr Val Cys Leu His Phe Tyr Thr Glu Leu Ser Ser Thr Arg Gly
            35                  40                  45

Tyr Ser Ile Phe Ser Tyr Ala Thr Lys Arg Gln Asp Asn Glu Ile Leu
```

```
                50                  55                  60
Ile Phe Trp Ser Lys Asp Ile Gly Tyr Ser Phe Thr Val Gly Gly Ser
 65                  70                  75                  80

Glu Ile Leu Phe Glu Val Pro Glu Val Thr Val Ala Pro Val His Ile
                 85                  90                  95

Cys Thr Ser Trp Glu Ser Ala Ser Gly Ile Val Glu Phe Trp Val Asp
                100                 105                 110

Gly Lys Pro Arg Val Arg Lys Ser Leu Lys Lys Gly Tyr Thr Val Gly
                115                 120                 125

Ala Glu Ala Ser Ile Ile Leu Gly Gln Glu Gln Asp Ser Phe Gly Gly
            130                 135                 140

Asn Phe Glu Gly Ser Gln Ser Leu Val Gly Asp Ile Gly Asn Val Asn
145                 150                 155                 160

Met Trp Asp Phe Val Leu Ser Pro Asp Glu Ile Asn Thr Ile Tyr Leu
                165                 170                 175

Gly Gly Pro Phe Ser Pro Asn Val Leu Asn Trp Arg Ala Leu Lys Tyr
                180                 185                 190

Glu Val Gln Gly Glu Val Phe Thr Lys Pro Gln Leu Trp Pro Xaa Xaa
            195                 200                 205

Xaa Xaa Xaa Xaa Xaa Xaa Xaa Xaa Xaa Xaa Xaa Xaa Xaa Xaa Xaa Xaa
            210                 215                 220

Xaa Xaa Lys Gln Val Gly Asn Lys Phe Phe Leu Thr Asn Gly Glu Ile
225                 230                 235                 240

Met Thr Phe Glu Lys Val Lys Ala Leu Cys Val Lys Phe Gln Ala Ser
                245                 250                 255

Val Ala Thr Pro Arg Asn Ala Ala Glu Asn Gly Ala Ile Gln Asn Leu
                260                 265                 270

Ile Lys Glu Glu Ala Phe Leu Gly Ile Thr Asp Glu Lys Thr Glu Gly
            275                 280                 285

Gln Phe Val Asp Leu Thr Gly Asn Arg Leu Thr Tyr Thr Asn Trp Asn
            290                 295                 300

Glu Gly Glu Pro Asn Asn Ala Gly Ser Asp Glu Asp Cys Val Leu Leu
305                 310                 315                 320

Leu Lys Asn Gly Gln Trp Asn Asp Val Pro Cys Ser Thr Ser His Leu
                325                 330                 335

Ala Val Cys Glu Phe Pro Ile
            340

<210> SEQ ID NO 36
<211> LENGTH: 343
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (118)..(137)
<223> OTHER INFORMATION: Any amino acid and this region may encompass 0
      to 20 residues, wherein some positions may be absent

<400> SEQUENCE: 36

Lys Gln Val Gly Asn Lys Phe Phe Leu Thr Asn Gly Glu Ile Met Thr
  1               5                  10                  15

Phe Glu Lys Val Lys Ala Leu Cys Val Lys Phe Gln Ala Ser Val Ala
                 20                  25                  30

Thr Pro Arg Asn Ala Ala Glu Asn Gly Ala Ile Gln Asn Leu Ile Lys
```

```
                 35                  40                  45
Glu Glu Ala Phe Leu Gly Ile Thr Asp Glu Lys Thr Glu Gly Gln Phe
             50                  55                  60

Val Asp Leu Thr Gly Asn Arg Leu Thr Tyr Thr Asn Trp Asn Glu Gly
 65                  70                  75                  80

Glu Pro Asn Asn Ala Gly Ser Asp Glu Asp Cys Val Leu Leu Leu Lys
                 85                  90                  95

Asn Gly Gln Trp Asn Asp Val Pro Cys Ser Thr Ser His Leu Ala Val
            100                 105                 110

Cys Glu Phe Pro Ile Xaa Xaa Xaa Xaa Xaa Xaa Xaa Xaa Xaa Xaa Xaa
            115                 120                 125

Xaa Xaa Xaa Xaa Xaa Xaa Xaa Xaa Gln Thr Asp Met Ser Arg Lys
            130                 135                 140

Ala Phe Val Phe Pro Lys Glu Ser Asp Thr Ser Tyr Val Ser Leu Lys
145                 150                 155                 160

Ala Pro Leu Thr Lys Pro Leu Lys Ala Phe Thr Val Cys Leu His Phe
                165                 170                 175

Tyr Thr Glu Leu Ser Ser Thr Arg Gly Tyr Ser Ile Phe Ser Tyr Ala
            180                 185                 190

Thr Lys Arg Gln Asp Asn Glu Ile Leu Ile Phe Trp Ser Lys Asp Ile
            195                 200                 205

Gly Tyr Ser Phe Thr Val Gly Gly Ser Glu Ile Leu Phe Glu Val Pro
            210                 215                 220

Glu Val Thr Val Ala Pro Val His Ile Cys Thr Ser Trp Glu Ser Ala
225                 230                 235                 240

Ser Gly Ile Val Glu Phe Trp Val Asp Gly Lys Pro Arg Val Arg Lys
                245                 250                 255

Ser Leu Lys Lys Gly Tyr Thr Val Gly Ala Glu Ala Ser Ile Ile Leu
            260                 265                 270

Gly Gln Glu Gln Asp Ser Phe Gly Gly Asn Phe Glu Gly Ser Gln Ser
            275                 280                 285

Leu Val Gly Asp Ile Gly Asn Val Asn Met Trp Asp Phe Val Leu Ser
290                 295                 300

Pro Asp Glu Ile Asn Thr Ile Tyr Leu Gly Gly Pro Phe Ser Pro Asn
305                 310                 315                 320

Val Leu Asn Trp Arg Ala Leu Lys Tyr Glu Val Gln Gly Glu Val Phe
                325                 330                 335

Thr Lys Pro Gln Leu Trp Pro
            340
```

<210> SEQ ID NO 37
<211> LENGTH: 488
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (263)..(282)
<223> OTHER INFORMATION: Any amino acid and this region may encompass 0
      to 20 residues, wherein some positions may be absent

<400> SEQUENCE: 37

```
Pro Lys Ser Ser Asp Lys Thr His Thr Cys Pro Pro Cys Pro Ala Pro
1               5                   10                  15

Glu Leu Leu Gly Gly Pro Ser Val Phe Leu Phe Pro Pro Lys Pro Lys
```

```
            20                  25                  30
Asp Thr Leu Met Ile Ser Arg Thr Pro Glu Val Thr Cys Val Val Val
        35                  40                  45
Asp Val Ser His Glu Asp Pro Glu Val Lys Phe Asn Trp Tyr Val Asp
    50                  55                  60
Gly Val Glu Val His Asn Ala Lys Thr Lys Pro Arg Glu Glu Gln Tyr
65                  70                  75                  80
Asp Ser Thr Tyr Arg Val Val Ser Val Leu Thr Val Leu His Gln Asp
                85                  90                  95
Trp Leu Asn Gly Lys Glu Tyr Lys Cys Lys Val Ser Asn Lys Ala Leu
            100                 105                 110
Pro Ala Pro Ile Glu Lys Thr Ile Ser Lys Ala Lys Gly Gln Pro Arg
        115                 120                 125
Glu Pro Gln Val Tyr Thr Leu Pro Pro Ser Arg Asp Glu Leu Thr Lys
    130                 135                 140
Asn Gln Val Ser Leu Thr Cys Leu Val Lys Gly Phe Tyr Pro Ser Asp
145                 150                 155                 160
Ile Ala Val Glu Trp Glu Ser Asn Gly Gln Pro Glu Asn Asn Tyr Lys
                165                 170                 175
Thr Thr Pro Pro Val Leu Asp Ser Asp Gly Ser Phe Phe Leu Tyr Ser
            180                 185                 190
Lys Leu Thr Val Asp Lys Ser Arg Trp Gln Gln Gly Asn Val Phe Ser
        195                 200                 205
Cys Ser Val Met His Glu Ala Leu His Asn His Tyr Thr Gln Lys Ser
    210                 215                 220
Leu Ser Leu Ser Pro Gly Ala Pro Asp Gly Asp Ser Ser Leu Ala Ala
225                 230                 235                 240
Ser Glu Arg Lys Ala Leu Gln Thr Glu Met Ala Arg Ile Lys Lys Trp
                245                 250                 255
Leu Thr Phe Ser Leu Gly Xaa Xaa Xaa Xaa Xaa Xaa Xaa Xaa Xaa
            260                 265                 270
Xaa Xaa Xaa Xaa Xaa Xaa Xaa Xaa Xaa Xaa Gln Thr Asp Met Ser Arg
        275                 280                 285
Lys Ala Phe Val Phe Pro Lys Glu Ser Asp Thr Ser Tyr Val Ser Leu
    290                 295                 300
Lys Ala Pro Leu Thr Lys Pro Leu Lys Ala Phe Thr Val Ala Leu His
305                 310                 315                 320
Phe Tyr Thr Glu Leu Ser Ser Thr Arg Gly Tyr Ser Ile Phe Ser Tyr
                325                 330                 335
Ala Thr Lys Arg Gln Asp Asn Glu Ile Leu Ile Phe Trp Ser Lys Asp
            340                 345                 350
Ile Gly Tyr Ser Phe Thr Val Gly Gly Ser Glu Ile Leu Phe Glu Val
        355                 360                 365
Pro Glu Val Thr Val Ala Pro Val His Ile Ala Thr Ser Trp Glu Ser
    370                 375                 380
Ala Ser Gly Ile Val Glu Phe Trp Val Asp Gly Lys Pro Arg Val Arg
385                 390                 395                 400
Lys Ser Leu Lys Lys Gly Tyr Thr Val Gly Ala Glu Ala Ser Ile Ile
                405                 410                 415
Leu Gly Gln Glu Gln Asp Ser Phe Gly Gly Asn Phe Glu Gly Ser Gln
            420                 425                 430
Ser Leu Val Gly Asp Ile Gly Asn Val Asn Met Trp Asp Phe Val Leu
        435                 440                 445
```

Ser Pro Asp Glu Ile Asn Thr Ile Tyr Leu Gly Gly Pro Phe Ser Pro
    450                 455                 460

Asn Val Leu Asn Trp Arg Ala Leu Lys Tyr Glu Val Gln Gly Glu Val
465                 470                 475                 480

Phe Thr Lys Pro Gln Leu Trp Pro
                485

<210> SEQ ID NO 38
<211> LENGTH: 215
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 38

Ala Lys Thr His His His His His His Gln Thr Asp Met Ser Arg Lys
1               5                   10                  15

Ala Phe Val Phe Pro Lys Glu Ser Asp Thr Ser Tyr Val Ser Leu Lys
            20                  25                  30

Ala Pro Leu Thr Lys Pro Leu Lys Ala Phe Thr Val Cys Leu His Phe
        35                  40                  45

Tyr Thr Glu Leu Ser Ser Thr Arg Gly Tyr Ser Ile Phe Ser Tyr Ala
    50                  55                  60

Thr Lys Arg Gln Asp Asn Glu Ile Leu Ile Phe Trp Ser Lys Asp Ile
65                  70                  75                  80

Gly Tyr Ser Phe Thr Val Gly Gly Ser Glu Ile Leu Phe Glu Val Pro
                85                  90                  95

Glu Val Thr Val Ala Pro Val His Ile Cys Thr Ser Trp Glu Ser Ala
            100                 105                 110

Ser Gly Ile Val Glu Phe Trp Val Asp Gly Lys Pro Arg Val Arg Lys
        115                 120                 125

Ser Leu Lys Lys Gly Tyr Thr Val Gly Ala Glu Ala Ser Ile Ile Leu
    130                 135                 140

Gly Gln Glu Gln Asp Ser Phe Gly Gly Asn Phe Glu Gly Ser Gln Ser
145                 150                 155                 160

Leu Val Gly Asp Ile Gly Asn Val Asn Met Trp Asp Phe Val Leu Ser
                165                 170                 175

Pro Asp Glu Ile Asn Thr Ile Tyr Leu Gly Gly Pro Phe Ser Pro Asn
            180                 185                 190

Val Leu Asn Trp Arg Ala Leu Lys Tyr Glu Val Gln Gly Glu Val Phe
        195                 200                 205

Thr Lys Pro Gln Leu Trp Pro
    210                 215

<210> SEQ ID NO 39
<211> LENGTH: 206
<212> TYPE: PRT
<213> ORGANISM: Homo sapiens

<400> SEQUENCE: 39

Gln Thr Asp Met Ser Arg Lys Ala Phe Val Phe Pro Lys Glu Ser Asp
1               5                   10                  15

Thr Ser Tyr Val Ser Leu Lys Ala Pro Leu Thr Lys Pro Leu Lys Ala
            20                  25                  30

Phe Thr Val Cys Leu His Phe Tyr Thr Glu Leu Ser Ser Thr Arg Gly
        35                  40                  45

Tyr Ser Ile Phe Ser Tyr Ala Thr Lys Arg Gln Asp Asn Glu Ile Leu
            50                  55                  60

Ile Phe Trp Ser Lys Asp Ile Gly Tyr Ser Phe Thr Val Gly Gly Ser
 65                  70                  75                  80

Glu Ile Leu Phe Glu Val Pro Glu Val Thr Val Ala Pro Val His Ile
                85                  90                  95

Cys Thr Ser Trp Glu Ser Ala Ser Gly Ile Val Glu Phe Trp Val Asp
               100                 105                 110

Gly Lys Pro Arg Val Arg Lys Ser Leu Lys Lys Gly Tyr Thr Val Gly
           115                 120                 125

Ala Glu Ala Ser Ile Ile Leu Gly Gln Glu Gln Asp Ser Phe Gly Gly
       130                 135                 140

Asn Phe Glu Gly Ser Gln Ser Leu Val Gly Asp Ile Gly Asn Val Asn
145                 150                 155                 160

Met Trp Asp Phe Val Leu Ser Pro Asp Glu Ile Asn Thr Ile Tyr Leu
               165                 170                 175

Gly Gly Pro Phe Ser Pro Asn Val Leu Asn Trp Arg Ala Leu Lys Tyr
               180                 185                 190

Glu Val Gln Gly Glu Val Phe Thr Lys Pro Gln Leu Trp Pro
           195                 200                 205

<210> SEQ ID NO 40
<211> LENGTH: 458
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (207)..(226)
<223> OTHER INFORMATION: Any amino acid and this region may encompass 0
      to 20 residues, wherein some positions may be absent

<400> SEQUENCE: 40

Gln Thr Asp Met Ser Arg Lys Ala Phe Val Phe Pro Lys Glu Ser Asp
  1               5                  10                  15

Thr Ser Tyr Val Ser Leu Lys Ala Pro Leu Thr Lys Pro Leu Lys Ala
               20                  25                  30

Phe Thr Val Cys Leu His Phe Tyr Thr Glu Leu Ser Ser Thr Arg Gly
            35                  40                  45

Tyr Ser Ile Phe Ser Tyr Ala Thr Lys Arg Gln Asp Asn Glu Ile Leu
            50                  55                  60

Ile Phe Trp Ser Lys Asp Ile Gly Tyr Ser Phe Thr Val Gly Gly Ser
 65                  70                  75                  80

Glu Ile Leu Phe Glu Val Pro Glu Val Thr Val Ala Pro Val His Ile
                85                  90                  95

Cys Thr Ser Trp Glu Ser Ala Ser Gly Ile Val Glu Phe Trp Val Asp
               100                 105                 110

Gly Lys Pro Arg Val Arg Lys Ser Leu Lys Lys Gly Tyr Thr Val Gly
           115                 120                 125

Ala Glu Ala Ser Ile Ile Leu Gly Gln Glu Gln Asp Ser Phe Gly Gly
       130                 135                 140

Asn Phe Glu Gly Ser Gln Ser Leu Val Gly Asp Ile Gly Asn Val Asn
145                 150                 155                 160

Met Trp Asp Phe Val Leu Ser Pro Asp Glu Ile Asn Thr Ile Tyr Leu
               165                 170                 175

Gly Gly Pro Phe Ser Pro Asn Val Leu Asn Trp Arg Ala Leu Lys Tyr
            180                 185                 190

Glu Val Gln Gly Glu Val Phe Thr Lys Pro Gln Leu Trp Pro Xaa Xaa
        195                 200                 205

Xaa Xaa Xaa Xaa Xaa Xaa Xaa Xaa Xaa Xaa Xaa Xaa Xaa Xaa Xaa Xaa
    210                 215                 220

Xaa Xaa Glu Pro Lys Ser Ser Asp Lys Thr His Thr Cys Pro Pro Cys
225                 230                 235                 240

Pro Ala Pro Glu Leu Leu Gly Gly Pro Ser Val Phe Leu Phe Pro Pro
                245                 250                 255

Lys Pro Lys Asp Thr Leu Met Ile Ser Arg Thr Pro Glu Val Thr Cys
            260                 265                 270

Val Val Val Asp Val Ser His Glu Asp Pro Glu Val Lys Phe Asn Trp
        275                 280                 285

Tyr Val Asp Gly Val Glu Val His Asn Ala Lys Thr Lys Pro Arg Glu
    290                 295                 300

Glu Gln Tyr Asp Ser Thr Tyr Arg Val Val Ser Val Leu Thr Val Leu
305                 310                 315                 320

His Gln Asp Trp Leu Asn Gly Lys Glu Tyr Lys Cys Lys Val Ser Asn
                325                 330                 335

Lys Ala Leu Pro Ala Pro Ile Glu Lys Thr Ile Ser Lys Ala Lys Gly
            340                 345                 350

Gln Pro Arg Glu Pro Gln Val Tyr Thr Leu Pro Pro Ser Arg Asp Glu
        355                 360                 365

Leu Thr Lys Asn Gln Val Ser Leu Thr Cys Leu Val Lys Gly Phe Tyr
    370                 375                 380

Pro Ser Asp Ile Ala Val Glu Trp Glu Ser Asn Gly Gln Pro Glu Asn
385                 390                 395                 400

Asn Tyr Lys Thr Thr Pro Pro Val Leu Asp Ser Asp Gly Ser Phe Phe
                405                 410                 415

Leu Tyr Ser Lys Leu Thr Val Asp Lys Ser Arg Trp Gln Gln Gly Asn
            420                 425                 430

Val Phe Ser Cys Ser Val Met His Glu Ala Leu His Asn His Tyr Thr
        435                 440                 445

Gln Lys Ser Leu Ser Leu Ser Pro Gly Ala
    450                 455

<210> SEQ ID NO 41
<211> LENGTH: 439
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 41

Gln Thr Asp Met Ser Arg Lys Ala Phe Val Phe Pro Lys Glu Ser Asp
1               5                   10                  15

Thr Ser Tyr Val Ser Leu Lys Ala Pro Leu Thr Lys Pro Leu Lys Ala
            20                  25                  30

Phe Thr Val Cys Leu His Phe Tyr Thr Glu Leu Ser Ser Thr Arg Gly
        35                  40                  45

Tyr Ser Ile Phe Ser Tyr Ala Thr Lys Arg Gln Asp Asn Glu Ile Leu
    50                  55                  60

Ile Phe Trp Ser Lys Asp Ile Gly Tyr Ser Phe Thr Val Gly Gly Ser 65                  70                  75                  80
Glu Ile Leu Phe Glu Val Pro Glu Val Thr Val Ala Pro Val His Ile
                    85                  90                  95

Cys Thr Ser Trp Glu Ser Ala Ser Gly Ile Val Glu Phe Trp Val Asp
                100                 105                 110

Gly Lys Pro Arg Val Arg Lys Ser Leu Lys Lys Gly Tyr Thr Val Gly
            115                 120                 125

Ala Glu Ala Ser Ile Ile Leu Gly Gln Glu Gln Asp Ser Phe Gly Gly
130                 135                 140

Asn Phe Glu Gly Ser Gln Ser Leu Val Gly Asp Ile Gly Asn Val Asn
145                 150                 155                 160

Met Trp Asp Phe Val Leu Ser Pro Asp Glu Ile Asn Thr Ile Tyr Leu
                165                 170                 175

Gly Gly Pro Phe Ser Pro Asn Val Leu Asn Trp Arg Ala Leu Lys Tyr
            180                 185                 190

Glu Val Gln Gly Glu Val Phe Thr Lys Pro Gln Leu Trp Pro Leu Glu
        195                 200                 205

Pro Lys Ser Ser Asp Lys Thr His Thr Cys Pro Pro Cys Pro Ala Pro
210                 215                 220

Glu Leu Leu Gly Gly Pro Ser Val Phe Leu Phe Pro Pro Lys Pro Lys
225                 230                 235                 240

Asp Thr Leu Met Ile Ser Arg Thr Pro Glu Val Thr Cys Val Val Val
                245                 250                 255

Asp Val Ser His Glu Asp Pro Glu Val Lys Phe Asn Trp Tyr Val Asp
            260                 265                 270

Gly Val Glu Val His Asn Ala Lys Thr Lys Pro Arg Glu Glu Gln Tyr
        275                 280                 285

Asp Ser Thr Tyr Arg Val Val Ser Val Leu Thr Val Leu His Gln Asp
    290                 295                 300

Trp Leu Asn Gly Lys Glu Tyr Lys Cys Lys Val Ser Asn Lys Ala Leu
305                 310                 315                 320

Pro Ala Pro Ile Glu Lys Thr Ile Ser Lys Ala Lys Gly Gln Pro Arg
                325                 330                 335

Glu Pro Gln Val Tyr Thr Leu Pro Pro Ser Arg Asp Glu Leu Thr Lys
            340                 345                 350

Asn Gln Val Ser Leu Thr Cys Leu Val Lys Gly Phe Tyr Pro Ser Asp
        355                 360                 365

Ile Ala Val Glu Trp Glu Ser Asn Gly Gln Pro Glu Asn Asn Tyr Lys
    370                 375                 380

Thr Thr Pro Pro Val Leu Asp Ser Asp Gly Ser Phe Phe Leu Tyr Ser
385                 390                 395                 400

Lys Leu Thr Val Asp Lys Ser Arg Trp Gln Gln Gly Asn Val Phe Ser
                405                 410                 415

Cys Ser Val Met His Glu Ala Leu His Asn His Tyr Thr Gln Lys Ser
            420                 425                 430

Leu Ser Leu Ser Pro Gly Ala
        435

<210> SEQ ID NO 42
<211> LENGTH: 232
<212> TYPE: PRT
<213> ORGANISM: Artificial Sequence
<220> FEATURE:
<223> OTHER INFORMATION: Description of Artificial Sequence: Synthetic
    polypeptide

<400> SEQUENCE: 42

```
Glu Pro Lys Ser Ser Asp Lys Thr His Thr Cys Pro Pro Cys Pro Ala
1               5                   10                  15

Pro Glu Leu Leu Gly Gly Pro Ser Val Phe Leu Phe Pro Pro Lys Pro
            20                  25                  30

Lys Asp Thr Leu Met Ile Ser Arg Thr Pro Glu Val Thr Cys Val Val
        35                  40                  45

Val Asp Val Ser His Glu Asp Pro Glu Val Lys Phe Asn Trp Tyr Val
    50                  55                  60

Asp Gly Val Glu Val His Asn Ala Lys Thr Lys Pro Arg Glu Glu Gln
65                  70                  75                  80

Tyr Asp Ser Thr Tyr Arg Val Val Ser Val Leu Thr Val Leu His Gln
                85                  90                  95

Asp Trp Leu Asn Gly Lys Glu Tyr Lys Cys Lys Val Ser Asn Lys Ala
            100                 105                 110

Leu Pro Ala Pro Ile Glu Lys Thr Ile Ser Lys Ala Lys Gly Gln Pro
        115                 120                 125

Arg Glu Pro Gln Val Tyr Thr Leu Pro Pro Ser Arg Asp Glu Leu Thr
130                 135                 140

Lys Asn Gln Val Ser Leu Thr Cys Leu Val Lys Gly Phe Tyr Pro Ser
145                 150                 155                 160

Asp Ile Ala Val Glu Trp Glu Ser Asn Gly Gln Pro Glu Asn Asn Tyr
                165                 170                 175

Lys Thr Thr Pro Pro Val Leu Asp Ser Asp Gly Ser Phe Phe Leu Tyr
            180                 185                 190

Ser Lys Leu Thr Val Asp Lys Ser Arg Trp Gln Gln Gly Asn Val Phe
        195                 200                 205

Ser Cys Ser Val Met His Glu Ala Leu His Asn His Tyr Thr Gln Lys
210                 215                 220

Ser Leu Ser Leu Ser Pro Gly Ala
225                 230
```

<210> SEQ ID NO 43
<211> LENGTH: 458
<212> TYPE: PRT
<213> ORGANISM: Artificial Sequence
<220> FEATURE:
<223> OTHER INFORMATION: Description of Artificial Sequence: Synthetic
    polypeptide
<220> FEATURE:
<221> NAME/KEY: MOD_RES
<222> LOCATION: (207)..(226)
<223> OTHER INFORMATION: Any amino acid and this region may encompass 0
    to 20 residues, wherein some positions may be absent

<400> SEQUENCE: 43

```
Gln Thr Asp Met Ser Arg Lys Ala Phe Val Phe Pro Lys Glu Ser Asp
1               5                   10                  15

Thr Ser Tyr Val Ser Leu Lys Ala Pro Leu Thr Lys Pro Leu Lys Ala
            20                  25                  30

Phe Thr Val Cys Leu His Phe Tyr Thr Glu Leu Ser Ser Thr Arg Gly
        35                  40                  45

Tyr Ser Ile Phe Ser Tyr Ala Thr Lys Arg Gln Asp Asn Glu Ile Leu
    50                  55                  60

Ile Phe Trp Ser Lys Asp Ile Gly Tyr Ser Phe Thr Val Gly Gly Ser
65                  70                  75                  80
```

```
Glu Ile Leu Phe Glu Val Pro Glu Val Thr Val Ala Pro Val His Ile
                 85                  90                  95

Cys Thr Ser Trp Glu Ser Ala Ser Gly Ile Val Glu Phe Trp Val Asp
            100                 105                 110

Gly Lys Pro Arg Val Arg Lys Ser Leu Lys Lys Gly Tyr Thr Val Gly
        115                 120                 125

Ala Glu Ala Ser Ile Ile Leu Gly Gln Glu Gln Asp Ser Phe Gly Gly
    130                 135                 140

Asn Phe Glu Gly Ser Gln Ser Leu Val Gly Asp Ile Gly Asn Val Asn
145                 150                 155                 160

Met Trp Asp Phe Val Leu Ser Pro Asp Glu Ile Asn Thr Ile Tyr Leu
                165                 170                 175

Gly Gly Pro Phe Ser Pro Asn Val Leu Asn Trp Arg Ala Leu Lys Tyr
            180                 185                 190

Glu Val Gln Gly Glu Val Phe Thr Lys Pro Gln Leu Trp Pro Xaa Xaa
        195                 200                 205

Xaa Xaa Xaa Xaa Xaa Xaa Xaa Xaa Xaa Xaa Xaa Xaa Xaa Xaa Xaa Xaa
    210                 215                 220

Xaa Xaa Glu Pro Lys Ser Ser Asp Lys Thr His Thr Cys Pro Pro Cys
225                 230                 235                 240

Pro Ala Pro Glu Leu Leu Gly Gly Pro Ser Val Phe Leu Phe Pro Pro
                245                 250                 255

Lys Pro Lys Asp Thr Leu Met Ile Ser Arg Thr Pro Glu Val Thr Cys
            260                 265                 270

Val Val Val Asp Val Ser His Glu Asp Pro Glu Val Lys Phe Asn Trp
        275                 280                 285

Tyr Val Asp Gly Val Glu Val His Asn Ala Lys Thr Lys Pro Arg Glu
    290                 295                 300

Glu Gln Tyr Asn Ser Thr Tyr Arg Val Val Ser Val Leu Thr Val Leu
305                 310                 315                 320

His Gln Asp Trp Leu Asn Gly Lys Glu Tyr Lys Cys Lys Val Ser Asn
                325                 330                 335

Lys Ala Leu Pro Ala Pro Ile Glu Lys Thr Ile Ser Lys Ala Lys Gly
            340                 345                 350

Gln Pro Arg Glu Pro Gln Val Tyr Thr Leu Pro Pro Ser Arg Asp Glu
        355                 360                 365

Leu Thr Lys Asn Gln Val Ser Leu Thr Cys Leu Val Lys Gly Phe Tyr
    370                 375                 380

Pro Ser Asp Ile Ala Val Glu Trp Glu Ser Asn Gly Gln Pro Glu Asn
385                 390                 395                 400

Asn Tyr Lys Thr Thr Pro Pro Val Leu Asp Ser Asp Gly Ser Phe Phe
                405                 410                 415

Leu Tyr Ser Lys Leu Thr Val Asp Lys Ser Arg Trp Gln Gln Gly Asn
            420                 425                 430

Val Phe Ser Cys Ser Val Met His Glu Ala Leu His Asn His Tyr Thr
        435                 440                 445

Gln Lys Ser Leu Ser Leu Ser Pro Gly Ala
    450                 455
```

<210> SEQ ID NO 44
<211> LENGTH: 438
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 44

```
Gln Thr Asp Met Ser Arg Lys Ala Phe Val Phe Pro Lys Glu Ser Asp
1               5                   10                  15

Thr Ser Tyr Val Ser Leu Lys Ala Pro Leu Thr Lys Pro Leu Lys Ala
            20                  25                  30

Phe Thr Val Cys Leu His Phe Tyr Thr Glu Leu Ser Ser Thr Arg Gly
        35                  40                  45

Tyr Ser Ile Phe Ser Tyr Ala Thr Lys Arg Gln Asp Asn Glu Ile Leu
    50                  55                  60

Ile Phe Trp Ser Lys Asp Ile Gly Tyr Ser Phe Thr Val Gly Gly Ser
65                  70                  75                  80

Glu Ile Leu Phe Glu Val Pro Glu Val Thr Val Ala Pro Val His Ile
                85                  90                  95

Cys Thr Ser Trp Glu Ser Ala Ser Gly Ile Val Glu Phe Trp Val Asp
            100                 105                 110

Gly Lys Pro Arg Val Arg Lys Ser Leu Lys Lys Gly Tyr Thr Val Gly
        115                 120                 125

Ala Glu Ala Ser Ile Ile Leu Gly Gln Glu Gln Asp Ser Phe Gly Gly
    130                 135                 140

Asn Phe Glu Gly Ser Gln Ser Leu Val Gly Asp Ile Gly Asn Val Asn
145                 150                 155                 160

Met Trp Asp Phe Val Leu Ser Pro Asp Glu Ile Asn Thr Ile Tyr Leu
                165                 170                 175

Gly Gly Pro Phe Ser Pro Asn Val Leu Asn Trp Arg Ala Leu Lys Tyr
            180                 185                 190

Glu Val Gln Gly Glu Val Phe Thr Lys Pro Gln Leu Trp Pro Glu Pro
        195                 200                 205

Lys Ser Ser Asp Lys Thr His Thr Cys Pro Pro Cys Pro Ala Pro Glu
    210                 215                 220

Leu Leu Gly Gly Pro Ser Val Phe Leu Phe Pro Pro Lys Pro Lys Asp
225                 230                 235                 240

Thr Leu Met Ile Ser Arg Thr Pro Glu Val Thr Cys Val Val Val Asp
                245                 250                 255

Val Ser His Glu Asp Pro Glu Val Lys Phe Asn Trp Tyr Val Asp Gly
            260                 265                 270

Val Glu Val His Asn Ala Lys Thr Lys Pro Arg Glu Glu Gln Tyr Asn
        275                 280                 285

Ser Thr Tyr Arg Val Val Ser Val Leu Thr Val Leu His Gln Asp Trp
    290                 295                 300

Leu Asn Gly Lys Glu Tyr Lys Cys Lys Val Ser Asn Lys Ala Leu Pro
305                 310                 315                 320

Ala Pro Ile Glu Lys Thr Ile Ser Lys Ala Lys Gly Gln Pro Arg Glu
                325                 330                 335

Pro Gln Val Tyr Thr Leu Pro Pro Ser Arg Asp Glu Leu Thr Lys Asn
            340                 345                 350

Gln Val Ser Leu Thr Cys Leu Val Lys Gly Phe Tyr Pro Ser Asp Ile
        355                 360                 365

Ala Val Glu Trp Glu Ser Asn Gly Gln Pro Glu Asn Asn Tyr Lys Thr
    370                 375                 380

Thr Pro Pro Val Leu Asp Ser Asp Gly Ser Phe Phe Leu Tyr Ser Lys
385                 390                 395                 400
```

Leu Thr Val Asp Lys Ser Arg Trp Gln Gln Gly Asn Val Phe Ser Cys
            405                 410                 415

Ser Val Met His Glu Ala Leu His Asn His Tyr Thr Gln Lys Ser Leu
        420                 425                 430

Ser Leu Ser Pro Gly Ala
        435

<210> SEQ ID NO 45
<211> LENGTH: 618
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 45
cagaccgata tgagccggaa agccttcgtg ttccctaaag agagcgatac cagctatgtg     60
agcctgaaag ccccactgac caaaccactg aaggccttca ccgtgtgcct gcacttttac    120
accgagctga gctccacacg agggtacagc atctttttcct atgctacaaa gaggcaggac   180
aacgaaatcc tgattttctg gtcaaaagat atcggctata gctttactgt gggcggatcc   240
gagattctgt cgaggtgcc cgaagtcaca gtggctcctg tccatatctg tacttcctgg    300
gagtcagcaa gcggcattgt cgaattctgg gtggacggaa agcctagggt gagaaaatct   360
ctgaagaaag atacacagt gggggccgag gctagtatca ttctggggca ggaacaggac    420
tcattcgggg gcaactttga aggctcccag tctctggtcg gggatatcgg caacgtgaac   480
atgtgggact ttgtcctgag cccagatgag atcaatacca tctacctggg agggcccttc   540
agccctaacg tgctgaattg gcgcgcactg aagtatgagg tccagggcga agtgtttaca   600 aaacccagc tgtggcca                                                  618

<210> SEQ ID NO 46
<211> LENGTH: 618
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 46
cagacagaca tgtcgaggaa ggcttttgtg tttcccaaag agtcggatac ttcctatgta     60
tccctcaaag caccccttaac gaagcctctc aaagccttca ctgtgtgcct ccacttctac   120
acggaactgt cctcgaccag agggtacagt attttctcgt atgctactaa gagacaagac   180
aatgagattc tcatattttg gtctaaggat ataggataca gttttacagt gggtgggtct   240
gaaatattat tcgaggttcc tgaagtcaca gtagctccag tacacatttg cacaagctgg   300
gagtccgcct cagggatcgt ggagttctgg gtagatggga agcccagggt gaggaagagt   360
ctgaagaagg atacactgt gggggcagaa gcaagcatca tcttggggca ggagcaggat    420
tccttcggtg gaactttga aggaagccag tccctggtgg gagacattgg aaatgtgaac    480
atgtgggact ttgtgctgtc accagatgag attaacacca tctatcttgg cgggcccttc   540
agtcctaatg tcctgaactg gcgggcactg aagtatgaag tgcaaggcga agtgttcacc   600
aaaccccagc tgtggccc                                                 618

<210> SEQ ID NO 47
<211> LENGTH: 618
<212> TYPE: DNA

<213> ORGANISM: Artificial Sequence
<220> FEATURE:
<223> OTHER INFORMATION: Description of Artificial Sequence: Synthetic
    polynucleotide

<400> SEQUENCE: 47

```
cagacagaca tgagcaggaa ggcttttgtg tttcccaaag agagcgatac ttcctatgtg    60
tccctcaaag caccgctgac caagcctctc aaagccttca ctgtgtgcct ccacttctac   120
accgaactgt ccagcacccg tgggtacagt attttcagct atgctactaa gagacaggac   180
aatgagattc tcatattttg gtctaaggat atcggataca gttttacagt gggtgggtct   240
gaaatactgt tcgaggtgcc tgaagtcaca gtggctccag tacacatttg tacaagctgg   300
gagtccgcct cagggatcgt ggagttctgg gtggatggga agcccagggt gaggaagagt   360
ctgaagaagg gatacactgt gggggcagaa gcaagcatca tcctggggca ggagcaggat   420
tccttcggtg gaacttttga aggaagccag tccctggtgg agacattgg aaatgtgaac    480
atgtgggact ttgtgctgtc accagatgag attaacacca tctatctggg cgggcccttc   540
agtcctaatg tcctgaactg gcgggcactg aagtatgaag tgcagggcga agtgttcacc   600
aaaccccagc tgtggccc                                                 618
```

<210> SEQ ID NO 48
<211> LENGTH: 618
<212> TYPE: DNA
<213> ORGANISM: Artificial Sequence
<220> FEATURE:
<223> OTHER INFORMATION: Description of Artificial Sequence: Synthetic
    polynucleotide

<400> SEQUENCE: 48

```
cagacagaca tgtcgaggaa ggcttttgtg tttcccaaag agtcggatac ttcctatgta    60
tccctcaaag caccgttaac gaagcctctc aaagccttca ctgtgtgcct ccacttctac   120
acggaactgt cctcgacccg tgggtacagt attttctcgt atgctactaa gagacaagac   180
aatgagattc tcatattttg gtctaaggat ataggataca gttttacagt gggtgggtct   240
gaaatattat tcgaggttcc tgaagtcaca gtagctccag tacacatttg tacttcctgg   300
gagtcagcaa gcggcattgt cgaattctgg gtggacggaa agcctagggt gagaaaatct   360
ctgaagaaag gatacacagt gggggccgag gctagtatca ttctggggca ggaacaggac   420
tcattcgggg gcaactttga aggctcccag tctctggtcg gggatatcgg caacgtgaac   480
atgtgggact ttgtcctgag cccagatgag atcaatacca tctacctggg agggcccttc   540
agccctaacg tgctgaattg gcgcgcactg aagtatgagg tccagggcga agtgtttaca   600
aaaccccagc tgtggcca                                                 618
```

<210> SEQ ID NO 49
<211> LENGTH: 618
<212> TYPE: DNA
<213> ORGANISM: Artificial Sequence
<220> FEATURE:
<223> OTHER INFORMATION: Description of Artificial Sequence: Synthetic
    polynucleotide

<400> SEQUENCE: 49

```
cagaccgata tgagccggaa agccttcgtg ttccctaaag agagcgatac cagctatgtg    60
agcctgaaag ccccactgac caaaccactg aaggccttca ccgtgtgcct gcacttttac   120
accgagctga gctccacacg agggtacagc atcttttcct atgctacaaa gaggcaggac   180
```

| | | |
|---|---|---|
| aacgaaatcc tgattttctg gtcaaaagat atcggctata gctttactgt gggcggatcc | 240 | |
| gagattctgt tcgaggtgcc cgaagtcaca gtggctcctg tccatatctg tacaagctgg | 300 | |
| gagtccgcct cagggatcgt ggagttctgg gtagatggga agcccagggt gaggaagagt | 360 | |
| ctgaagaagg gatacactgt gggggcagaa gcaagcatca tcttggggca ggagcaggat | 420 | |
| tccttcggtg ggaactttga aggaagccag tccctggtgg gagacattgg aaatgtgaac | 480 | |
| atgtgggact ttgtgctgtc accagatgag attaacacca tctatcttgg cgggcccttc | 540 | |
| agtcctaatg tcctgaactg gcgggcactg aagtatgaag tgcaaggcga agtgttcacc | 600 | |
| aaacccccagc tgtggccc | 618 | |

<210> SEQ ID NO 50
<211> LENGTH: 618
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 50

| | | |
|---|---|---|
| cagaccgata tgagccggaa agccttcgtg ttccctaaag agagcgatac cagctatgtg | 60 | |
| agcctgaaag ccccactgac caaaccactg aaggccttca ccgtgtgcct gcacttttac | 120 | |
| accgagctga gctccacacg agggtacagc atcttttcgt atgctactaa gagacaagac | 180 | |
| aatgagattc tcatattttg gtctaaggat ataggataca gttttacagt gggtgggtct | 240 | |
| gaaatattat tcgaggttcc tgaagtcaca gtagctccag tacacatttg tacaagctgg | 300 | |
| gagtccgcct cagggatcgt ggagttctgg gtagatggga agcccagggt gaggaagagt | 360 | |
| ctgaagaagg gatacactgt gggggcagaa gcaagcatca tcttggggca ggagcaggat | 420 | |
| tccttcggtg ggaactttga aggaagccag tccctggtgg gagacattgg aaatgtgaac | 480 | |
| atgtgggact ttgtgctgtc accagatgag atcaatacca tctacctggg agggcccttc | 540 | |
| agccctaacg tgctgaattg gcgcgcactg aagtatgagg tccagggcga agtgtttaca | 600 | |
| aaacccccagc tgtggcca | 618 | |

<210> SEQ ID NO 51
<211> LENGTH: 618
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 51

| | | |
|---|---|---|
| cagacagaca tgtcgaggaa ggcttttgtg tttcccaaag agtcggatac ttcctatgta | 60 | |
| tccctcaaag caccgttaac gaagcctctc aaagccttca ctgtgtgcct ccacttctac | 120 | |
| acggaactgt cctcgacccg tgggtacagt attttctcct atgctacaaa gaggcaggac | 180 | |
| aacgaaatcc tgattttctg gtcaaaagat atcggctata gctttactgt gggcggatcc | 240 | |
| gagattctgt tcgaggtgcc cgaagtcaca gtggctcctg tccatatctg tacttcctgg | 300 | |
| gagtcagcaa gcggcattgt cgaattctgg gtggacggaa agcctagggt gagaaaatct | 360 | |
| ctgaagaaag gatacacagt gggggccgag gctagtatca ttctggggca ggaacaggac | 420 | |
| tcattcgggg gcaactttga aggctcccag tctctggtcg gggatatcgg caacgtgaac | 480 | |
| atgtgggact ttgtcctgag cccagatgag attaacacca tctatcttgg cgggcccttc | 540 | |
| agtcctaatg tcctgaactg gcgggcactg aagtatgaag tgcaaggcga agtgttcacc | 600 | |

-continued

```
aaacccagc tgtggccc                                                618

<210> SEQ ID NO 52
<211> LENGTH: 618
<212> TYPE: DNA
<213> ORGANISM: Homo sapiens

<400> SEQUENCE: 52
cagacagaca tgtcgaggaa ggcttttgtg tttcccaaag agtcggatac ttcctatgta    60
tccctcaaag caccgttaac gaagcctctc aaagccttca ctgtgtgcct ccacttctac   120
acggaactgt cctcgacccg tgggtacagt attttctcgt atgctactaa gagacaagac   180
aatgagattc tcatattttg gtctaaggat ataggataca gttttacagt gggtgggtct   240
gaaatattat tcgaggttcc tgaagtcaca gtagctccag tacacatttg tacaagctgg   300
gagtccgcct cagggatcgt ggagttctgg gtagatggga agcccagggt gaggaagagt   360
ctgaagaagg gatacactgt gggggcagaa gcaagcatca tcttggggca ggagcaggat   420
tccttcggtg ggaactttga aggaagccag tccctggtgg gagacattgg aaatgtgaac   480
atgtgggact ttgtgctgtc accagatgag attaacacca tctatcttgg cgggcccttc   540
agtcctaatg tcctgaactg gcgggcactg aagtatgaag tgcaaggcga agtgttcacc   600 aaacccagc tgtggccc                                                 618

<210> SEQ ID NO 53
<211> LENGTH: 6
<212> TYPE: PRT
<213> ORGANISM: Artificial Sequence
<220> FEATURE:
<223> OTHER INFORMATION: Description of Artificial Sequence: Synthetic
      6xHis tag

<400> SEQUENCE: 53

His His His His His His
1               5
```